(12) United States Patent
Houmard et al.

(10) Patent No.: US 7,786,351 B2
(45) Date of Patent: Aug. 31, 2010

(54) RECOMBINANT DNA CONSTRUCTS AND METHODS FOR CONTROLLING GENE EXPRESSION

(75) Inventors: Nancy Houmard, North Stonington, CT (US); Shihshieh Huang, Woodland, CA (US); Thomas Malvar, North Stonington, CT (US)

(73) Assignee: Monsanto Technology, LLC, St. Louis, MO (US)

( * ) Notice: Subject to any disclaimer, the term of this patent is extended or adjusted under 35 U.S.C. 154(b) by 357 days.

(21) Appl. No.: 11/545,086

(22) Filed: Oct. 10, 2006

(65) Prior Publication Data

US 2007/0089192 A1      Apr. 19, 2007

Related U.S. Application Data

(60) Provisional application No. 60/736,525, filed on Nov. 14, 2005, provisional application No. 60/726,106, filed on Oct. 13, 2005.

(51) Int. Cl.
*C12N 15/82* (2006.01)
*C07H 21/04* (2006.01)

(52) U.S. Cl. .................... 800/287; 800/278; 536/24.1

(58) Field of Classification Search .................. None
See application file for complete search history.

(56) References Cited

OTHER PUBLICATIONS

Whitelaw et al. Aug. 2003, Genbank Accession No. CG266326.*
Sequence alignment.*
Kim et al. 1994, Plant Molecular Biology 24: 105-11.*
Oommenn et al 1994, The Plant Cell 6:1789-1803.*
Megraw et al. (2006) "MicroRNA promoter element discovery in Arabidopsis." RNA, 12:1612-1619.
Wang et al. (2006) "Significant sequence similarities in promoters and precursors of *Arabidopsis thaliana* non-conserved microRNAs." Bioinformatics, 22:2585-2589.
U.S. Appl. No. 11/545,082, Huang, Shihshieh, entire document.
U.S. Appl. No. 11/544,928, Huang, Shihshieh, entire document.
U.S. Appl. No. 11/545,030, Huang, Shihshieh, entire document.
U.S. Appl. No. 11/544,944, Huang, Shihshieh, entire document.
U.S. Appl. No. 11/545,105, Huang, Shihshieh, entire document.
U.S. Appl. No. 11/544,953, Huang, Shihshieh, entire document.
U.S. Appl. No. 11/545,106, Huang, Shihshieh, entire document.
U.S. Appl. No. 11/545,088, Huang, Shihshieh, entire document.
U.S. Appl. No. 11/545,098, Huang, Shihshieh, entire document.
U.S. Appl. No. 11/544,962, Huang, Shihshieh, entire document.
U.S. Appl. No. 11/545,027, Huang, Shihshieh, entire document.
U.S. Appl. No. 11/545,076, Huang, Shihshieh, entire document.
U.S. Appl. No. 11/545,084, Huang, Shihshieh, entire document.
U.S. Appl. No. 11/544,959, Huang, Shihshieh, entire document.
U.S. Appl. No. 11/544,954, Huang, Shihshieh, entire document.
U.S. Appl. No. 11/303,745, Huang, Shihshieh, entire document.
U.S. Appl. No. 11/544,942, Huang, Shihshieh, entire document.
U.S. Appl. No. 11/544,940, Huang, Shihshieh, entire document.
U.S. Appl. No. 11/544,960, Huang, Shihshieh, entire document.
U.S. Appl. No. 11/544,961, Huang, Shihshieh, entire document.
U.S. Appl. No. 11/545,075, Huang, Shihshieh, entire document.
U.S. Appl. No. 11/545,029, Huang, Shihshieh, entire document.
U.S. Appl. No. 11/545,072, Huang, Shihshieh, entire document.
U.S. Appl. No. 11/545,071, Huang, Shihshieh, entire document.
U.S. Appl. No. 11/545,099, Huang, Shihshieh, entire document.
05857084.7-1212/1824967, Aug. 29, 2007, Monsanto Technology, LLC, entire document.

* cited by examiner

*Primary Examiner*—David H Kruse
*Assistant Examiner*—Li Zheng
(74) *Attorney, Agent, or Firm*—Maria Margarita D. Unson; Thomas E. Kelley

(57) ABSTRACT

The present invention provides molecular constructs and methods for use thereof, including constructs including heterologous miRNA recognition sites, constructs for gene suppression including a gene suppression element embedded within an intron flanked on one or on both sides by non-protein-coding sequence, constructs containing engineered miRNA or miRNA precursors, and constructs for suppression of production of mature microRNA in a cell. Also provided are transgenic plant cells, plants, and seeds containing such constructs, and methods for their use. The invention further provides transgenic plant cells, plants, and seeds containing recombinant DNA for the ligand-controlled expression of a target sequence, which may be endogenous or exogenous. Also disclosed are novel miRNAs and miRNA precursors from crop plants including maize and soy.

8 Claims, 30 Drawing Sheets

FIGURE 5
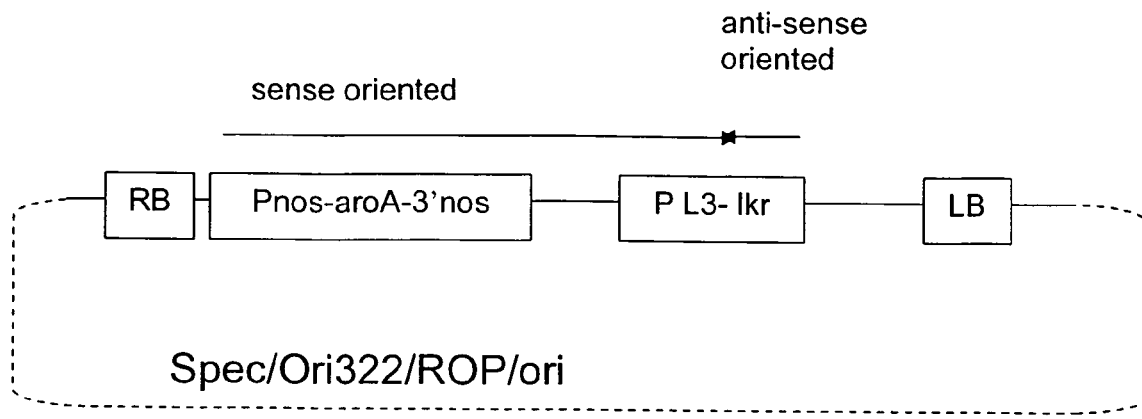
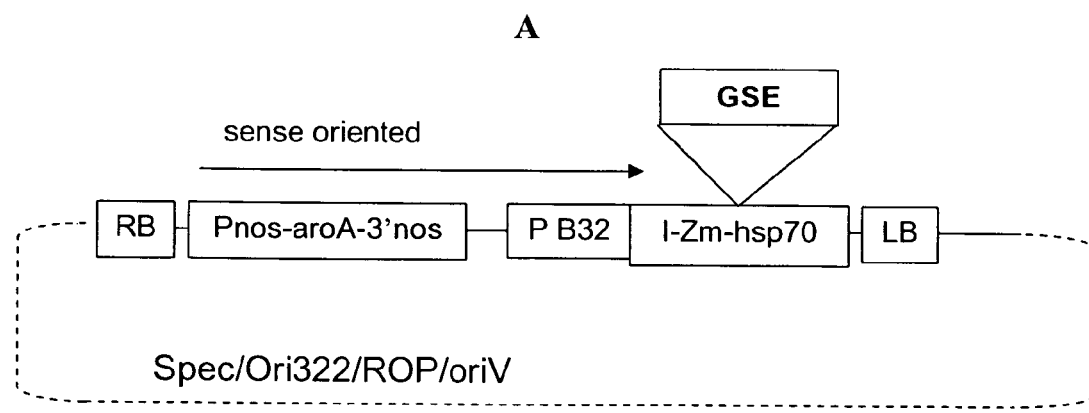
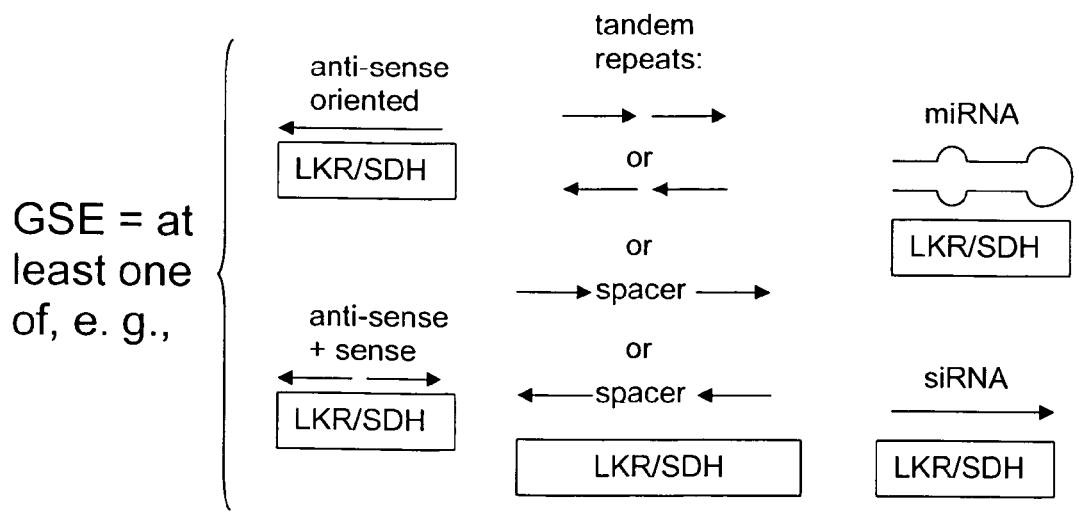

FIGURE 6
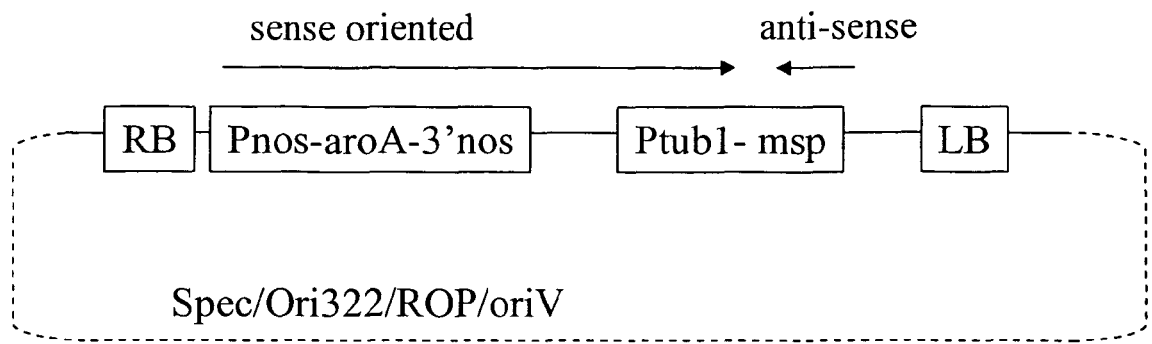
A
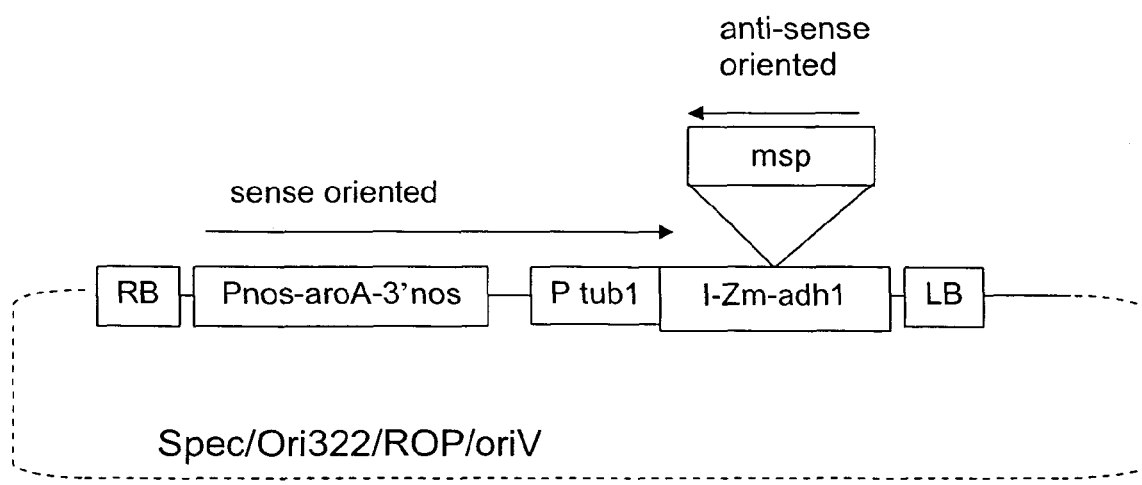

FIGURE 8
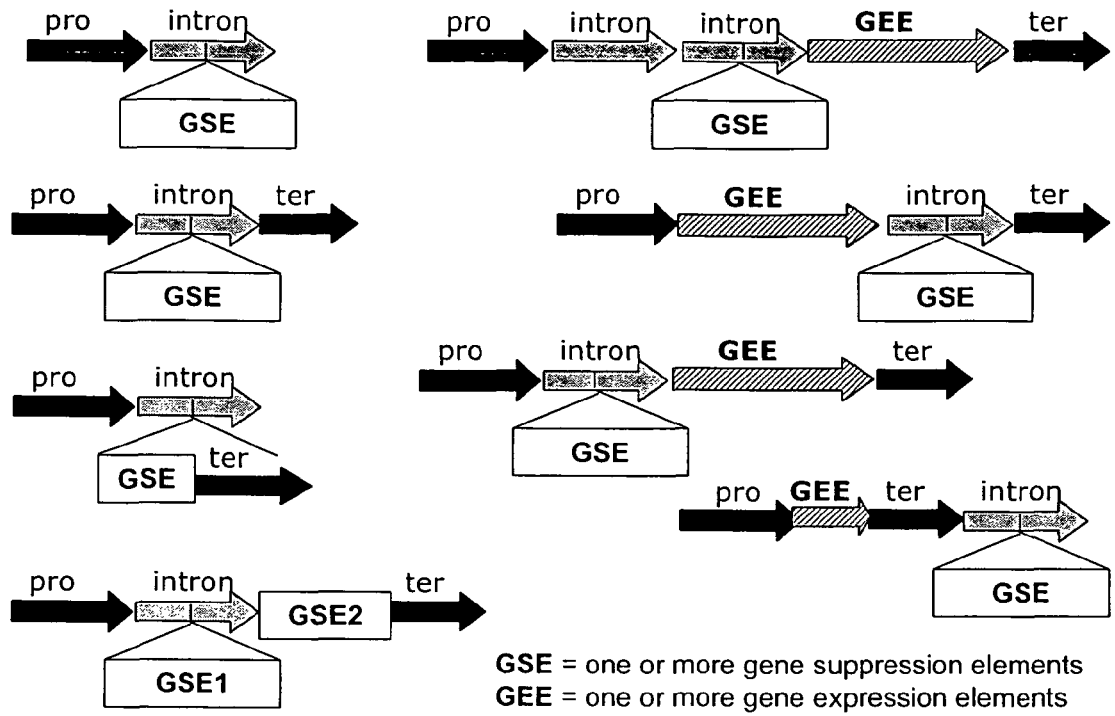
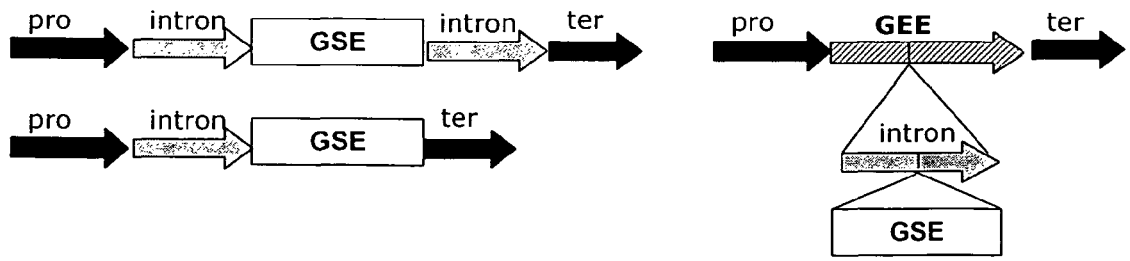
A

FIGURE 11

```
>MRT4577_318026C Zm-MIR164e   (fold-back portion of SEQ ID NO. 10)
    152 tggtgagaaggtccctgttggagaagcagggcacgtgcag 191
        |||||||||| || || ||||||||  | ||||| ||||
    353 accactcttcc-ggcaccacctcttcccctcgtgc-cgtc 315

>MRT4577_179508C,MRT4577_58555C Zm-MIR319-like(fold-back portion ofSEQ ID NO.12)
    783 ggatcggagggagcacccttcagtccaagcaaagacggtgcgag 826
        |||| | || ||||  |||||||||||| ||  | |||||| ||
    971 cctaccttctctcgcaggaagtcaggtgagtccccgccacgatc 928

>MRT4577_260136C Zm-MIR393b   (fold-back portion of SEQ ID NO. 14)
     39 agtggaggactccaaagggatcgcattgatctaacctgc 77
        ||||||| | ||||||||||| ||| ||| || | ||||
    151 tcacctcttaaggtttccctaacgtgact-gactagacg 114

>MRT4577_22487C Zm-MIR399G   (fold-back portion of SEQ ID NO. 16)
    131 agctgaagacagttgta-ggcagctctcctctggcagg 167
        |||||||||||||.|.| ||||.|||||||| |||||||
    335 tcgacttctgtcagcgtcccgttgagaggaaaccgtcc 298

>MRT4577_267767C Zm-MIR408B   (fold-back portion of SEQ ID NO. 18)
     66 ggagacagggacgaggcagagcatgggtaggggc 100
        |||| |||||| ||||||| ||| ||| |||| ||
    216 cctcggtcccttctccgtcacgt-cccctccctcg 183

>ZMRC1_cluster1_Zm-MIR397   (fold-back portion of SEQ ID NO. 22)
    327 aagcaaaggcatcattgagcgcagcgttgatgagccagccgc 368
        ||||||||| | |||||| |||||| || |||||| |||||
    428 ttcgtttccgcattaactcacgtcgcgaccactcgg-cggcg 388

>BC-gmXLIB3544002Ag05b1 Gm-MIR393a   (fold-back portion of SEQ ID NO. 24)
    461 aggaggcatccaaagggatcgcattgatcccaaat 495
        |||||. ||||||||||||| ||| |||||||||||
    575 tcctctttaggtttccctatcgt-actagggttta 542

>GLYMA-06JUN02-CLUSTER7414_5 Gm-MIR393b   (fold-back portion of SEQ ID NO. 26)
     86 ttattgtgggtggagagttccaaagggatcgcattgatctaat 128
        ||| || |.||||.||||||  |||||||||||| |||||.|||
    241 aatctcaactacctttcaaggattccctagcgt-actaggtta 200

>LIB5119-036-A1-PF1-B6 Gm-MIR399   (fold-back portion of SEQ ID NO. 28)
      3 gttgcagctgcattacagggcaagttctccattggcaggtagc 45
        |||||||  | ||. | ||||||  ||||| ||||||||.| ||
    131 caacgtcctcttagcgacccgtt-tagaggaaaccgtctaacg 90

>gC-gmleLIB3762P080h12b1 Gm-MIR164a   (fold-back portion of SEQ ID NO. 30)
    191 gagaagctccttgttggagaagcagggcacgtgcaa 226
          |||||.| || ||||||||||||  |.||||||||||
    292 ctctttg-ggcacaacctcttcccctcgtgcacgtt 258

>GM_651_A2_G05_MR Gm-MIR164c   (fold-back portion of SEQ ID NO. 34)
    177 attatgtgcatgttgtgcaagatggagaagcagggcacgtgcaatactaactcat 231
        || | |||| |||||| || |||||.||| ||||||.|| | ||||||| ||
    356 tattccacg-acaaca-gtactacccctttctccccgtgtacttcttgattgatta 304
```

FIGURE 12

>MRT3847_253879C.2 Glycine max miRNA (fold-back portion of SEQ ID NO. 38)
    94 acaggaucguccugagaccaaaugagcagcuga 126
        |||.| || ||||||| || |||||||||||
   185 uguucccgcuggacucuugucuacucgucgacu 153

>MRT3847_268725C Gm-MIR408 (fold-back portion of SEQ ID NO. 39)
    282 gacaaagcaggggaacaggcagagcatg 309
       |||| ||| ||||| |||||| |||||
   405 ctgtctcggtcccttctccgtcacgtac 378

FIGURE 13

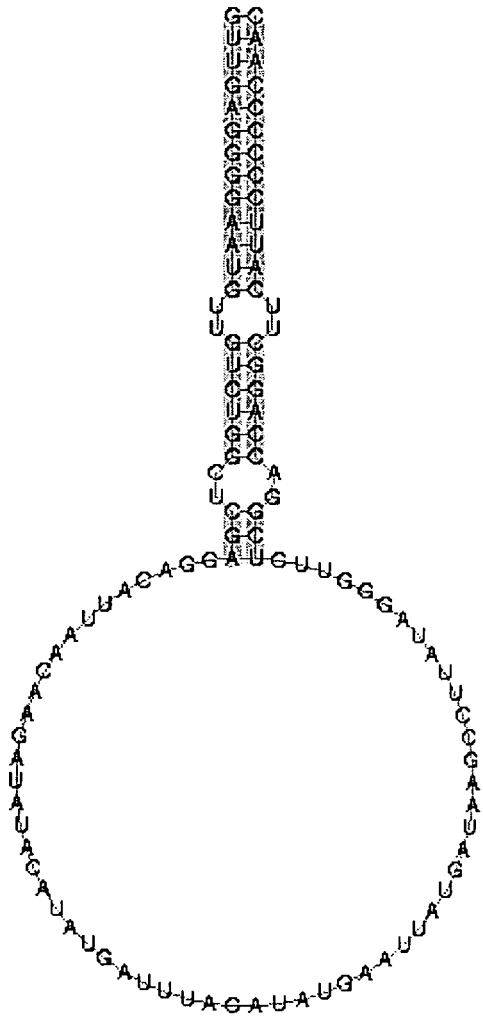

>ZM4683.C4_Segment_6065_6446:Segment{304..176}
/ZM_BACS/LIB4683/edit_dir/LIB4683.fasta.scree.ace.5 from 339 to 26663
(SEQ ID NO. 43)
GTTAAGGGGTCTGTTGTCTGGTTCAAGGTCGCCACAGCAGGCAAATAAAGCCCATTTCGC
GCTTAGCATGCACCATGCATGATGGGTGTACCTGTTGGTGATCTCGGACCAGGCTTCAAT
CCCTTTAAC >ZM4133.C1_Segment_5776_6156:Segment{261..176}
/projects/gsc/BACS/LIB4133/edit_dir/LIB4133.fasta.screen.ace.6 (whole
contig) (SEQ ID NO. 44)
GTCGAGGGGAATGACGTCCGGTCCGAACGAGCCACGGCTGCTGCTGCGCCGCCGCGGGCT
TCGGACCAGGCTTCATTCCCCGTGAC

FIGURE 15

```
         ---------|---------|---------|---------|---------|
    1 acacgctgaaaccatcttccacacactcaagccacactattggagaacac  50

51 acagggacaacacaccataaccgccgccgccggtagaagATGGCGCCCAC 100
                                             M  A  P  T   5

101 CGTGATGATGGCCTCGTCGGCCACCGCCGTCGCTCCGTTCCaGGGGCTCA 150
    6  V  M  M  A  S  S  A  T  A  V  A  P  F  Q  G  L  K 22

151 AGTCCACCGCCAGCCTCCCCGTCGCCCGCCGCTCCTCCAGAAGCCTCGGC 200
   23  S  T  A  S  L  P  V  A  R  R  S  S  R  S  L  G   38

201 AACGTCAGCAACGGCGGAAGGATCCGGTGCATGCAGGTGTGGCCggcCTA 250
   39 N  V  S  N  G  G  R  I  R  C  M  Q  V  W  P  A  Y  55

251 CGGCAACAAGAAGTTCGAGACGCTGTCGTACCTGCCGCCGCTGTCGAccG 300
   56  G  N  K  K  F  E  T  L  S  Y  L  P  P  L  S  T  G 72

301 GCGGgcgcatccgctgcatgcaggcCATGgccTTCTTCAAcCGGGTgATc 350
   73   G  R  I  R  C  M  Q  A  M  A  F  F  N  R  V  I   88

351 ACCCTcACgGTgCCgTCgTCAGACGTGGTCAACTACTCgGAgATcTAcCA 400
   89 T  L  T  V  P  S  S  D  V  V  N  Y  S  E  I  Y  Q 105

401 GGTgGCTCCTCAGTATGTcAACCAgGCcCTGACccTGGCcAAGTAcTTcC 450
  106  V  A  P  Q  Y  V  N  Q  A  L  T  L  A  K  Y  F  Q 122

451 AgGGCGCcATcGACGGcAGCACCCTgAGGTTCGAcTTCGAgAAgGCGTTA 500
  123    G  A  I  D  G  S  T  L  R  F  D  F  E  K  A  L  138

501 CAgATcGCCAACGACATcCCGCAgGCcGCgGTgGTcAACACCCTgAAcCA 550
  139  Q  I  A  N  D  I  P  Q  A  A  V  V  N  T  L  N  Q 155

551 GACCGTCCAGCAGGGGACCGTCCAGGTCAGCGTcATGATCGAcAAGATcG 600
  156  T  V  Q  Q  G  T  V  Q  V  S  V  M  I  D  K  I  V 172

601 TGGACATCATGAAgAATGTCCTGTCCATCGTGATAGAcAACAAGAAGTTT 650
  173   D  I  M  K  N  V  L  S  I  V  I  D  N  K  K  F  188

651 TGGGATCAGGTCACGGCTGCcATcACcAAcACCTTCACgAAcCTGAACag 700
  189 W  D  Q  V  T  A  A  I  T  N  T  F  T  N  L  N  S 205

701 cCAgGAgTCgGAGgccTGGATCTTCTATTAcAAgGAgGACGCCCACAAGA 750
  206  Q  E  S  E  A  W  I  F  Y  Y  K  E  D  A  H  K  T 222

751 CGTCCTAcTAtTAcAACATCCTCTTCGCcATCCAGGACGAAGAGACGGGt 800
  223    S  Y  Y  Y  N  I  L  F  A  I  Q  D  E  E  T  G  238

801 GGcGTGATGGCcACGcTGCCCATCGCCTTCGACATCAGTGTgGACATCGA 850
  239 G  V  M  A  T  L  P  I  A  F  D  I  S  V  D  I  E 255

851 GAAgGAgAAgGTCCTGTTCGTgACcATcAAGGACACTGAGAATTACGCCG 900
  256  K  E  K  V  L  F  V  T  I  K  D  T  E  N  Y  A  V 272

901 TCACCGTCAAGGCGATCAACGTGGTcCAGGCACTccAgTCTAGCAGGGAT 950
  273   T  V  K  A  I  N  V  V  Q  A  L  Q  S  S  R  D  288

951 TCTAAGGTGGTTGATGCGTTCAAATCGCCaCGGCACTTACCCCGGAAGAG 1000
  289 S  K  V  V  D  A  F  K  S  P  R  H  L  P  R  K  R 305

1001 GCATAAGATTTGCTCTAACTCGtgatgActgcTGGATGCAGAGGTATTAT 1050
  306  H  K  I  C  S  N  *  *            miRNA162 site 1051 CGatgcgtttggacgtatgctcattcaggttggagccaatttggttgatg 1100

1101 tgtgtgcgagttcttgcgagtctgatgagacatctctgtattgtgtttct 1150

1151 ttccccagtgttttctgtacttgtgtaatcggctaatcgccaacagattc 1200

1201 ggcgatgaataaatgagaaataaattgttctgattttgagtg 1242
         ---------|---------|---------|---------|---------|
```

SEQ ID NO. 220

FIGURE 16

```
       ---------|---------|---------|---------|---------|
  1 ACACGCTGAcaagctGACTCTAGcagatCctctagaaccatcttccacac  50

51 actcaagccacactattggagaacacacagggacaacacaccataaGATC 100

101 CAAGGGAGGCCTCCGCCGCCGCCGGTAGAAGTGATCAACcATGgccTTCT 150
                                             M  A  F  F  6

151 TCAAcCGGGTgATcACCCTcACgGTgCCgTCgTCAGACGTGGTCAACTAC 200
  7  N  R  V  I  T  L  T  V  P  S  S  D  V  V  N  Y  22

201 TCgGAgATcTAcCAGGTgGCTCCTCAGTATGTcAACCAgGCcCTGACccT 250
 23  S  E  I  Y  Q  V  A  P  Q  Y  V  N  Q  A  L  T  L  39

251 GGCcAAGTAcTTcCAgGGCGCcATcGACGGcAGCACCCTgAGGTTCGAcT 300
 40  A  K  Y  F  Q  G  A  I  D  G  S  T  L  R  F  D  F 56

301 TCGAgAAgGCGTTACAgATcGCCAACGACATcCCGCAgGCcGCgGTgGTc 350
 57  E  K  A  L  Q  I  A  N  D  I  P  Q  A  A  V  V  72

351 AACACCCTgAAcCAGACCGTCCAGCAGGGGACCGTCCAGGTCAGCGTcAT 400
 73  N  T  L  N  Q  T  V  Q  Q  G  T  V  Q  V  S  V  M  89

401 GATCGAcAAGATcGTGGACATCATGAAgAATGTCCTGTCCATCGTGATAG 450
 90   I  D  K  I  V  D  I  M  K  N  V  L  S  I  V  I  D 106

451 AcAACAAGAAGTTTTGGGATCAGGTCACGGCTGCcATcACcAACACCTTC 500
107   N  K  K  F  W  D  Q  V  T  A  A  I  T  N  T  F  122

501 ACGAAcCTGAACagcCAgGAgTCgGAGgccTGGATCTTCTATTAcAAgGA 550
123  T  N  L  N  S  Q  E  S  E  A  W  I  F  Y  Y  K  E 139

551 gGACGCCCACAAGACGTCcTAcTAtTAcAACATCCTCTTCGCcATCCAGG 600
140  D  A  H  K  T  S  Y  Y  Y  N  I  L  F  A  I  Q  D 156

601 ACGAAGAGACGGGtGGcGTGATGGCcACgcTGCCCATCGCCTTCGACATC 650
157  E  E  T  G  V  M  A  T  L  P  I  A  F  D  I    172

651 AGTGTgGACATCGAGAAgGAgAAgGTCCTGTTCGTgACCATCAAGGAcAC 700
173  S  V  D  I  E  K  E  K  V  L  F  V  T  I  K  D  T 189

701 TGAGAATTACGCCGTCACCGTCAAGGCGATCAACGTGGTCCAGGCACTcc 750
190   E  N  Y  A  V  T  V  K  A  I  N  V  V  Q  A  L  Q 206

751 AgTCTAGCAGGGATTCTAAGGTGGTTGATGCGTTCAAATCGCCaCGGCAC 800
207    S  S  R  D  S  K  V  V  D  A  F  K  S  P  R  H 222

801 TTACCCCGGAAGAGGCATAAGATTTGCTCTAACTCGtgatgAATgTACGT 850
223 L  P  R  K  R  H  K  I  C  S  N  *  *       miRNA164

851 GCCCTGCTTCTCCATCTGCATGCGTTTGGACGTATGCTCATTCAGGTTGG 900

901 AGCCAATTTGGTTGATGTGTGTGCGAGTTCTTGCGAGTCTGATGAGACAT 950

951 CTCTGT 956
    ---------|---------|---------|---------|---------|
```

SEQ ID NO. 221

FIGURE 17
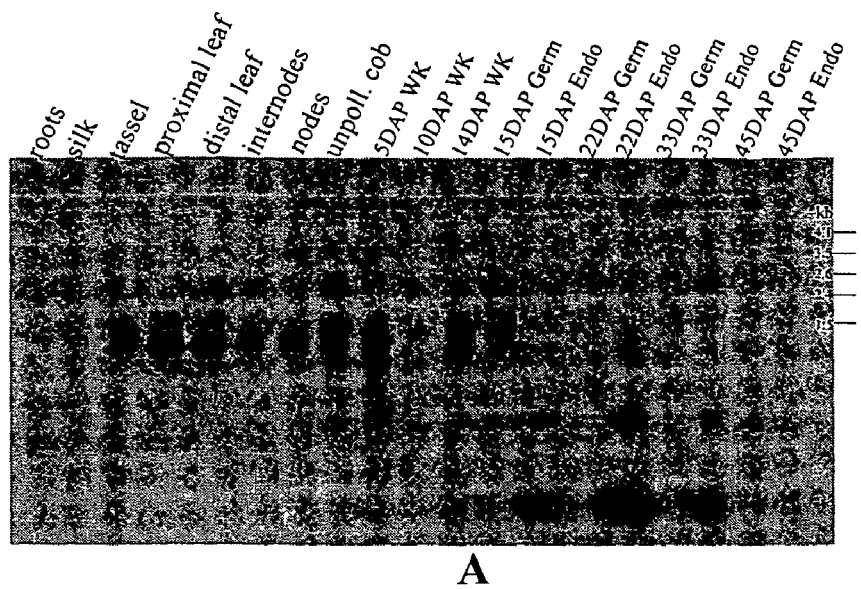
A
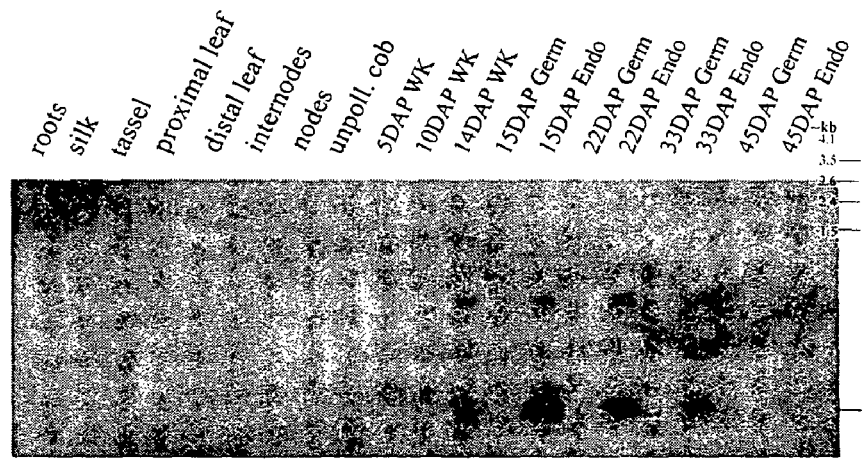
B
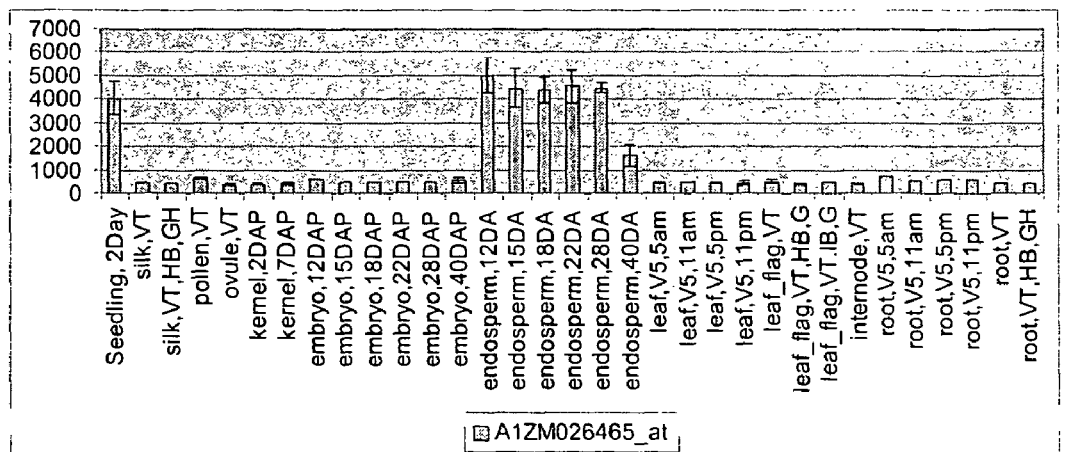
C

FIGURE 19
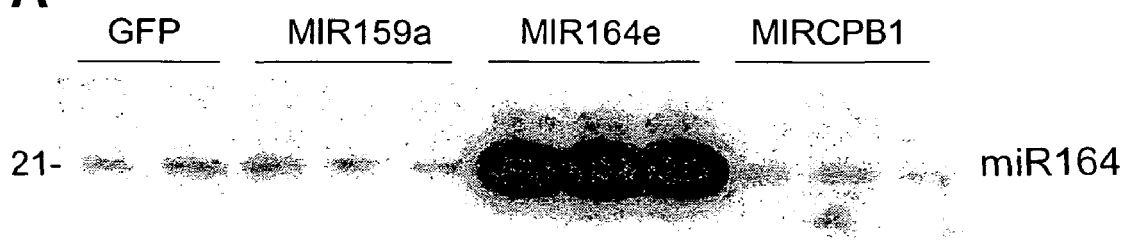
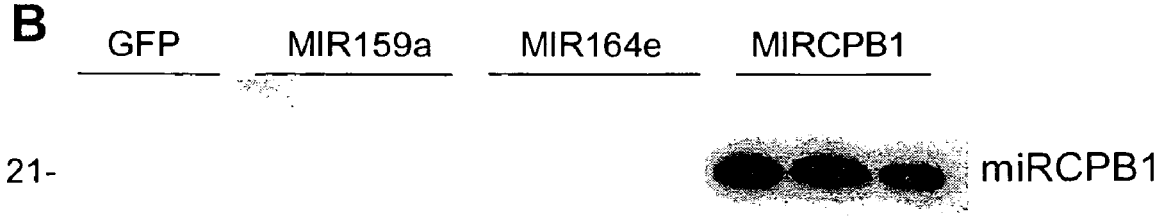

FIGURE 20
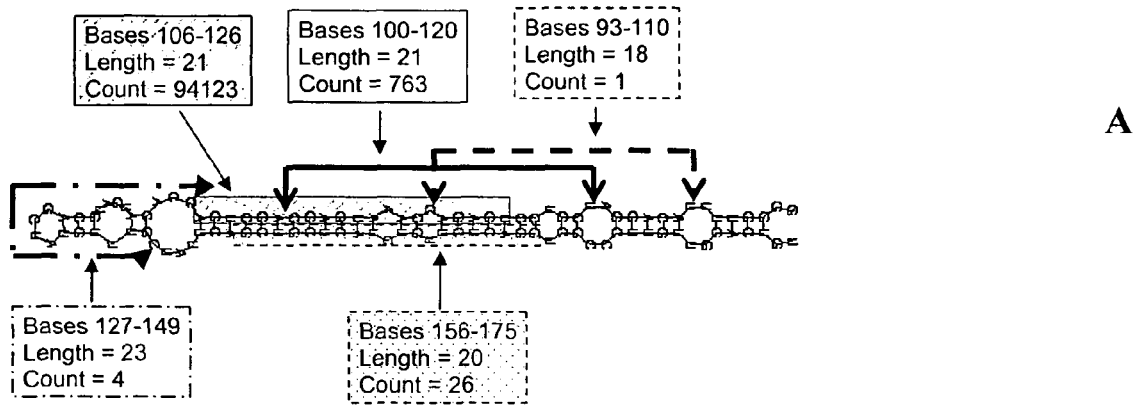
A
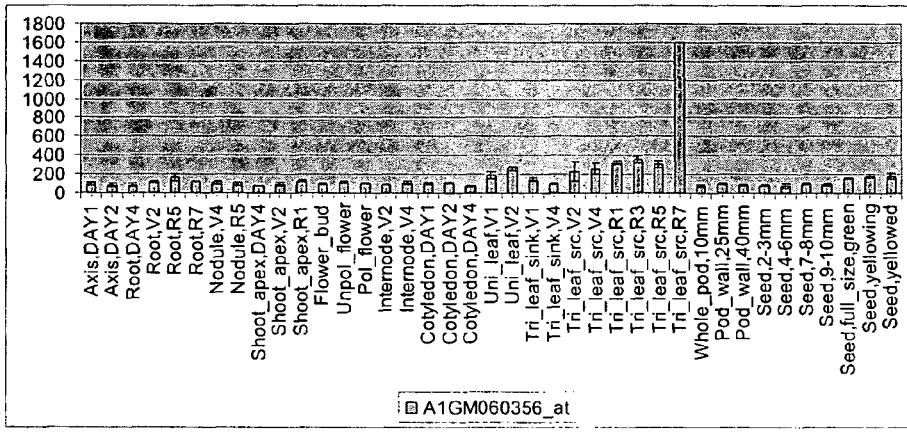
B
miRNA (3' - 5')   AGUCGACGAGUAAACCAGAGU (SEQ ID NO. 234)
Target (5' - 3') (bases 153-173)   Ccagcugcucauuuggucacu (SEQ ID NO. 250)
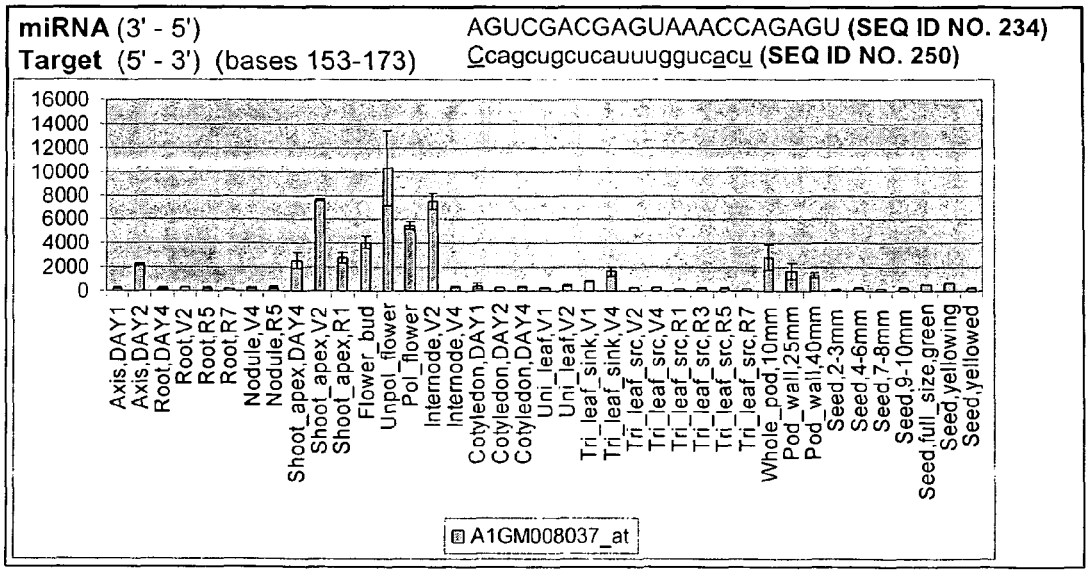
C

FIGURE 21
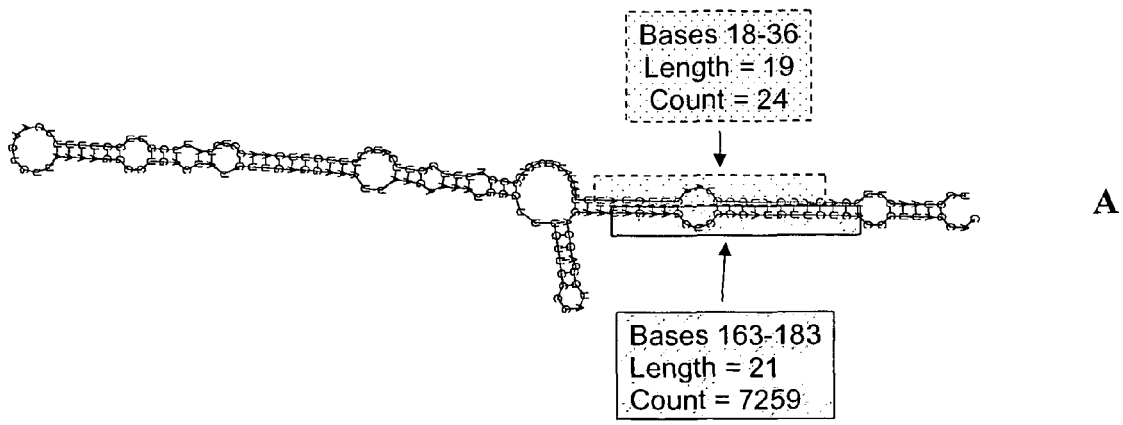
A
| miRNA (3' - 5') | ACUCUUGUACCCCUCGAAGAU (SEQ ID NO. 237) |
|---|---|
| Target (5' - 3') (bases 1111-1131) | Agaggacaugggga g guucua (SEQ ID NO. 251) |
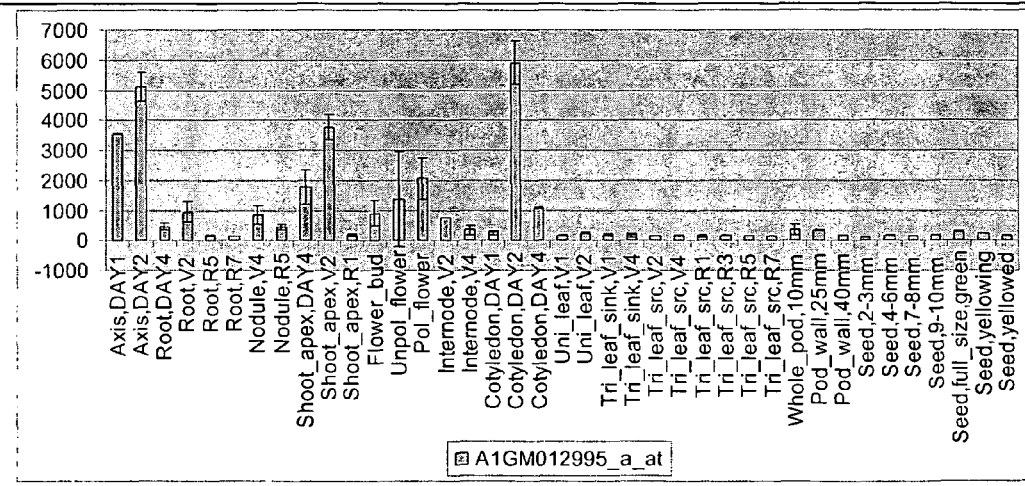
B

FIGURE 24
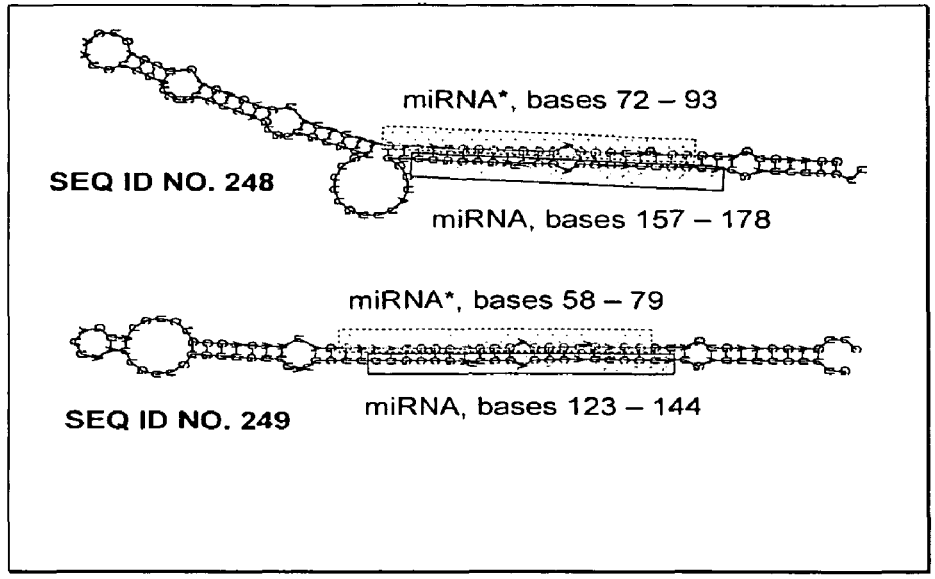
A
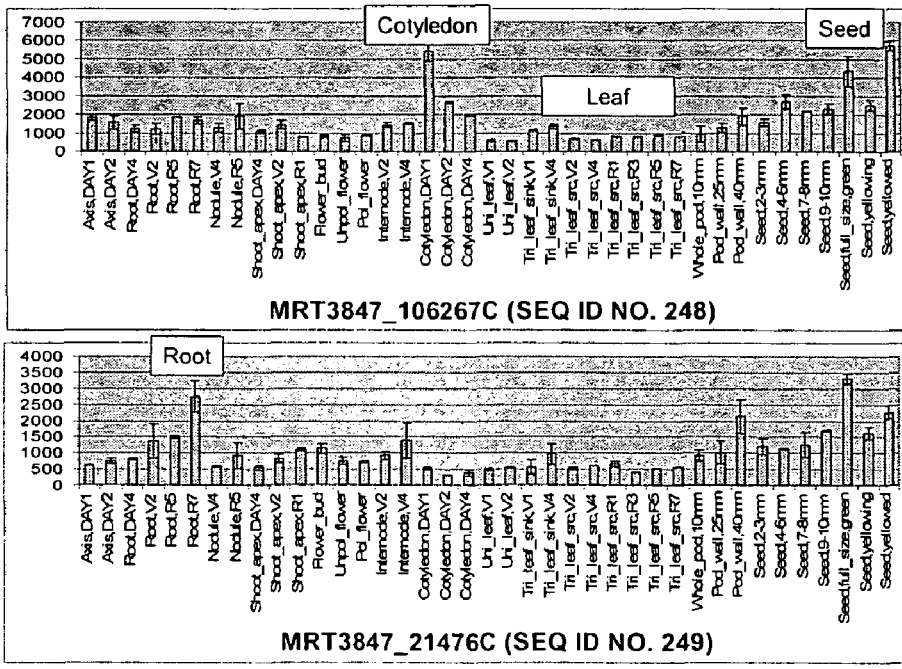
B

FIGURE 25

| Promoter<br>e.g. pB32 | 5' intron<br>e.g. ADH1 | Gene of interest<br>e.g. cordapA | polyA site<br>e.g. nos 3' | Inverted repeat for target gene<br>e.g. LKR' |

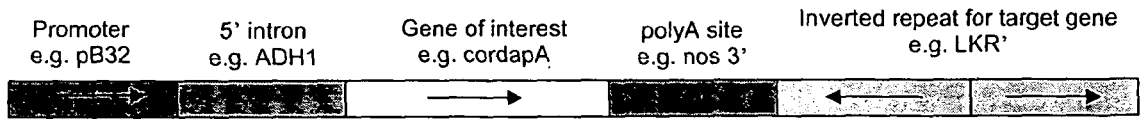

| Promoter<br>e.g. pB32 | 5' intron<br>e.g. ADH1 | Gene of interest<br>e.g. cordapA | polyA site<br>e.g. nos 3' | Inverted repeat for target gene<br>e.g. LKR' |

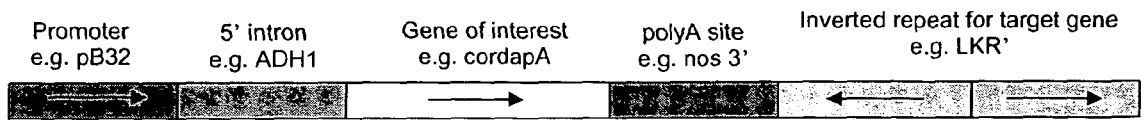

| Promoter<br>e.g. pB32 | 5' intron<br>e.g. ADH1 | Gene of interest<br>e.g. cordapA | polyA site<br>e.g. nos 3' | AS for target gene<br>e.g. LKR | polyA site<br>e.g. nos 3' |

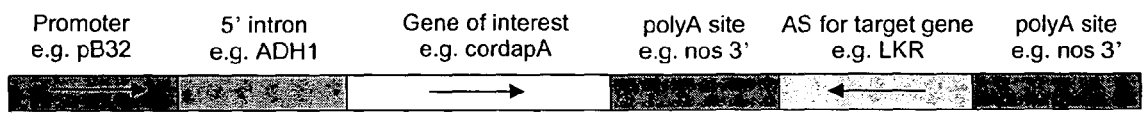

| Promoter<br>e.g. pB32 | 5' intron<br>e.g. ADH1 | Gene of interest<br>e.g. cordapA | polyA site<br>e.g. nos 3' | AS for target gene<br>e.g. LKR |

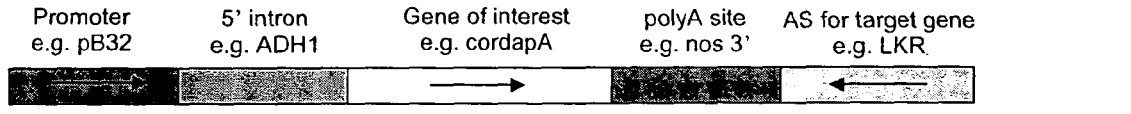

| Promoter<br>e.g. pRact1 | 5' intron<br>e.g. ract-1 | Gene of interest<br>e.g. B.t. gene | polyA site<br>e.g. nos 3' | Inverted repeat for target gene<br>e.g. CRW V-ATPase | polyA site<br>e.g. nos 3' |

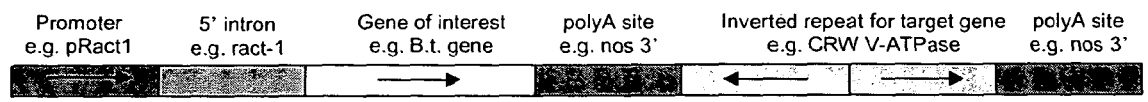

| Promoter<br>e.g. pRact1 | 5' intron<br>e.g. ract-1 | Gene of interest<br>e.g. B.t. gene | polyA site<br>e.g. nos 3' | Inverted repeat for target gene<br>e.g. CRW V-ATPase |

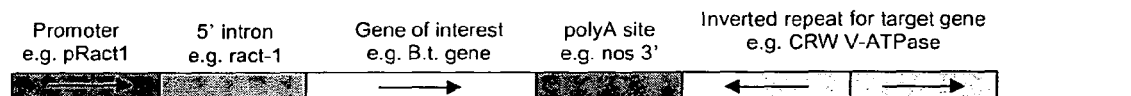

| e35S | GUS | nos 3' polyA site | Inverted repeat for target gene<br>LUC |

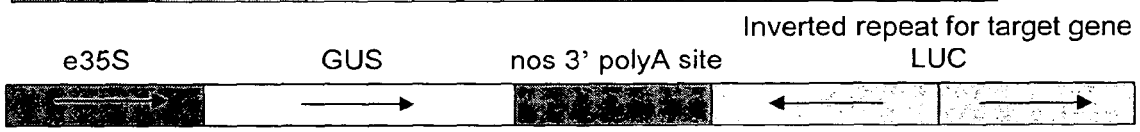

| e35S | GUS | nos 3' polyA site | Antisense LUC | polyA site<br>e.g. nos 3' |

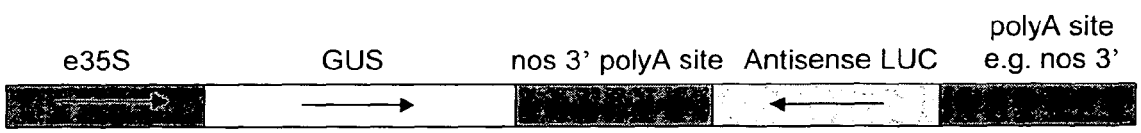

| e35S | GUS | nos 3' polyA site | Antisense LUC |

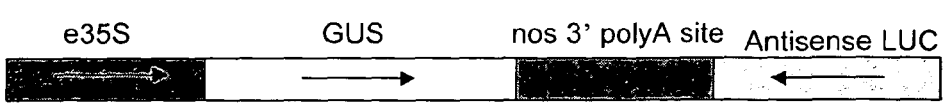

FIGURE 26
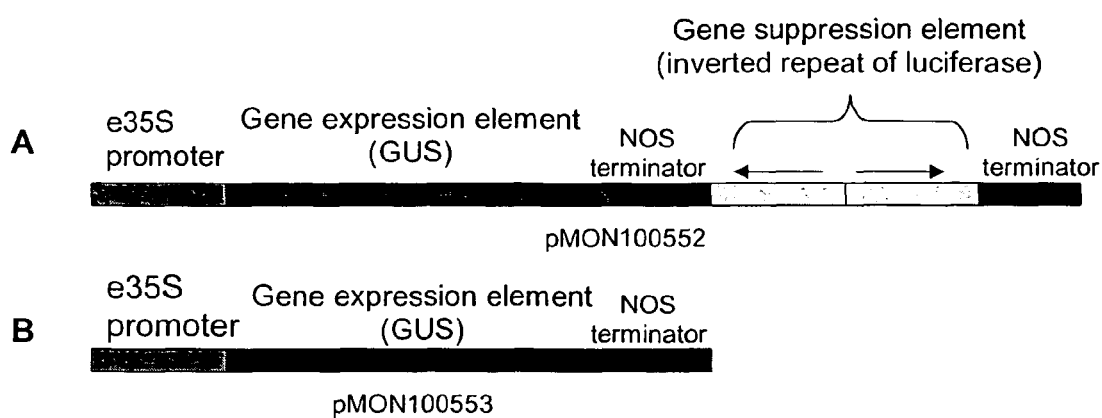
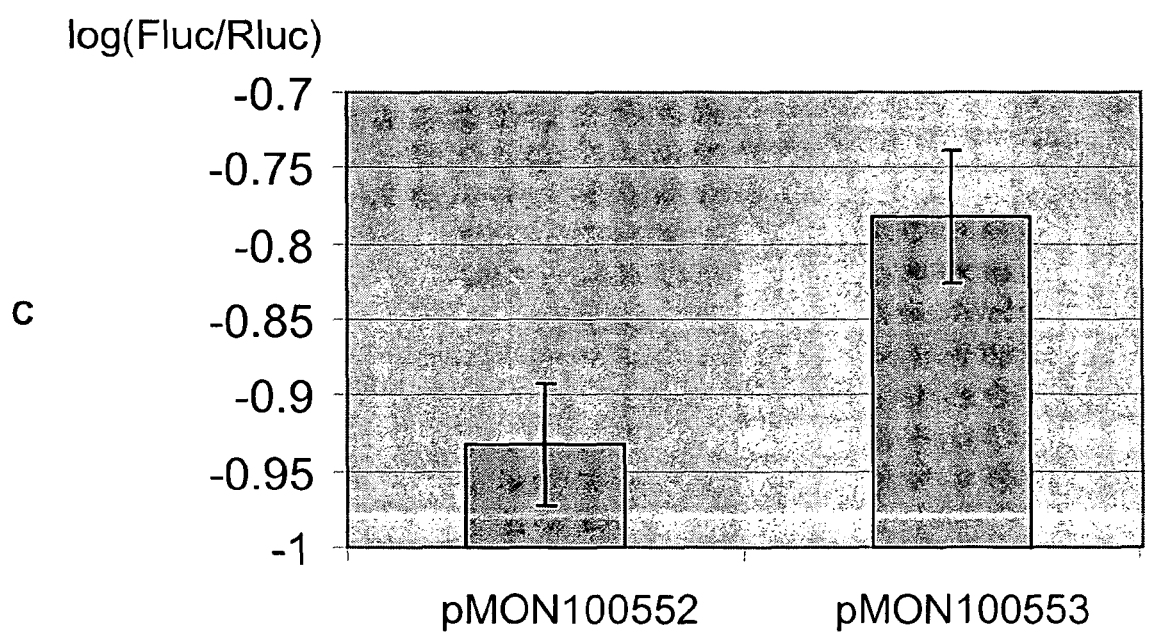

FIGURE 28
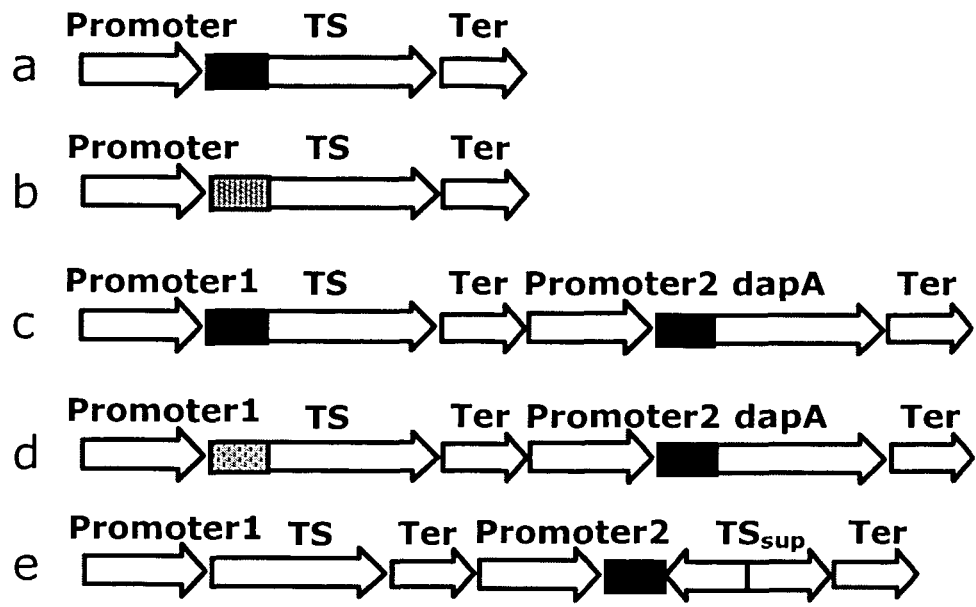
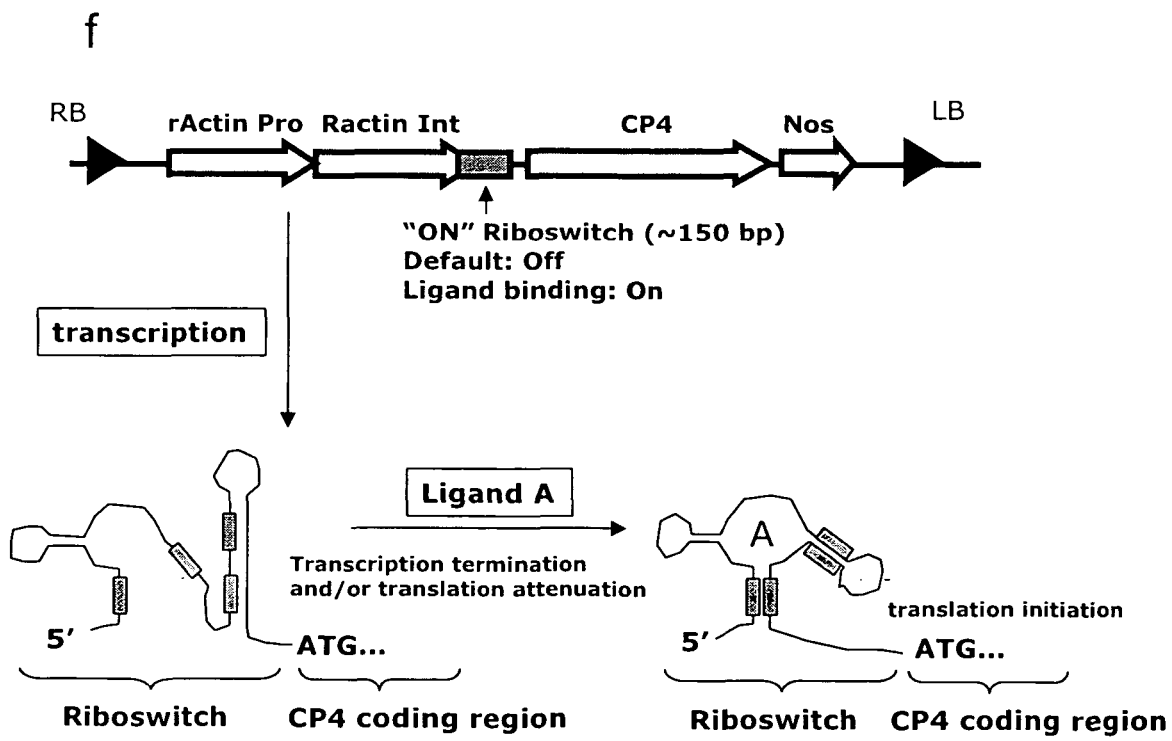

FIGURE 29
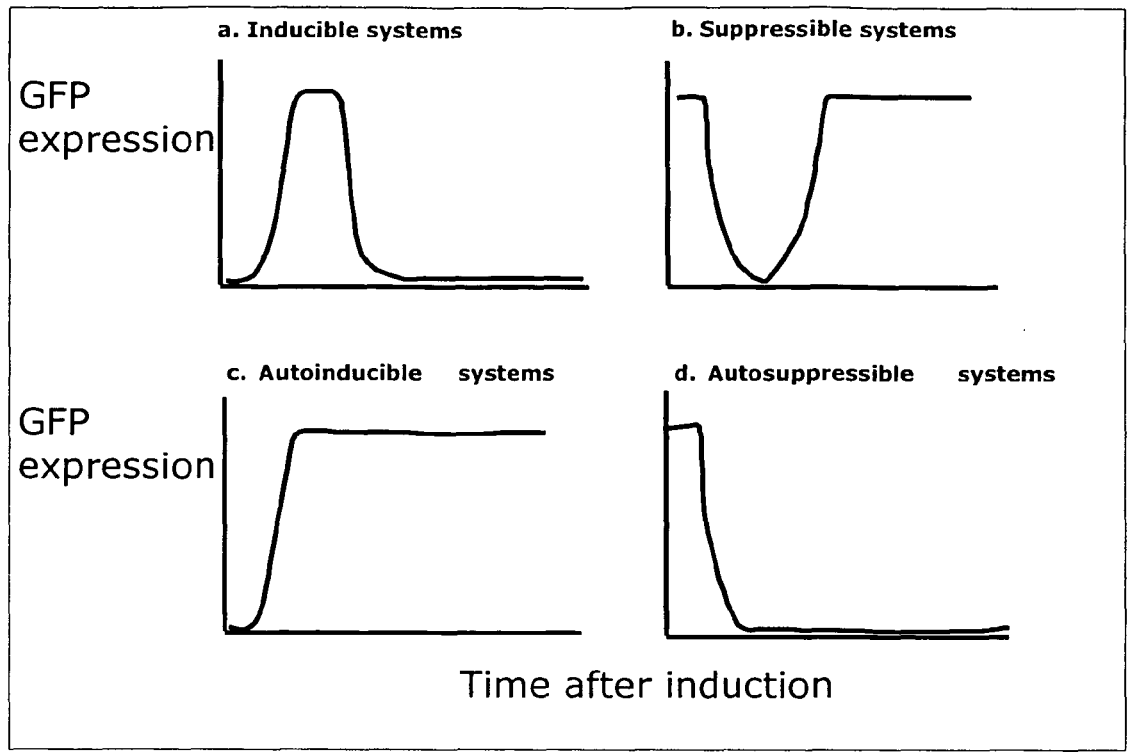
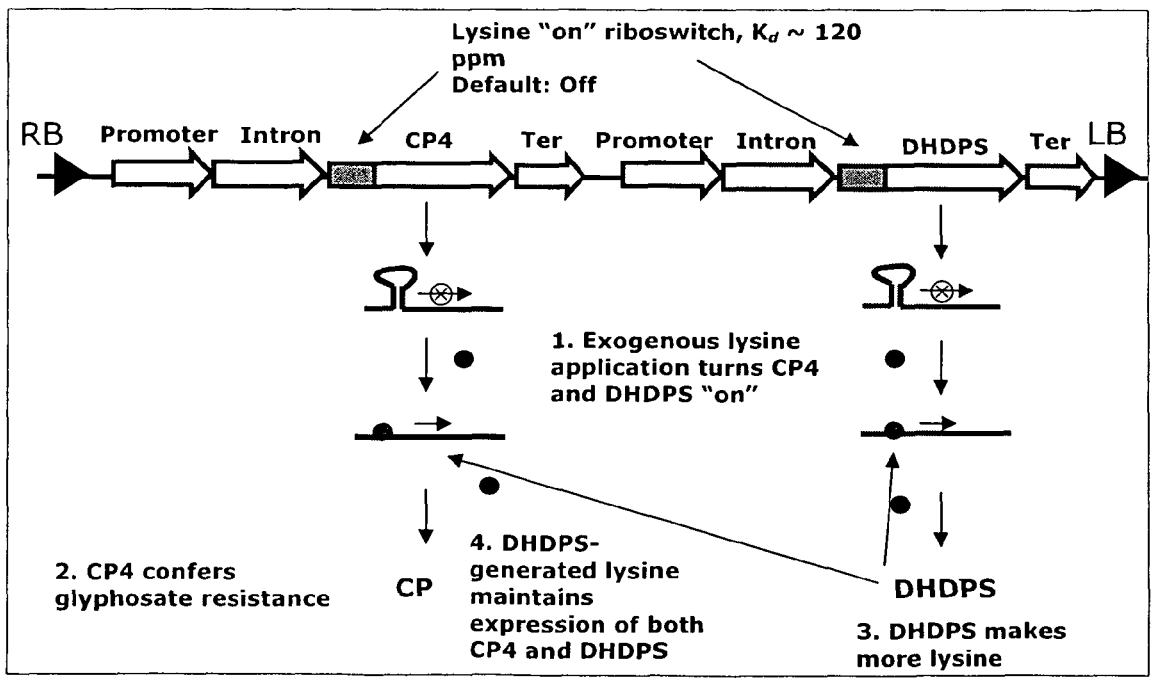

RECOMBINANT DNA CONSTRUCTS AND METHODS FOR CONTROLLING GENE EXPRESSION

PRIORITY CLAIMS AND INCORPORATION OF SEQUENCE LISTINGS

This application claims the benefit of priority of U.S. Provisional Patent Applications 60/638,256, which was filed on 21 Dec. 2004, 60/639,094, which was filed on 24 Dec. 2004, 60/701,124, which was filed on 19 Jul. 2005, 60/711,834, which was filed on 26 Aug. 2005, 60/720,005, which was filed on 24 Sep. 2005, 60/726,106, which was filed on 13 Oct. 2005, and 60/736,525, which was filed on 14 Nov. 2005, all of which are incorporated by reference in their entirety herein. The sequence listings contained in the files "53429A.ST25.txt" (file size of 15 kilobytes recorded on 21 Dec. 2004, and filed with provisional application 60/638,256 on 21 Dec. 2004), "38-21(53709)B.ST25.txt" (file size of 4 kilobytes, recorded on 23 Dec. 2004, and filed with provisional application 60/639,094 on 24 Dec. 2004), "38-15 (53429)B.rpt" (file size of 7 kilobytes, recorded on 19 Jul. 2005, filed with provisional application 60/701,124 on 19 Jul. 2005), "38-15(54068)A.rpt" (file size of 6 kilobytes, recorded on 26 Aug. 2005, filed with provisional application 60/711,834 on 26 Aug. 2005), "38-21(54176)A.rpt" (file size of 29 kilobytes, recorded on 23 Sep. 2005, and filed with provisional 60/720,005 on 24 Sep. 2005), "38-21(54232) A.rpt" (file size of 61 kilobytes, recorded on 12 Oct. 2005, and filed with provisional application 60/726,106 on 13 Oct. 2005) are incorporated by reference in their entirety herein. Incorporation by reference of the sequence listing contained in the file named "38-15(53429)C.ST25.txt", which is 97 kilobytes (measured in MS-Windows) and located in computer readable form on a compact disk created on 15 Dec. 2005 and filed with the specification on 15 Dec. 2005, and of the replacement sequence listing contained in the file named "38-15(53429)C.rpt", which is 97 kilobytes (measured in MS-Windows) and located in computer readable form on a compact disk created on 28 Sep. 2006, and filed on 29 Sep. 2006 is cancelled. The replacement sequence listing contained in the file named "53429_100_replacementseqlisting.txt", which is 102 kilobytes (measured in MS-Windows), created on 2 Feb. 2010, and electronically filed via EFS-Web on 10 Feb. 2010 is incorporated herein by reference.

FIELD OF THE INVENTION

The present invention discloses molecular constructs and methods for the control of gene expression, for example, gene suppression in plants or in plant pests or pathogens or suppressing expression of a target RNA in a specific cell. Also disclosed are transgenic eukaryotes, including transgenic plant cells, plants, and seeds, whose genome includes molecular constructs for controlling expression of an endogenous or an exogenous gene.

BACKGROUND OF THE INVENTION

Nucleic acid aptamers include DNA or RNA sequences that can recognize and specifically bind, often with high affinity, a particular molecule or ligand. See, for example, reports describing in vitro aptamer selection by Tuerk and Gold (1990) *Science*, 249:505-510, Ellington and Szostak (1990) *Nature*, 346:818-822, and Ellington and Szostak (1992) *Nature*, 355:850-852, as well as Jenison et al. (1994) *Science*, 263:1425-1429, which demonstrated the ability of an RNA aptamer to distinguish between theophylline and caffeine (which differ by a single methyl group) by four orders of magnitude. Similar to antibodies that bind specific antigens or receptors that bind specific molecules, aptamers are useful alone, to bind to a specific ligand (see, for example, Shi et al. (1999) *Proc. Natl. Acad. Sci. USA*, 96:10033-10038, which describes a multivalent RNA aptamer effective as a protein antagonist), and in combination, e.g., as a molecular "escort" for delivery of an agent to a specific location, cell, or tissue (see, for example, Hicke and Stephens (2000) *J. Clin. Investigation*, 106:923-928) or as part of a riboswitch. Riboswitches are complex folded RNA sequences including an aptamer domain for a specific ligand. Naturally occurring riboswitches have been found mainly in bacteria, and more recently in fungi (Kubodera et al. (2003) *FEBS Lett.*, 555: 516-520) and plants (Sudarsan et al. (2003) *RNA*, 9:644-647, which is incorporated by reference). Many riboswitches contain conserved domains within species (Barrick et al., (2004) *Proc. Natl. Acad. Sci. USA*, 101:6421-6426, which is incorporated by reference). Riboswitches that act in a "cis" fashion (i.e., that control expression of an operably linked sequence) are known to occur in the non-coding regions of mRNAs in prokaryotes, where they control gene expression by harnessing allosteric structural changes caused by ligand binding. For a review of "cis" riboswitches, see Mandal and Breaker (2004a) *Nature Rev. Mol. Cell. Biol.*, 5:451-463, which is incorporated by reference. Riboswitches that act in a "trans" fashion (i.e., that control expression of a sequence not operably linked to the riboswitch) have also been designed, see, for example, Bayer and Smolke (2005) *Nature Biotechnol.*, 23:337-343, which is incorporated by reference.

Most known naturally occurring riboswitches are "off" switches, wherein the default state is "on" (i.e., the gene under the riboswitch's control is expressed), and ligand binding turns the gene "off". In prokaryotes, these riboswitches have been found mainly in the 5' untranslated region (5' UTR) of mRNAs encoding biosynthesis genes; in eukaryotes, riboswitches have been found in the 3' untranslated region (3' UTR) or within introns (Sudarsan et al. (2003) *RNA*, 9:644-647; Templeton and Moorhead (2004) *Plant Cell*, 16:2252-2257). When an increased concentration of a particular metabolite or ligand is "sensed" by the riboswitch (bound by the aptamer domain), the riboswitch "switches off" gene expression through transcription termination and/or translation attenuation; see, for example, FIG. 2 in Mandal and Breaker (2004a) *Nature Rev. Mol. Cell. Biol.*, 5:451-463 and FIG. 4 in Sudarsan et al. (2003) *RNA*, 9:644-647.

At least two types of "on" riboswitches have been reported, wherein the default state is "off" and ligand binding turns the gene "on". Expression of ydhL, encoding a purine exporter, is turned on by adenine binding to the ydhL aptamer; see Mandal and Breaker (2004b) *Nature Struct. Mol. Biol.*, 11:29-35). Similarly lysine "on" riboswitches have been proposed to activate the expression of lysine exporter or degradation genes; see Rodionov et al. (2003) *Nucleic Acids Res.*, 31:6748-6757. There are also lysine "off" riboswitches that control the expression of lysine biosynthesis genes; see Sudarsan et al (2003) *Genes Dev.*, 17:2688-2697.

A typical riboswitch is composed of an aptamer domain that remains largely conserved, and a regulatory domain that can vary more widely during evolution. In a non-limiting example, the coenzyme-$B_{12}$ riboswitch controls gene expression by two main mechanisms, as dictated by the architecture of the regulatory domain (see FIG. 2 in Mandal and Breaker (2004a) *Nature Rev. Mol. Cell. Biol.*, 5:451-463). If the regulatory domain contains a "terminator stem", the binding of coenzyme-$B_{12}$ to its aptamer triggers transcriptional termination. If the expression platform contains an "anti-ribosome binding site stem", the binding of coenzyme-$B_{12}$ to its aptamer triggers translational attenuation. In some instances, it is believed that transcription and translation can be controlled simultaneously.

The present invention provides a novel transgenic plant having in its genome recombinant DNA that transcribes to at least one RNA aptamer to which a ligand binds, and can further include at least one regulatory RNA domain capable of regulating the target sequence. Depending on the design of the recombinant DNA, the regulatory RNA can act "in trans" or "in cis" in the transgenic plants to control expression of an endogenous or of an exogenous target sequence, and the ligand can be exogenous or endogenous. Transgenic plants of the invention are preferably stably transgenic plants in which a desired trait, or an altered trait, is achieved in the transgenic plant (or in a seed or progeny plant of the transgenic plant) according to whether or not the ligand is bound to the aptamer and the resulting expression (or suppression) of the target sequence.

Current methods to suppress a gene include, for example, the use of antisense, co-suppression, and RNA interference. Anti-sense gene suppression in plants is described by Shewmaker et al. in U.S. Pat. Nos. 5,107,065, 5453,566, and 5,759, 829. Gene suppression in bacteria using DNA which is complementary to mRNA encoding the gene to be suppressed is disclosed by Inouye et al. in U.S. Pat. Nos. 5,190,931, 5,208,149, and 5,272,065. RNA interference or double-stranded RNA-mediated gene suppression has been described by, e.g., Redenbaugh et al. in "Safety Assessment of Genetically Engineered Fruits and Vegetables", CRC Press, 1992; Chuang et al. (2000) *PNAS*, 97:4985-4990; Wesley et al. (2001) *Plant J.*, 27:581-590.

The efficiency of anti-sense gene suppression is typically low. Redenbaugh et al. in "Safety Assessment of Genetically Engineered Fruits and Vegetables", CRC Press, 1992, report a transformation efficiency ranging from 1% to 20% (page 113) for tomato transformed with a construct designed for anti-sense suppression of the polygalacturonase gene. Chuang et al. reported in *PNAS*, (2000) 97:4985-4990 that anti-sense constructs, sense constructs, and constructs where anti-sense and sense DNA are driven by separate promoters had either no, or weak, genetic interference effects as compared to potent and specific genetic interference effects from dsRNA constructs (see FIG. 1 and Table 1, *PNAS*, (2000) 97:4985-4990). See also Wesley et al. who report in *The Plant Journal*, (2001) 27:581-590, e.g., at Table 1, the comparative efficiency of hairpin RNA, sense constructs, and anti-sense constructs at silencing a range of genes in a range of plant species with a clear indication that the efficiency for anti-sense constructs is typically about an order of magnitude lower than the efficiency for hairpin RNA.

Matzke et al. in Chapter 3 ("Regulation of the Genome by double-stranded RNA") of "RNAi—A Guide to Gene Silencing", edited by Hannon, Cold Spring Harbor Laboratory Press, 2003, discuss the use of polyadenylation signals in promoter inverted repeat constructs. At page 58, they state that "the issue of whether to put polyadenylation signals in promoter inverted repeat constructs is unsettled because the nature of the RNA triggering RdDM [RNA-directed DNA methylation] is unresolved. Depending on whether short RNA or dsRNA is involved in RdDM, the decision to include a polyadenylation site might differ depending on the experimental system used. If dsRNA is involved in RdDM, then a polyadenylation signal is not required because dsRNA forms rapidly by intramolecular folding when the entire inverted repeat is transcribed. Indeed, nonpolyadenylated dsRNAs might be retained in the nucleus and induce RdDM more efficiently than polyadenylated dsRNAs. Matzke et al. continue: "If short RNAs guide homologous DNA methylation, then the situation in plants and mammals differ. In plants, which probably possess a nuclear form of Dicer, non-polyadenylated dsRNAs would still be optimal because they should feed preferentially into a nuclear pathway for dsRNA processing."

Carmichael et al. in U.S. Pat. Nos. 5,908,779 and 6,265, 167 disclose methods and constructs for expressing and accumulating anti-sense RNA in the nucleus using a construct that comprises a promoter, anti-sense sequences, and sequences encoding a cis- or trans-ribozyme. The cis-ribozyme is incorporated into the anti-sense construct in order to generate 3' ends independently of the polyadenylation machinery and thereby inhibit transport of the RNA molecule to the cytoplasm. Carmichael demonstrated the use of the construct in mouse NIH 3T3 cells.

Various other nucleic acid constructs and methods for gene suppression have been described in recent publications. Shewmaker et al. (U.S. Pat. No. 5,107,565) disclose constructs for gene silencing that can contain two or more repetitive anti-sense sequence in tandem for modulating one or more genes. Resistance to a virus was achieved in a transgenic plant by use of a transgene containing a direct repeat of the virus's movement protein (Sijen et al. (1996) *Plant Cell*, 8:2277-2294). Another report demonstrated that nucleic acid constructs containing a promoter, a terminator, and direct or interrupted tandem repeats of either sense or anti-sense sequences, could induce gene silencing in plants (Ma and Mitra (2002) *Plant J*, 31:37-49. The expression of 1-aminocyclopropane-1-carboxylic acid (ACC) oxidase was down-regulated in transgenic tomatoes containing a nucleic acid construct including a direct repeat of the ACC oxidase 5' untranslated region sequence in the anti-sense orientation (Hamilton et al. (1998) *Plant J.*, 15:737-346). Waterhouse and Wang (U.S. Patent Application Publication 2003/ 0165894) disclose a method for reducing phenotypic expression using nucleic acid constructs that transcribe to aberrant RNAs including unpolyadenylated RNAs. Clemente et al. disclose nucleic acid constructs including sense or anti-sense sequences lacking a normal 3' untranslated region and optionally including a ribozyme, that transcribe to unpolyadenylated RNA. All of the patents cited in this paragraph are incorporated by reference in their entirety herein.

DNA is either coding (protein-coding) DNA or non-coding DNA. Non-coding DNA includes many kinds of non-translatable (non-protein-coding) sequence, including 5' untranslated regions, promoters, enhancers, or other non-coding transcriptional regions, 3' untranslated regions, terminators, and introns. The term "intron" is generally applied to segments of DNA (or the RNA transcribed from such segments) that are located between exons (protein-encoding segments of the DNA), wherein, during maturation of the messenger RNA, the introns present are enzymatically "spliced out" or removed from the RNA strand by a cleavage/ligation process that occurs in the nucleus in eukaryotes. Lin et al. (2003) *Biochem. Biophys. Res. Comm.*, 310:754-760, and Lin et al. U.S. Patent Application Publications 2004/0106566 and 2004/0253604, which are incorporated by reference in their entirety herein, disclose methods for inducing gene silencing using nucleic acid constructs containing a gene silencing molecule (sense or anti-sense or both) within an intron flanked by multiple protein-coding exons, wherein, upon splicing and removal of the intron, the protein-coding exons are linked to form a mature mRNA encoding a protein with desired function and the gene silencing molecule is released.

However, apart from introns found between protein-encoding exons, there are other non-coding DNA sequences that can be spliced out of a maturing messenger RNA. One example of these are spliceable sequences that that have the ability to enhance expression in plants (in some cases, especially in monocots) of the downstream coding sequence; these spliceable sequences are naturally located in the 5' untranslated region of some plant genes, as well as in some viral genes (e.g., the tobacco mosaic virus 5' leader sequence or "omega" leader described as enhancing expression in plant genes by Gallie and Walbot (1992) *Nucleic Acids Res.*, 20:4631-4638). These spliceable sequences or "expression-enhancing introns" can be artificially inserted in the 5' untranslated region of a plant gene between the promoter but before any protein-coding exons. For example, it was reported that inserting a maize alcohol dehydrogenase (Zm-Adh1) or Bronze-1 expression-enhancing intron 3' to a promoter (e.g., Adh1, cauliflower mosaic virus 35S, or nopaline synthase promoters) but 5' to a protein-coding sequence (e.g., chloramphenicol acetyltransferase, luciferase, or neomycin phosphotransferase II) greatly stimulated expression of the protein (Callis et al. (1987) *Genes Dev.*, 1:1183-1200). The Adhlintron greatly stimulated expression of a reporter gene (Mascarenkas et al. (1990) *Plant Mol. Biol.*, 15:913-920). Cis-acting elements that increase transcription of a downstream coding sequence in transformed plant cells were reported to occur in the 5' untranslated region of the rice actin 1 (Os-Act1) gene (Wang et al. (1992) *Mol. Cell. Biol.*, 12:3399-3406). The rice Act1 gene was further characterized to contain a 5' expression-enhancing intron that is located upstream of the first protein-coding exon and that is essential for efficient expression of coding sequence under the control of the Act1 promoter (McElroy et al. (1990) *Plant Cell*, 2:163-171). The Shrunken-1 (Sh-1) intron was reported to give about 10 times higher expression than constructs containing the Adh-1 intron (Vasil et al. (1989) *Plant Physiol.*, 91:1575-1579). The maize sucrose synthase intron, when placed between a promoter and the firs protein-coding exon, also increases expression of the encoded protein, and splicing of the intron is required for this enhanced expression to occur (Clancy and Hannah (2002) *Plant Physiol.*, 130:918-929). Expression-enhancing introns have also been characterized for heat shock protein 18 (hsp18) (Silva et al. (1987) *J. Cell Biol.*, 105:245) and the 82 kilodalton heat shock protein (hsp82) (Semrau et al. (1989) J. Cell Biol., 109, p. 39A, and Mettler et al. (May 1990) N.A.T.O. Advanced Studies Institute on Molecular Biology, Elmer, Bavaria). U.S. Pat. Nos. 5,593,874 and 5,859,347 describe improved recombinant plant genes including a chimeric plant gene with an expression-enhancing intron derived from the 70 kilodalton maize heat shock protein (hsp70) in the non-translated leader positioned 3' from the gene promoter and 5' from the first protein-coding exon. All of the patents and publications cited in this paragraph are incorporated by reference herein.

The present inventors have found that, unexpectedly, introns can be utilized to deliver a gene suppression element in the absence of any protein-coding exons (coding sequence). In the present invention, an intron, such as an expression-enhancing intron (preferred in certain embodiments), is interrupted by embedding within the intron a gene suppression element, wherein, upon transcription, the gene suppression element is excised from the intron to function in suppressing a target gene. Thus, no protein-coding exons are required to provide the gene suppressing function of the recombinant DNA constructs disclosed herein.

MicroRNAs (miRNAs) are non-protein coding RNAs, generally of between about 19 to about 25 nucleotides (commonly about 20-24 nucleotides in plants), that guide cleavage in trans of target transcripts, negatively regulating the expression of genes involved in various regulation and development pathways (Bartel (2004) *Cell*, 116:281-297). In some cases, miRNAs serve to guide in-phase processing of siRNA primary transcripts (see Allen et al. (2005) *Cell*, 121:207-221, which is incorporated herein by reference).

Some microRNA genes (MIR genes) have been identified and made publicly available in a database ("miRBase", available on line at microrna.sanger.ac.uk/sequences). Additional MIR genes and mature miRNAs are also described in U.S. Patent Application Publications 2005/0120415 and 2005/144669A1, which is incorporated by reference herein. MIR genes have been reported to occur in inter-genic regions, both isolated and in clusters in the genome, but can also be located entirely or partially within introns of other genes (both protein-coding and non-protein-coding). For a recent review of miRNA biogenesis, see Kim (2005) *Nature Rev. Mol. Cell. Biol.*, 6:376-385. Transcription of MIR genes can be, at least in some cases, under promotional control of a MIR gene's own promoter. MIR gene transcription is probably generally mediated by RNA polymerase II (see, e.g., Aukerman. and Sakai (2003) *Plant Cell*, 15:2730-2741; Parizotto et al. (2004) *Genes Dev.*, 18:2237-2242), and therefore could be amenable for gene silencing approaches that have been used in other polymerase II-transcribed genes. The primary transcript (which can be polycistronic) termed a "pri-miRNA", a miRNA precursor molecule that can be quite large (several kilobases) and contains one or more local double-stranded or "hairpin" regions as well as the usual 5' "cap" and polyadenylated tail of an mRNA. See, for example, FIG. 1 in Kim (2005) *Nature Rev. Mol. Cell. Biol.*, 6:376-385.

In animal cells, this pri-miRNA is believed to be "cropped" by the nuclear RNase III Drosha to produce a shorter miRNA precursor molecule known as a "pre-miRNA". Following nuclear processing by Drosha, pre-miRNAs are exported to the nucleus where the enzyme Dicer generates the short, mature miRNAs. See, for example, Lee et al. (2002) *EMBO Journal*, 21:4663-4670; Reinhart et al. (2002) *Genes & Dev.*, 16:161611626; Lund et al. (2004) *Science*, 303:95-98; and Millar and Waterhouse (2005) *Funct. Integr Genomics*, 5:129-135, which are incorporated by reference herein. In contrast, in plant cells, microRNA precursor molecules are believed to be largely processed in the nucleus. Whereas in animals both miRNAs and siRNAs are believed to result from activity of the same DICER enzyme, in plants miRNAs and siRNAs are formed by distinct DICER-like (DCL) enzymes, and in *Arabidopsis* a nuclear DCL enzyme is believed to be required for mature miRNA formation (Xie et al. (2004) *PLoS Biol.*, 2:642-652, which is incorporated by reference herein). Additional reviews on microRNA biogenesis and function are found, for example, in Bartel (2004) *Cell*, 116:281-297; Murchison and Hannon (2004) *Curr. Opin. Cell Biol.*, 16:223-229; and Dugas and Bartel (2004) *Curr. Opin. Plant Biol.*, 7:512-520. MicroRNAs can thus be described in terms of RNA (e.g., RNA sequence of a mature miRNA or a miRNA precursor RNA molecule), or in terms of DNA (e.g., DNA sequence corresponding to a mature miRNA RNA sequence or DNA sequence encoding a MIR gene or fragment of a MIR gene or a miRNA precursor).

MIR gene families appear to be substantial, estimated to account for 1% of at least some genomes and capable of influencing or regulating expression of about a third of all genes (see, for example, Tomari et al. (2005) *Curr. Biol.*, 15:R61-64; G. Tang (2005) *Trends Biochem. Sci.*, 30:106-14; Kim (2005) *Nature Rev. Mol. Cell. Biol.*, 6:376-385). Because miRNAs are important regulatory elements in eukaryotes, including animals and plants, transgenic suppression of miRNAs could, for example, lead to the understanding of important biological processes or allow the manipulation of certain pathways useful, for example, in biotechnological applications. For example, miRNAs are involved in regulation of cellular differentiation, proliferation and apoptosis, and are probably involved in the pathology of at least some diseases, including cancer, where miRNAs may function variously as oncogenes or as tumor suppressors. See, for example, O'Donnell et al. (2005) *Nature,* 435:839-843; Cai et al. (2005) *Proc. Natl. Acad. Sci. USA,* 102:5570-5575; Morris and McManus (2005) *Sci. STKE,* pe41 (available online at stke.sciencemag.org/cgi/reprint/sigtrans;2005/297/pe41.pdf). MicroRNA (MIR) genes have identifying characteristics, including conservation among plant species, a stable foldback structure, and processing of a specific miRNA/miRNA* duplex by Dicer-like enzymes (Ambros et al. (2003) *RNA,* 9:277-279). These characteristics have been used to identify miRNAs and their corresponding genes in plants (Xie et al. (2005) *Plant Physiol.,* 138:2145-2154; Jones-Rhoades and Bartel (2004) *Mol. Cell,* 14:787-799; Reinhart et al. (2002) *Genes Dev.,* 16:1616-1626; Sunkar and Zhu (2004) *Plant Cell,* 16:2001-2019). Publicly available microRNA genes are catalogued at miRBase (Griffiths-Jones et al. (2003) *Nucleic Acids Res.,* 31:439-441).

MiRNAs have been found to be expressed in very specific cell types in *Arabidopsis* (see, for example, Kidner and Martienssen (2004) *Nature,* 428:81-84, Millar and Gubler (2005) *Plant Cell,* 17:705-721). Suppression can be limited to a side, edge, or other division between cell types, and is believed to be required for proper cell type patterning and specification (see, for example, Palatnik et al. (2003) *Nature,* 425:257-263). Suppression of a GFP reporter gene containing an endogenous miR171 recognition site was found to limit expression to specific cells in transgenic *Arabidopsis* (Parizotto et al. (2004) *Genes Dev.,* 18:2237-2242). Recognition sites of miRNAs have been validated in all regions of an mRNA, including the 5' untranslated region, coding region, and 3' untranslated region, indicating that the position of the miRNA target site relative to the coding sequence may not necessarily affect suppression (see, for example, Jones-Rhoades and Bartel (2004). *Mol. Cell,* 14:787-799, Rhoades et al. (2002) *Cell,* 110:513-520, Allen et al. (2004) *Nat. Genet.,* 36:1282-1290, Sunkar and Zhu (2004) *Plant Cell,* 16:2001-2019).

The invention provides novel recombinant DNA constructs and methods for use thereof for suppression of production of mature miRNA in a cell, where the constructs are designed to target at least one miRNA precursor or at least one promoter of a miRNA precursor. Using constructs of the invention, suppression of production of mature miRNA can occur in the nucleus or in the cytoplasm or in both. In plants, microRNA precursor molecules are believed to be largely processed in the nucleus. Thus, in many preferred embodiments of the recombinant DNA construct of the invention, particularly (but not limited to) embodiments where the suppression occurs in a plant cell, suppression preferably occurs wholly or substantially in the nucleus. Another potential advantage of the invention is that miRNA precursors (especially pri-miRNAs, and to a lesser extent pre-miRNAs) offer substantially larger target sequences than does a mature miRNA.

In a preferred embodiment, the constructs and methods of the invention are designed to target nuclear-localized miRNA precursors (such as pri-miRNAs and pre-miRNA) prior to their export from the nucleus; such embodiments provide an advantage over conventional gene suppression constructs (e.g., containing inverted repeats) that typically result in accumulation of dsRNA in the cytoplasm. In such embodiments, recombinant DNA constructs of the invention include a gene suppression element designed to remain in the nucleus after transcription, for example, a gene suppression element that is transcribed to RNA lacking functional nuclear export signals. Such embodiments are particularly preferred for use, e.g., in plants, where processing of miRNA is believed to occur largely in the nucleus. In one preferred embodiment of the invention, the recombinant DNA construct includes a suppression element (e.g., one or more inverted repeats, antisense sequence, tandem repeats, or other suppression elements) embedded within a spliceable intron. The resulting suppression transcript remains in the nucleus, preferably resulting in the nuclear degradation of the target pri-miRNA or pre-miRNA, or alternatively, resulting in transcriptional silencing of a target MIR gene promoter, which, in turn, reduces the accumulation of the mature miRNA.

In other embodiments, recombinant DNA constructs of the invention include a suppression element transcribable to RNA that is exported from the nucleus to the cytoplasm, where, for example, the transcribed and exported RNA targets a cytoplasmic pre-miRNA. Such embodiments are particularly useful where miRNA processing at least partly occurs in the cytoplasm, e.g., in animal cells. In such embodiments, the suppression element is preferably transcribed to RNA including functional nuclear export signals.

In multicellular eukaryotes, including plants, microRNAs (miRNAs) regulate endogenous genes by a post-transcriptional cleavage mechanism in a cell-type specific manner. The invention further provides a recombinant DNA construct, and methods for the use thereof, wherein the construct includes transcribable DNA that transcribes to RNA including (a) at least one exogenous miRNA recognition site recognizable by a mature miRNA expressed in a specific cell, and (b) target RNA to be suppressed in the specific cell, whereby said target RNA is expressed in cells other than said specific cell. These constructs are useful for suppressing expression of a target RNA in a specific cell of a multicellular eukaryote (but allowing expression in other cells), including transcribing in the multicellular eukaryote a recombinant DNA construct including a promoter operably linked to DNA that transcribes to RNA including: (a) at least one exogenous miRNA recognition site recognizable by a mature miRNA expressed in a specific cell, and (b) target RNA to be suppressed in the specific cell, wherein the mature miRNA guides cleavage of target RNA in the specific cell, whereby expression of the target RNA is suppressed in the specific cell relative to its expression in cells lacking expression of the mature miRNA.

The present invention further provides novel mature miRNA sequences and MIR gene sequences from crop plants, including maize and soybean. The mature miRNAs processed from these genes belong to canonical families conserved across distantly related plant species. These MIR genes and their encoded mature miRNAs are useful, e.g., for modifying developmental pathways, e.g., by affecting cell differentiation or morphogenesis (see, for example, Palatnik et al. (2003) *Nature,* 425:257-263; Mallory et al. (2004) *Curr. Biol.,* 14:1035-1046), to serve as sequence sources for engineered (non-naturally occurring) miRNAs that are designed to target sequences other than the transcripts targeted by the naturally occurring miRNA sequence (see, for example, Parizotto et al. (2004) *Genes Dev.,* 18:2237-2242, and U.S. Patent Application Publications 2004/3411A1, 2005/0120415, which are incorporated by reference herein), and to stabilize dsRNA. A MIR gene itself (or its native 5' or 3' untranslated regions, or its native promoter or other elements involved in its transcription) is useful as a target sequence for gene suppression (e.g., by methods of the present invention), where suppression of the miRNA encoded by the MIR gene is desired. Promoters of MIR genes can have very specific expression patterns (e.g., cell-specific, tissue-specific, or temporally specific), and thus are useful in recombinant constructs to induce such specific transcription of a DNA sequence to which they are operably linked.

SUMMARY OF THE INVENTION

The present invention discloses a transgenic plant cell, as well as transgenic plants and transgenic seed of such plants, having in its genome recombinant DNA for the ligand-controlled expression of a target sequence. One aspect of this invention provides a transgenic plant cell having in its genome recombinant DNA including transcribable DNA including DNA that transcribes to an RNA aptamer capable of binding to a ligand. In some embodiments of the invention, the recombinant DNA further includes at least one T-DNA border. In many embodiments, the transcribable DNA further includes DNA that transcribes to regulatory RNA capable of regulating expression of a target sequence, wherein the regulation of the target sequence is dependent on the conformation of the regulatory RNA, and the conformation of the regulatory RNA is allosterically affected by the binding state of the RNA aptamer.

Another aspect of the invention provides a method of reducing damage to a plant by an invertebrate pest or by a bacterial, fungal, or viral pathogen of said plant, including transcribing in the plant a recombinant DNA construct including transcribable DNA including DNA that transcribes to an RNA aptamer capable of binding to a ligand, wherein the ligand comprises at least part of a molecule endogenous to the pest or pathogen, and whereby binding of the RNA aptamer to the ligand reduces damage to the plant by the pest or pathogen, relative to damage in the absence of transcription of the recombinant DNA construct. In particularly preferred embodiments, the pest or pathogen is an invertebrate pest of the plant, and the ligand includes at least part of a molecule of the digestive tract lining of the invertebrate pest.

Another aspect of the invention provides a recombinant DNA construct including: (a) transcribable DNA including DNA that transcribes to an RNA aptamer capable of binding to a ligand; and (b) DNA sequence that transcribes to double-stranded RNA flanking said transcribable DNA. In some embodiments, the recombinant DNA construct further includes DNA that transcribes to regulatory RNA capable of regulating expression of a target sequence, wherein the regulation is dependent on the conformation of the regulatory RNA, and the conformation of the regulatory RNA is allosterically affected by the binding state of the RNA aptamer.

The present invention discloses recombinant DNA constructs for suppression of at least one target gene, as well as methods for their use. In one aspect, the present invention provides a recombinant DNA construct for plant transformation including a first gene suppression element for suppressing at least one first target gene, wherein the gene suppression element is embedded in an intron, and wherein the intron is located adjacent to at least one element selected from the group consisting of a promoter element and a terminator element. The construct can optionally include at least one T-DNA border, a second gene suppression element, a gene expression element, or both. The invention further provides transgenic plant cells and transgenic plants and seeds derived therefrom, containing such a recombinant DNA construct, and a method for effecting gene suppression by expressing such a recombinant DNA construct in a transgenic plant.

In another aspect, the present invention provides a transgenic seed having in its genome a recombinant DNA construct for suppressing at least one first target gene, including DNA capable of initiating transcription in a plant and operably linked to a first transcribable heterologous DNA, wherein said first transcribable heterologous DNA is embedded in an intron. The invention further provides a transgenic plant grown from the transgenic seed, and methods for gene suppression or for concurrent gene suppression and gene expression, that include growing such transgenic plants. A potential advantage of the use of constructs of this invention is avoidance of unintentional systemic spreading of gene suppression.

Another aspect of the invention discloses recombinant DNA constructs and methods for suppression of production of mature microRNA in a cell, for example, by targeting for suppression a miRNA precursor or a promoter of a miRNA gene In one aspect, the present invention provides a recombinant DNA construct for suppressing production of mature microRNA (miRNA) in a cell, including a promoter element operably linked to a suppression element for suppression of at least one target microRNA precursor. The recombinant DNA constructs include at least one suppression element for suppression of at least one target microRNA precursor. The suppression element suppresses at least one target sequence selected from a target sequence of the at least one target microRNA precursor, or a target sequence of a promoter of the at least one target microRNA precursor, or both.

In another aspect, the present invention provides a transgenic plant having in its genome the recombinant DNA construct of the invention (i.e., a recombinant DNA construct for suppressing production of mature microRNA (miRNA) in a cell, including a promoter element operably linked to a suppression element for suppression of at least one target microRNA precursor), as well as seed and progeny of such transgenic plants.

In still another aspect, the present invention provides a method to suppress expression of a target sequence in a plant cell, including transcribing in a plant cell a recombinant DNA construct including a transcribable engineered miRNA precursor, derived from the fold-back structure of a maize or soybean MIR sequence or their complements, designed to suppress a target sequence, whereby expression of the target sequence is suppressed relative to its expression in the absence of transcription of the recombinant DNA construct.

In a further aspect, the present invention provides a recombinant DNA construct including a promoter operably linked to DNA that transcribes to RNA including (a) at least one exogenous miRNA recognition site recognizable by a mature miRNA expressed in a specific cell, and (b) target RNA to be suppressed in the specific cell, whereby said target RNA is expressed in cells other than said specific cell.

In yet another aspect, the present invention provides methods for suppressing expression of a target RNA in a specific cell of a multicellular eukaryote, including transcribing in the multicellular eukaryote a recombinant DNA construct including a promoter operably linked to DNA that transcribes to RNA including: (a) at least one exogenous miRNA recognition site recognizable by a mature miRNA expressed in a specific cell, and (b) target RNA to be suppressed in the specific cell, wherein the mature miRNA guides cleavage of target RNA in the specific cell, whereby expression of the target RNA is suppressed in the specific cell relative to its expression in cells lacking expression of the mature miRNA.

Other specific embodiments of the invention are disclosed in the following detailed description.

BRIEF DESCRIPTION OF THE DRAWINGS

FIG. 5A is a schematic map of a vector including an enhanced anti-sense construct and described in Example 4. The plasmid includes an aroA gene as an herbicidal selectable marker, and a recombinant DNA construct for enhanced anti-sense gene suppression, consisting of a seed-specific maize L3 oleosin promoter operably linked to transcribable DNA consisting of about 300 base pairs of a maize lysine ketoglutarate reductase (LKR) gene (LKR region of the lysine ketoglutarate reductase/saccharopine dehydrogenase gene, LKR/SDH) in an anti-sense orientation, wherein a functional polyadenylation site is absent in this transcribable DNA, and left T-DNA border (LB) and right T-DNA border (RB) elements. FIG. 5B depicts a recombinant DNA construct of the present invention for gene suppression and described in Example 4, including left T-DNA border (LB) and right T-DNA border (RB) elements, and a promoter element operably linked to an intron (maize heat shock protein 70 intron, I-Zm-hsp70) within which is embedded a first gene suppression element for suppressing at least one first target gene (in this example, maize lysine ketoglutarate reductase/saccharopine dehydrogenase gene (LKR/SDH)). The first gene suppression element can include any gene suppression element as described above under the heading "Gene Suppression Elements" wherein the intron is located adjacent to the promoter element. In the specific, non-limiting embodiment depicted in FIG. 5B, the promoter element is an endosperm-specific maize B32 promoter (nucleotides 848 through 1259 of GenBank accession number X70153, see also Hartings et al. (1990) *Plant Mol. Biol.*, 14:1031-1040, which is incorporated herein by reference), although other promoter elements could be used. This specific embodiment also includes an aroA gene as an herbicidal selectable marker; other selectable marker or reporter genes can be used. As shown in the lower part of FIG. 5B, the intron-embedded gene suppression element ("GSE") can include any one or more gene suppression elements as described under "Gene Suppression Elements".

FIG. 6A is a schematic map of a vector including an enhanced anti-sense construct as described in Example 5. The vector includes an aroA gene as an herbicidal selectable marker and a recombinant DNA construct for enhanced anti-sense gene suppression, consisting of a TUB-1 root specific promoter from *Arabidopsis thaliana* operably linked to transcribable DNA consisting of anti-sense oriented DNA of a nematode major sperm protein (msp) of a soybean cyst nematode, wherein a functional polyadenylation site is absent in this transcribable DNA. The plasmid also includes left T-DNA border (LB) and right T-DNA border (RB) elements. FIG. 6B is a schematic map of a recombinant DNA construct of the present invention as described in Example 5, which includes an aroA gene as an herbicidal selectable marker and a recombinant DNA construct of the present invention for gene suppression, including left T-DNA border (LB) and right T-DNA border (RB) elements, and a TUB-1 root specific promoter from *Arabidopsis thaliana* operably linked to an intron (maize alcohol dehydrogenase intron, I-Zm-adh1) within which is embedded a first transcribable heterologous DNA that includes an anti-sense DNA segment that is anti-sense to the target gene, nematode major sperm protein of a soybean cyst nematode, wherein a functional polyadenylation site is absent in this transcribable heterologous DNA.

FIG. 8A schematically depicts non-limiting recombinant DNA constructs of the invention as described in Example 8. For use in *Agrobacterium*-mediated transformation of plant cells, at least one T-DNA border is generally included in each construct (not shown). These constructs include a promoter element ("pro"), an intron flanked on one or on both sides by non-protein-coding DNA, an optional terminator element ("ter"), at least one first gene suppression element ("GSE" or "GSE1") for suppressing at least one first target gene, and can optionally include at least one second gene suppression element ("GSE2") for suppressing at least one second target gene, at least one gene expression element ("GEE") for expressing at least one gene of interest, or both. In embodiments containing a gene expression element, the gene expression element can be located adjacent to (outside of) the intron. In one variation of this embodiment (not shown), the gene suppression element (embedded in an intron flanked on one or on both sides by non-protein-coding DNA) is located 3' to the terminator. In other constructs of the invention (not shown), a gene suppression element (not intron-embedded) is located 3' to the terminator (see Example 22). FIG. 8B schematically depicts examples of recombinant DNA constructs distinct from those of the present invention. These constructs can contain a gene suppression element that is located adjacent to an intron or between two discrete introns (that is to say, not embedded within a single intron), or can include a gene expression element including a gene suppression element embedded within an intron which is flanked on both sides by protein-coding DNA (e.g., protein-coding exons that make up a gene expression element).

These gene suppression elements and transcribable exogenous DNAs can include: DNA that includes at least one anti-sense DNA segment that is anti-sense to at least one segment of the at least one first target gene, or DNA that includes multiple copies of at least one anti-sense DNA segment that is anti-sense to at least one segment of the at least one first target gene (FIG. 9A); DNA that includes at least one sense DNA segment that is at least one segment of the at least one first target gene, or DNA that includes multiple copies of at least one sense DNA segment that is at least one segment of the at least one first target gene (FIG. 9B); DNA that transcribes to RNA for suppressing the at least one first target gene by forming double-stranded RNA and includes at least one anti-sense DNA segment that is anti-sense to at least one segment of the at least one target gene and at least one sense DNA segment that is at least one segment of the at least one first target gene (FIG. 9C); DNA that transcribes to RNA for suppressing the at least one first target gene by forming a single double-stranded RNA and includes multiple serial anti-sense DNA segments that are anti-sense to at least one segment of the at least one first target gene and multiple serial sense DNA segments that are at least one segment of the at least one first target gene (FIG. 9D); DNA that transcribes to RNA for suppressing the at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of inverted repeats (FIG. 9E); and DNA that includes nucleotides derived from a miRNA (see also FIG. 5B), or DNA that includes nucleotides of a siRNA (FIG. 9F). FIG. 9F depicts various non-limiting arrangements of double-stranded RNA (dsRNA) that can be transcribed from embodiments of the gene suppression elements and transcribable exogenous DNAs useful in the recombinant DNA constructs of the invention. When such dsRNA is formed, it can suppress one or more target genes, and can form a single double-stranded RNA or multiple double strands of RNA, or a single dsRNA "stem" or multiple "stems". Where multiple dsRNA "stems" are formed, they can be arranged in "hammerheads" or "cloverleaf" arrangements. Spacer DNA is optional and can include sequence that transcribes to an RNA (e.g., a large loop of antisense sequence of the target gene or an aptamer) that assumes a secondary structure or three-dimensional configuration that confers on the transcript a desired characteristic, such as increased stability, increased half-life in vivo, or cell or tissue specificity.

FIG. 11 depicts fold-back structures of maize and soy MIR sequences, as described in detail in Example 14. Nucleotides corresponding to the mature miRNA are indicated by bold font, Watson-Crick base-pairing by a vertical line, and base-pairing mismatches by a dot.

FIG. 12 depicts fold-back structures of maize and soy MIR sequences, as described in detail in Example 15. Nucleotides corresponding to the mature miRNA are indicated by bold font, Watson-Crick base-pairing by a vertical line, and base-pairing mismatches by a dot.

FIG. 13 depicts a miR166 consensus fold-back structure (SEQ ID NO:347) (Griffiths-Jones (2004) *Nucleic Acids Res.*, 32, Database Issue, D109-D111, which is incorporated by reference herein) with the nucleotides corresponding to the mature miRNA indicated by the shaded nucleotides, as described in Example 16.

FIG. 15 depicts a non-limiting example of transcribable DNA sequence including an exogenous miRNA recognition site, chloroplast-targeted TIC809 with a miRNA162 recognition site (in bold text) located in the 3' untranslated region (SEQ ID NO. 220), as described in detail in Example 18. The translated amino acid sequence (SEQ ID NO:348) is also shown.

FIG. 16 depicts a non-limiting example of transcribable DNA sequence including an exogenous miRNA recognition site, non-chloroplast-targeted TIC809 with a miRNA164 recognition site (in bold text) located in the 3' untranslated region (SEQ ID NO. 221), as described in detail in Example 18. The translated amino acid sequence (SEQ ID NO:349) is also shown.

FIG. 17 depicts the strong and specific endosperm expression of the miR167g microRNA (SEQ ID NO. 4) cloned from maize endosperm, as described in detail in Example 19. Northern blots of RNA from maize (LH59) tissues probed with an end-labeled mature miR167 22-mer LNA probe specific for SEQ ID NO. 4 (FIG. 17A) or with a ~400 bp miR167g gene-specific probe (FIG. 17B). Transcription profiling of maize tissues corroborated the Northern blot results (FIG. 17C); the transcript corresponding to miR167g was abundantly and specifically expressed in endosperm tissue (abundances are categorized as follows: >5000, high abundance, $97^{th}$ percentile; 700-5000, moderate abundance, $20^{th}$ percentile; 400-700, average abundance; 200-400, low abundance; <200, not detected). Selected abbreviations: "DAP" or "DA", days after pollination; "WK", whole kernel, "endo", endosperm.

FIG. 19 depicts Northern blots from a transient expression assay in Nicotiana benthamiana. Small RNA blots were hybridized to probes specific for the mature miRNAs predicted to be processed from miR164e (SEQ ID NO. 228) (FIG. 19A) and from an miRNA engineered to target Colorado potato beetle vacuolar ATPase (SEQ ID NO. 229) (FIG. 19B), as described in detail in Example 20. Results show that the predicted mature miRNAs were processed efficiently in vivo.

FIG. 20 depicts results described in detail in Example 21. FIG. 20A depicts the fold-back structure of SEQ ID NO. 236, the predicted miRNA precursor for SEQ ID NO. 234; the mature miRNA is located at bases 106-126, the corresponding miRNA* at bases 156-175, and another abundant miRNA was also found to be located at bases 100-120 in the stem of the fold-back structure. "Count" refers to the number of occurrences of a small RNA in the filtered set of 381,633 putative miRNA sequences that was analyzed. FIG. 20B depicts a transcription profile in soy tissues for the miRNA precursor SEQ ID NO. 236. FIG. 20C depicts a transcription profile in soy tissues for a predicted target, polyphenol oxidase (SEQ ID NO. 250) for the mature miRNA (SEQ ID NO. 234).

FIG. 21 depicts results described in detail in Example 21. FIG. 21A depicts the fold-back structure of SEQ ID NO. 239, the predicted miRNA precursor for SEQ ID NO. 237; the mature miRNA is located at bases 163-183, and the miRNA* at bases 18-63. "Count" refers to the number of occurrences of a small RNA in the filtered set of 381,633 putative miRNA sequences that was analyzed. FIG. 21B depicts a transcription profile in soy tissues for a predicted target, polyphenol oxidase (SEQ ID NO. 251) for the mature miRNA (SEQ ID NO. 237).

FIG. 22A depicts the fold-back structure of SEQ ID NO. 242, the predicted miRNA precursor for SEQ ID NO. 240; the mature miRNA is located at bases 87-107, and the miRNA* at bases 150-169. "Count" refers to the number of occurrences of a small RNA in the filtered set of 381,633 putative miRNA sequences that was analyzed.

FIG. 23A depicts the fold-back structure of SEQ ID NO. 245, the predicted miRNA precursor for SEQ ID NO. 243; the mature miRNA is located at bases 61-81, and the miRNA* at bases 109-129. "Count" refers to the number of occurrences of a small RNA in the filtered set of 381,633 putative miRNA sequences that was analyzed.

FIG. 24 depicts results described in detail in Example 21. FIG. 24A (top) depicts the fold-back structure of SEQ ID NO. 248, one of the predicted miRNA precursors for SEQ ID NO. 246; the mature miRNA is located at bases 157-178, and the miRNA* at bases 72-93. FIG. 24A (bottom) depicts the fold-back structure of SEQ ID NO. 249, another predicted miRNA precursors for SEQ ID NO. 246; the mature miRNA is located at bases 123-144, and the miRNA* at bases 58-79. "Count" refers to the number of occurrences of a small RNA in the filtered set of 381,633 putative miRNA sequences that was analyzed. FIG. 24B (top) depicts a transcription profile in soy tissues for the miRNA precursor SEQ ID NO. 248. FIG. 24B (bottom) depicts a transcription profile in soy tissues for the miRNA precursor SEQ ID NO. 249.

FIG. 25 depicts various embodiments of recombinant DNA constructs including a gene suppression element 3' to a terminator, as described in detail in Example 22.

FIG. 26 depicts constructs and results described in detail in Example 22. FIG. 26A depicts a recombinant DNA construct (pMON100552) for suppressing a target gene (luciferase), containing a gene suppression element 3' to a terminator. FIG. 26A depicts a control construct (pMON100553). Y-axis values are given as the logarithm of the ratio of logarithm of the ratio of firefly luciferase to Renilla luciferase, "log(Fluc/Rluc)"; error bars are 95% confidence intervals.

FIG. 28 depicts non-limiting embodiments of recombinant DNA useful in making transgenic plants of the invention, as described in Example 24. Abbreviations: "TS", target sequence; "Ter", terminator; a gene expression element represented by a non-limiting gene of interest "dapA", cordapA; "$TSs_{up}$", a gene suppression element. FIG. 24F depicts one mechanism for an "on" riboswitch acting in cis. "RB", right T-DNA border element; "LB", left T-DNA border element.

FIG. 29, top panel, depicts different systems of controlling expression of a target sequence (in this non-limiting example, of green fluorescent protein, "GFP") as described in Example 28. The bottom panel depicts a non-limiting example of a riboswitch autoinduced by its own ligand (lysine), as described in Example 28.

DETAILED DESCRIPTION OF THE INVENTION

Figure 1:
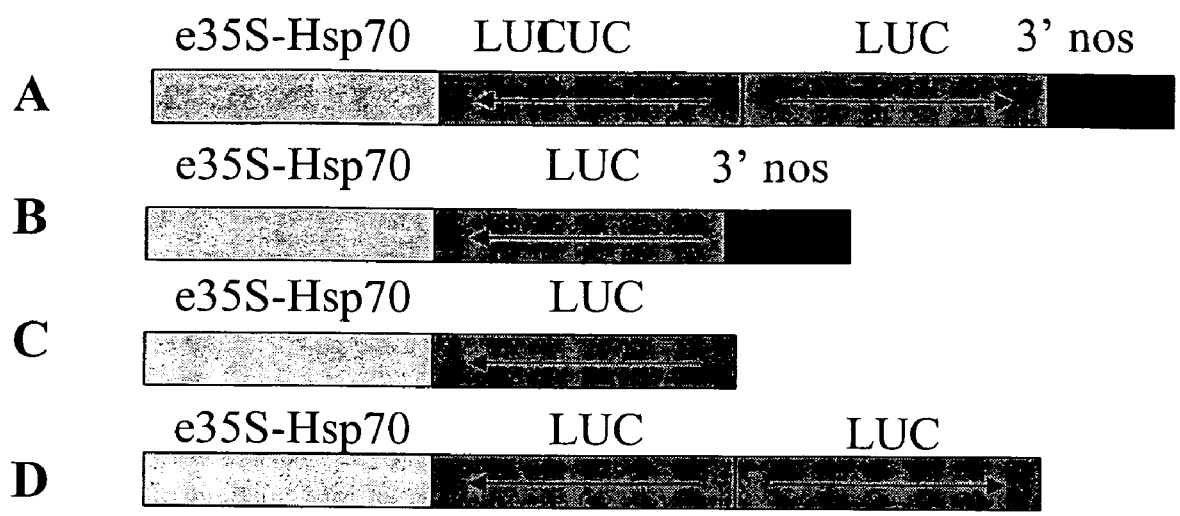
FIG. 1 schematically illustrates DNA vectors as described in Example 1. Legend: pale grey regions labelled "e35X-Hsp70": a chimeric promoter element including an enhanced CaMV35S promoter linked to an enhancer element (an intron from heat shock protein 70 of *Zea mays*, Pe35S-Hsp70 intron); medium grey regions labeled "LUC": DNA coding for firefly luciferase; dark grey regions labeled "3' nos": a 3'UTR DNA from *Agrobacterium tumefaciens* nopaline synthase gene. Vectors are conventionally depicted as transcribing from left (5') to right (3'). Arrows indicate orientation of the luciferase segments as sense (arrowhead to right) or anti-sense (arrowhead to left).

Unless defined otherwise, all technical and scientific terms used have the same meaning as commonly understood by one of ordinary skill in the art to which this invention belongs. Generally, the nomenclature used and the manufacture or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Where a term is provided in the singular, the inventors also contemplate aspects of the invention described by the plural of that term. The nomenclature used and the laboratory procedures described below are those well known and commonly employed in the art. Where there are discrepancies in terms and definitions used in references that are incorporated by reference, the terms used in this application shall have the definitions given. Other technical terms used have their ordinary meaning in the art that they are used, as exemplified by a variety of technical dictionaries. The inventors do not intend to be limited to a mechanism or mode of action. Reference thereto is provided for illustrative purposes only.

I. Selective Expression of a Target Sequence in Transgenic Plant Cells, Plants, and Seeds The present invention provides a transgenic plant cell having in its genome recombinant DNA including transcribable DNA including DNA that transcribes to an RNA aptamer capable of binding to a ligand. In some embodiments of the invention, for example, in transgenic plant cells made transgenic by *Agrobacterium*-mediated transformation, the recombinant DNA further includes at least one T-DNA border. In many embodiments, the transcribable DNA further includes DNA that transcribes to regulatory RNA capable of regulating expression of a target sequence, wherein the regulation of the target sequence is dependent on the conformation of the regulatory RNA, and the conformation of the regulatory RNA is allosterically affected by the binding state of the RNA aptamer.

Further provided by the invention is a transgenic plant including a regenerated plant prepared from a transgenic plant cell having in its genome recombinant DNA including transcribable DNA including DNA that transcribes to an RNA aptamer capable of binding to a ligand, or a progeny plant (which may be a hybrid progeny plant) of the regenerated plant. Such transgenic plants may be plants of any developmental stage, including seed, and include transgenic plants grown from such seed. Also claimed are plant tissues regenerated from the transgenic plant cell of the invention.

In preferred embodiments, the transgenic plant cell or plant having in its genome recombinant DNA including transcribable DNA including DNA that transcribes to an RNA aptamer capable of binding to a ligand has at least one altered trait, relative to a plant lacking the recombinant DNA, as described in detail under the heading "Making and Using Transgenic Plant Cells and Plants". In these embodiments, the altered trait is typically obtained by providing the ligand to at least some cells or tissues of the transgenic plant. In one preferred embodiment, the altered trait is provided by contacting the transgenic plant with an exogenous ligand that binds to the aptamer. In some of these embodiments, the exogenous ligand is physically applied to the plant (e.g., a synthetic or natural ligand applied to the plant as a foliar spray or root solution), or applied (e.g., as a coating or soak) to transgenic seed of the transgenic plant. For example, the altered trait may be obtained by contacting the transgenic plant with an herbicide (e.g., glyphosate or dicamba) that binds to an aptamer specific for the herbicide, thus turning "on" or "off" the regulatory RNA. In other embodiments, the ligand is an exogenous ligand produced by or found in a pest or pathogen of the transgenic plant, or a ligand (e.g., an allelochemical) produced by adjacent plants of the same or different species as the transgenic plant. In another preferred embodiment, the altered trait is obtained through the binding of an endogenous ligand to the aptamer. In such embodiments, the ligand is endogenous to the transgenic plant, e.g., a ligand produced constitutively, or in a specific cell or tissue, or under biotic or abiotic stress, or at a particular developmental or seasonal time. In a non-limiting example, the altered trait is obtained during a period of stress (biotic or abiotic), wherein a ligand, such as a stress-responsive molecule or hormone (e.g., salicylic acid, jasmonic acid, ethylene, glutathione, ascorbate, auxins, cytokinins), is endogenously produced by the transgenic plant, and binds to an aptamer specific for the stress-responsive molecule. In yet another example, the altered trait may be obtained in response to a pest or pathogen of the transgenic plant, wherein the aptamer is specific for a ligand produced by the plant in response to the pest or pathogen.

Transcribable DNA: The transcribable DNA includes DNA that transcribes to an RNA aptamer capable of binding to a ligand. By "transcribable" is meant that the DNA is capable of being transcribed to RNA. Thus, in preferred embodiments, the recombinant DNA further includes a promoter operably linked to the transcribable DNA. Promoters of use in the invention are preferably promoters functional in a plant cells, as described under the heading "Promoter Elements". Suitable promoters can be constitutive or non-constitutive promoters. In various embodiments, the promoter element can include a promoter selected from the group consisting of a constitutive promoter, a spatially specific promoter, a temporally specific promoter, a developmentally specific promoter, and an inducible promoter. In one embodiment of the invention, the promoter is a pol II promoter. In another embodiment, the promoter is a pol III promoter (see, for example, Eckstein (2005) *Trends Biochem. Sci.*, 30:445-452).

In many preferred embodiments, the transcribable DNA further includes DNA that transcribes to regulatory RNA capable of regulating expression of a target sequence, wherein the regulation is dependent on the conformation of the regulatory RNA, and the conformation of the regulatory RNA is allosterically affected by the binding state of the RNA aptamer, that is to say, the conformation of the regulatory RNA is allosterically influenced by the conformation of the RNA aptamer, which in turn is determined by whether the RNA aptamer is occupied or unoccupied by the specific ligand.

Figure 27:
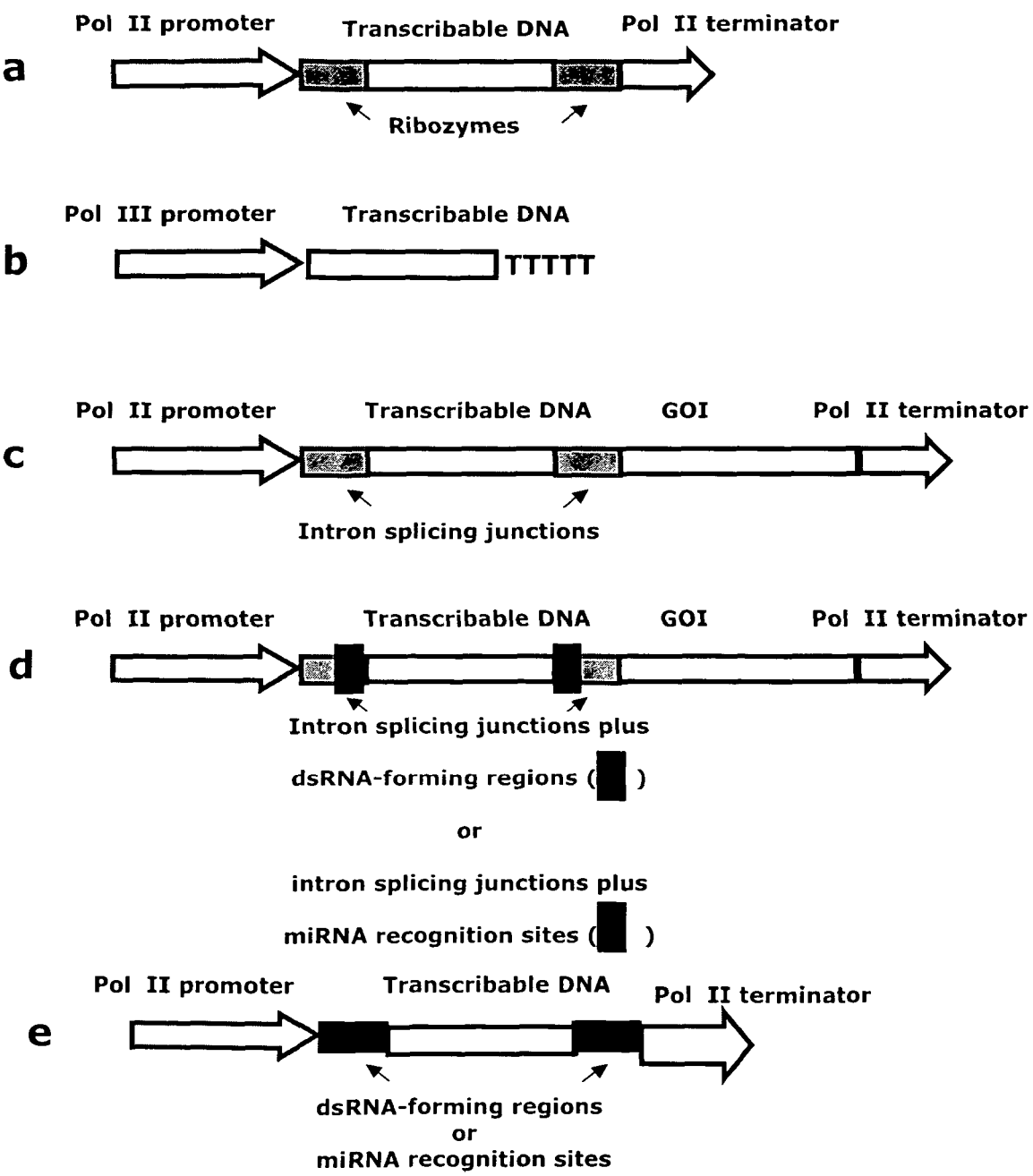
FIG. 27 schematically depicts non-limiting embodiments of the recombinant DNA useful in making transgenic plants of the invention. The transcribable DNA includes DNA that transcribes to at least one RNA aptamer domain, and can further include DNA that transcribes to an RNA regulatory domain (which can act "in cis" or "in trans"). Useful promoters include any promoter capable of transcribing the transcribable DNA in a transgenic plant of the invention, e.g., a pol II promoter or a pol III promoter. Various embodiments can include introns, double-stranded RNA-forming regions, and/or microRNA recognition sites. Some embodiments can further include one or more separate gene expression elements or gene suppression elements (shown here as a gene of interest, "GOI", which can be positioned upstream or downstream of the transcribable DNA).

In some embodiments, the transcribable DNA is optionally flanked on one or both sides by a ribozyme (e.g., a self-cleaving ribozyme or a hairpin ribozyme) (see, e.g., FIG. 27A). See, for example, Esteban et al. (1997) *J. Biol. Chem.*, 272:13629-13639, which describes the effects of conformation on hairpin ribozyme kinetics and provides guidelines for hairpin ribozyme sequence modification, and Najafi-Shoushtari et al. (2004) *Nucleic Acids Res.*, 32:3212-3219, which describes conformationally controlled hairpin ribozymes. In other embodiments, the transcribable DNA is optionally embedded within a spliceable intron (see, e.g., FIG. 27C). Introns suitable for use in the invention are preferably introns that are spliceable in planta; plant-sourced introns are especially preferred. Non-limiting examples of especially preferred plant introns include a rice actin 1 intron (I-Os-Act1), a maize heat shock protein intron (I-Zm-hsp70), and a maize alcohol dehydrogenase intron (I-Zm-adh1). Embodiments where the transcribable DNA is flanked by intron splicing sites can further include additional sequence to allow cleavage of the transcript, e.g., DNA that transcribes to RNA including at least one microRNA recognition site or DNA that transcribes to RNA capable of forming double-stranded RNA (dsRNA) (see, e.g., FIG. 27D). In other embodiments, the transcribable DNA includes DNA that transcribes to RNA sequence that can be processed in an RNAi pathway (i.e., to produce small interfering RNAs or microRNAs, see, for example, Xie et al. (2004) *PLoS Biol.*, 2:642-652; Bartel (2004) *Cell*, 116:281-297; Murchison and Hannon (2004) *Curr. Opin. Cell Biol.*, 16:223-229; and Dugas and Bartel (2004) *Curr. Opin. Plant Biol.*, 7:512-520, which are incorporated by reference). In non-limiting examples, the transcribable DNA is optionally flanked by DNA that transcribes to RNA including at least one microRNA recognition site (see, e.g., FIG. 27E). In these embodiments, the miRNA recognition site is preferably a miRNA recognition site recognized by a miRNA endogenous to the plant in which transcription occurs. In a non-limiting example, the transcribable DNA is flanked on both sides by a miRNA recognition site that is recognized by a mature miRNA that is expressed in an inducible or a spatially or temporally specific manner. In yet other embodiments, the transcribable DNA is optionally flanked on one or both sides by DNA that transcribes to RNA capable of forming double-stranded RNA (dsRNA) (see, e.g., FIG. 27E), for example, by forming an inverted repeat where the transcribable DNA is located in the middle "spacer" or "loop" region, or by forming separate dsRNA regions on one or both sides of the transcribable DNA, which may be processed to small interfering RNAs or to mature microRNAs. In certain embodiments, the transcribable DNA can further include at least one gene expression (or suppression) element for the expression of any gene or genes or interest (including coding or non-coding sequence), as described under the heading "Gene Expression Elements" (see, e.g., FIG. 27C and FIG. 1D, where a gene expression element is represented by a gene of interest, "GOI", and FIG. 28C and FIG. 28D, where a gene expression element is represented by a specific gene of interest, cordapA, "dapA", and FIG. 28E, where a gene suppression element is represented by "$TS_{sup}$").

RNA Aptamers: Nucleic acid aptamers are nucleic acid molecules that bind to a ligand through binding mechanism that is not primarily based on Watson-Crick base-pairing (in contrast, for example, to the base-pairing that occurs between complementary, anti-parallel nucleic acid strands to form a double-stranded nucleic acid structure). See, for example, Ellington and Szostak (1990) Nature, 346:818-822. A nucleic acid aptamer generally includes a primary nucleotide sequence that allows the aptamer to form a secondary structure (e.g., by forming stem-loop structures) that allows the aptamer to bind to its ligand. Binding of the aptamer to its ligand is preferably specific, allowing the aptamer to distinguish between two or more molecules that are structurally similar (see, for example, Bayer and Smolke (2005) Nature Biotechnol., 23:337-343). Aptamers useful in the invention can, however, be monovalent (binding a single ligand) or multivalent (binding more than one individual ligand, e.g., binding one unit of two or more different ligands). See, for example, Di Giusto and King (2004) J. Biol. Chem., 279: 46483-46489, describing the design and construction of multivalent, circular DNA aptamers, which is incorporated by reference.

Aptamers useful in the invention can include DNA, RNA, nucleic acid analogues (e.g., peptide nucleic acids), locked nucleic acids, chemically modified nucleic acids, or combinations thereof. See, for example, Schmidt et al. (2004) Nucleic Acids Res., 32:5757-5765, who describe locked nucleic acid aptamers. In one preferred embodiment of the invention, the aptamer is an RNA aptamer. In a particularly preferred embodiment, the aptamer is produced by transcription in planta. Examples of aptamers can be found, for example, in the public Aptamer Database, available on line at aptamer.icmb.utexas.edu (Lee et al. (2004) Nucleic Acids Res., 32(1):D95-100).

Aptamers can be designed for a given ligand by various procedures known in the art, including in vitro selection or directed evolution techniques. See, for example, "SELEX" ("systematic evolution of ligands by exponential enrichment"), as described in Tuerk and Gold (1990) Science, 249: 505-510, Ellington and Szostak (1990) Nature, 346:818-822, Ellington and Szostak (1992) Nature, 355:850-852, selection of bifunctional RNA aptamers by chimeric SELEX, as described by Burke and Willis (1998), RNA, 4:1165-1175, selection using ligands bound to magnetic particles as described by Murphy et al. (2003) Nucleic Acids Res., 31:e110, an automated SELEX technique described by Eulberg et al. (2005) Nucleic Acids Res., 33(4):e45, and a SELEX-type technique for obtaining aptamers raised against recombinant molecules expressed on cell surfaces, as descried by Ohuchi et al (2005) Nucleic Acid Symposium Series, 49:351-352 Selection can begin with a random pool of RNAs, from a partially structured pool of RNAs (see, for example, Davis and Szostak (2002) Proc. Natl. Acad. Sci. USA, 99: 11616-11621), or from a pool of degenerate RNAs (see, for example, Geiger et al. (1996) Nucleic Acids Res., 24: 1029-1036). Secondary structure models, folding, and hybridization behavior for a given RNA sequence can be predicted using algorithms, e.g., as described by Zuker (2003) Nucleic Acids Res., 31: 3406-3415. Thus, aptamers for a given ligand can be designed de novo using suitable selection. One non-limiting example of aptamer design and selection is described in detail in Weill et al. (2004) Nucleic Acids Res., 32:5045-5058, which describes isolation of various ATP-binding aptamers and secondary selection of aptamers that bind cordycepin (3' deoxyadenosine). Another non-limiting example of aptamer design is given in Huang and Szostak (2003) RNA, 9:1456-1463, which describes the in vitro evolution of novel aptamers with new specificities and new secondary structures from a starting aptamer. All citations in this paragraph are specifically incorporated by reference.

Ligands useful in the invention can include amino acids or their biosynthetic or catabolic intermediates, peptides, proteins, glycoproteins, lipoproteins, carbohydrates, fatty acids and other lipids, steroids, terpenoids, hormones, nucleic acids, aromatics, alkaloids, natural products or synthetic compounds (e.g., dyes, pharmaceuticals, antibiotics, herbicides), inorganic ions, and metals, in short, any molecule (or part of a molecule) that can be recognized and be bound by a nucleic acid secondary structure by a mechanism not primarily based on Watson-Crick base pairing. In this way, the recognition and binding of ligand and aptamer is analogous to that of antigen and antibody, or of biological effector and receptor. Ligands can include single molecules (or part of a molecule), or a combination of two or more molecules (or parts of a molecule), and can include one or more macromolecular complexes (e.g., polymers, lipid bilayers, liposomes, cellular membranes or other cellular structures, or cell surfaces). See, for example, Plummer et al. (2005) Nucleic Acids Res., 33:5602-5610, which describes selection of aptamers that bind to a composite small molecule-protein surface; Zhuang et al. (2002) J. Biol. Chem., 277:13863-13872, which describes the association of insect mid-gut receptor proteins with lipid rafts, which affects the binding of Bacillus thuringiensis insecticidal endotoxins; and Homann and Goringer (1999) Nucleic Acids Res., 27:2006-2014, which describes aptamers that bind to live trypanosomes; these citations are incorporated by reference.

Non-limiting examples of specific ligands include vitamins such as coenzyme $B_{12}$ and thiamine pyrophosphate, flavin mononucleotide, guanine, adenosine, S-adenosylmethionine, S-adenosylhomocysteine, coenzyme A, lysine, tyrosine, dopamine, glucosamine-6-phosphate, caffeine, theophylline, antibiotics such as chloramphenicol and neomycin, herbicides such as glyphosate and dicamba, proteins including viral or phage coat proteins and invertebrate epidermal or digestive tract surface proteins, and RNAs including viral RNA, transfer-RNAs (t-RNAs), ribosomal RNA (rRNA), and RNA polymerases such as RNA-dependent RNA polymerase (RdRP). One class of RNA aptamers useful in the invention are "thermoswitches" that do not bind a ligand but are thermally responsive, that is to say, the aptamer's conformation is determined by temperature. See, for example, Box 3 in Mandal and Breaker (2004) *Nature Rev. Mol. Cell. Biol.*, 5:451-463, which is incorporated by reference.

An aptamer can be described by its binding state, that is, whether the aptamer is bound (or unbound) to its respective ligand. The binding site (or three-dimensional binding domain or domains) of an aptamer can be described as occupied or unoccupied by the ligand. Similarly, a population of a given aptamer can be described by the fraction of the population that is bound or unbound to the ligand. The affinity of an aptamer for its ligand can be described in terms of the rate of association (binding) of the aptamer with the ligand and the rate of dissociation of the ligand from the aptamer, e.g., by the equilibrium association constant (K) or by its reciprocal, the affinity constant ($K_a$) as is well known in the art. These rates can be determined by methods similar to those commonly used for determining binding kinetics of ligands and receptors or antigens and antibodies, such as, but not limited to, equilibrium assays, competition assays, surface plasmon resonance, and predictive models. The affinity of an aptamer for its ligand can be selected, e.g., during in vitro evolution of the aptamer, or further modified by changes to the aptamer's primary sequence, where such changes can be guided by calculations of binding energy or by algorithms, e.g., as described by Zuker (2003) *Nucleic Acids Res.*, 31:3406-3415 or Bayer and Smolke (2005) *Nature Biotechnol.*, 23:337-343.

The binding state of an aptamer preferably at least partially determines the secondary structure (e.g., the formation of double-stranded or single stranded regions) and the three-dimensional conformation of the aptamer. In embodiments where the transcribable DNA further includes DNA that transcribes to regulatory RNA capable of regulating expression of a target sequence, the binding state of the aptamer allosterically affects the conformation of the regulatory RNA and thus the ability of the regulatory RNA to regulate expression of the target sequence.

In one preferred embodiments, the aptamer (transcribed RNA) is flanked by DNA that transcribes to RNA capable of forming double-stranded RNA (dsRNA) (FIG. 27E). In some of these embodiments, the dsRNA is processed by an RNAi (siRNA or miRNA) mechanism, whereby the aptamer is cleaved from the rest of the transcript. In other, particularly preferred embodiments, the two transcribed RNA regions flanking the aptamer form at least partially double-stranded RNA "stem" between themselves, wherein the aptamer serves as a "spacer" or "loop" in a stem-loop structure; such an arrangement is expected to enhance the stability or half-life of the transcript in a manner analogous to that observed for DNA (see, for example, Di Giusto and King (2004) *J. Biol. Chem.*, 279:46483-46489, which is incorporated by reference). Transgenic plants having in their genome DNA that transcribes to such aptamers having enhanced stability are particularly desirable, e.g., where the aptamer functions to inhibit or kill a pathogen or pest of the transgenic plant.

Target Sequence: The regulatory RNA is capable of regulating expression of a target sequence, wherein the regulation of the target sequence is dependent on the conformation of the regulatory RNA, and the conformation of the regulatory RNA is allosterically affected by the binding state of the RNA aptamer. Any target sequence may be chosen, including one or more target sequences selected from a gene native to the transgenic plant of the invention, a transgene in the transgenic plant, and a gene native to a pest or pathogen of the transgenic plant. The target sequence can include a sequence that expresses a gene of interest (e.g., an RNA encoding a protein), or a sequence that suppresses a gene of interest (e.g., an RNA that is processed to an siRNA or miRNA that in turn suppresses the gene of interest).

The regulatory RNA can regulate the transcription and/or translation of any target nucleic acid sequence or sequences of interest. In some embodiments, the recombinant DNA further includes a second gene regulatory element for regulating (i.e., suppressing or expressing) at least one second target sequence that is in addition to the target sequence regulated by the regulatory RNA. Whether a first target sequence or a second target sequence, the target sequence can include a single sequence or part of a single sequence that is targeted for regulation, or can include, for example, multiple consecutive segments of a target sequence, multiple non-consecutive segments of a target sequence, multiple alleles of a target sequence, or multiple target sequences from one or more species.

The target sequence can be translatable (coding) sequence, or can be non-coding sequence (such as non-coding regulatory sequence), or both. The target sequence can include at least one eukaryotic target sequence, at least one non-eukaryotic target sequence, or both. A target sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans. Suitable target sequences are further described as "target genes" under the heading "Target Genes".

Non-limiting examples of a target sequence include non-translatable (non-coding) sequence, such as, but not limited to, 5' untranslated regions, promoters, enhancers, or other non-coding transcriptional regions, 3' untranslated regions, terminators, and introns. Target sequences can also include genes encoding microRNAs, small interfering RNAs, RNA components of ribosomes or ribozymes, small nucleolar RNAs, and other non-coding RNAs (see, for example, non-coding RNA sequences provided publicly at rfam.wustl.edu; Erdmann et al. (2001) *Nucleic Acids Res.*, 29:189-193; Gottesman (2005) *Trends Genet.*, 21:399-404; Griffiths-Jones et al. (2005) *Nucleic Acids Res.*, 33:121-124, which are incorporated by reference). One specific example of a target sequence includes a microRNA recognition site (that is, the site on an RNA strand to which a mature miRNA binds and induces cleavage). Another specific example of a target sequence includes a microRNA precursor sequence, that is, the primary transcript encoding a microRNA, or the RNA intermediates processed from this primary transcript (e.g., a nuclear-limited pri-miRNA or a pre-miRNA which can be exported from the nucleus into the cytoplasm). See, for example, Lee et al. (2002) *EMBO Journal*, 21:4663-4670; Reinhart et al. (2002) *Genes & Dev.*, 16:161611626; Lund et al. (2004) *Science*, 303:95-98; and Millar and Waterhouse (2005) *Funct. Integr Genomics*, 5:129-135, which are incorporated by reference. Target microRNA precursor DNA sequences can be native to the transgenic plant of the invention, or can be native to a pest or pathogen of the transgenic plant. Target sequences can also include translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). A target sequence can be a native gene targeted for expression control (e.g., suppression), with or without concurrent expression (or suppression) of an exogenous transgene, for example, by including a gene expression (or suppression) element in the same or in a separate recombinant DNA construct. For example, it can be desirable to replace a native gene with an exogenous transgene homologue.

One preferred embodiment of the invention provides transgenic plant cells (or transgenic plants, progeny plants, or seeds derived from the transgenic plant cells) having in their genome a recombinant DNA including transcribable DNA including DNA that transcribes to an RNA aptamer capable of binding to a ligand, for suppressing a plant pest or pathogen (e.g., viruses, bacteria, fungi, and invertebrates such as insects, nematodes, and molluscs).

Examples of such embodiments include transgenic plant cells (or transgenic plants, progeny plants, or seeds derived from the transgenic plant cells) having in their genome a recombinant DNA including transcribable DNA including DNA that transcribes to one or more RNA aptamers that bind to one or more ligands involved in a pest or pathogen's ability to recognize, invade, or feed on a plant, or in the pest or pathogen's ability to recruit additional individuals of its species, or in the pest or pathogen's ability to grow, metamorphose, or reproduce. Non-limiting examples of ligands suitable for this approach include the insect mid-gut brush border receptor proteins that are recognized by *Bacillus thuringiensis* insecticidal endotoxins. See, for example, Knight et al. (1995) *J. Biol. Chem.*, 270:17765-17770, and Gill et al. (1995) *J. Biol. Chem.*, 270:27277-27282, which describe the isolation, identification, and cloning of examples of such receptor proteins; Gomez et al. (2001) *J. Biol. Chem.*, 276: 28906-28912, and Daniel et al. (2002) *Appl. Env. Microbiol.*, 68:2106-2112, which describe techniques for identifying binding epitopes of such receptor proteins and for studying their binding affinities; Jurat-Fuentes and Adang (2001) *Appl. Env. Microbiol.*, 67:323-329, and Jurat-Fuentes et al. (2001), *Appl. Env. Microbiol.*, 67:872-879, which describe endotoxin-receptor binding assays involving either membrane blots or surface plasmon resonance measured binding of brush border membrane vesicles to endotoxin; all of these are incorporated by reference. Other examples of suitable ligands to which RNA aptamers of the invention bind include steroid receptors, such as estrogen receptors, androgen receptors, retinoid receptors, and ecdysone receptors (see, for example, Saez et al. (2000) *Proc. Natl. Acad. Sci. USA*, 97:14512-14517. Where ligands are receptor molecules or receptor complexes, RNA aptamers of the invention can optionally act as antagonists or as agonists.

One aspect of the invention provides transgenic plants wherein the target sequence is selected to provide resistance to a plant pest or pathogen, for example, resistance to a nematode such as soybean cyst nematode or root knot nematode or to a pest insect. Thus, target sequences (i.e., "target genes") of interest can also include endogenous genes of plant pests and pathogens as described in detail under "Target Genes". Pests and pathogens of interest include invertebrates (including nematodes, molluscs, and insects), fungi, bacteria, mollicute, and viruses, as described in detail under "Target Genes". Thus, a target sequence need not be endogenous to the plant in which the recombinant DNA is transcribed. It is envisioned that recombinant DNA of the invention can be transcribed in a plant and used to control expression of a target sequence endogenous to a pathogen or pest that may infest the plant.

Regulatory RNA: In many embodiments, the transcribable DNA further includes DNA that transcribes to regulatory RNA capable of regulating expression of a target sequence, wherein the regulation of the target sequence is dependent on the conformation of the regulatory RNA, and the conformation of the regulatory RNA is allosterically affected by the binding state of the RNA aptamer. Such combinations of an aptamer with a regulator RNA domain are commonly known as riboswitches. The regulatory RNA is typically downstream of the aptamer but the two domains may overlap; see, e.g., Najafi-Shoushtari and Famulok (2005) *RNA*, 111:1514-1520, which is incorporated by reference and describes a hairpin ribozyme that includes an aptamer domain and is competitively regulated by flavin mononucleotide and an oligonucleotide complementary to the aptamer domain. In some embodiments, the regulatory RNA is operably linked to the target sequence, and acts "in cis". In other embodiments, the regulatory RNA is not operably linked to the target sequence, and acts "in trans".

In riboswitch embodiments including an aptamer and a regulatory RNA, the riboswitch regulates expression of the target sequence by any suitable mechanism. One non-limiting mechanism is transcriptional regulation by the ligand-dependent formation of an intrinsic terminator stem (an extended stem-loop structure typically followed by a run of 6 or more U residues) that causes RNA polymerase to abort transcription, e.g., before a complete mRNA is formed. In "off" riboswitches, in the absence of sufficient ligand, the unbound aptamer domain permits formation of an "antiterminator stem", which prevents formation of the intrinsic terminator stem and thus allows transcription to proceed; thus, the default state of the riboswitch is "on" (i.e., transcription normally proceeds) and the ligand must be added to turn the riboswitch off. In "on" riboswitches that use this mechanism, the aptamer domain must be in the bound (ligand-occupied) conformation to permit formation of the "antiterminator stem" and allow transcription. Another mechanism is translation regulation, where ligand binding causes structural changes in full-length mRNAs and thereby permits (or prevents) ribosomes from binding to the ribosomal binding site (RBS); the formation of an "anti-anti-RBS" stem and an "anti-RBS" stem is also mutually exclusive. In "on" riboswitches that use this mechanism, absence of the ligand allows formation of an anti-anti-RBS, and thus a structurally unencumbered RBS to which the ribosome can bind. A combination of both transcriptional and translational regulation is also possible. For a detailed discussion of regulation mechanisms, see Mandal and Breaker (2004) *Nature Rev. Mol. Cell Biol.*, 5:451-463, which is incorporated by reference.

In some embodiments, the regulatory RNA includes a ribozyme, e.g., a self-cleaving ribozyme, a hammerhead ribozyme, or a hairpin ribozyme. Certain embodiments of the regulatory RNA include RNA sequence that is complementary or substantially complementary to the target sequence. One non-limiting example is where the regulatory RNA includes an anti-sense segment that is complementary or substantially complementary to the target sequence. See, for example, Bayer and Smolke (2005) *Nature Biotechnol.*, 23:337-343, where the regulatory RNA includes both an anti-sense segment complementary to the target sequence, and a sense segment complementary to the anti-sense segment, wherein the anti-sense segment and sense segment are capable of hybridizing to each other to form an intramolecular double-stranded RNA.

In embodiments where regulation of a target sequence involves Watson-Crick base-pairing of the regulatory RNA to the target sequence (e.g., in trans-acting embodiments, see, e.g., Bayer and Smolke (2005) *Nature Biotechnol.*, 23:337-343), the target sequence of interest can be more specifically targeted by designing the regulatory RNA to include regions substantially non-identical to a non-target sequence. Non-target sequences can include any gene for which the expression is preferably not modified, either in a plant transcribing the recombinant DNA construct or in organisms that may come into contact with RNA transcribed from the recombinant DNA construct. A non-target sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans).

In one embodiment of the invention, the target sequence is a gene endogenous to a given species, such as a given plant (such as, but not limited to, agriculturally or commercially important plants, including monocots and dicots), and the non-target sequence can be, for example, a gene of a non-target species, such as another plant species or a gene of a virus, fungus, bacterium, invertebrate, or vertebrate, even a human. One non-limiting example is where it is desirable to design either the aptamer, or the regulatory RNA, or both, in order to modify the expression of a target sequence that is a gene endogenous to a single species (e.g., Western corn rootworm, *Diabrotica virgifera virgifera* LeConte) but to not modify the expression of a non-target sequence such as genes from related, even closely related, species (e.g., Northern corn rootworm, *Diabrotica barberi* Smith and Lawrence, or Southern corn rootworm, *Diabrotica undecimpunctata*).

In other embodiments (e.g., where it is desirable to modify the expression of a target sequence across multiple species), it may be desirable to design the aptamer, or the regulatory RNA, or both, to modify the expression of a target sequence common to the multiple species in which the expression of the target sequence is to be modified. Thus, the aptamer, or the regulatory RNA, or both, can be selected to be specific for one taxon (e.g., specific to a genus, family, or even a larger taxon such as a phylum, e.g., arthropoda) but not for other taxa (for example, plants or vertebrates or mammals). In one non-limiting example of this embodiment, a regulatory RNA can be selected so as to target pathogenic fungi (e.g., a *Fusarium* spp.) but not target any gene sequence from beneficial fungi (e.g., beneficial soil mycorrhizal fungi).

In another non-limiting example of this embodiment, the aptamer, or the regulatory RNA, or both, to regulate gene expression in corn rootworm can be selected to be specific to all members of the genus *Diabrotica*. For example, a regulatory RNA including a *Diabrotica*-targeted suppression element (e.g., anti-sense RNA, double-stranded RNA, microRNA, or tandem RNA repeats) can be selected so as to not target any gene sequence from beneficial coleopterans (for example, predatory coccinellid beetles, commonly known as ladybugs or ladybirds) or other beneficial insect species.

The required degree of specificity of a regulatory RNA that includes a gene suppression element (e.g., anti-sense RNA, double-stranded RNA, microRNA, or tandem RNA repeats) for suppression of a target sequence depends on various factors. For example, where the gene suppression element includes double-stranded RNA (dsRNA), factors can include the size of the smaller dsRNA fragments that are expected to be produced by the action of Dicer, and the relative importance of decreasing the dsRNA's potential to suppress non-target sequences. For example, where the dsRNA fragments are expected to be 21 base pairs in size, one particularly preferred embodiment can be to include in the regulatory RNA a sequence capable of forming dsRNA and encoding regions substantially non-identical to a non-target sequence, such as regions within which every contiguous fragment including at least 21 nucleotides matches fewer than 21 (e.g., fewer than 21, or fewer than 20, or fewer than 19, or fewer than 18, or fewer than 17) out of 21 contiguous nucleotides of a non-target sequence. In another embodiment, regions substantially non-identical to a non-target sequence include regions within which every contiguous fragment including at least 19 nucleotides matches fewer than 19 (e.g., fewer than 19, or fewer than 18, or fewer than 17, or fewer than 16) out of 19 contiguous nucleotides of a non-target sequence.

In some embodiments, it may be desirable to design the aptamer, the regulatory RNA, or both, to include regions predicted to not generate undesirable polypeptides, for example, by screening the aptamer, the regulatory RNA, or both, for sequences that may encode known undesirable polypeptides or close homologues of these. Undesirable polypeptides include, but are not limited to, polypeptides homologous to known allergenic polypeptides and polypeptides homologous to known polypeptide toxins. Publicly available sequences encoding such undesirable potentially allergenic peptides are available, for example, the Food Allergy Research and Resource Program (FARRP) allergen database (available at allergenonline.com) or the Biotechnology Information for Food Safety Databases (available at www.iit.edu/~sgendel/fa.htm) (see also, for example, Gendel (1998) *Adv. Food Nutr. Res.*, 42:63-92, which is incorporated by reference). Undesirable sequences can also include, for example, those polypeptide sequences annotated as known toxins or as potential or known allergens and contained in publicly available databases such as GenBank, EMBL, SwissProt, and others, which are searchable by the Entrez system (www.ncbi.nih.gov/Entrez). Non-limiting examples of undesirable, potentially allergenic peptide sequences include glycinin from soybean, oleosin and agglutinin from peanut, glutenins from wheat, casein, lactalbumin, and lactoglobulin from bovine milk, and tropomyosin from various shellfish (allergenonline.com). Non-limiting examples of undesirable, potentially toxic peptides include tetanus toxin tetA from *Clostridium tetani*, diarrheal toxins from *Staphylococcus aureus*, and venoms such as conotoxins from *Conus* spp. and neurotoxins from arthropods and reptiles (www.ncbi.nih.gov/Entrez).

In one non-limiting example, a proposed aptamer, regulatory RNA, or both, can be screened to eliminate those transcribable sequences encoding polypeptides with perfect homology to a known allergen or toxin over 8 contiguous amino acids, or with at least 35% identity over at least 80 amino acids; such screens can be performed on any and all possible reading frames in both directions, on potential open reading frames that begin with ATG, or on all possible reading frames, regardless of whether they start with an ATG or not. When a "hit" or match is made, that is, when a sequence that encodes a potential polypeptide with perfect homology to a known allergen or toxin over 8 contiguous amino acids (or at least about 35% identity over at least about 80 amino acids), is identified, the DNA sequences corresponding to the hit can be avoided, eliminated, or modified when selecting sequences to be used in the aptamer, the regulatory RNA, or both.

Figure 4:
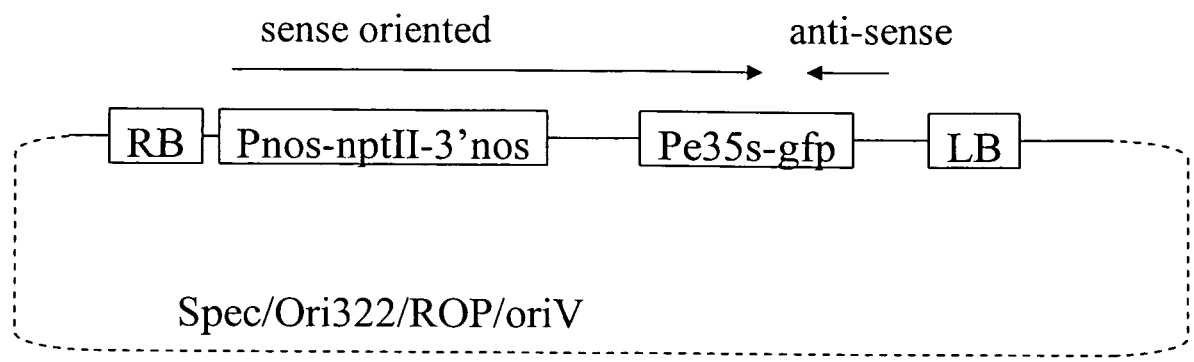
FIG. 4 is a schematic map of a plasmid including an enhanced anti-sense construct as described in Example 3.

Avoiding, elimination of, or modification of, an undesired sequence can be achieved by any of a number of methods known to those skilled in the art. In some cases, the result can be novel sequences that are believed to not exist naturally. For example, avoiding certain sequences can be accomplished by joining together "clean" sequences into novel chimeric sequences to be used in a gene suppression element.

Where the regulatory RNA includes double-stranded RNA (dsRNA) for silencing a target gene, applicants recognize that in some dsRNA-mediated gene silencing, it is possible for imperfectly matching dsRNA sequences to be effective at gene silencing. For example, it has been shown that mismatches near the center of a miRNA complementary site has stronger effects on the miRNA's gene silencing than do more distally located mismatches. See, for example, FIG. 4 in Mallory et al. (2004) *EMBO J.*, 23:3356-3364, which is incorporated by reference. In another example, it has been reported that, both the position of a mismatched base pair and the identity of the nucleotides forming the mismatch influence the ability of a given siRNA to silence a target sequence, and that adenine-cytosine mismatches, in addition to the G:U wobble base pair, were well tolerated (see Du et al. (2005) *Nucleic Acids Res.*, 33:1671-1677, which is incorporated by reference). Thus, a regulatory RNA that includes double-stranded RNA need not always have 100% sequence identity with the intended target sequence, but generally would preferably have substantial sequence identity with the intended target sequence, such as about 95%, about 90%, about 85%, or about 80% sequence identity with the intended target sequence. One skilled in the art would be capable of judging the importance given to screening for regions predicted to be more highly specific to the first target sequence or predicted to not generate undesirable polypeptides, relative to the importance given to other criteria, such as, but not limited to, the percent sequence identity with the intended first target sequence or the predicted gene silencing efficiency of a given sequence. For example, it may be desirable for a given regulatory RNA that includes double-stranded RNA for gene silencing to be active across several species, and therefore one skilled in the art can determine that it is more important to include in the regulatory RNA regions specific to the several species of interest, but less important to screen for regions predicted to have higher gene silencing efficiency or for regions predicted to generate undesirable polypeptides.

In many embodiments, the transgenic plant cell has in its genome recombinant DNA including transcribable DNA including (a) DNA that transcribes to an RNA aptamer capable of binding to a ligand, and (b) DNA that transcribes to regulatory RNA capable of regulating expression of a target sequence, wherein the regulation is dependent on the conformation of the regulatory RNA, and the conformation of said regulatory RNA is allosterically affected by the binding state of said RNA aptamer. In these embodiments, binding of the aptamer to its ligand results in a specific change in the expression of the target sequence, which may be an increase or a decrease in expression, depending on the design of the recombinant DNA.

In one embodiment, binding of the ligand to the RNA aptamer results in an increase of expression of the target sequence relative to expression in the absence of the binding. In another embodiment, binding of the ligand to the RNA aptamer results in a decrease of expression of the target sequence relative to expression in the absence of the binding.

Some embodiments are characterized by "autoinducibility". In one such embodiment, binding of the ligand to the RNA aptamer results in an increase of expression of the target sequence relative to expression in the absence of the binding, wherein the increase of expression results in a level of the ligand sufficient to maintain the increase of expression. In another embodiment, binding of the ligand to the RNA aptamer results in a decrease of expression of the target sequence relative to expression in the absence of the binding, the decrease of expression resulting in a level of the ligand sufficient to maintain the increase of expression.

Thus, another aspect of the invention is a method of modifying expression of a gene of interest in a plant cell, including transcribing in a transgenic plant cell of the invention, or a plant, progeny plant, or seed or other plant tissue derived from such a transgenic plant cell, recombinant or heterologous DNA that transcribes to (a) an RNA aptamer capable of binding to a ligand, and (b) regulatory RNA capable of regulating expression of a target sequence, wherein the regulation is dependent on the conformation of the regulatory RNA, and wherein the conformation of the regulatory RNA is allosterically affected by the binding state of the RNA aptamer, whereby expression of the gene of interest is modified relative to its expression in the absence of transcription of the recombinant DNA construct.

Method of Reducing Invertebrate Pest Damage to a Plant: The present invention also provides a method of reducing damage to a plant by a pest or pathogen of the plant, including transcribing in the plant a recombinant DNA construct including transcribable DNA including DNA that transcribes to an RNA aptamer capable of binding to a ligand, wherein the ligand includes at least part of a molecule endogenous to the pest or pathogen, and whereby binding of the RNA aptamer to the ligand reduces damage to the plant by the pest or pathogen, relative to damage in the absence of transcription of the recombinant DNA construct. The ligand can include at least part of any molecule that is part of a pest's anatomy (e.g., a coat or surface protein or macromolecular structure), or is produced or secreted by the pest or pathogen (e.g., an enzyme secreted by a pathogen in invasion of a plant cell)

In particularly preferred embodiments, the pest or pathogen is an invertebrate pest of the transgenic plant, and the ligand includes at least part of a molecule of the digestive tract lining of the invertebrate pest, e.g., insect mid-gut brush border receptor proteins that are recognized by *Bacillus thuringiensis* insecticidal endotoxins (see discussion above under the heading "RNA Aptamers"). Invertebrate pests of interest are listed above under the heading "Target Sequences".

The invention also contemplates and claims an analogous method for improving resistance in a transgenic plant to bacterial, fungal, or viral pathogens. The method reduces damage to a transgenic plant by a bacterial, fungal, or viral pathogen of the plant, including the step of transcribing in the plant a recombinant DNA construct including transcribable DNA including DNA that transcribes to an RNA aptamer capable of binding to a ligand, wherein the ligand includes at least part of a molecule endogenous to the bacterial, fungal, or viral pathogen, and whereby binding of the RNA aptamer to the ligand reduces damage to the plant by the bacterial, fungal, or viral pathogen, relative to damage in the absence of transcription of the recombinant DNA construct. Bacterial, fungal, and viral pathogens of interest are provided under the heading "Target Genes".

Recombinant DNA Constructs: The present invention further provides a recombinant DNA construct including: (a) transcribable DNA including DNA that transcribes to an RNA aptamer capable of binding to a ligand; and (b) DNA sequence that transcribes to double-stranded RNA flanking said transcribable DNA. In some embodiments, the recombinant DNA construct further includes DNA that transcribes to regulatory RNA capable of regulating expression of a target sequence, wherein the regulation is dependent on the conformation of the regulatory RNA, and the conformation of the regulatory RNA is allosterically affected by the binding state of the RNA aptamer. The transcribable DNA is DNA that is capable of being transcribed in a eukaryotic cell, preferably an animal cell or a plant cell.

The double-stranded RNA (dsRNA) is preferably RNA that is capable of being processed through an RNAi pathway (i.e., to produce small interfering RNAs or microRNAs, see, for example, Xie et al. (2004) *PLoS Biol.*, 2:642-652; Bartel (2004) *Cell*, 116:281-297; Murchison and Hannon (2004) *Curr. Opin. Cell Biol.*, 16:223-229; and Dugas and Bartel (2004) *Curr. Opin. Plant Biol.*, 7:512-520, which are incorporated by reference). The RNAi pathway can be that found in animals or that found in plants. See, e.g., Lee et al. (2002) *EMBO Journal*, 21:4663-4670; Reinhart et al. (2002) *Genes & Dev.*, 16:161611626; Lund et al. (2004) *Science*, 303:95-98; and Millar and Waterhouse (2005) *Funct. Integr Genomics*, 5:129-135, which are incorporated by reference. Whereas in animals both miRNAs and siRNAs are believed to result from activity of the same DICER enzyme, in plants miRNAs and siRNAs are formed by distinct DICER-like (DCL) enzymes, and in *Arabidopsis* a nuclear DCL enzyme is believed to be required for mature miRNA formation (Xie et al. (2004) *PLoS Biol.*, 2:642-652, which is incorporated by reference).

In non-limiting examples, the transcribable DNA is optionally flanked on one or both sides by DNA that transcribes to RNA capable of forming double-stranded RNA (dsRNA) (for example, by forming an inverted repeat where the transcribable DNA is located in the middle "spacer" region, or by forming separate dsRNA regions on one or both sides of the transcribable DNA, which may be processed to small interfering RNAs, to microRNA precursors such as pre-miRNAs, or to mature microRNAs). In yet other embodiments, the transcribable DNA is optionally flanked by DNA that transcribes to RNA including at least one microRNA recognition site. In these embodiments, the miRNA recognition site is preferably a miRNA recognition site recognized by a miRNA endogenous to the plant in which transcription occurs. In a non-limiting example, the transcribable DNA is flanked on both sides by a miRNA recognition site that is recognized by a mature miRNA that is expressed in an inducible or a spatially or temporally specific manner. The transcribable DNA can further include at least one gene expression element.

The invention further provides a transgenic eukaryotic cell including in its genome a recombinant DNA construct including: (a) transcribable DNA including DNA that transcribes to an RNA aptamer capable of binding to a ligand; and (b) DNA sequence that transcribes to double-stranded RNA flanking said transcribable DNA. Such cells may be animal cells or plant cells. Also provided is a transgenic plant having in its genome a recombinant DNA construct including: (a) transcribable DNA including DNA that transcribes to an RNA aptamer capable of binding to a ligand; and (b) DNA sequence that transcribes to double-stranded RNA flanking said transcribable DNA Methods for preparing and using the recombinant DNA constructs, and for making transgenic cells and transgenic plants, are described under the headings "Making and Using Recombinant DNA Constructs" and "Making and Using Transgenic Plant Cells and Transgenic Plants".

II. Recombinant DNA Constructs Containing Introns and Gene Suppression Elements

The present invention provides a recombinant DNA construct for plant transformation including a promoter operably linked to a first gene suppression element for suppressing at least one first target gene, wherein said first gene suppression element is embedded in an intron flanked on one or on both sides by non-protein-coding DNA. In some embodiments, the recombinant DNA construct consists entirely of non-protein-coding DNA (e.g., a promoter, a gene suppression element that is embedded in an intron and that transcribes to a non-coding RNA, and an optional terminator). Thus, the invention includes the use of an intron to deliver a gene suppression element in the absence of any protein-coding exons.

In some embodiments, the intron is located adjacent to at least one element selected from the group consisting of the promoter and a terminator, that is to say, directly contiguous (or essentially directly, with no substantial intervening sequence) with the promoter or with a terminator or with both. In one specific embodiment, the intron is directly (or essentially directly) 3' to the promoter. The intron can also optionally be directly (or essentially directly) 5' to a terminator, if a terminator is present in the recombinant DNA construct. Where the intron is adjacent to a terminator element, any intervening sequence preferably does not include a self-splicing ribozyme. In one preferred embodiment, the intron containing the gene suppression element is flanked directly (on the 5' end) by the promoter element, and (on the 3' end) by the terminator element if one is present.

The inventors have unexpectedly found that transcription can continue downstream of a terminator at least sufficiently to allow transcription of a gene suppression element located 3' to the terminator (downstream of a polyadenylation sequence). Thus another aspect of the invention is a recombinant DNA construct including a promoter, a terminator, transcribable sequence (which can include coding or non-coding sequence or both, and can include, e.g., a gene expression element, a gene suppression element, an aptamer, or a riboswitch) between the promoter and the terminator, and at least one gene suppression element that is 3' to the terminator. In various embodiments, at least one gene suppression element (such as any one or more of those described under "Gene Suppression Elements"), whether embedded in an intron or not, is located downstream of a terminator and sufficiently proximate to the terminator to permit transcription of the gene suppression element. In a specific embodiment, the intron is located downstream of a terminator and sufficiently proximate to the terminator to permit transcription of the intron. In one preferred but non-limiting embodiment, the intron is directly (or essentially directly) 3' to a terminator. Introns can affect the expression of adjacent sequences (e.g., depending on the intron's splicing efficiency), and thus one advantage of placing a gene suppression element (or intron containing a gene suppression element) 3' to a terminator includes allowing expression of a sequence between the promoter and the terminator, wherein the expression is not influenced by in the manner that it may be if the gene suppression element (or intron containing a gene suppression element) was also located between the promoter and the terminator. Another advantage includes the likelihood that a gene suppression element 3' to a terminator will be processed as an aberrant transcript (e.g., converted to double-stranded RNA in an RNA-dependent RNA polymerase manner even in the absence of inverted repeat sequences), which can increase the efficiency of gene suppression (see Examples 1, 2, and 3, which illustrate that lack of sequences necessary for polyadenylation enhanced the efficiency of a gene suppression element). Yet another advantage is that this approach reduces the need for multiple promoter elements, especially useful when stacking multiple genetic constructs to be expressed in a single cell.

The recombinant DNA construct contains one or more first gene suppression element for suppressing at least one first target gene and embedded in an intron flanked on one or on both sides by non-protein-coding DNA. Suitable gene suppression elements are described under the heading "Gene Suppression Elements". Where the recombinant DNA construct contains more than one first gene suppression element, each of these first gene suppression elements can include one or more elements as described herein. The first target gene can include a single gene or part of a single gene that is targeted for suppression, or can include, for example, multiple consecutive segments of a first target gene, multiple non-consecutive segments of a first target gene, multiple alleles of a first target gene, or multiple first target genes from one or more species. Suitable first target genes are described under the heading "Target Genes".

Introns of use in the recombinant DNA construct are described under the heading "Introns". The intron is located adjacent to at least one element selected from the group consisting of a promoter element and a terminator element, as described under the headings "Promoter Elements" and "Terminator Elements" respectively. Preferably, upon transcription of the recombinant DNA construct, the first gene suppression element is spliced out of the intron. In some embodiments, the recombinant DNA construct is designed so that the RNA transcribed from the first gene suppression element, when spliced out of the intron, lacks at least one of a functional polyadenylation signal or a functional polyadenylation site (or any other element that facilitates transport of a transcribed RNA into the cytoplasm), or lacks a 3' untranslated region; the resulting transcribed RNA (and gene suppression by the transcribed RNA) is preferably localized in the nucleus. In other embodiments, the recombinant DNA construct is designed so that the RNA transcribed from the first gene suppression element, when spliced out of the intron, is transported out of the nucleus for gene suppression in the cytoplasm.

In various embodiments of the invention, the recombinant DNA constructs are optionally characterized by any one or more of the following. The recombinant DNA construct can further include at least one of: (a) at least one T-DNA border region, as described under "T-DNA Borders"; (b) spacer DNA, as described under "Spacer DNA"; (c) a gene expression element for expressing at least one gene of interest, wherein the gene expression element is located adjacent to the intron; (d) a gene expression element for expressing at least one gene of interest, wherein said gene expression element is located adjacent to said first gene suppression element and within said intron; and (e) a second gene suppression element for suppressing at least one second target gene, wherein the second gene suppression element is located outside of (e.g., adjacent to) the intron. These further aspects are described in more detail below.

In some embodiments, the recombinant DNA construct further includes a gene expression element for expressing at least one gene of interest, wherein the gene expression element is located adjacent to the intron. The gene of interest can include a single gene or multiple genes. Gene expression elements are further described under the heading "Gene Expression Elements".

In yet other embodiments, the recombinant DNA construct further includes a second gene suppression element for suppressing at least one second target gene, wherein the second gene suppression element is located outside of, e.g., adjacent to, the intron. The at least one second target gene can include a single gene or part of a single gene that is targeted for suppression, or can include, for example, multiple consecutive segments of a second target gene, multiple non-consecutive segments of a second target gene, multiple alleles of a second target gene, or multiple second target genes from one or more species. Suitable second target genes are described under the heading "Target Genes".

Gene Suppression Elements: The gene suppression element can be transcribable DNA of any suitable length, and will generally include at least about 19 to about 27 nucleotides (for example 19, 20, 21, 22, 23, or 24 nucleotides) for every target gene that the recombinant DNA construct is intended to suppress. In many embodiments the gene suppression element includes more than 23 nucleotides (for example, more than about 30, about 50, about 100, about 200, about 300, about 500, about 1000, about 1500, about 2000, about 3000, about 4000, or about 5000 nucleotides) for every target gene that the recombinant DNA construct is intended to suppress.

Suitable gene suppression elements useful in the recombinant DNA constructs of the invention include at least one element (and, in some embodiments, multiple elements) selected from the group consisting of:

(a) DNA that includes at least one anti-sense DNA segment that is anti-sense to at least one segment of the at least one first target gene;

(b) DNA that includes multiple copies of at least one anti-sense DNA segment that is anti-sense to at least one segment of the at least one first target gene;

(c) DNA that includes at least one sense DNA segment that is at least one segment of the at least one first target gene;

(d) DNA that includes multiple copies of at least one sense DNA segment that is at least one segment of the at least one first target gene;

(e) DNA that transcribes to RNA for suppressing the at least one first target gene by forming double-stranded RNA and includes at least one anti-sense DNA segment that is anti-sense to at least one segment of the at least one target gene and at least one sense DNA segment that is at least one segment of the at least one first target gene;

(f) DNA that transcribes to RNA for suppressing the at least one first target gene by forming a single double-stranded RNA and includes multiple serial anti-sense DNA segments that are anti-sense to at least one segment of the at least one first target gene and multiple serial sense DNA segments that are at least one segment of the at least one first target gene;

(g) DNA that transcribes to RNA for suppressing the at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of inverted repeats;

(h) DNA that includes nucleotides derived from a miRNA, preferably a plant miRNA;

(i) DNA that includes nucleotides of a siRNA;

(j) DNA that transcribes to an RNA aptamer capable of binding to a ligand; and (k) DNA that transcribes to an RNA aptamer capable of binding to a ligand, and DNA that transcribes to regulatory RNA capable of regulating expression of the first target gene, wherein the regulation is dependent on the conformation of the regulatory RNA, and the conformation of the regulatory RNA is allosterically affected by the binding state of the RNA aptamer.

Any of these gene suppression elements, whether transcribing to a single double-stranded RNA or to multiple double-stranded RNAs, can be designed to suppress more than one target gene, including, for example, more than one allele of a target gene, multiple target genes (or multiple segments of at least one target gene) from a single species, or target genes from different species.

Anti-Sense DNA Segments: In one embodiment, the at least one anti-sense DNA segment that is anti-sense to at least one segment of the at least one first target gene includes DNA sequence that is anti-sense or complementary to at least a segment of the at least one first target gene, and can include multiple anti-sense DNA segments, that is, multiple copies of at least one anti-sense DNA segment that is anti-sense to at least one segment of the at least one first target gene. Multiple anti-sense DNA segments can include DNA sequence that is anti-sense or complementary to multiple segments of the at least one first target gene, or to multiple copies of a segment of the at least one first target gene, or to segments of multiple first target genes, or to any combination of these. Multiple anti-sense DNA segments can be fused into a chimera, e.g., including DNA sequences that are anti-sense to multiple segments of one or more first target genes and fused together.

The anti-sense DNA sequence that is anti-sense or complementary to (that is, can form Watson-Crick base-pairs with) at least a segment of the at least one first target gene has preferably at least about 80%, or at least about 85%, or at least about 90%, or at least about 95% complementarity to at least a segment of the at least one first target gene. In one preferred embodiment, the DNA sequence that is anti-sense or complementary to at least a segment of the at least one first target gene has between about 95% to about 100% complementarity to at least a segment of the at least one first target gene. Where the at least one anti-sense DNA segment includes multiple anti-sense DNA segments, the degree of complementarity can be, but need not be, identical for all of the multiple anti-sense DNA segments.

Sense DNA Segments: In another embodiment, the at least one sense DNA segment that is at least one segment of the at least one first target gene includes DNA sequence that corresponds to (that is, has a sequence that is identical or substantially identical to) at least a segment of the at least one first target gene, and can include multiple sense DNA segments, that is, multiple copies of at least one sense DNA segment that corresponds to (that is, has the nucleotide sequence of) at least one segment of the at least one first target gene. Multiple sense DNA segments can include DNA sequence that is or that corresponds to multiple segments of the at least one first target gene, or to multiple copies of a segment of the at least one first target gene, or to segments of multiple first target genes, or to any combination of these. Multiple sense DNA segments can be fused into a chimera, that is, can include DNA sequences corresponding to multiple segments of one or more first target genes and fused together.

The sense DNA sequence that corresponds to at least a segment of the target gene has preferably at least about 80%, or at least about 85%, or at least about 90%, or at least about 95% sequence identity to at least a segment of the target gene. In one preferred embodiment, the DNA sequence that corresponds to at least a segment of the target gene has between about 95% to about 100% sequence identity to at least a segment of the target gene. Where the at least one sense DNA segment includes multiple sense DNA segments, the degree of sequence identity can be, but need not be, identical for all of the multiple sense DNA segments.

Multiple Copies: Where the gene suppression element includes multiple copies of anti-sense or multiple copies of sense DNA sequence, these multiple copies can be arranged serially in tandem repeats. In some embodiments, these multiple copies can be arranged serially end-to-end, that is, in directly connected tandem repeats. In some embodiments, these multiple copies can be arranged serially in interrupted tandem repeats, where one or more spacer DNA segment can be located adjacent to one or more of the multiple copies. Tandem repeats, whether directly connected or interrupted or a combination of both, can include multiple copies of a single anti-sense or multiple copies of a single sense DNA sequence in a serial arrangement or can include multiple copies of more than one anti-sense DNA sequence or of more than one sense DNA sequence in a serial arrangement.

Double-stranded RNA: In those embodiments wherein the gene suppression element includes either at least one anti-sense DNA segment that is anti-sense to at least one segment of the at least one target gene or at least one sense DNA segment that is at least one segment of the at least one target gene, RNA transcribed from either the at least one anti-sense or at least one sense DNA may become double-stranded by the action of an RNA-dependent RNA polymerase. See, for example, U.S. Pat. No. 5,283,184, which is incorporated by reference herein.

In yet other embodiments, the gene suppression element can include DNA that transcribes to RNA for suppressing the at least one first target gene by forming double-stranded RNA and includes at least one anti-sense DNA segment that is anti-sense to at least one segment of the at least one target gene (as described above under the heading "Anti-sense DNA Segments") and at least one sense DNA segment that is at least one segment of the at least one first target gene (as described above under the heading "Sense DNA Segments"). Such a gene suppression element can further include spacer DNA segments. Each at least one anti-sense DNA segment is complementary to at least part of a sense DNA segment in order to permit formation of double-stranded RNA by intramolecular hybridization of the at least one anti-sense DNA segment and the at least one sense DNA segment. Such complementarity between an anti-sense DNA segment and a sense DNA segment can be, but need not be, 100% complementarity; in some embodiments, this complementarity can be preferably at least about 80%, or at least about 85%, or at least about 90%, or at least about 95% complementarity.

Figure 9:
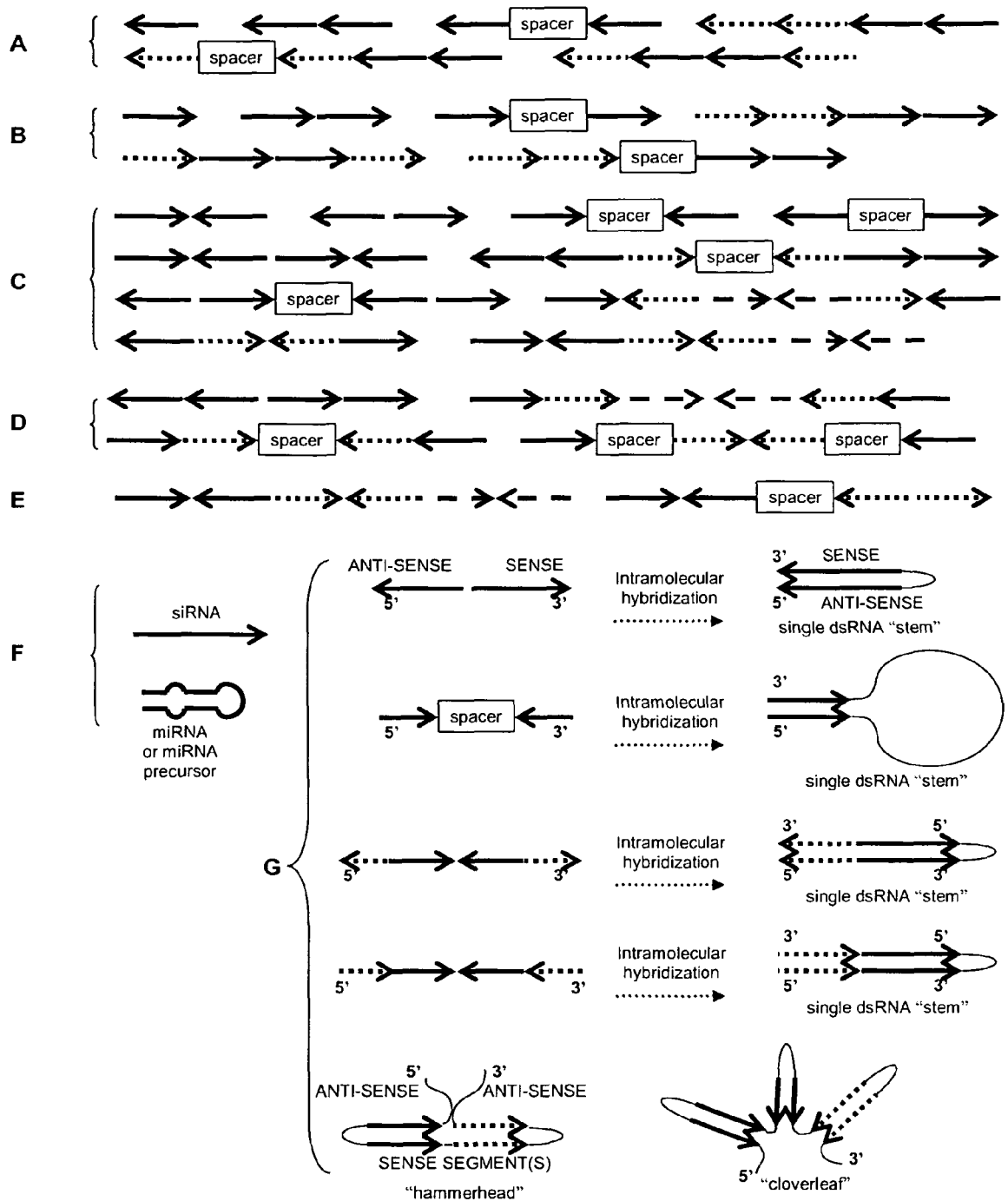
FIG. 9 depicts various non-limiting examples of gene suppression elements and transcribable exogenous DNAs useful in the recombinant DNA constructs of the invention. Where drawn as a single strand (FIGS. 9A through 9E), these are conventionally depicted in 5' to 3' (left to right) transcriptional direction, where the arrows indicate anti-sense sequence (arrowhead pointing to the left), or sense sequence (arrowhead pointing to the right). Where drawn as double-stranded (antiparallel) transcripts (FIGS. 9F and 9G), the 5' and 3' transcriptional directionality is as shown. Solid lines, dashed lines, and dotted lines indicate sequences that target different target genes.

The double-stranded RNA can be in the form of a single dsRNA "stem" (region of base-pairing between sense and anti-sense strands), or can have multiple dsRNA "stems". In one embodiment, the gene suppression element can include DNA that transcribes to RNA for suppressing the at least one first target gene by forming essentially a single double-stranded RNA and includes multiple serial anti-sense DNA segments that are anti-sense to at least one segment of the at least one first target gene and multiple serial sense DNA segments that are at least one segment of the at least one first target gene; the multiple serial anti-sense and multiple serial sense segments can form a single double-stranded RNA "stem" or multiple "stems" in a serial arrangement (with or without non-base paired spacer DNA separating the multiple "stems"). In another embodiment, the gene suppression element includes DNA that transcribes to RNA for suppressing the at least one first target gene by forming multiple dsRNA "stems" of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of dsRNA "stems" (such as, but not limited to "inverted repeats"). Such multiple dsRNA "stems" can further be arranged in series or clusters to form tandem inverted repeats, or structures resembling "hammerhead" or "cloverleaf" shapes. Any of these gene suppression elements can further include spacer DNA segments found within a dsRNA "stem" (for example, as a spacer between multiple anti-sense or sense DNA segments or as a spacer between a base-pairing anti-sense DNA segment and a sense DNA segment) or outside of a double-stranded RNA "stem" (for example, as a loop region separating a pair of inverted repeats). In cases where base-pairing anti-sense and sense DNA segment are of unequal length, the longer segment can act as a spacer. FIGS. 5B and 9 depict illustrations of possible embodiments of these gene suppression constructs.

miRNAs: In a further embodiment, the gene suppression element can include DNA that includes nucleotides derived from a miRNA (microRNA), that is, a DNA sequence that corresponds to a miRNA native to a virus or a eukaryote of interest (including plants and animals, especially invertebrates), or a DNA sequence derived from such a native miRNA but modified to include nucleotide sequences that do not correspond to the native miRNA. While miRNAs have not to date been reported in fungi, fungal miRNAs, should they exist, are also suitable for use in the invention. A particularly preferred embodiment includes a gene suppression element containing DNA that includes nucleotides derived from a viral or plant miRNA.

In a non-limiting example, the nucleotides derived from a miRNA can include DNA that includes nucleotides corresponding to the loop region of a native miRNA and nucleotides that are selected from a target gene sequence. In another non-limiting example, the nucleotides derived from a miRNA can include DNA derived from a miRNA precursor sequence, such as a native pri-miRNA or pre-miRNA sequence, or nucleotides corresponding to the regions of a native miRNA and nucleotides that are selected from a target gene sequence number such that the overall structure (e.g., the placement of mismatches in the stem structure of the pre-miRNA) is preserved to permit the pre-miRNA to be processed into a mature miRNA. In yet another embodiment, the gene suppression element can include DNA that includes nucleotides derived from a miRNA and capable of inducing or guiding in-phase cleavage of an endogenous transcript into trans-acting siRNAs, as described by Allen et al. (2005) *Cell*, 121:207-221, which is incorporated by reference in its entirety herein. Thus, the DNA that includes nucleotides derived from a miRNA can include sequence naturally occurring in a miRNA or a miRNA precursor molecule, synthetic sequence, or both.

siRNAs: In yet another embodiment, the gene suppression element can include DNA that includes nucleotides of a small interfering RNA (siRNA). The siRNA can be one or more native siRNAs (such as siRNAs isolated from a non-transgenic eukaryote or from a transgenic eukaryote), or can be one or more DNA sequences predicted to have siRNA activity (such as by use of predictive tools known in the art, see, for example, Reynolds et al (2004) *Nature Biotechnol.*, 22:326-330, which is incorporated by reference in its entirety herein). Multiple native or predicted siRNA sequences can be joined in a chimeric siRNA sequence for gene suppression. Such a DNA that includes nucleotides of a siRNA preferably includes at least 19 nucleotides, and in some embodiments preferably includes at least 21, at least 22, at least 23, or at least 24 nucleotides. In other embodiments, the DNA that includes nucleotides of a siRNA can contain substantially more than 21 nucleotides, for example, more than about 50, about 100, about 300, about 500, about 1000, about 3000, or about 5000 nucleotides or greater.

Introns: As used herein, "intron" or "intron sequence" generally means non-coding DNA sequence from a natural gene, which retains in the recombinant DNA constructs of this invention its native capability to be excised from pre-mRNA transcripts, e.g., native intron sequences found with associated protein coding RNA regions, wherein the native introns are spliced, allowing exons to be assembled into mature mRNAs before the RNA leaves the nucleus. Such an excisable intron has a 5' splice site and a 3' splice site. Introns can be self-splicing or non-self-splicing (that is, requiring enzymes or a spliceosome for splicing to occur) and can be selected for different splicing efficiency.

Introns suitable for use in constructs of the invention can be viral introns (e.g., Yamada et al. (1994) *Nucleic Acids Res.*, 22:2532-2537), eukaryotic introns (including animal, fungal, and plant introns), archeal or bacterial introns (e.g., Belfort et al. (1995) *J. Bacteriol.*, 177:3897-3903), or any naturally occurring or artificial (e.g., Yoshimatsu and Nagawa (1989) *Science*, 244:1346-1348) DNA sequences with intron-like functionality in the plant in which the recombinant DNA construct of the invention is to be transcribed. While essentially any intron can be used in the practice of this invention as a host for embedded DNA, particularly preferred are introns that are introns that enhance expression in a plant or introns that are derived from a 5' untranslated leader sequence. Where a recombinant DNA construct of the invention is used to transform a plant, plant-sourced introns can be especially preferred. Examples of especially preferred plant introns include a rice actin 1 intron (I-Os-Act1) (Wang et al. (1992) *Mol. Cell. Biol.*, 12:3399-3406; McElroy et al. (1990) *Plant Cell*, 2:163-171), a maize heat shock protein intron (I-Zm-hsp70) (U.S. Pat. Nos. 5,593,874 and 5,859,347), and a maize alcohol dehydrogenase intron (I-Zm-adh1) (Callis et al. (1987) *Genes Dev.*, 1:1183-1200). Other examples of introns suitable for use in the invention include the tobacco mosaic virus 5' leader sequence or "omega" leader (Gallie and Walbot (1992) *Nucleic Acids Res.*, 20:4631-4638), the Shrunken-1 (Sh-1) intron (Vasil et al. (1989) *Plant Physiol.*, 91:1575-1579), the maize sucrose synthase intron (Clancy and Hannah (2002) *Plant Physiol.*, 130:918-929), the heat shock protein 18 (hsp18) intron (Silva et al. (1987) *J. Cell Biol.*, 105:245), and the 82 kilodalton heat shock protein (hsp82) intron (Semrau et al. (1989) *J. Cell Biol.*, 109, p. 39A, and Mettler et al. (May 1990) N.A.T.O. Advanced Studies Institute on Molecular Biology, Elmer, Bavaria).

Promoter Elements: Where the recombinant DNA construct is to be transcribed in an animal cell, the promoter element is functional in an animal. Where the recombinant DNA construct is to be transcribed in an plant cell, the promoter element is functional in a plant. Preferred promoter elements include promoters that have promoter activity in a plant transformed with the recombinant DNA constructs of the invention. Suitable promoters can be constitutive or non-constitutive promoters. In various embodiments, the promoter element can include a promoter selected from the group consisting of a constitutive promoter, a spatially specific promoter, a temporally specific promoter, a developmentally specific promoter, and an inducible promoter.

Non-constitutive promoters suitable for use with the recombinant DNA constructs of the invention include spatially specific promoters, temporally specific promoters, and inducible promoters. Where transcription of the construct is to occur in a plant cell, spatially specific promoters can include organelle-, cell-, tissue-, or organ-specific promoters functional in a plant (e.g., a plastid-specific, a root-specific, a pollen-specific, or a seed-specific promoter for suppressing expression of the first target RNA in plastids, roots, pollen, or seeds, respectively). In many cases a seed-specific, embryo-specific, aleurone-specific, or endosperm-specific promoter is especially useful. Where transcription of the construct is to occur in an animal cell, spatially specific promoters include promoters that have enhanced activity in a particular animal cell or tissue (e.g., enhanced or specific promoter activity in nervous tissue, liver, muscle, eye, blood, marrow, breast, prostate, gonads, or other tissues). Temporally specific promoters can include promoters that tend to promote expression during certain developmental stages in an animal or plant's growth or reproductive cycle, or during different times of day or night, or at different seasons in a year. Inducible promoters include promoters induced by chemicals (e.g., exogenous or synthetic chemicals as well as endogenous pheromones and other signaling molecules) or by environmental conditions such as, but not limited to, biotic or abiotic stress (e.g., water deficit or drought, heat, cold, high or low nutrient or salt levels, high or low light levels, or pest or pathogen infection). An expression-specific promoter can also include promoters that are generally constitutively expressed but at differing degrees or "strengths" of expression, including promoters commonly regarded as "strong promoters" or as "weak promoters".

In one particularly preferred embodiment, the promoter element includes a promoter element functional in a plant transformed with a recombinant DNA construct of the invention. Non-limiting specific examples include an opaline synthase promoter isolated from T-DNA of *Agrobacterium*, and a cauliflower mosaic virus 35S promoter, among others, as well as enhanced promoter elements or chimeric promoter elements, e.g., an enhanced cauliflower mosaic virus (CaMV) 35S promoter linked to an enhancer element (an intron from heat shock protein 70 of *Zea mays*). Many expression-specific promoters functional in plants and useful in the method of the invention are known in the art. For example, U.S. Pat. Nos. 5,837,848; 6,437,217 and 6,426,446 disclose root specific promoters; U.S. Pat. No. 6,433,252 discloses a maize L3 oleosin promoter; U.S. Patent Application Publication 2004/0216189 discloses a promoter for a plant nuclear gene encoding a plastid-localized aldolase; U.S. Pat. No. 6,084,089 discloses cold-inducible promoters; U.S. Pat. No. 6,140,078 discloses salt inducible promoters; U.S. Pat. No. 6,294,714 discloses light-inducible promoters; U.S. Pat. No. 6,252,138 discloses pathogen-inducible promoters; and U.S. Patent Application Publication 2004/0123347 A1 discloses water deficit-inducible promoters. All of the above-described patents and patent publications disclosing promoters and their use, especially in recombinant DNA constructs functional in plants, are incorporated herein by reference.

The promoter element can include nucleic acid sequences that are not naturally occurring promoters or promoter elements or homologues thereof but that can regulate expression of a gene. Examples of such "gene independent" regulatory sequences include naturally occurring or artificially designed RNA sequences that include a ligand-binding region or aptamer and a regulatory region (which can be cis-acting). See, for example, Isaacs et al. (2004) *Nat. Biotechnol.*, 22:841-847, Bayer and Smolke (2005) *Nature Biotechnol.*, 23:337-343, Mandal and Breaker (2004) *Nature Rev. Mol Cell Biol.*, 5:451-463, Davidson and Ellington (2005) *Trends Biotechnol.*, 23:109-112, Winkler et al. (2002) *Nature*, 419:952-956, Sudarsan et al. (2003) *RNA*, 9:644-647, and Mandal and Breaker (2004) *Nature Struct. Mol. Biol.*, 11:29-35, all of which are incorporated by reference herein. Such "riboregulators" could be selected or designed for specific spatial or temporal specificity, for example, to regulate translation of the exogenous gene only in the presence (or absence) of a given concentration of the appropriate ligand.

Terminator Elements: In some embodiments, the recombinant DNA construct includes both a promoter element and a functional terminator element. Where it is functional, the terminator element includes a functional polyadenylation signal and polyadenylation site, allowing RNA transcribed from the recombinant DNA construct to be polyadenylated and processed for transport into the cytoplasm.

In other embodiments, a functional terminator element is absent. In some embodiments where a functional terminator element is absent, at least one of a functional polyadenylation signal and a functional polyadenylation site is absent. In other embodiments, a 3' untranslated region is absent. In these cases, the recombinant DNA construct is transcribed as unpolyadenylated RNA and is preferably not transported into the cytoplasm.

T-DNA Borders: T-DNA borders refer to the DNA sequences or regions of DNA that define the start and end of an *Agrobacterium* T-DNA (tumor DNA) and function in cis for transfer of T-DNA into a plant genome by *Agrobacterium*-mediated transformation (see, e.g., Hooykaas and Schilperoort (1992) *Plant Mol. Biol.*, 19:15-38). In one preferred embodiment of the recombinant DNA construct of the invention, the intron in which is embedded the gene suppression element is located between a pair of T-DNA borders, which can be a set of left and right T-DNA borders, a set of two left T-DNA borders, or a set of two right T-DNA borders. In another embodiment, the recombinant DNA construct includes a single T-DNA border and an intron-embedded gene suppression element.

Spacer DNA: Spacer DNA segments can include virtually any DNA (such as, but not limited to, translatable DNA sequence encoding a gene of interest, translatable DNA sequence encoding a marker or reporter gene; transcribable DNA derived from an intron, which upon transcription can be excised from the resulting transcribed RNA; transcribable DNA sequence encoding RNA that forms a structure such as a loop or stem or an aptamer capable of binding to a specific ligand; spliceable DNA such as introns and self-splicing ribozymes; transcribable DNA encoding a sequence for detection by nucleic acid hybridization, amplification, or sequencing; and a combination of these). Spacer DNA can be found, for example, between parts of a gene suppression element, or between different gene suppression elements. In some embodiments, spacer DNA is itself sense or anti-sense sequence of the target gene. In some preferred embodiments, the RNA transcribed from the spacer DNA (e.g., a large loop of antisense sequence of the target gene or an aptamer) assumes a secondary structure or three-dimensional configuration that confers on the transcript a desired characteristic, such as increased stability, increased half-life in vivo, or cell or tissue specificity.

Target Genes: The recombinant DNA construct can be designed to suppress any first target gene. In some embodiments, the construct further includes a second gene suppression element for suppressing at least one second target gene, wherein the second gene suppression element is located adjacent to the intron. Whether a first or a second target gene, the target gene can include a single gene or part of a single gene that is targeted for suppression, or can include, e.g., multiple consecutive segments of a target gene, multiple non-consecutive segments of a target gene, multiple alleles of a target gene, or multiple target genes from one or more species.

The target gene can be translatable (coding) sequence, or can be non-coding sequence (such as non-coding regulatory sequence), or both, and can include at least one gene selected from the group consisting of a eukaryotic target gene, a non-eukaryotic target gene, a microRNA precursor DNA sequence, and a microRNA promoter. The target gene can be native (endogenous) to the cell (e.g., a cell of a plant or animal) in which the recombinant DNA construct of the invention is transcribed, or can be native to a pest or pathogen of the plant or animal in which the construct is transcribed. The target gene can be an exogenous gene, such as a transgene in a plant.

The target gene can include a single gene or part of a single gene that is targeted for suppression, or can include, for example, multiple consecutive segments of a target gene, multiple non-consecutive segments of a target gene, multiple alleles of a target gene, or multiple target genes from one or more species. A target gene sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans.

Non-limiting examples of a target gene include non-translatable (non-coding) sequence, such as, but not limited to, 5' untranslated regions, promoters, enhancers, or other non-coding transcriptional regions, 3' untranslated regions, terminators, and introns. Target genes can also include genes encoding microRNAs, small interfering RNAs, RNA components of ribosomes or ribozymes, small nucleolar RNAs, and other non-coding RNAs (see, for example, non-coding RNA sequences provided publicly at rfam.wustl.edu; Erdmann et al. (2001) *Nucleic Acids Res.*, 29:189-193; Gottesman (2005) *Trends Genet.*, 21:399-404; Griffiths-Jones et al. (2005) *Nucleic Acids Res.*, 33:121-124, which are incorporated by reference herein). One specific example of a target gene includes a microRNA precursor DNA sequence, that is, the primary DNA transcript encoding a microRNA, or the RNA intermediates processed from this primary transcript (e.g., a nuclear-limited pri-miRNA or a pre-miRNA which can be exported from the nucleus into the cytoplasm), or a microRNA promoter. See, for example, Lee et al. (2002) *EMBO Journal*, 21:4663-4670; Reinhart et al. (2002) *Genes & Dev.*, 16:161611626; Lund et al. (2004) *Science*, 303:95-98; and Millar and Waterhouse (2005) *Funct. Integr Genomics*, 5:129-135, which are incorporated by reference herein. In one non-limiting embodiment, the target gene includes nucleotides of a loop region of at least one target microRNA precursor. In plants, microRNA precursor molecules (e.g., primary miRNA transcripts) are believed to be largely processed in the nucleus, and thus recombinant DNA constructs of the invention that are transcribed to non-polyadenylated suppression transcripts are expected to suppress these and other nuclear-localized target genes in plants more effectively than conventional gene suppression constructs that result in, e.g., double-stranded RNA molecules localized in the cytoplasm. Target microRNA precursor DNA sequences can be native to the transgenic plant in which the recombinant DNA construct of the invention is transcribed, or can be native to a pest or pathogen of the transgenic plant. Target genes can also include translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). A target gene can be a native gene targeted for suppression, with or without concurrent expression of an exogenous transgene, for example, by including a gene expression element in the same or in a separate recombinant DNA construct. For example, it can be desirable to replace a native gene with an exogenous transgene homologue.

It can be useful to provide transgenic plants having in their genome a DNA construct for suppressing a gene which is exogenous to the host plant but endogenous to a plant pest or pathogen (e.g., viruses, bacteria, fungi, and invertebrates such as insects, nematodes, and molluscs). Thus, one aspect of the invention provides recombinant DNA constructs wherein the target gene is selected to provide resistance to a plant pest or pathogen, for example, resistance to a nematode such as soybean cyst nematode or root knot nematode or to a pest insect. Thus, target genes of interest can also include endogenous genes of plant pests and pathogens. Pest invertebrates include, but are not limited to, pest nematodes (e.g., cyst nematodes *Heterodera* spp. especially soybean cyst nematode *Heterodera glycines*, root knot nematodes *Meloidogyne* spp., lance nematodes *Hoplolaimus* spp., stunt nematodes *Tylenchorhynchus* spp., spiral nematodes *Helicotylenchus* spp., lesion nematodes *Pratylenchus* spp., ring nematodes *Criconema* spp., and foliar nematodes *Aphelenchus* spp. or *Aphelenchoides* spp.), pest molluscs (slugs and snails), and pest insects (e.g., corn rootworms, *Lygus* spp., aphids, corn borers, cutworms, armyworms, leafhoppers, Japanese beetles, grasshoppers, and other pest coelepterans, dipterans, and lepidopterans). Plant pathogens of interest include fungi (e.g., the fungi that cause powdery mildew, rust, leaf spot and blight, damping-off, root rot, crown rot, cotton boll rot, stem canker, twig canker, vascular wilt, smut, or mold, including, but not limited to, *Fusarium* spp., *Phakospora* spp., *Rhizoctonia* spp., *Aspergillus* spp., *Gibberella* spp., *Pyricularia* spp., *Alternaria* spp., and *Phytophthora* spp.), bacteria (e.g., the bacteria that cause leaf spotting, fireblight, crown gall, and bacterial wilt), mollicutes (e.g., the mycoplasmas that cause yellows disease and spiroplasmas such as *Spiroplasma kunkelii*, which causes corn stunt), and viruses (e.g., the viruses that cause mosaics, vein banding, flecking, spotting, or abnormal growth). See also G. N. Agrios, "Plant Pathology" (Fourth Edition), Academic Press, San Diego, 1997, 635 pp., which is incorporated by reference herein, for descriptions of fungi, bacteria, mollicutes (including mycoplasmas and spiroplasmas), viruses, nematodes, parasitic higher plants, and flagellate protozoans, all of which are plant pests or pathogens of interest. See also the continually updated compilation of plant pests and pathogens and the diseases caused by such on the American Phytopathological Society's "Common Names of Plant Diseases", compiled by the Committee on Standardization of Common Names for Plant Diseases of The American Phytopathological Society, 1978-2005, available online at www.apsnet.org/online/common/top.asp, which is incorporated by reference herein.

Non-limiting examples of fungal plant pathogens of particular interest include *Phakospora pachirhizi* (Asian soy rust), *Puccinia sorghi* (corn common rust), *Puccinia polysora* (corn Southern rust), *Fusarium oxysporum* and other *Fusarium* spp., *Alternaria* spp., *Penicillium* spp., *Pythium aphanidermatum* and other *Pythium* spp., *Rhizoctonia solani*, *Exserohilum turcicum* (Northern corn leaf blight), *Bipolaris maydis* (Southern corn leaf blight), *Ustilago maydis* (corn smut), *Fusarium graminearum* (*Gibberella zeae*), *Fusarium verticilliodes* (*Gibberella moniliformis*), *F. proliferatum* (*G. fujikuroi* var. *intermedia*), *F. subglutinans* (*G. subglutinans*), *Diplodia maydis*, *Sporisorium holci-sorghi*, *Colletotrichum*

*graminicola, Setosphaeria turcica, Aureobasidium zeae, Phytophthora infestans, Phytophthora sojae, Sclerotinia sclerotiorum*, and the numerous fungal species provided in Tables 4 and 5 of U.S. Pat. No. 6,194,636, which is incorporated in its entirety by reference herein.

Non-limiting examples of bacterial pathogens include *Pseudomonas avenae, Pseudomonas andropogonis, Erwinia stewartii, Pseudomonas syringae* pv. *syringae*, and the numerous bacterial species listed in Table 3 of U.S. Pat. No. 6,194,636, which is incorporated in its entirety by reference herein.

Non-limiting examples of viral plant pathogens of particular interest include maize dwarf mosaic virus (MDMV), sugarcane mosaic virus (SCMV, formerly MDMV strain B), wheat streak mosaic virus (WSMV), maize chlorotic dwarf virus (MCDV), barley yellow dwarf virus (BYDV), banana bunchy top virus (BBTV), and the numerous viruses listed in Table 2 of U.S. Pat. No. 6,194,636, which is incorporated in its entirety by reference herein.

Non-limiting examples of invertebrate pests include pests capable of infesting the root systems of crop plants, e.g., northern corn rootworm (*Diabrotica barberi*), southern corn rootworm (*Diabrotica undecimpunctata*), Western corn rootworm (*Diabrotica virgifera*), corn root aphid (*Anuraphis maidiradicis*), black cutworm (*Agrotis ipsilon*), glassy cutworm (*Crymodes devastator*), dingy cutworm (*Feltia ducens*), claybacked cutworm (*Agrotis gladiaria*), wireworm (*Melanotus* spp., *Aeolus mellillus*), wheat wireworm (*Aeolus mancus*), sand wireworm (*Horistonotus uhlerii*), maize bilibug (*Sphenophorus maidis*), timothy bilibug (*Sphenophorus zeae*), bluegrass billbug (*Sphenophorus parvulus*), southern corn billbug (*Sphenophorus callosus*), white grubs (*Phyllophaga* spp.), seedcorn maggot (*Delia platura*), grape colaspis (*Colaspis brunnea*), seedcorn beetle (*Stenolophus lecontei*), and slender seedcorn beetle (*Clivinia impressifrons*), as well as the parasitic nematodes listed in Table 6 of U.S. Pat. No. 6,194,636, which is incorporated in its entirety by reference herein.

Target genes from pests can include invertebrate genes for major sperm protein, alpha tubulin, beta tubulin, vacuolar ATPase, glyceraldehyde-3-phosphate dehydrogenase, RNA polymerase II, chitin synthase, cytochromes, miRNAs, miRNA precursor molecules, miRNA promoters, as well as other genes such as those disclosed in Table II of United States Patent Application Publication 2004/0098761 A1, which is incorporated by reference herein. Target genes from pathogens can include genes for viral translation initiation factors, viral replicases, miRNAs, miRNA precursor molecules, fungal tubulin, fungal vacuolar ATPase, fungal chitin synthase, enzymes involved in fungal cell wall biosynthesis, cutinases, melanin biosynthetic enzymes, polygalacturonases, pectinases, pectin lyases, cellulases, proteases, and other genes involved in invasion and replication of the pathogen in the infected plant. Thus, a target gene need not be endogenous to the plant in which the recombinant DNA construct is transcribed. A recombinant DNA construct of the invention can be transcribed in a plant and used to suppress a gene of a pathogen or pest that may infest the plant.

Specific, non-limiting examples of suitable target genes also include amino acid catabolic genes (such as, but not limited to, the maize LKR/SDH gene encoding lysine-ketoglutarate reductase (LKR) and saccharopine dehydrogenase (SDH), and its homologues), maize zein genes, genes involved in fatty acid synthesis (e.g., plant microsomal fatty acid desaturases and plant acyl-ACP thioesterases, such as, but not limited to, those disclosed in U.S. Pat. Nos. 6,426,448, 6,372,965, and 6,872,872), genes involved in multi-step biosynthesis pathways, where it may be of interest to regulate the level of one or more intermediates, such as genes encoding enzymes for polyhydroxyalkanoate biosynthesis (see, for example, U.S. Pat. No. 5,750,848); and genes encoding cell-cycle control proteins, such as proteins with cyclin-dependent kinase (CDK) inhibitor-like activity (see, for example, genes disclosed in International Patent Application Publication Number WO 05007829A2). Target genes can include genes encoding undesirable proteins (e.g., allergens or toxins) or the enzymes for the biosynthesis of undesirable compounds (e.g., undesirable flavor or odor components). Thus, one embodiment of the invention is a transgenic plant or tissue of such a plant that is improved by the suppression of allergenic proteins or toxins, e.g., a peanut, soybean, or wheat kernel with decreased allergenicity. Target genes can include genes involved in fruit ripening, such as polygalacturonase. Target genes can include genes where expression is preferably limited to a particular cell or tissue or developmental stage, or where expression is preferably transient, that is to say, where constitutive or general suppression, or suppression that spreads through many tissues, is not necessarily desired. Thus, other examples of suitable target genes include genes encoding proteins that, when expressed in transgenic plants, make the transgenic plants resistant to pests or pathogens (see, for example, genes for cholesterol oxidase as disclosed in U.S. Pat. No. 5,763,245); genes where expression is pest- or pathogen-induced; and genes which can induce or restore fertility (see, for example, the barstar/barnase genes described in U.S. Pat. No. 6,759,575); all the publications and patents cited in this paragraph are incorporated by reference in their entirety herein.

The recombinant DNA constructs of the invention can be designed to be more specifically suppress the target gene, by designing the gene suppression element or elements to include regions substantially non-identical to a non-target gene sequence. Non-target genes can include any gene not intended to be silenced or suppressed, either in a plant transcribing the recombinant DNA construct or in organisms that may come into contact with RNA transcribed from the recombinant DNA construct. A non-target gene sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans).

In one embodiment, the target gene is a gene endogenous to a given species, such as a given plant (such as, but not limited to, agriculturally or commercially important plants, including monocots and dicots), and the non-target gene can be, e.g., a gene of a non-target species, such as another plant species or a gene of a virus, fungus, bacterium, invertebrate, or vertebrate, even a human. One non-limiting example is where the gene suppression element is designed to suppress a target gene that is a gene endogenous to a single species (e.g., Western corn rootworm, *Diabrotica virgifera virgifera* LeConte) but to not suppress a non-target gene such as genes from related, even closely related, species (e.g., Northern corn rootworm, *Diabrotica barberi* Smith and Lawrence, or Southern corn rootworm, *Diabrotica undecimpunctata*).

In other embodiments (e.g., where it is desirable to suppress a target gene across multiple species), it may be desirable to design the gene suppression element to suppress a target gene sequence common to the multiple species in which the target gene is to be silenced. Thus, a gene suppression element can be selected to be specific for one taxon (for example, specific to a genus, family, or even a larger taxon such as a phylum, e.g., arthropoda) but not for other taxa (e.g., plants or vertebrates or mammals). In one non-limiting example of this embodiment, a gene suppression element for gene silencing can be selected so as to target pathogenic fungi (e.g., a *Fusarium* spp.) but not target any gene sequence from beneficial fungi.

In another non-limiting example of this embodiment, a gene suppression element for gene silencing in corn rootworm can be selected to be specific to all members of the genus *Diabrotica*. In a further example of this embodiment, such a *Diabrotica*-targeted gene suppression element can be selected so as to not target any gene sequence from beneficial coleopterans (for example, predatory coccinellid beetles, commonly known as ladybugs or ladybirds) or other beneficial insect species.

The required degree of specificity of a gene suppression element for suppression of a target gene depends on various factors. For example, where the gene suppression element contains DNA that transcribes to RNA for suppressing a target gene by forming double-stranded RNA (dsRNA), factors can include the size of the smaller dsRNA fragments that are expected to be produced by the action of Dicer, and the relative importance of decreasing the dsRNA's potential to suppress non-target genes. For example, where the dsRNA fragments are expected to be 21 base pairs in size, one particularly preferred embodiment can be to include in the gene suppression element DNA that transcribes to dsRNA and that encodes regions substantially non-identical to a non-target gene sequence, such as regions within which every contiguous fragment including at least 21 nucleotides matches fewer than 21 (e.g., fewer than 21, or fewer than 20, or fewer than 19, or fewer than 18, or fewer than 17) out of 21 contiguous nucleotides of a non-target gene sequence. In another embodiment, regions substantially non-identical to a non-target gene sequence include regions within which every contiguous fragment including at least 19 nucleotides matches fewer than 19 (e.g., fewer than 19, or fewer than 18, or fewer than 17, or fewer than 16) out of 19 contiguous nucleotides of a non-target gene sequence.

In some embodiments, it may be desirable to design the gene suppression element to include regions predicted to not generate undesirable polypeptides, for example, by screening the gene suppression element for sequences that may encode known undesirable polypeptides or close homologues of these. Undesirable polypeptides include, but are not limited to, polypeptides homologous to known allergenic polypeptides and polypeptides homologous to known polypeptide toxins. Publicly available sequences encoding such undesirable potentially allergenic peptides are available, for example, the Food Allergy Research and Resource Program (FARRP) allergen database (available at allergenonline.com) or the Biotechnology Information for Food Safety Databases (available at www.iit.edu/~sgendel/fa.htm) (see also, for example, Gendel (1998) *Adv. Food Nutr. Res.*, 42:63-92, which is incorporated by reference herein). Undesirable sequences can also include, for example, those polypeptide sequences annotated as known toxins or as potential or known allergens and contained in publicly available databases such as GenBank, EMBL, SwissProt, and others, which are searchable by the Entrez system (www.ncbi.nih.gov/Entrez). Non-limiting examples of undesirable, potentially allergenic peptide sequences include glycinin from soybean, oleosin and agglutinin from peanut, glutenins from wheat, casein, lactalbumin, and lactoglobulin from bovine milk, and tropomyosin from various shellfish (allergenonline.com). Non-limiting examples of undesirable, potentially toxic peptides include tetanus toxin tetA from *Clostridium tetani*, diarrheal toxins from *Staphylococcus aureus*, and venoms such as conotoxins from *Conus* spp. and neurotoxins from arthropods and reptiles (www.ncbi.nih.gov/Entrez).

In one non-limiting example, a gene suppression element is screened to eliminate those transcribable sequences encoding polypeptides with perfect homology to a known allergen or toxin over 8 contiguous amino acids, or with at least 35% identity over at least 80 amino acids; such screens can be performed on any and all possible reading frames in both directions, on potential open reading frames that begin with ATG, or on all possible reading frames, regardless of whether they start with an ATG or not. When a "hit" or match is made, that is, when a sequence that encodes a potential polypeptide with perfect homology to a known allergen or toxin over 8 contiguous amino acids (or at least about 35% identity over at least about 80 amino acids), is identified, the DNA sequences corresponding to the hit can be avoided, eliminated, or modified when selecting sequences to be used in a gene suppression element.

Avoiding, elimination of, or modification of, an undesired sequence can be achieved by any of a number of methods known to those skilled in the art. In some cases, the result can be novel sequences that are believed to not exist naturally. For example, avoiding certain sequences can be accomplished by joining together "clean" sequences into novel chimeric sequences to be used in a gene suppression element.

Where the gene suppression element contains DNA that transcribes to RNA for suppressing a target gene by forming double-stranded RNA (dsRNA), applicants recognize that in some dsRNA-mediated gene silencing, it is possible for imperfectly matching dsRNA sequences to be effective at gene silencing. For example, it has been shown that mismatches near the center of a miRNA complementary site has stronger effects on the miRNA's gene silencing than do more distally located mismatches. See, for example, FIG. 4 in Mallory et al. (2004) *EMBO J.*, 23:3356-3364, which is incorporated by reference herein. In another example, it has been reported that, both the position of a mismatched base pair and the identity of the nucleotides forming the mismatch influence the ability of a given siRNA to silence a target gene, and that adenine-cytosine mismatches, in addition to the G:U wobble base pair, were well tolerated (see Du et al. (2005) *Nucleic Acids Res.*, 33:1671-1677, which is incorporated by reference herein). Thus, the DNA that transcribes to RNA for suppressing a target gene by forming double-stranded RNA need not always have 100% sequence identity with the intended target gene, but generally would preferably have substantial sequence identity with the intended target gene, such as about 95%, about 90%, about 85%, or about 80% sequence identity with the intended target gene. One skilled in the art would be capable of judging the importance given to screening for regions predicted to be more highly specific to the first target gene or predicted to not generate undesirable polypeptides, relative to the importance given to other criteria, such as, but not limited to, the percent sequence identity with the intended first target gene or the predicted gene silencing efficiency of a given sequence. For example, it may be desirable for a given DNA sequence for dsRNA-mediated gene silencing to be active across several species, and therefore one skilled in the art can determine that it is more important to include in the gene suppression element regions specific to the several species of interest, but less important to screen for regions predicted to have higher gene silencing efficiency or for regions predicted to generate undesirable polypeptides.

Gene Expression Element: The recombinant DNA constructs of the invention can further include a gene expression element. Any gene or genes of interest can be expressed by the gene expression element, including coding or non-coding sequence or both, and can include naturally occurring sequences or artificial or chimeric sequences or both. Where the gene expression element encodes a protein, such constructs preferably include a functional terminator element to permit transcription and translation of the gene expression element.

In some embodiments, the recombinant DNA construct further includes a gene expression element for expressing at least one gene of interest, wherein the gene expression element is located adjacent to the intron. In other embodiments, the recombinant DNA construct further includes a gene expression element for expressing at least one gene of interest, wherein the gene expression element is located adjacent to the first gene suppression element and within the intron; in such cases, the gene expression element can be operably linked to a functional terminator element that is itself also within the intron. The gene of interest to be expressed by the gene expression element can include at least one gene selected from the group consisting of a eukaryotic target gene, a non-eukaryotic target gene, and a microRNA precursor DNA sequence. The gene of interest can include a single gene or multiple genes (such as multiple copies of a single gene, multiple alleles of a single gene, or multiple genes including genes from multiple species). In one embodiment, the gene expression element can include self-hydrolyzing peptide sequences, e.g., located between multiple sequences coding for one or more polypeptides (see, for example, the 2A and "2A-like" self-cleaving sequences from various species, including viruses, trypanosomes, and bacteria, disclosed by Donnelly et al. (2001), *J. Gen. Virol.*, 82:1027-1041, which is incorporated herein by reference). In another embodiment, the gene expression element can include ribosomal "skip" sequences, e.g., located between multiple sequences coding for one or more polypeptides (see, for example, the aphthovirus foot-and-mouth disease virus (FMDV) 2A ribosomal "skip" sequences disclosed by Donnelly et al. (2001), *J. Gen. Virol.*, 82:1013-1025, which is incorporated herein by reference).

A gene of interest can include any coding or non-coding sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, and mammals. Non-limiting examples of a non-coding sequence to be expressed by a gene expression element include, but not limited to, 5' untranslated regions, promoters, enhancers, or other non-coding transcriptional regions, 3' untranslated regions, terminators, intron, microRNAs, microRNA precursor DNA sequences, small interfering RNAs, RNA components of ribosomes or ribozymes, small nucleolar RNAs, and other non-coding RNAs. Non-limiting examples of a gene of interest further include, but are not limited to, translatable (coding) sequence, such as genes encoding transcription factors and genes encoding enzymes involved in the biosynthesis or catabolism of molecules of interest (such as amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). A gene of interest can be a gene native to the plant in which the recombinant DNA construct of the invention is to be transcribed, or can be a non-native gene. A gene of interest can be a marker gene, for example, a selectable marker gene encoding antibiotic, antifungal, or herbicide resistance, or a marker gene encoding an easily detectable trait (e.g., phytoene synthase or other genes imparting a particular pigment to the plant), or a gene encoding a detectable molecule, such as a fluorescent protein, luciferase, or a unique polypeptide or nucleic acid "tag" detectable by protein or nucleic acid detection methods, respectively). Selectable markers are genes of interest of particular utility in identifying successful processing of constructs of the invention.

In some embodiments of the invention, the recombinant DNA constructs are designed to suppress at least one endogenous gene and to simultaneously express at least one exogenous gene. In one non-limiting example, the recombinant DNA construct includes a gene suppression element for suppressing a endogenous (maize) lysine ketoglutarate reductase/saccharopine dehydrogenase (LKR/SDH) gene and a gene expression element for expressing an exogenous (bacterial) dihydrodipicolinic acid synthase protein, where the construct is transcribed in a maize (*Zea mays*) plant; such a construct would be especially useful for providing maize with enhanced levels of lysine. In another non-limiting example, the recombinant DNA construct includes a gene suppression element for suppressing at least one endogenous (maize) zein gene and a gene expression element for expressing an exogenous or modified zein protein, where the construct is transcribed in a maize (*Zea mays*) plant; such a construct would be especially useful for providing maize with modified zein content, e.g., zeins with modified amino acid composition.

Second Gene Suppression Element: In some embodiments, the recombinant DNA construct further includes a second gene suppression element for suppressing at least one second target gene, wherein the second gene suppression element is located adjacent to the intron. The second gene suppression element can include any element as described above under "Gene Suppression Elements". In these embodiments, where the construct includes a functional terminator element, the construct can be designed so that the first gene suppression element, which is embedded in the intron, preferably causes nuclear suppression of the first target gene, whereas the second gene suppression element preferably causes extra-nuclear or cytoplasmic suppression of the second target gene. The second target gene can be any gene or genes as described above under the heading "Target Genes", and can include coding or non-coding sequence or both. The second target gene or genes can be endogenous or exogenous to the plant in which the recombinant DNA construct is transcribed, and can include multiple target genes.

Methods of Gene Suppression and Methods for Screening for Traits: The present invention provides a method of effecting gene suppression, including (a) providing a transgenic plant comprising a regenerated plant prepared from a transgenic plant cell containing a recombinant DNA construct for plant transformation including a promoter operably linked to a first gene suppression element for suppressing at least one first target gene, wherein said first gene suppression element is embedded in an intron flanked on one or on both sides by non-protein-coding DNA, or a progeny plant of said regenerated plant; and (b) transcribing said recombinant DNA construct in said transgenic plant; wherein said transcribing produces RNA that is capable of suppressing said at least one first target gene in said transgenic plant, whereby said at least one first target gene is suppressed relative to its expression in the absence of transcription of said recombinant DNA construct.

In some embodiments, the at least one first target gene is at least one gene selected from the group consisting of a gene native to said transgenic plant, a transgene in said transgenic plant, a gene native to a viral, a bacterial, a fungal, or an invertebrate pest or pathogen of said transgenic seed or of said transgenic plant, a microRNA precursor sequence, and a microRNA promoter. The at least one first target gene can be multiple target genes. In other embodiments, the gene suppression is nuclear suppression of a microRNA precursor sequence or a microRNA promoter. Gene suppression by the method of the invention can be spatially specific, temporally specific, developmentally specific, or inducible gene suppression. In another embodiment of the method, the recombinant DNA construct further includes a gene expression element for expressing at least one gene of interest, wherein the gene expression element is located outside of (e.g., adjacent to) the intron, and wherein the gene suppression is effected with concurrent expression of the at least one gene of interest in the transgenic plant.

In one preferred embodiment of the method, the resulting gene suppression is non-systemic suppression of a gene native to the transgenic plant or a transgene in the transgenic plant, for example, to provide non-systemic, tissue-specific suppression of at least one target gene in the transgenic plant, which can be useful, for example, for limiting gene suppression to specific tissue, such as in seeds or roots in plants, wherein the target gene can be native to the transgenic plant in which the construct is transcribed or native to a pest or pathogen of said plant. In such embodiments, it is preferred that the transcribable heterologous DNA is transcribed to RNA that remains in the nucleus, for example, to a messenger RNA (mRNA) that lacks processing signals such as polyadenylation for transport of the mRNA to the cytoplasm. In one particular example of this embodiment, the gene suppression is non-systemic, nuclear suppression of a microRNA precursor DNA sequence or of a microRNA promoter. The method can employ the recombinant DNA constructs of this invention to modify the lipid, protein, carbohydrate, or amino acid composition or content of plant seeds by non-systemically suppressing enzymes in biosynthetic pathways for such components. In a non-limiting specific example, transgenic maize having recombinant DNA for suppressing lysine ketoglutarate reductase (LKR/SDH) can be produced using a recombinant DNA construct of this invention consisting of an endosperm-specific or a seed-specific promoter operably linked to, an intron containing, for example, tandem copies of anti-sense oriented DNA from the maize endogenous gene encoding LKR/SDH. Suppression of LKR/SDH is non-systemic (depending on the promoter, limited to the endosperm or to the seed), and seed from such a transgenic maize plant with the recombinant DNA construct will have increased lysine as compared to seed of substantially equivalent genotype but without the recombinant DNA.

The present invention further provides a method of concurrently effecting gene suppression of at least one target gene and gene expression of at least one gene of interest, including growing a transgenic plant from a transgenic seed having in its genome a recombinant DNA construct for suppressing at least one first target gene, including DNA capable of initiating transcription in a plant and operably linked to a first transcribable heterologous DNA, wherein the first transcribable heterologous DNA is embedded in an intron, and wherein the recombinant DNA construct further includes a gene expression element for expressing the at least one gene of interest, the gene expression element being located adjacent to the intron, and wherein, when the recombinant DNA construct is transcribed in the transgenic plant, transcribed RNA that is capable of suppressing the at least one first target gene and transcribed RNA encoding the at least one gene of interest are produced, whereby the at least one first target gene is suppressed relative to its expression in the absence of transcription of the recombinant DNA construct and the at least one gene of interest is expressed. The transcribed RNA that is capable of suppressing the at least one first target gene is transcribed from the intron-embedded first transcribable heterologous DNA. The transcribed RNA encoding the at least one gene of interest is transcribed from the gene expression element. Where the transcribed RNA encoding the at least one gene of interest includes coding region for a protein to be expressed, it is preferably transcribed as RNA capable of transport into the cytoplasm for translation. The intron-embedded first transcribable heterologous DNA can be designed to suppress a single or multiple target genes. The gene expression element can be designed to express a single or multiple target genes. Optionally, the recombinant DNA construct can include a second transcribable heterologous DNA for suppression at least one second target gene, wherein the second transcribable heterologous DNA is transcribed into RNA capable of transport into the cytoplasm; in such embodiments of the method, the at least one first target gene is preferably suppressed by nuclear suppression, and the at least one second target gene is preferably suppressed by cytoplasmic suppression.

In one embodiment of the method, transgenic plants are produced that have a modified nutritional content, or that produce seed having a modified nutritional content. In particularly preferred embodiment, the method is useful for providing transgenic maize producing seed with enhanced levels of lysine, tryptophan, methionine, oil, or a combination of any of these. In one non-limiting example, the method makes use of a recombinant DNA construct that includes (a) a gene suppression element (embedded in an intron flanked on one or both sides by non-protein-coding DNA) for suppressing a endogenous (maize) lysine ketoglutarate reductase/saccharopine dehydrogenase (LKR/SDH) gene, and, optionally, (b) a gene expression element for expressing an exogenous (e.g., a bacterial) dihydrodipicolinic acid synthase protein, where the construct is transcribed in a maize (Zea mays) plant. This method preferably provides transgenic maize producing seed with enhanced levels of lysine (free or protein-bound or both). In another non-limiting example of the method, the recombinant DNA construct includes a gene suppression element (embedded in an intron flanked on one or both sides by non-protein-coding DNA) for suppressing at least one endogenous (maize) zein synthesis gene (e.g., an alpha-zein, such as a 19-kiloDalton alpha-zein or a 22-kiloDalton alpha-zein, or a gene encoding any one or more of the alpha-, beta-, gamma-, and delta-zeins) and optionally for suppressing an endogenous (maize) lysine catabolic enzyme gene (lysine ketoglutarate reductase/saccharopine dehydrogenase or LKR/SDH), and a gene expression element for expressing an exogenous lysine synthesis gene sequence encoding enzymes for synthesis of lysine or its precursors (e.g., aspartate kinase (AK) and dihydrodipicolinic acid synthase (DHDPS), and homologues of these genes). This method preferably provides transgenic maize producing seed with enhanced levels of lysine (free or protein-bound or both), and more preferably provides transgenic maize producing seed with enhanced levels of two or more of lysine, tryptophan, and oil. Also preferred are methods using similar recombinant DNA constructs to transform maize, where, for example, the gene expression element is used to express other biosynthetic genes of interest, such as asparagine synthase or a modified zein or other storage protein, wherein the resulting transgenic maize produces seed containing modified free amino acid or protein content, preferably with enhanced levels of lysine, tryptophan, methionine, oil, or a combination of these.

The present invention further provides a method of concurrently effecting gene suppression of at least one target gene and gene expression of at least one gene of interest, including: (a) providing a transgenic plant comprising a regenerated plant prepared from a transgenic plant cell containing a recombinant DNA construct for plant transformation including a promoter operably linked to a first gene suppression element for suppressing at least one first target gene, wherein the first gene suppression element is embedded in an intron flanked on one or on both sides by non-protein-coding DNA, or a progeny plant of the regenerated plant, wherein the recombinant DNA construct further includes a gene expression element for expressing the at least one gene of interest and the gene expression element is located adjacent to the intron; and (b) transcribing the recombinant DNA construct in the transgenic plant, wherein, when the recombinant DNA construct is transcribed in the transgenic plant, transcribed RNA that is capable of suppressing the at least one first target gene and transcribed RNA encoding the at least one gene of interest are produced, whereby the at least one first target gene is suppressed relative to its expression in the absence of transcription of the recombinant DNA construct and the at least one gene of interest is concurrently expressed.

The present invention also provides a method of screening for traits in a transgenic plant resulting from suppression of an endogenous gene, wherein the method includes: (a) providing a transgenic plant includes a regenerated plant prepared from a transgenic plant cell containing a recombinant DNA construct for plant transformation including a promoter operably linked to a first gene suppression element for suppressing at least one first target gene, wherein the first gene suppression element is embedded in an intron flanked on one or on both sides by non-protein-coding DNA, or a progeny plant of the regenerated plant; (b) transcribing the recombinant DNA construct in said transgenic plant; and (c) analyzing the transgenic plant for the traits. The method can optionally further include screening for transcription of the gene suppression element. In some embodiments of the method wherein the recombinant DNA construct further includes at least one gene expression element, the screening can optionally further include detection of expression of a gene encoded by the gene expression element.

The methods of the invention make use of procedures to introduce the recombinant DNA constructs into a transgenic plant cell, and the production of transgenic plants or progeny plants from such cells. Such procedures are described under the heading "Making and Using Transgenic Plant Cells and Plants". Detecting or measuring the gene suppression (or concurrent gene expression) obtained by transcription of the construct can be achieved by any suitable methods, including protein detection methods (e.g., western blots, ELISAs, and other immunochemical methods), measurements of enzymatic activity, or nucleic acid detection methods (e.g., Southern blots, northern blots, PCR, RT-PCR, fluorescent in situ hybridization). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, NY, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Peña (editor) "Transgenic Plants: Methods and Protocols", Humana Press, 2004, which are incorporated by reference herein.

Other suitable methods for detecting or measuring gene suppression (or concurrent gene expression) include measurement of any other trait that is a direct or proxy indication of gene suppression (or concurrent gene expression) in the plant in which the construct is transcribed, relative to one in which the construct is not transcribed, e.g., gross or microscopic morphological traits, growth rates, yield, reproductive or recruitment rates, resistance to pests or pathogens, or resistance to biotic or abiotic stress (e.g., water deficit stress, salt stress, nutrient stress, heat or cold stress). Such methods can use direct measurements of a phenotypic trait or proxy assays (e.g., plant part assays such as leaf or root assays to determine tolerance of abiotic stress).

III. Recombinant DNA Constructs for Suppressing Production of Mature miRNA and Methods of Use Thereof Another aspect of the invention provides a recombinant DNA construct for suppressing production of mature microRNA in a cell, including a promoter element operably linked to a gene suppression element for suppression of at least one target sequence selected from the at least one target microRNA precursor or a promoter of the at least one target microRNA precursor or both. In one non-limiting embodiment, the target sequence includes nucleotides of a loop region of at least one target microRNA precursor (that is, at least some nucleotides in any single-stranded region forming a loop-like or gap-like domain in a stem-loop RNA structure of a pri-miRNA or a pre-miRNA). Target microRNA precursor DNA sequences can be native (endogenous) to the cell (e.g., a cell of a plant or animal) in which the recombinant DNA construct of the invention is transcribed, or can be native to a pest or pathogen of the plant or animal in which the recombinant DNA construct of the invention is transcribed.

Using constructs of the invention, suppression of production of mature miRNA can occur in the nucleus or in the cytoplasm or in both. In many preferred embodiments, particularly (but not limited to) embodiments where the suppression occurs in a plant cell, suppression preferably occurs wholly or substantially in the nucleus, and the gene suppression element is preferably transcribed to RNA lacking functional nuclear export signals. In these embodiments, the RNA transcribed from such a gene suppression element preferably remains in the nucleus and results in enhanced nuclear suppression of production of mature miRNA; such a gene suppression element is preferably characterized by at least one of the following: (a) at least one of a functional polyadenylation signal and a functional polyadenylation site is absent; (b) a 3' untranslated region is absent; (c) a self-splicing ribozyme is located adjacent to and 3' to the suppression element; and/or (d) the suppression element is embedded in an intron, preferably an intron flanked on one or on both sides by non-protein-coding DNA.

The recombinant DNA construct for suppressing production of mature microRNA in a cell includes at least one gene suppression element selected from the group consisting of: (a) DNA that includes at least one anti-sense DNA segment that is anti-sense to at least one segment of the at least one target sequence; (b) DNA that includes multiple copies of at least one anti-sense DNA segment that is anti-sense to at least one segment of the at least one target sequence; (c) DNA that includes at least one sense DNA segment that is at least one segment of the at least one target sequence; (d) DNA that includes multiple copies of at least one sense DNA segment that is at least one segment of the at least one target sequence;

(e) DNA that transcribes to RNA for suppressing the at least one first target sequence by forming double-stranded RNA and includes at least one anti-sense DNA segment that is anti-sense to at least one segment of the at least one target sequence and at least one sense DNA segment that is at least one segment of the at least one target sequence; (f) DNA that transcribes to RNA for suppressing the at least one first target sequence by forming a single double-stranded RNA and includes multiple serial anti-sense DNA segments that are anti-sense to at least one segment of the at least one target sequence and multiple serial sense DNA segments that are at least one segment of the at least one target sequence; (g) DNA that transcribes to RNA for suppressing the at least one first target sequence by forming multiple double strands of RNA and includes multiple anti-sense DNA segments that are anti-sense to at least one segment of the at least one target sequence and multiple sense DNA segments that are at least one segment of the at least one target sequence, and wherein the multiple anti-sense DNA segments and the multiple sense DNA segments are arranged in a series of inverted repeats; (h) DNA that includes nucleotides derived from a miRNA (which can be an animal, plant, or viral miRNA and is preferably a viral or an animal miRNA where the construct is to be transcribed in an animal cell, and preferably a viral or a plant miRNA where the construct is to be transcribed in a plant cell); and (i) DNA that includes nucleotides of a siRNA; (j) DNA that transcribes to an RNA aptamer capable of binding to a ligand; and (k) DNA that transcribes to an RNA aptamer capable of binding to a ligand, and DNA that transcribes to regulatory RNA capable of regulating expression of the first target gene, wherein the regulation is dependent on the conformation of the regulatory RNA, and the conformation of the regulatory RNA is allosterically affected by the binding state of the RNA aptamer. In some embodiments, the gene suppression element suppresses multiple target microRNA precursors or multiple microRNA promoters or a combination of both. In some embodiments, the target sequence includes nucleotides of a loop region of the at least one target microRNA precursor.

Where the recombinant DNA construct is to be transcribed in an animal cell, the promoter includes a promoter element functional in an animal, and the at least one target microRNA precursor is endogenous to the animal or a eukaryotic pest or pathogen of the animal. Where the recombinant DNA construct is to be transcribed in a plant cell, the promoter element is functional in a plant, and the at least one target microRNA precursor is endogenous to the plant or to a eukaryotic pest or eukaryotic pathogen of the plant. In various embodiments, the recombinant DNA construct includes a promoter element which can be selected from the group consisting of a constitutive promoter, a spatially specific promoter, a temporally specific promoter, a developmentally specific promoter, and an inducible promoter.

In various embodiments, the recombinant DNA construct for suppressing production of mature microRNA in a cell optionally includes at least one of: (a) at least one T-DNA border; (b) spacer DNA; (c) a gene expression element for expressing at least one gene of interest; and (d) a second gene suppression element for suppressing at least one second target gene, wherein the second gene suppression element is located adjacent to the intron. In various embodiments, the recombinant DNA construct is further characterized by any of the following conditions: (a) the terminator element includes a functional polyadenylation signal and polyadenylation site; or (b) at least one of a functional polyadenylation signal and a functional polyadenylation site is absent in the terminator element; or (c) a 3' untranslated region is absent.

The invention further provides a method of effecting suppression of mature microRNA production in a eukaryotic cell, including transcribing in a eukaryotic cell a recombinant DNA construct for suppressing production of mature microRNA in a cell, including a promoter element operably linked to a gene suppression element for suppression of at least one target sequence selected from the at least one target microRNA precursor or a promoter of the at least one target microRNA precursor or both, whereby mature microRNA production is suppressed relative to its production in the absence of transcription of the recombinant DNA construct. In one preferred embodiment of the method, the suppression is nuclear suppression, and the suppression element is transcribed in the cell to RNA lacking functional nuclear export signals. The suppression element suppresses at least one target sequence selected from at least one target microRNA precursor molecule or a promoter of the at least one microRNA precursor molecule, or both. The method can include transcription of the recombinant DNA construct in a cell of an animal, wherein the at least one target microRNA precursor is endogenous to the animal or a eukaryotic or viral pest or pathogen of the animal. The method can include transcription of the recombinant DNA construct in a cell of a plant, wherein the at least one target microRNA precursor is endogenous to the plant or a eukaryotic or viral pest or pathogen of the plant. In various embodiments, the recombinant DNA construct further includes a gene expression element for expressing at least one gene of interest, wherein the suppression of mature microRNA production is effected with concurrent expression of the at least one gene of interest in the cell.

In preferred embodiments, the mature miRNA to be suppressed is a plant miRNA in a plant cell. Suppression can be of a consensus sequence of multiple mature miRNAs or multiple miRNA precursors, or of a miRNA promoter that promotes transcription of multiple miRNAs, or of a consensus sequence of multiple miRNA promoters. In preferred embodiments, the mature miRNA is a miRNA of a crop plant, such as, but not limited to, a miRNA of any of the plant species enumerated under the heading "Transgenic Plants". Especially preferred are methods where the mature miRNA to be suppressed is a maize or soybean mature microRNA. In preferred embodiments, the target microRNA precursor molecule is derived from the fold-back structure of a crop plant mature miRNA, such as a maize or soybean MIR sequence selected from the MIR sequences identified in Tables 3, 4, 5, 6, 9, and 10, and their complements. In specifically claimed embodiments, the target microRNA precursor molecule is derived from the fold-back structure of a maize or soybean MIR sequence selected from the group consisting of SEQ ID NO. 6, 7, 8, 9, 10, 12, 14, 16, 18, 20, 22, 24, 28, 30, 32, 34, 38, 39, 43, 44, 227, 228, 236, 239, 242, 245, 248, and 249, and their complements.

Promoters and other elements useful in the recombinant DNA constructs for suppressing production of mature microRNA in a cell are described in detail under the headings "Gene Suppression Elements", "Promoter Elements", "Introns", "Terminator Elements", "T-DNA Borders", "Spacer DNA", and "Gene Expression Elements", and elsewhere in this disclosure. Techniques for making and using recombinant DNA constructs of the invention, for making transgenic plant cells and transgenic plants, seeds, and progeny plants, and for assaying the effects of transcribing the recombinant DNA constructs, are described in detail under the headings "Making and Using Recombinant DNA Constructs", "Making and Using Transgenic Plant Cells and Transgenic Plants", and elsewhere in this disclosure.

IV. Engineered Heterologous miRNA for Controlling Gene Expression

Engineered miRNAs and trans-acting siRNAs (ta-siRNAs) are useful for gene suppression with increased specificity. The invention provides a recombinant DNA construct including a transcribable engineered miRNA precursor designed to suppress a target sequence, wherein the transcribable engineered miRNA precursor is derived from the fold-back structure of a MIR gene, preferably a maize or soybean MIR sequence selected from the group consisting of the MIR sequences identified in Tables 3, 4, 5, 6, 9, and 10, and their complements. In specifically claimed embodiments, the transcribable engineered miRNA precursor is derived from the fold-back structure of a maize or soybean MIR sequence selected from the group consisting of SEQ ID NO. 6, 7, 8, 9, 10, 12, 14, 16, 18, 20, 22, 24, 28, 30, 32, 34, 38, 39, 43, 44, 227, 228, 236, 239, 242, 245, 248, and 249, and their complements. These miRNA precursors are also useful for directing in-phase production of siRNAs (e.g., heterologous sequence designed to be processed in a trans-acting siRNA suppression mechanism in planta). The invention further provides a method to suppress expression of a target sequence in a plant cell, including transcribing in a plant cell a recombinant DNA construct including a transcribable engineered miRNA precursor designed to suppress a target sequence, wherein the transcribable engineered miRNA precursor is derived from the fold-back structure of a MIR gene, preferably a maize or soybean MIR sequence selected from the group consisting of the MIR sequences identified in Tables 2, 3, and 4, and their complements, whereby expression of the target sequence is suppressed relative to its expression in the absence of transcription of the recombinant DNA construct. In specifically claimed embodiments, the transcribable engineered miRNA precursor is derived from the fold-back structure of a maize or soybean MIR sequence selected from the group consisting of SEQ ID NO. 6, 7, 8, 9, 10, 12, 14, 16, 18, 20, 22, 24, 28, 30, 32, 34, 38, 39, 43, 44, 227, 228, 236, 239, 242, 245, 248, and 249, and their complements.

The mature miRNAs produced, or predicted to be produced, from these miRNA precursors may be engineered for use in suppression of a target gene, e.g., in transcriptional suppression by the miRNA, or to direct in-phase production of siRNAs in a trans-acting siRNA suppression mechanism (see Allen et al. (2005) *Cell*, 121:207-221, Vaucheret (2005) *Science STKE*, 2005:pe43, and Yoshikawa et al. (2005) *Genes Dev.*, 19:2164-2175, all of which are incorporated by reference herein). Plant miRNAs generally have near-perfect complementarity to their target sequences (see, for example, Llave et al. (2002) *Science*, 297:2053-2056, Rhoades et al. (2002) *Cell*, 110:513-520, Jones-Rhoades and Bartel (2004) *Mol. Cell*, 14:787-799, all of which are incorporated by reference herein). Thus, the mature miRNAs can be engineered to serve as sequences useful for gene suppression of a target sequence, by replacing nucleotides of the mature miRNA sequence with nucleotides of the sequence that is targeted for suppression; see, for example, methods disclosed by Parizotto et al. (2004) *Genes Dev.*, 18:2237-2242 and especially U.S. Patent Application Publications 2004/0053411A1, 2004/0268441A1, 2005/0144669, and 2005/0037988 all of which are incorporated by reference herein. When engineering a novel miRNA to target a specific sequence, one strategy is to select within the target sequence a region with sequence that is as similar as possible to the native miRNA sequence. Alternatively, the native miRNA sequence can be replaced with a region of the target sequence, preferably a region that meets structural and thermodynamic criteria believed to be important for miRNA function (see, for example, U.S. Patent Application Publication 2005/0037988). Sequences are preferably engineered such that the number and placement of mismatches in the stem structure of the fold-back region or pre-miRNA is preserved. Thus, an engineered miRNA or engineered miRNA precursor can be derived from any of the mature miRNA sequences, or their corresponding miRNA precursors (including the fold-back portions of the corresponding MIR genes) disclosed herein. The engineered miRNA precursor can be cloned and expressed (transiently or stably) in a plant cell or tissue or intact plant.

Promoters and other elements useful in the recombinant DNA constructs including a transcribable engineered miRNA precursor designed to suppress a target sequence are described in detail under the headings "Gene Suppression Elements", "Promoter Elements", "Introns", "Terminator Elements", "T-DNA Borders", "Spacer DNA", and "Gene Expression Elements", and elsewhere in this disclosure. Techniques for making and using recombinant DNA constructs of the invention, for making transgenic plant cells containing the recombinant DNA constructs and transgenic plants, seeds, and progeny plants derived therefrom, and for assaying the effects of transcribing the recombinant DNA constructs, are described in detail under the headings "Making and Using Recombinant DNA Constructs", "Making and Using Transgenic Plant Cells and Transgenic Plants", and elsewhere in this disclosure.

V. Recombinant DNA Constructs Including Exogenous miRNA Recognition Sites and Methods for Use Thereof One aspect of the invention provides a recombinant DNA construct including transcribable DNA that transcribes to RNA including (a) at least one exogenous miRNA recognition site recognizable by a mature miRNA expressed in a specific cell of a multicellular eukaryote, and (b) target RNA to be suppressed in the specific cell, whereby said target RNA is expressed in cells other than said specific cell. The multicellular eukaryote can be any multicellular eukaryote (e.g., plant, animal, or fungus), and is preferably a plant or an animal. The constructs are prepared by methods known in the art, for example, as disclosed below under the heading "Making and Using Recombinant DNA Constructs of the Invention".

Generally, the recombinant DNA construct includes a promoter operably linked to the transcribable DNA. Suitable promoters include any promoter that is capable of transcribing DNA in the cell where transcription is desired, and are generally promoters functional in a eukaryotic cell, e.g., the promoters listed below under the heading "Promoter Elements". Where the specific cell is an animal cell, the promoter is a promoter functional in the animal cell. Where the specific cell is a plant cell, the promoter is a promoter functional in the plant cell. In one embodiment of the invention, the promoter is preferably a constitutive promoter or a promoter that allows expression in cells not limited to the specific cell in which expression of the target RNA is to be suppressed. The recombinant DNA construct can optionally include a terminator, e.g., a functional terminator that allows polyadenylation of the transcript.

Mature miRNA: By mature miRNA is meant the small RNA processed from a miRNA precursor (e.g., pri-miRNA or pre-miRNA), that is capable of recognizing and binding to a specific sequence ("miRNA recognition site") within an RNA transcript, and guiding the cleavage of that transcript. In one preferred, non-limiting embodiment of the invention, the mature miRNA is a crop plant miRNA, such as a maize miRNA or a soy miRNA. Non-limiting examples of specific miRNAs are provided in the Examples.

Target RNA: The target RNA is any RNA of interest, and can include at least one of non-coding RNA, a suppression element; and a gene expression element, or any combination of these. Non-coding RNA can include RNA that functions as a suppression element (such as those described under the heading "Gene Suppression Elements") as well as RNA with a secondary structure conferring upon it a desired function, e.g., RNA ribozymes or RNA aptamers that can bind a specific ligand. The target RNA can include a gene expression element (described under the heading "Gene Expression Elements") and can include coding or non-coding sequence from any species.

miRNA Recognition Site: The at least one miRNA recognition site is exogenous, that is, occurring in other than a naturally occurring or native context. One or more (identical or different) exogenous miRNA recognition sites can be variously located in the recombinant DNA construct: (a) in the 5' untranslated region of the target RNA, or (b) in the 3' untranslated region of the target RNA, or (c) within the target RNA. Inclusion of the exogenous miRNA recognition site within a coding region may be constrained by the requirements of the amino acid sequence, but is possible if the inclusion does not produce translated polypeptides with undesirable characteristics (e.g., loss or decrease of function). Any miRNA recognition site may be used in carrying out the invention; particularly preferred are any of the miRNA recognition sites provided in Tables 8, 11, and 12, and specifically claimed are the miRNA recognition sites having SEQ ID NOS. 64-219 and 250-346.

In one non-limiting embodiment, it may be desirable to express the target RNA under a non-specific (e.g., a "strong" constitutive promoter) throughout most cells, but not in specific cells, of a multicellular eukaryote such as a plant. Thus, the at least one exogenous miRNA recognition site is generally chosen according to knowledge of spatial or temporal expression of the corresponding mature miRNA that recognizes and binds to the miRNA recognition site.

Cleavage of a target RNA transcript and the subsequent suppression of the target RNA is dependent on base pairing between the mature miRNA and its cognate miRNA recognition site. Thus, the at least one exogenous miRNA recognition site is designed to have sufficient sequence complementarity to the mature miRNA to allow recognition and binding by the mature miRNA. In plants, sequence complementarity of a miRNA and its recognition site is typically high, e.g., perfect complementarity between 19, 20, or 21 out of 21 nucleotides (in the case of a mature miRNA that is 21 nucleotides in length), that is, complementarity of about 90% or greater. A similar degree of complementarity is preferable for recognition sites for plant miRNAs of any length (e.g., 20, 21, 22, 23, and 24 nucleotides). The sequence requirements for mature miRNA binding to a recognition site, and methods for predicting miRNA binding to a given sequence, are discussed, for example, in Llave et al. (2002) *Science*, 297:2053-2056, Rhoades et al. (2002) *Cell*, 110:513-520, Jones-Rhoades and Bartel (2004) *Mol. Cell*, 14:787-799, Schwab et al (2005) *Developmental Cell*, 8:517-527, and Xie et al. (2005) *Plant Physiol.*, 138:2145-2154, all of which are incorporated by reference herein. When designing a miRNA recognition site as well as its exact location in or adjacent to a target RNA, it is also preferable to avoid sequences that have undesirable characteristics, such sequences encoding undesirable polypeptides, as described under the heading "Target Genes". When designing target RNA as a transgene to be expressed, the unintentional introduction of an exogenous miRNA recognition site is preferably avoided where suppression by a mature miRNA is not desired.

One preferred aspect of the invention includes a transgenic plant cell or a transgenic plant containing in its genome the recombinant DNA construct including at least one exogenous miRNA recognition site and target RNA. Suitable transgenic plants include a regenerated plant prepared from a transgenic plant cell having in its genome the recombinant DNA construct including at least one exogenous miRNA recognition site and target RNA, or a progeny plant of such a regenerated plant; progeny plants include plants of any developmental stage (including seeds) and include hybrid progeny plants. One preferred embodiment is a transgenic crop plant wherein the mature miRNA that recognizes the exogenous miRNA recognition site is a maize or soybean miRNA (e.g., a miRNA derived from the fold-back structure of a maize or soybean MIR sequence selected from the MIR sequences identified in Tables 3, 4, 5, 6, 9, and 10, and their complements, or more specifically, a MIR sequence selected from SEQ ID NO. 6, 7, 8, 9, 10, 12, 14, 16, 18, 20, 22, 24, 28, 30, 32, 34, 38, 39, 43, 44, 227, 228, 236, 239, 242, 245, 248, and 249, and their complements).

These constructs are useful in methods, as disclosed and claimed herein, for suppressing expression of a target RNA in a specific cell of a multicellular eukaryote, including transcribing in the multicellular eukaryote a recombinant DNA construct including a promoter operably linked to DNA that transcribes to RNA including: (a) at least one exogenous miRNA recognition site recognizable by a mature miRNA expressed in a specific cell, and (b) target RNA to be suppressed in the specific cell, wherein the mature miRNA guides cleavage of target RNA in the specific cell, whereby expression of the target RNA is suppressed in the specific cell relative to its expression in cells lacking expression of the mature miRNA. Suitable multicellular eukaryotes include plants (e.g., mosses, ferns, monocots, and dicots) and animals (including mammals and other vertebrates). Where the multicellular eukaryote is a plant, the mature miRNA is preferably a plant mature miRNA; in some embodiments, the mature miRNA is preferably a mature miRNA from a crop plant such as, but not limited to, maize or soy (e.g., a miRNA derived from the fold-back structure of a maize or soybean MIR sequence selected from the MIR sequences identified in Tables 3, 4, 5, 6, 9, and 10, and their complements, or more specifically, a MIR sequence selected from SEQ ID NO. 6, 7, 8, 9, 10, 12, 14, 16, 18, 20, 22, 24, 28, 30, 32, 34, 38, 39, 43, 44, 227, 228, 236, 239, 242, 245, 248, and 249, and their complements).

In some embodiments, the recombinant DNA construct further includes a gene expression element for expressing at least one gene of interest (as described in detail below under "Gene Expression Element"), wherein the expression of the target RNA is suppressed with concurrent expression of the at least one gene of interest in the specific cell. In other embodiments, the target RNA includes a gene suppression element embedded in an intron, preferably an intron flanked on one or on both sides by non-protein-coding DNA, as described under "II. Recombinant DNA Constructs Containing Introns and Gene Suppression Elements".

Promoters and other elements useful in the recombinant DNA constructs including at least one exogenous miRNA recognition site and target RNA are described in detail under the headings "Gene Suppression Elements", "Promoter Elements", "Introns", "Terminator Elements", "T-DNA Borders", "Spacer DNA", and "Gene Expression Elements", and elsewhere in this disclosure. Techniques for making and using recombinant DNA constructs of the invention, for making transgenic plant cells containing the recombinant DNA constructs and transgenic plants, seeds, and progeny plants derived therefrom, and for assaying the effects of transcribing the recombinant DNA constructs, are described in detail under the headings "Making and Using Recombinant DNA Constructs", "Making and Using Transgenic Plant Cells and Transgenic Plants", and elsewhere in this disclosure.

Making and Using Recombinant DNA Constructs: The recombinant DNA constructs of the present invention can be made by any method suitable to the intended application, taking into account, for example, the type of expression desired and convenience of use in the plant in which the construct is to be transcribed. General methods for making and using DNA constructs and vectors are well known in the art and described in detail in, for example, handbooks and laboratory manuals including Sambrook and Russell, "Molecular Cloning: A Laboratory Manual" (third edition), Cold Spring Harbor Laboratory Press, NY, 2001, which is incorporated herein by reference. An example of useful technology for building DNA constructs and vectors for transformation is disclosed in US Patent Application Publication 2004/0115642 A1, incorporated herein by reference. DNA constructs can also be built using the GATEWAY™ cloning technology (available from Invitrogen Life Technologies, Carlsbad, Calif.), which uses the site-specific recombinase LR cloning reaction of the Integrase/att system from bacteriophage lambda vector construction, instead of restriction endonucleases and ligases. The LR cloning reaction is disclosed in U.S. Pat. Nos. 5,888,732 and 6,277,608, and in U.S. Patent Application Publications 2001/283529, 2001/282319 and 2002/0007051, all of which are incorporated herein by reference. The GATEWAY™ Cloning Technology Instruction Manual, which is also supplied by Invitrogen, provides concise directions for routine cloning of any desired DNA into a vector comprising operable plant expression elements. Another alternative vector fabrication method employs ligation-independent cloning as disclosed by Aslandis et al. (1990) *Nucleic Acids Res.*, 18:6069-6074 and Rashtchian et al. (1992) *Biochem.*, 206:91-97, where a DNA fragment with single-stranded 5' and 3' ends is ligated into a desired vector which can then be amplified in vivo.

In certain embodiments, the DNA sequence of the recombinant DNA construct includes sequence that has been codon-optimized for the plant in which the recombinant DNA construct is to be expressed. For example, a recombinant DNA construct to be expressed in a plant can have all or parts of its sequence (e.g., the first gene suppression element or the gene expression element) codon-optimized for expression in a plant. See, e.g., U.S. Pat. No. 5,500,365; De Amicis and Marchetti (2000) *Nucleic Acid Res.*, 28:3339-3346, which are incorporated by reference herein.

In certain embodiments, the DNA sequence of the recombinant DNA construct includes sequence that has been codon-optimized for the cell (e.g., an animal, plant, or fungal cell) in which the construct is to be expressed. For example, a construct to be expressed in a plant cell can have all or parts of its sequence (e.g., the first gene suppression element or the gene expression element) codon-optimized for expression in a plant. See, for example, U.S. Pat. No. 5,500,365; De Amicis and Marchetti (2000) *Nucleic Acid Res.*, 28:3339-3346, which are incorporated by reference herein.

Making and Using Transgenic Plant Cells and Transgenic Plants: The invention provides and claims a transgenic plant cell having in its genome any of the recombinant DNA constructs presently disclosed. The transgenic plant cell can be an isolated plant cell (e.g., individual plant cells or cells grown in or on an artificial culture medium), or can be a plant cell in undifferentiated tissue (e.g., callus or any aggregation of plant cells). The transgenic plant cell can be a plant cell in at least one differentiated tissue selected from the group consisting of leaf (e.g., petiole and blade), root, stem (e.g., tuber, rhizome, stolon, bulb, and corm) stalk (e.g., xylem, phloem), wood, seed, fruit (e.g., nut, grain, fleshy fruits), and flower (e.g., stamen, filament, anther, pollen, carpel, pistil, ovary, ovules). The invention further provides a transgenic plant having in its genome any of the recombinant DNA constructs presently disclosed, including a regenerated plant prepared from the transgenic plant cells claimed herein, or a progeny plant (which can be a hybrid progeny plant) of the regenerated plant, or seed of such a transgenic plant. Also provided is a transgenic seed having in its genome any of the recombinant DNA constructs presently disclosed, and a transgenic plant grown from such transgenic seed.

The transgenic plant cell or plant of the invention can be any suitable plant cell or plant of interest. Stably transformed transgenic plants are particularly preferred. In many preferred embodiments, the transgenic plant is a fertile transgenic plant from which seed can be harvested, and thus the invention further claims seed of such transgenic plants, wherein the seed is preferably also transgenic, that is, preferably contains the recombinant construct of the invention.

Where a recombinant DNA construct is used to produce a transgenic plant cell or transgenic plant of the invention, the transformation can include any of the well-known and demonstrated methods and compositions. Suitable methods for plant transformation include virtually any method by which DNA can be introduced into a cell, such as by direct delivery of DNA (e.g., by PEG-mediated transformation of protoplasts, by electroporation, by agitation with silicon carbide fibers, and by acceleration of DNA coated particles), by *Agrobacterium*-mediated transformation, by viral or other vectors, etc. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice) and U.S. Pat. No. 6,399,861 (maize), and U.S. Pat. No. 6,403,865 (maize), all of which are incorporated by reference.

Another preferred method of plant transformation is *Agrobacterium*-mediated transformation. In one preferred embodiment of the invention, the transgenic plant cell of the invention is obtained by transformation by means of *Agrobacterium* containing a binary Ti plasmid system, wherein the *Agrobacterium* carries a first Ti plasmid and a second, chimeric plasmid containing at least one T-DNA border of a wild-type Ti plasmid, a promoter functional in the transformed plant cell and operably linked to a gene suppression construct of the invention. See, for example, U.S. Pat. No. 5,159,135; De Framond (1983) *Biotechnology*, 1:262-269; and Hoekema et al., (1983) *Nature*, 303:179, which are incorporated by reference. In such a binary system, the smaller plasmid, containing the T-DNA border or borders, can be conveniently constructed and manipulated in a suitable alternative host, such as *E. coli*, and then transferred into *Agrobacterium*.

Detailed procedures for *Agrobacterium*-mediated transformation of plants, especially crop plants, include, for example, procedures disclosed in U.S. Pat. Nos. 5,004,863, 5,159,135, and 5,518,908 (cotton); U.S. Pat. Nos. 5,416,011, 5,569,834, 5,824,877 and 6,384,301 (soy); U.S. Pat. No. 5,591,616 (maize); U.S. Pat. No. 5,981,840 (maize); U.S. Pat. No. 5,463,174 (brassicas), all of which are incorporated by reference. Similar methods have been reported for, among others, peanut (Cheng et al. (1996) *Plant Cell Rep.*, 15: 653); asparagus (Bytebier et al. (1987) *Proc. Natl. Acad. Sci. U.S.A.*, 84:5345); barley (Wan and Lemaux (1994) *Plant Physiol.,* 104:37); rice (Toriyama et al. (1988) *Bio/Technology,* 6:10; Zhang et al. (1988) *Plant Cell Rep.,* 7:379; wheat (Vasil et al. (1992) *Bio/Technology,* 10:667; Becker et al. (1994) *Plant J.,* 5:299), and alfalfa (Masoud et al. (1996) *Transgen. Res.,* 5:313). See also U.S. Patent Application Publication 2003/0167537 A1, incorporated by reference, for a description of vectors, transformation methods, and production of transformed *Arabidopsis thaliana* plants where transcription factors are constitutively expressed by a CaMV35S promoter. Transgenic plant cells and transgenic plants can also be obtained by transformation with other vectors, such as, but not limited to, viral vectors (e.g., tobacco etch potyvirus (TEV), barley stripe mosaic virus (BSMV), and the viruses referenced in Edwardson and Christie, "The Potyvirus Group: Monograph No. 16, 1991, Agric. Exp. Station, Univ. of Florida, which is incorporated by reference), plasmids, cosmids, YACs (yeast artificial chromosomes), BACs (bacterial artificial chromosomes) or any other suitable cloning vector, when used with an appropriate transformation protocol, e.g., bacterial infection (e.g., with *Agrobacterium* as described above), binary bacterial artificial chromosome constructs, direct delivery of DNA (e.g., via PEG-mediated transformation, desiccation/inhibition-mediated DNA uptake, electroporation, agitation with silicon carbide fibers, and microprojectile bombardment). It would be clear to one of skill in the art that various transformation methodologies can be used and modified for production of stable transgenic plants from any number of plant species of interest. All of the above-described patents and publications disclosing materials and methods for plant transformation are incorporated by reference in their entirety.

Transformation methods to provide transgenic plant cells and transgenic plants containing stably integrated recombinant DNA are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos or parts of embryos, and gametic cells such as microspores, pollen, sperm, and egg cells. It is contemplated that any cell from which a fertile plant can be regenerated can be useful as a recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (e.g., various media and recipient target cells, transformation of immature embryos, and subsequent regeneration of fertile transgenic plants) are disclosed, for example, in U.S. Pat. Nos. 6,194,636 and 6,232,526 and U.S. Application Publication 2004/0216189, which are incorporated by reference.

In general transformation practice, DNA is introduced into only a small percentage of target cells in any one transformation experiment. Marker genes are generally used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the recombinant DNA. Commonly used selective marker genes include those conferring resistance to antibiotics such as kanamycin or paromomycin (nptII), hygromycin B (aph IV) and gentamycin (aac3 and aacC4) or resistance to herbicides such as glufosinate (bar or pat) and glyphosate (EPSPS). Examples of useful selective marker genes and selection agents are illustrated in U.S. Pat. Nos. 5,550,318, 5,633,435, 5,780,708, and 6,118,047, all of which are incorporated by reference. Screenable markers or reporters, such as markers that provide an ability to visually identify transformants can also be employed. Non-limiting examples of useful screenable markers include, for example, a gene expressing a protein that produces a detectable color by acting on a chromogenic substrate (e.g., beta-glucuronidase (GUS) (uidA) or luciferase (luc)) or that itself is detectable, such as green fluorescent protein (GFP) (gfp) or an immunogenic molecule. Those of skill in the art will recognize that many other useful markers or reporters are available for use.

Detecting or measuring the resulting change in expression of the target gene (or concurrent expression of a gene of interest) obtained by transcription of the recombinant construct in the transgenic plant of the invention can be achieved by any suitable methods, including protein detection methods (e.g., western blots, ELISAs, and other immunochemical methods), measurements of enzymatic activity, or nucleic acid detection methods (e.g., Southern blots, northern blots, PCR, RT-PCR, fluorescent in situ hybridization). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, NY, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Peña (editor) "Transgenic Plants: Methods and Protocols", Humana Press, 2004, which are incorporated by reference.

Other suitable methods for detecting or measuring the resulting change in expression of the target gene (or concurrent expression of a gene of interest) obtained by transcription of the recombinant DNA in the transgenic plant of the invention include measurement of any other trait that is a direct or proxy indication of expression of the target gene (or concurrent expression of a gene of interest) in the transgenic plant in which the recombinant DNA is transcribed, relative to one in which the recombinant DNA is not transcribed, e.g., gross or microscopic morphological traits, growth rates, yield, reproductive or recruitment rates, resistance to pests or pathogens, or resistance to biotic or abiotic stress (e.g., water deficit stress, salt stress, nutrient stress, heat or cold stress). Such methods can use direct measurements of a phenotypic trait or proxy assays (e.g., in plants, these assays include plant part assays such as leaf or root assays to determine tolerance of abiotic stress).

The recombinant DNA constructs of the invention can be stacked with other recombinant DNA for imparting additional traits (e.g., in the case of transformed plants, traits including herbicide resistance, pest resistance, cold germination tolerance, water deficit tolerance, and the like) for example, by expressing or suppressing other genes. Constructs for coordinated decrease and increase of gene expression are disclosed in U.S. Patent Application Publication 2004/0126845 A1, incorporated by reference.

Seeds of transgenic, fertile plants can be harvested and used to grow progeny generations, including hybrid generations, of transgenic plants of this invention that include the recombinant DNA construct in their genome. Thus, in addition to direct transformation of a plant with a recombinant DNA construct, transgenic plants of the invention can be prepared by crossing a first plant having the recombinant DNA with a second plant lacking the construct. For example, the recombinant DNA can be introduced into a plant line that is amenable to transformation to produce a transgenic plant, which can be crossed with a second plant line to introgress the recombinant DNA into the resulting progeny. A transgenic plant of the invention with one recombinant DNA (effecting change in expression of a target gene) can be crossed with a plant line having other recombinant DNA that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s).

Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e.g., usually 6 to 8 generations, to produce a progeny plant with substantially the same genotype as one original transgenic parental line but for the recombinant DNA of the other transgenic parental line.

Yet another aspect of the invention is a transgenic plant grown from the transgenic seed of the invention. This invention contemplates transgenic plants grown directly from transgenic seed containing the recombinant DNA as well as progeny generations of plants, including inbred or hybrid plant lines, made by crossing a transgenic plant grown directly from transgenic seed to a second plant not grown from the same transgenic seed.

Crossing can include, for example, the following steps:

(a) plant seeds of the first parent plant (e.g., non-transgenic or a transgenic) and a second parent plant that is transgenic according to the invention;

(b) grow the seeds of the first and second parent plants into plants that bear flowers;

(c) pollinate a flower from the first parent with pollen from the second parent; and (d) harvest seeds produced on the parent plant bearing the fertilized flower.

It is often desirable to introgress recombinant DNA into elite varieties, e.g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", and then the selected progeny are mated back to the superior recurrent parent "A". After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e., one or more transformation events.

Through a series of breeding manipulations, a selected DNA construct can be moved from one line into an entirely different line without the need for further recombinant manipulation. One can thus produce inbred plants which are true breeding for one or more DNA constructs. By crossing different inbred plants, one can produce a large number of different hybrids with different combinations of DNA constructs. In this way, plants can be produced which have the desirable agronomic properties frequently associated with hybrids ("hybrid vigor"), as well as the desirable characteristics imparted by one or more DNA constructs.

Genetic markers can be used to assist in the introgression of one or more DNA constructs of the invention from one genetic background into another. Marker assisted selection offers advantages relative to conventional breeding in that it can be used to avoid errors caused by phenotypic variations. Further, genetic markers can provide data regarding the relative degree of elite germplasm in the individual progeny of a particular cross. For example, when a plant with a desired trait which otherwise has a non-agronomically desirable genetic background is crossed to an elite parent, genetic markers can be used to select progeny which not only possess the trait of interest, but also have a relatively large proportion of the desired germplasm. In this way, the number of generations required to introgress one or more traits into a particular genetic background is minimized. The usefulness of marker assisted selection in breeding transgenic plants of the current invention, as well as types of useful molecular markers, such as but not limited to SSRs and SNPs, are discussed in PCT Application Publication WO 02/062129 and U.S. Patent Application Publications Nos. 2002/0133852, 2003/0049612, and 2003/0005491, each of which is incorporated by reference in their entirety.

In certain transgenic plant cells and transgenic plants of the invention, it may be desirable to concurrently express (or suppress) a gene of interest while also regulating expression of a target gene. Thus, in some embodiments, the transgenic plant contains recombinant DNA further including a gene expression (or suppression) element for expressing at least one gene of interest, and regulation of expression of a target gene is preferably effected with concurrent expression (or suppression) of the at least one gene of interest in the transgenic plant.

Thus, as described herein, the transgenic plant cells or transgenic plants of the invention can be obtained by use of any appropriate transient or stable, integrative or non-integrative transformation method known in the art or presently disclosed. The recombinant DNA constructs can be transcribed in any plant cell or tissue or in a whole plant of any developmental stage. Transgenic plants can be derived from any monocot or dicot plant, such as, but not limited to, plants of commercial or agricultural interest, such as crop plants (especially crop plants used for human food or animal feed), wood- or pulp-producing trees, vegetable plants, fruit plants, and ornamental plants. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Preferred dicot plants include, but are not limited to, canola, cotton, potato, quinoa, amaranth, buckwheat, safflower, soybean, sugarbeet, and sunflower, more preferably soybean, canola, and cotton. Preferred monocots include, but are not limited to, wheat, oat, barley, maize, rye, triticale, rice, ornamental and forage grasses, sorghum, millet, and sugarcane, more preferably maize, wheat, and rice.

The ultimate goal in plant transformation is to produce plants which are useful to man. In this respect, transgenic plants of the invention can be used for virtually any purpose deemed of value to the grower or to the consumer. For example, one may wish to harvest the transgenic plant itself, or harvest transgenic seed of the transgenic plant for planting purposes, or products can be made from the transgenic plant or its seed such as oil, starch, ethanol or other fermentation products, animal feed or human food, pharmaceuticals, and various industrial products. For example, maize is used extensively in the food and feed industries, as well as in industrial applications. Further discussion of the uses of maize can be found, for example, in U.S. Pat. Nos. 6,194,636, 6,207,879, 6,232,526, 6,426,446, 6,429,357, 6,433,252, 6,437,217, and 6,583,338 and PCT Publications WO 95/06128 and WO 02/057471, each of which is incorporated by reference in its entirety.

Thus, in preferred embodiments, a transgenic plant of the invention has at least one altered trait, relative to a plant lacking said recombinant DNA construct, selected from the group of traits consisting of:

(a) improved abiotic stress tolerance;

(b) improved biotic stress tolerance;

(c) improved resistance to a pest or pathogen of the plant;

(d) modified primary metabolite composition;

(e) modified secondary metabolite composition;

(f) modified trace element, carotenoid, or vitamin composition;

(g) improved yield;

(h) improved ability to use nitrogen or other nutrients;

(i) modified agronomic characteristics;

(j) modified growth or reproductive characteristics; and (k) improved harvest, storage, or processing quality.

The invention further provides a method of providing at least one altered plant tissue, including: (a) providing a transgenic plant including a regenerated plant prepared from a transgenic plant cell having in its genome any of the recombinant DNA constructs presently disclosed, or a progeny plant of the regenerated plant; and (b) transcribing the recombinant DNA construct in at least one tissue of the transgenic plant, whereby an altered trait in the at least one tissue results, relative to tissue wherein the recombinant DNA construct is not transcribed, the altered trait being selected from:

(i) improved abiotic stress tolerance;

(ii) improved biotic stress tolerance;

(iii) improved resistance to a pest or pathogen of the plant;

(iv) modified primary metabolite composition;

(v) modified secondary metabolite composition;

(vi) modified trace element, carotenoid, or vitamin composition;

(vii) improved yield;

(viii) improved ability to use nitrogen or other nutrients;

(ix) modified agronomic characteristics;

(x) modified growth or reproductive characteristics; and (xi) improved harvest, storage, or processing quality.

In preferred embodiments of the method of providing at least one altered plant tissue, the transgenic plant from which such tissue is obtained is a crop plant as described herein.

In particularly preferred embodiments, the transgenic plant is characterized by: improved tolerance of abiotic stress (e.g., tolerance of water deficit or drought, heat, cold, non-optimal nutrient or salt levels, non-optimal light levels) or of biotic stress (e.g., crowding, allelopathy, or wounding); by improved resistance to a pest or pathogen (e.g., insect, nematode, fungal, bacterial, or viral pest or pathogen) of the plant; by a modified primary metabolite (e.g., fatty acid, oil, amino acid, protein, sugar, or carbohydrate) composition; a modified secondary metabolite (e.g., alkaloids, terpenoids, polyketides, non-ribosomal peptides, and secondary metabolites of mixed biosynthetic origin) composition; a modified trace element (e.g., iron, zinc), carotenoid (e.g., beta-carotene, lycopene, lutein, zeaxanthin, or other carotenoids and xanthophylls), or vitamin (e.g., tocopherols) composition; improved yield (e.g., improved yield under non-stress conditions or improved yield under biotic or abiotic stress); improved ability to use nitrogen or other nutrients; modified agronomic characteristics (e.g., delayed ripening; delayed senescence; earlier or later maturity; improved shade tolerance; improved resistance to root or stalk lodging; improved resistance to "green snap" of stems; modified photoperiod response); modified growth or reproductive characteristics (e.g., intentional dwarfing; intentional male sterility, useful, e.g., in improved hybridization procedures; improved vegetative growth rate; improved germination; improved male or female fertility); improved harvest, storage, or processing quality (e.g., improved resistance to pests during storage, improved resistance to breakage, improved appeal to consumers); or any combination of these traits.

In one preferred embodiment, transgenic seed, or seed produced by the transgenic plant, has modified primary metabolite (e.g., fatty acid, oil, amino acid, protein, sugar, or carbohydrate) composition, a modified secondary metabolite (e.g., alkaloids, terpenoids, polyketides, non-ribosomal peptides, and secondary metabolites of mixed biosynthetic origin) composition, a modified trace element (e.g., iron, zinc), carotenoid (e.g., beta-carotene, lycopene, lutein, zeaxanthin, or other carotenoids and xanthophylls), or vitamin (e.g., tocopherols), composition, an improved harvest, storage, or processing quality, or a combination of these. For example, it can be desirable to modify the amino acid (e.g., lysine, methionine, tryptophan, or total protein), oil (e.g., fatty acid composition or total oil), carbohydrate (e.g., simple sugars or starches), trace element, carotenoid, or vitamin content of seeds of crop plants (e.g., canola, cotton, safflower, soybean, sugarbeet, sunflower, wheat, maize, or rice), preferably in combination with improved seed harvest, storage, or processing quality, and thus provide improved seed for use in animal feeds or human foods. In another instance, it can be desirable to change levels of native components of the transgenic plant or seed of a transgenic plant, for example, to decrease levels of proteins with low levels of lysine, methionine, or tryptophan, or to increase the levels of a desired amino acid or fatty acid, or to decrease levels of an allergenic protein or glycoprotein (e.g., peanut allergens including ara h 1, wheat allergens including gliadins and glutenins, soy allergens including P34 allergen, globulins, glycinins, and conglycinins) or of a toxic metabolite (e.g., cyanogenic glycosides in cassava, solanum alkaloids in members of the Solanaceae).

EXAMPLES

Example 1

This example illustrates the construction and use of vectors designed for double-stranded RNAi suppression or for anti-sense suppression of a luciferase gene. The gene suppression experiments used were similar to a dual luciferase assay described by Horstmann et al. (2004) *BMC Biotechnol.*, 4:13, which is incorporated by reference herein. A prior art vector, "vector 1A", designed for double-stranded RNAi suppression of a luciferase gene was constructed as depicted in FIG. 1A with an RNAi transcription unit with a polyadenylation site including (a) a chimeric promoter including an enhanced CaMV35S promoter linked to an enhancer element (an intron from heat shock protein 70 of *Zea mays*, Pe35S-Hsp intron), (b) an inverted repeat of DNA coding for firefly luciferase (LUC) with anti-sense oriented DNA followed by a sense oriented DNA, and (c) a 3'UTR DNA from *Agrobacterium tumefaciens* nopaline synthase gene (3'NOS) which provides a polyadenylation (polyA) site. Elements of the plasmid comprising the RNAi transcription unit had a DNA sequence of SEQ ID NO. 1. See Table 1 for a description of the elements within SEQ ID NO. 1.

TABLE 1

| Element | Nucleotide position in SEQ ID NO. 1 |
| --- | --- |
| CaMV e35S promoter | 1-614 |
| Hsp 70 intron | 645-1448 |
| Firefly luciferase anti-sense | 1455-1025 |
| Firefly luciferase sense | 2082-2502 |
| 3' UTR from nopaline synthase | 2515-2767 |

A prior art vector, "vector 1B", designed for anti-sense suppression of a luciferase gene and containing a polyA site was constructed as depicted in FIG. 1B with an anti-sense transcription unit including (a) the CaMV e35S-Hsp 70 intron chimeric promoter as described in Table 1, (b) the firefly luciferase anti-sense sequence described in Table 2, and (c) the 3' UTR from nopaline synthase as described in Table 1.

A novel vector, "vector 1C", designed for double-stranded RNAi suppression of a luciferase gene was constructed as depicted in FIG. 1C with an RNAi transcription unit without a polyadenylation site and including (a) the CaMV e35S-Hsp 70 intron chimeric promoter as described in Table 1, and (b) an inverted repeat of DNA coding for firefly luciferase, including the firefly luciferase anti-sense and firefly luciferase sense sequences described in Table 1. The RNAi transcription unit did not have 3'UTR DNA sequence providing a functional polyadenylation site.

Another novel vector, "vector 1D", designed for anti-sense suppression of a luciferase gene and without a functional polyadenylation site was constructed as depicted in FIG. 1D with an anti-sense transcription unit without polyadenylation site and including (a) the CaMV e35S-Hsp 70 intron chimeric promoter and (b) the firefly luciferase anti-sense sequence described in Table 1. The RNAi transcription unit did not have 3'UTR DNA sequence providing a functional polyadenylation site.

Maize protoplasts were prepared as previously described by Sheen (1990) *Plant Cell*, 2:1027-1038, which is incorporated by reference herein. Each of the four vectors 1A through 1D was electroporated together with reporter vectors for firefly luciferase and *Renilla* luciferase into three separate volumes of maize protoplasts. Two sets of firefly luciferase suppression experiments were performed to confirm the enhanced ability for gene suppression exhibited by the constructs without a functional polyadenylation site (vectors 1C and 1D) relative to the anti-sense construct with a functional polyadenylation site (vector 1B). The relative level of suppression of the target gene, firefly luciferase, was indicated by the ratio of firefly luciferase to *Renilla* luciferase "ffLUC/rLUC", and the results of the two experiments are given in Table 2.

TABLE 2

| | | Average ffLUC/rLUC | |
| --- | --- | --- | --- |
| Vector | Description of Construct | First experiment | Second experiment |
| 1A | RNAi with polyA site | 1862 | 2387 |
| 1B | anti-sense with polyA site | 6089 | 13988 |
| 1C | RNAi without polyA site | 3620 | 5879 |
| 1D | anti-sense without polyA site | 2238 | 4762 |

Example 2

Figure 2:
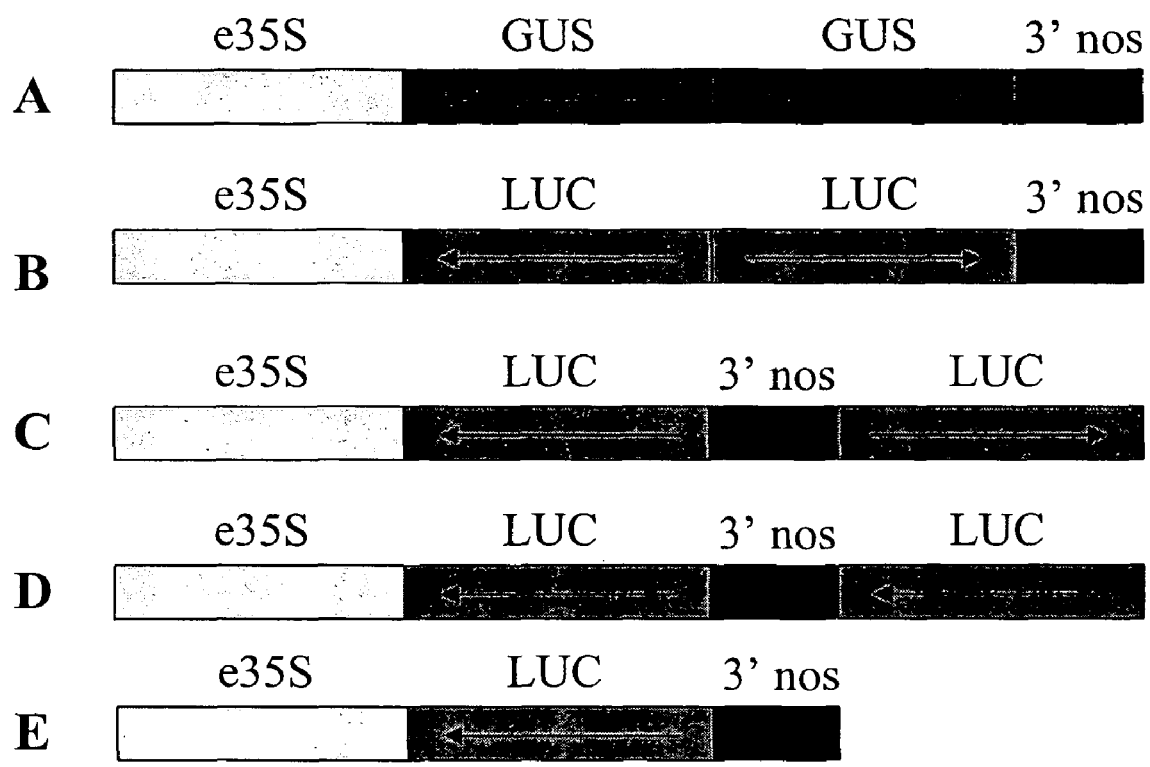
FIG. 2 schematically illustrates DNA vectors as described in Example 2. Legend: pale grey regions labelled "e35s": a chimeric promoter including an enhanced CaMV35S promoter linked to an enhancer element (an intron from heat shock protein 70 of *Zea mays*, Pe35S-Hsp70 intron); medium grey regions labeled "GUS": DNA coding for beta-glucuronidase; medium grey regions labeled "LUC": DNA coding for firefly luciferase; dark grey regions labeled "3' nos": a 3'UTR DNA from *Agrobacterium tumefaciens* nopaline synthase gene. Vectors are conventionally depicted as transcribing from left (5') to right (3'). Arrows indicate orientation of the luciferase segments as sense (arrowhead to right) or anti-sense (arrowhead to left).

This example further illustrates the construction and use of vectors designed for double-stranded RNAi suppression or for anti-sense suppression of a luciferase gene. The gene suppression experiments used were similar to a dual luciferase assay described by Horstmann et al. (2004) *BMC Biotechnol.*, 4:13. The vectors illustrated in FIG. 2 were constructed. Vector 2A (FIG. 2A), a control vector not encoding anti-sense or double-stranded RNA for the target gene (firefly luciferase), consisted of (a) the CaMV e35S-Hsp 70 intron chimeric promoter as described in Example 1 and Table 1, (b) an inverted repeat of DNA coding for beta-glucuronidase (GUS) (uidA) with anti-sense oriented DNA followed by a sense oriented DNA, and (c) a 3'UTR DNA from *Agrobacterium tumefaciens* nopaline synthase gene (3'NOS) as described in Example 1 and Table 1, which provides a polyadenylation (polyA) site. Vector 2B (FIG. 2B), a prior art vector designed for double-stranded RNAi suppression of a luciferase gene, consisted of (a) the CaMV e35S-Hsp 70 intron chimeric promoter as described in Example 1 and Table 1, (b) an inverted repeat of DNA coding for firefly luciferase (LUC) with anti-sense oriented DNA followed by a sense oriented DNA, as described in Example 1 and Table 1, and (c) a 3'UTR DNA from *Agrobacterium tumefaciens* nopaline synthase gene (3'NOS) as described in Example 1 and Table 1, which provides a polyadenylation (polyA) site. Vector 2C (FIG. 2C), a novel vector, consisted of (a) the CaMV e35S-Hsp 70 intron chimeric promoter as described in Example 1 and Table 1, (b) the firefly luciferase anti-sense sequence, as described in Example 1 and Table 1, (c) spacer DNA consisting of a 3'UTR DNA from *Agrobacterium tumefaciens* nopaline synthase gene (3'NOS) as described in Example 1 and Table 1, and (d) the firefly luciferase sense sequence, as described in Example 1 and Table 1. Vector 2D (FIG. 2D), a novel vector, consisted of (a) the CaMV e35S-Hsp 70 intron chimeric promoter as described in Example 1 and Table 1, (b) a first copy of the firefly luciferase anti-sense sequence, as described in Example 1 and Table 1, (c) spacer DNA consisting of a 3'UTR DNA from *Agrobacterium* lumefaciens nopaline synthase gene (3'NOS) as described in Example 1 and Table 1, and (d) a second copy of the firefly luciferase anti-sense sequence. Vector 2E (FIG. 2E), a prior art vector designed for anti-sense RNA suppression of a luciferase gene, consisted of (a) the CaMV e35S-Hsp 70 intron chimeric promoter as described in Example 1 and Table 1, (b) the firefly luciferase anti-sense sequence, as described in Example 1 and Table 1, and (c) a 3'UTR DNA from *Agrobacterium tumefaciens* nopaline synthase gene (3'NOS) as described in Example 1 and Table 1, which provides a polyadenylation (polyA) site.

Figure 3:
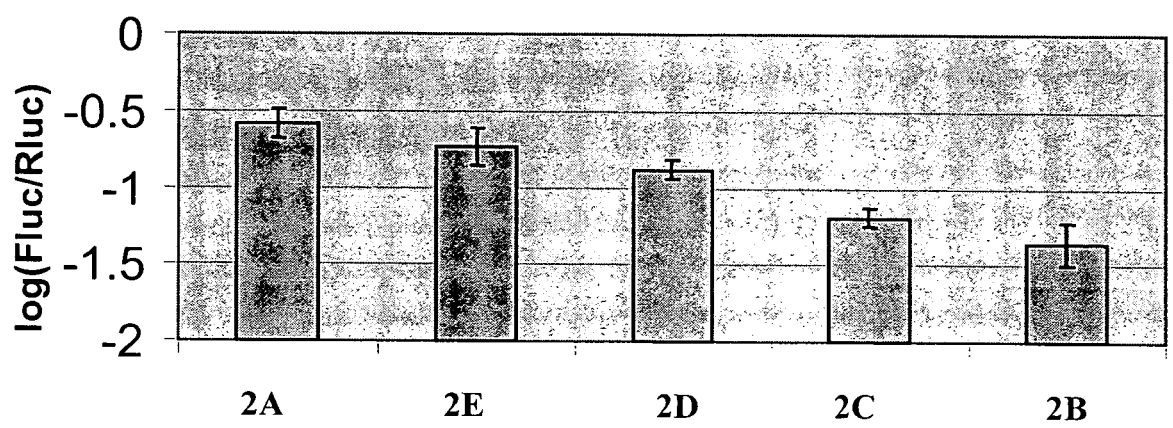
FIG. 3 depicts results of the experiments described in Example 2. X-axis indicates the vectors (see FIG. 2) used. Y-axis values are given as the logarithm of the ratio of logarithm of the ratio of firefly luciferase to *Renilla* luciferase, "log(Fluc/Rluc)"; error bars are 95% confidence intervals.

Each of the four vectors was electroporated together with reporter vectors for firefly luciferase and *Renilla* luciferase into three separate volumes of maize protoplasts prepared as previously described by Sheen (1990) *Plant Cell*, 2:1027-1038. Firefly luciferase suppression experiments were performed, and the relative level of suppression of the target gene, firefly luciferase, was indicated by the logarithm of the ratio of firefly luciferase to *Renilla* luciferase, "log(Fluc/Rluc)", as depicted in FIG. 3.

Example 3

This example describes transformation of a crop plant (maize) with an enhanced anti-sense construct. A plasmid for binary vector *Agrobacterium*-mediated transformation of maize is constructed including the elements shown in FIG. 4. Specifically, the plasmid includes an nptII gene as an antibiotic selectable marker and a recombinant DNA construct for enhanced anti-sense gene suppression, consisting of a CaMV35S promoter operably linked to transcribable DNA consisting of about 300 base pairs of a green fluorescent protein (gfp) gene in an anti-sense orientation, wherein a functional polyadenylation site is absent in this transcribable DNA. The plasmid also includes left T-DNA border (LB) and right T-DNA border (RB) elements. A control plasmid for RNAi suppression of green fluorescent protein (GFP) is constructed by adding to the enhanced anti-sense construct shown in FIG. 4 a repeat of the gfp DNA in the sense orientation followed by a 3' NOS element including a functional polyadenylation site. Maize callus for transformation is selected from a transgenic maize line expressing GFP. Both the plasmid with the enhanced anti-sense construct and the control plasmid with the RNAi construct are inserted into maize callus by *Agrobacterium*-mediated transformation. Events are selected as being resistant to kanamycin. The efficiency of suppression with enhanced anti-sense constructs is substantially the same as with the RNAi constructs.

Example 4

This example illustrates the use of a recombinant DNA construct for non-systemic suppression of a target gene in specific tissue of a transgenic plant. Specifically, this example describes transformation of a crop plant (maize) with an enhanced anti-sense construct. A plasmid for binary vector *Agrobacterium*-mediated transformation of corn is constructed including the elements shown in FIG. 5A. Specifically, the plasmid includes an aroA gene as an herbicidal selectable marker and a recombinant DNA construct for enhanced anti-sense gene suppression, consisting of a seed-specific maize L3 oleosin promoter (as disclosed in U.S. Pat. No. 6,433,252, incorporated herein by reference) operably linked to transcribable DNA consisting of about 300 base pairs of the LKR domain of a maize lysine ketoglutarate reductase/saccharopine dehydrogenase gene (LKR/SDH) in an anti-sense orientation, wherein a functional polyadenylation site is absent in this transcribable DNA. The plasmid also includes left T-DNA border (LB) and right T-DNA border (RB) elements. The plasmid with the enhanced anti-sense construct is inserted into maize callus by *Agrobacterium*-mediated transformation. Events are selected as being resistance to glyphosate herbicide and grown into transgenic maize plants to produce F1 seed. Mature seeds from each event are analyzed to determine success of transformation and suppression of LKR/SDH. The mature transgenic seeds are dissected to extract protein for Western analysis. Seed from transgenic maize plants shows reduction in LKR/SDH and increased lysine as compared to wild type.

In a further development of this approach, a recombinant DNA construct of the present invention is constructed as follows. A plasmid for binary vector *Agrobacterium*-mediated transformation of corn is constructed as shown in FIG. 5B, which includes a recombinant DNA construct of the present invention for gene suppression, including left and right T-DNA borders containing between them a promoter element operably linked to an intron (maize heat shock protein 70 intron, I-Zm-hsp70) within which is embedded a first gene suppression element for suppressing at least one first target gene (in this non-limiting example, the at least one first target gene includes coding sequence from the LKR domain, coding sequence from the SDH domain, or non-coding sequence of the maize lysine ketoglutarate reductase/saccharopine dehydrogenase gene (LKR/SDH), or any combination of these). The first gene suppression element can include any gene suppression element as described above under the heading "Gene Suppression Elements" wherein the intron is located adjacent to the promoter element. In the specific, non-limiting embodiment depicted in FIG. 5B, the promoter element is an endosperm-specific maize B32 promoter (nucleotides 848 through 1259 of GenBank accession number X70153, see also Hartings et al. (1990) *Plant Mol. Biol.*, 14:1031-1040, which is incorporated herein by reference), although other promoter elements could be used. This specific embodiment also includes an aroA gene as an herbicidal selectable marker; other selectable marker or reporter genes can be used, e.g., a selectable marker conferring glyphosate resistance, epsps-cp4 (5-enolpyruvylshikimate-3-phosphate synthase from *Agrobacterium tumefaciens* strain CP4). The intron-embedded gene suppression element includes any one or more gene suppression elements, including, for example, single or multiple copies of sense or anti-sense, tandem or interrupted repeats, single or multiple sense/anti-sense pairs able to form dsRNA for gene suppression, gene suppression sequences derived from an miRNA, sequences including siRNAs, or combinations of any of these. The construct optionally includes a gene expression element (e.g., transcribable or translatable DNA outside of the intron), a second gene suppression element, or both.

In one non-limiting example, the gene suppression element includes an about 300 base-pair anti-sense DNA segment that is anti-sense to the target gene, maize lysine ketoglutarate reductase/saccharopine dehydrogenase gene (LKR/SDH), wherein a functional polyadenylation site is absent in this transcribable heterologous DNA. The plasmid also includes left T-DNA border (LB) and right T-DNA border (RB) elements. The plasmid with the intron-embedded transcribable heterologous DNA is inserted into maize callus by *Agrobacterium*-mediated transformation. Events are selected as being resistance to glyphosate herbicide and grown into transgenic maize plants to produce F1 seed. Mature seeds from each event are analyzed to determine success of transformation and suppression of LKR/SDH. The mature transgenic seeds are dissected to extract protein for Western analysis. Seed from transgenic maize plants shows endosperm-specific reduction in LKR/SDH and increased lysine as compared to wild type.

Example 5

This example illustrates use of recombinant DNA constructs for pest control in plants producing by means of gene suppression in a specific tissue of a transgenic plant. Specifically, this example describes transformation of a crop plant (soybean) with an enhanced anti-sense construct. A plasmid for binary vector *Agrobacterium*-mediated transformation of soybean is constructed including the elements shown in FIG. 6. Specifically, the plasmid includes an aroA gene as an herbicidal selectable marker and a recombinant DNA construct for enhanced anti-sense gene suppression, consisting of a TUB-1 root specific promoter from *Arabidopsis thaliana* (disclosed in FIG. 1 of U.S. Patent Application Publication 2004/078841 A1, incorporated by reference herein) operably linked to transcribable DNA consisting of anti-sense oriented DNA of a nematode major sperm protein (msp) of a soybean cyst nematode (disclosed as SEQ ID NO:5 in U.S. Patent Application Publication 2004/0098761 A1, incorporated herein by reference), wherein a functional polyadenylation site is absent in this transcribable DNA. The plasmid also includes left T-DNA border (LB) and right T-DNA border (RB) elements. The plasmid with the enhanced anti-sense construct is inserted into soybean callus by *Agrobacterium*-mediated transformation. Events are selected as being resistance to glyphosate herbicide. Reduction in soybean cyst nematode infestation as compared to wild type is observed.

In a further development of this approach, a recombinant DNA construct of the present invention is constructed as follows. A plasmid for binary vector *Agrobacterium*-mediated transformation of corn is constructed, which includes an aroA gene as an herbicidal selectable marker and a recombinant DNA construct of the present invention for gene suppression, consisting of a TUB-1 root specific promoter from *Arabidopsis thaliana* (disclosed in FIG. 1 of U.S. Patent Application Publication 2004/078841 A1, incorporated by reference herein) operably linked to an intron (maize alcohol dehydrogenase intron, I-Zm-adh1) within which is embedded a first gene suppression element for suppression of an endogenous gene of a crop plant pest (soybean cyst nematode); in this specific, non-limiting example, the gene suppression element is transcribable heterologous DNA that includes an anti-sense DNA segment that is anti-sense to the target gene, nematode major sperm protein of a soybean cyst nematode (disclosed as SEQ ID NO:5 in U.S. Patent Application Publication 2004/0098761 A1, incorporated herein by reference), wherein the resulting transcribed RNA is unpolyadenylated. As a selectable marker, the plasmid alternatively uses a gene conferring glyphosate resistance, epsps-cp4 (5-enolpyruvylshikimate-3-phosphate synthase from *Agrobacterium tumefaciens* strain CP4). Other promoters, first transcribable heterologous DNAs, or introns can be substituted; the construct optionally includes a gene expression element, a second transcribable heterologous DNA for suppressing a second target gene, or both. The plasmid optionally contains a transcribable or translatable gene expression element outside of the intron. The plasmid also includes left T-DNA border (LB) and right T-DNA border (RB) elements. The plasmid with the enhanced anti-sense construct is inserted into soybean callus by *Agrobacterium*-mediated transformation. Events are selected as being resistance to glyphosate herbicide. Reduction in soybean cyst nematode infestation as compared to wild type is observed.

Example 6

This example illustrates a recombinant DNA construct of the invention, specifically, a construct including a gene suppression element that contains intron-embedded tandem repeats. More specifically, this illustrates a construct including a suppression element that contains intron-embedded tandem repeats for suppression of at least one target microRNA precursor. The tandem repeats are designed to suppress at least one target sequence selected from said at least one target microRNA precursor or a promoter of said at least one target microRNA precursor or both. This example also describes methods for testing recombinant DNA constructs for their ability to silence a target gene, and optionally for their ability to concurrently express a gene of interest.

Gene silencing by tandem repeats may operate through a nuclear-localized heterochromatin-associated RNAi pathway. See, for example, Sijen et al. (1996) *Plant Cell*, 8:2277-2294, Ma and Mitra (2002) *Plant J*, 31:37-49, Zilberman et al. (2003) *Science*, 299:716-719, and Martienssen (2003) *Nat. Genet.*, 35:213-214, which are incorporated by reference herein. The present invention provides recombinant DNA constructs for enhanced nuclear-localized gene silencing (e.g., suppression of production of mature microRNA). Non-limiting examples of such constructs are constructs with one or more suppression elements including tandem repeats, where the tandem repeats are embedded in an intron; such constructs can optionally include a gene expression element (FIG. 7A), which can be upstream (5', not shown) or downstream (3', as shown) of the intron. Two other approaches for enhancing nuclear-localized gene silencing by tandem repeats are tandem repeats that are transcribed but not processed for transport into the cytoplasm, e.g., transcribed from constructs lacking a functional terminator, as shown in FIG. 7B, and tandem repeats under transcriptional control of two opposing promoters, as shown in FIG. 7C. By embedding tandem repeats in an intron (e.g., FIG. 7A), transgenic transcripts splice out the tandem repeat containing intron in the nucleus. By removing or omitting a functional terminator of a transgene cassette (e.g., FIG. 7B), the resulting RNA transcripts containing tandem repeats are without a polyA signal and more likely to accumulate in the nucleus. In a construct where tandem repeats are flanked by opposing or convergent promoters (e.g., FIG. 7C), one promoter will transcribe the sense strand, and the other will transcribe the antisense strand; these two complementary strands can form a dsRNA. The purpose for this is to provide the initial dsRNA substrate for a Dicer or a Dicer-like enzyme. Thus, for example, Dicer produces siRNAs, and RDR2-dependent amplification of dsRNA and siRNAs, facilitated by the tandem repeat configuration, maintains the silencing pathway for these sequences.

Figure 7:
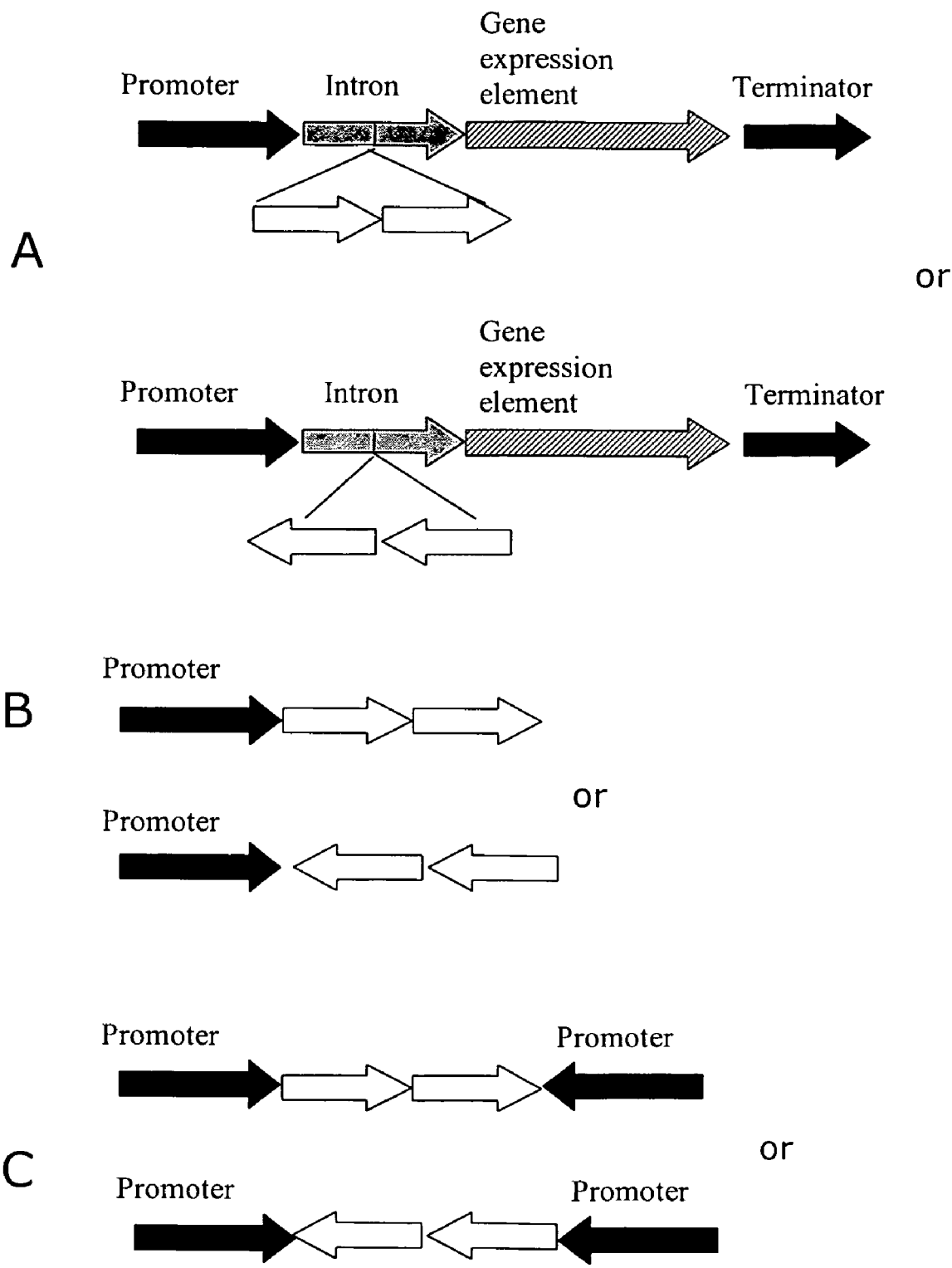
FIG. 7A depicts a gene suppression element useful in a recombinant DNA construct of the invention, including intron-embedded tandem repeats for enhancing nuclear-localized gene silencing as described in Example 6. Such an element can be combined with at least one T-DNA border in the construct for *Agrobacterium*-mediated transformation of a plant cell. The constructs optionally include a gene expression element, which can be upstream (5') or downstream (3') of the intron. In a variation of this embodiment (not shown), the intron-embedded tandem repeats are located 3' to the terminator.
FIG. 7B shows another vector useful for nuclear-localized gene silencing by tandem repeats, wherein the vector includes tandem repeats transcribed from constructs lacking a functional terminator. In a variation of this embodiment (not shown), the tandem repeats are located 3' to the terminator.
FIG. 7C shows yet another vector useful for nuclear-localized gene silencing by tandem repeats, wherein the vector includes tandem repeats under transcriptional control of two opposing promoters.

In the non-limiting examples shown in FIG. 7, there are two copies in the tandem repeat. Also encompassed by the invention are embodiments with the copy number of the tandem repeat ranging from 2 to about 100, as well as embodiments with tandem or interrupted repeats of one or more sequences (in non-limiting examples, these could include, e.g., AABB, AABAA, AABAABAA, AABAABB, ABBBBAA, AAABBB, AABBAA, and other arrangements, where A and B represent discrete sequences, each of which can be repeated). The size of each repeat is preferably at least about 19, or at least about 21, or at least about 50, at least about 100, at least about 200, or at least about 500 nucleotides in length. Preferably, at least two of the repeats are in the tandem repeat orientation. Unique or non-repeated sequences, including repeats of a second sequence, can optionally occur as "spacers" between some or all of the repeated units. Such spacers are preferably at least about 4, at least about 10, or at least about 20 nucleotides in length. Having unique sequences between facilitate assembly and/or verification of the tandem repeats. The repeats can be arranged in either the sense or antisense orientation, or, for example, where there are repeats of more than one sequence, each sequence can independently be in an arrangement of tandem sense repeats or tandem anti-sense repeats.

Example 7

This example describes non-limiting methods for testing any of the recombinant DNA constructs of the invention for their ability to silence a target gene, and optionally for their ability to concurrently express a gene of interest. Constructs can be designed and tested in transient assays by various means known to one skilled in the art, for example, protoplast transient transformation and *Agrobacterium* infiltration assays. For example, constructs can be designed where the target gene is a gene easily assayed for suppression (e.g., green fluorescent protein or GFP, luciferase or luc, or other reporter or marker genes commonly used). Such transient assays can generally be used to test any recombinant DNA constructs, e.g., constructs containing intron-embedded gene suppression elements (including gene suppression elements other than tandem repeats) for their ability to suppress a target gene.

In one non-limiting example, experiments to assay for gene suppression of a target gene (the reporter gene, luciferase) are carried out with a maize protoplast model system. Maize protoplasts are prepared as previously described by Sheen (1990) *Plant Cell*, 2:1027-1038, which is incorporated by reference herein. Polyethylene glycol (PEG)-mediated transformations (see, for example, Armstrong et al. (1990), *Plant Cell Rep.*, 9:335-339, which is incorporated by reference herein) are performed in deep well (2 milliliters/well) 96-well plates. Separate vectors containing either firefly luciferase or *Renilla* luciferase are employed as reporters. The firefly luciferase reporter vector includes a chimeric promoter including a chimeric promoter including an enhanced cauliflower mosaic virus (CaMV) 35S promoter linked to an enhancer element (an intron from heat shock protein 70 of *Zea mays*), the coding sequence of the firefly luciferase gene luc, and a 3' untranslated region (3' UTR) DNA from *Agrobacterium tumefaciens* nopaline synthase gene (3'NOS) which provides a polyadenylation (polyA) site. The *Renilla* luciferase reporter vector includes the same chimeric promoter, the coding sequence of the *Renilla* luciferase gene luc, and the same 3'NOS UTR terminator. Generally, 1.3 micrograms firefly luciferase reporter vector DNA, 0.6 micrograms *Renilla* luciferase reporter vector DNA, and additional plasmid (pUC18) DNA are added to each well in order to maintain the total amount of RNA plus DNA constant at 12.5 micrograms per well. To each well is added 160 microliters ($2 \times 10^6$ protoplasts per milliliter) of maize protoplasts. Protoplasts are made transformation-competent by treatment with a solution containing 4 grams PEG 4000, 2 milliliters water, 3 milliliters 0.8 molar mannitol, and 1 milliliter $Ca(NO_3)_2$. The protoplasts are co-transformed with the test recombinant DNA constructs of the invention, where the target gene is firefly luciferase, together with the reporter vectors for firefly luciferase and *Renilla* luciferase, into 4 separate volumes of maize protoplasts; the test constructs can be delivered in a vector. The relative level of suppression of the target gene, firefly luciferase, is indicated by the intensity of firefly luciferase emission ("Fluc") normalized to *Renilla* luciferase emission (Rluc). A negative control test vector is, for example, one similar to the test vectors containing the gene suppression elements but containing a gene suppression element targeting a non-relevant gene such as beta-glucuronidase (GUS) (uidA). A positive control test vector is, for example, one similar to the test vector but containing, for example, the full-length firefly luc gene. The relative level of suppression of the target gene, firefly luciferase, is given as the logarithm of the ratio of firefly luciferase emission to *Renilla* luciferase emission, "log(Fluc/Rluc)".

Transient assays such as the one described in the preceding paragraph can be designed to optionally simultaneously assay for expression of a gene of interest. For example, a model gene of interest can include GFP. The experiments are carried out as in the preceding paragraph, where the test recombinant DNA constructs can contain both a first gene suppression element for suppressing the target gene and a gene expression element for expressing a gene of interest such as GFP. The expression of GFP can be simultaneously monitored by spectrophotometry as is the firefly and *Renilla* luciferase emission.

Example 8

This example describes various non-limiting embodiments of recombinant DNA constructs of the invention and useful in making transgenic eukaryotes (including transgenic plant cells, plants, and seeds) of the invention. One non-limiting application of these constructs is, for example, suppression of at least one target miRNA precursor or miRNA promoter, or non-systemic gene suppression of a gene endogenous to a plant or to a pest or pathogen of the plant.

FIG. 8A schematically depicts non-limiting examples of recombinant DNA constructs of the invention for suppression of at least one target gene. These constructs include at least one first gene suppression element ("GSE" or "GSE1") for suppressing at least one first target gene, wherein the first gene suppression element is embedded in an intron flanked on one or on both sides by non-protein-coding DNA. These constructs utilize an intron (in many embodiments, an intron derived from a 5' untranslated region or an expression-enhancing intron is preferred) to deliver a gene suppression element without requiring the presence of any protein-coding exons (coding sequence). The constructs can optionally include at least one second gene suppression element ("GSE2") for suppressing at least one second target gene, at least one gene expression element ("GEE") for expressing at least one gene of interest (which can be coding or non-coding sequence or both), or both. In embodiments containing an optional gene expression element, the gene expression element can be located outside of (e.g., adjacent to) the intron. In some embodiments, the intron containing the first gene suppression element is 3' to a terminator.

To more clearly differentiate recombinant DNA constructs of the invention (containing at least one gene suppression element embedded within a single intron flanked on one or on both sides by non-protein-coding DNA) from the prior art, FIG. 8B schematically depicts examples of prior art recombinant DNA constructs. These constructs can contain a gene suppression element that is located adjacent to an intron flanked by protein-coding sequence, or between two discrete introns (wherein the gene suppression element is not embedded in either of the two discrete introns), or can include a gene expression element including a gene suppression element embedded within an intron which is flanked by multiple exons (e.g., exons including the coding sequence of a protein).

Example 9

This example describes various non-limiting embodiments of gene suppression constructs of the invention. FIG. 9 depicts various non-limiting examples of gene suppression elements and transcribable exogenous DNAs useful in the recombinant DNA constructs of the invention. Where drawn as a single strand (FIGS. 9A through 9E), these are conventionally depicted in 5' to 3' (left to right) transcriptional direction; the arrows indicate anti-sense sequence (arrowhead pointing to the left), or sense sequence (arrowhead pointing to the right). These gene suppression elements and transcribable exogenous DNAs can include: DNA that includes at least one anti-sense DNA segment that is anti-sense to at least one segment of the at least one first target gene, or DNA that includes multiple copies of at least one anti-sense DNA segment that is anti-sense to at least one segment of the at least one first target gene (FIG. 9A); DNA that includes at least one sense DNA segment that is at least one segment of the at least one first target gene, or DNA that includes multiple copies of at least one sense DNA segment that is at least one segment of the at least one first target gene (FIG. 9B); DNA that transcribes to RNA for suppressing the at least one first target gene by forming double-stranded RNA and includes at least one anti-sense DNA segment that is anti-sense to at least one segment of the at least one target gene and at least one sense DNA segment that is at least one segment of the at least one first target gene (FIG. 9C); DNA that transcribes to RNA for suppressing the at least one first target gene by forming a single double-stranded RNA and includes multiple serial anti-sense DNA segments that are anti-sense to at least one segment of the at least one first target gene and multiple serial sense DNA segments that are at least one segment of the at least one first target gene (FIG. 9D); DNA that transcribes to RNA for suppressing the at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of inverted repeats (FIG. 9E); and DNA that includes nucleotides derived from a miRNA, or DNA that includes nucleotides of a siRNA (FIG. 9F).

FIG. 9F depicts various non-limiting arrangements of double-stranded RNA that can be transcribed from embodiments of the gene suppression elements and transcribable exogenous DNAs useful in the recombinant DNA constructs of the invention. When such double-stranded RNA is formed, it can suppress one or more target genes, and can form a single double-stranded RNA or multiple double strands of RNA, or a single double-stranded RNA "stem" or multiple "stems". Where multiple double-stranded RNA "stems" are formed, they can be arranged in "hammerheads" or "cloverleaf" arrangements.

Example 10

This example describes various non-limiting embodiments of recombinant DNA constructs of the invention and useful in making transgenic eukaryotes (including transgenic plant cells, plants, and seeds) of the invention. More specifically, this example describes embodiments of gene suppression constructs that transcribe to RNA capable of forming multiple double-stranded "stems" and suppress one or more target genes.

To form a double "hairpin" molecule or a double-stranded RNA structure resembling a "hammerhead", a recombinant DNA construct is designed to include a single-stranded, contiguous DNA sequence including two non-identical pairs of self-complementary sequences is used, wherein the DNA can transcribe to RNA also including two non-identical pairs of self-complementary sequences that can form two separate double-stranded RNA "stems". Each member of a non-identical pair of self-complementary sequences preferably includes at least about 19 to about 27 nucleotides (for example 19, 20, 21, 22, 23, or 24 nucleotides) for every target gene that the recombinant DNA construct is intended to suppress; in many embodiments the pair of self-complementary sequence can be larger than at least about 19 to about 27 base pairs (for example, more than about 30, about 50, about 100, about 200, about 300, about 500, about 1000, about 1500, about 2000, about 3000, about 4000, or about 5000 base pairs) for every target gene that the recombinant DNA construct is intended to suppress. Each non-identical pair of self-complementary sequences can be separated by spacer DNA, for example, additional nucleotides that can form a loop connecting the two strands of RNA forming a double-stranded hairpin, or that can separate adjacent double-stranded RNA "stems". Spacer DNA can include nucleotides that are located at the distal end of one or both members of the pair the self-complementary sequences, for example, where inclusion of these nucleotides as "spacer" sequence facilitates the formation of the double-stranded RNA structures, or facilitates the assembly and maintenance of these sequences in plasmids. Spacer DNA can include sequence encoding an aptamer. The non-identical pair of self-complementary sequences can include sequence derived from a single segment of a single target gene, multiple copies of a single segment of a single target gene, multiple segments of a single target gene, segments of multiple target genes, or any combination of these, with or without spacer DNA. Multiple "hairpins" can be formed in an analogous fashion by including more than two non-identical pairs of self-complementary sequences that can form two separate double-stranded RNA "stems".

Figure 10:
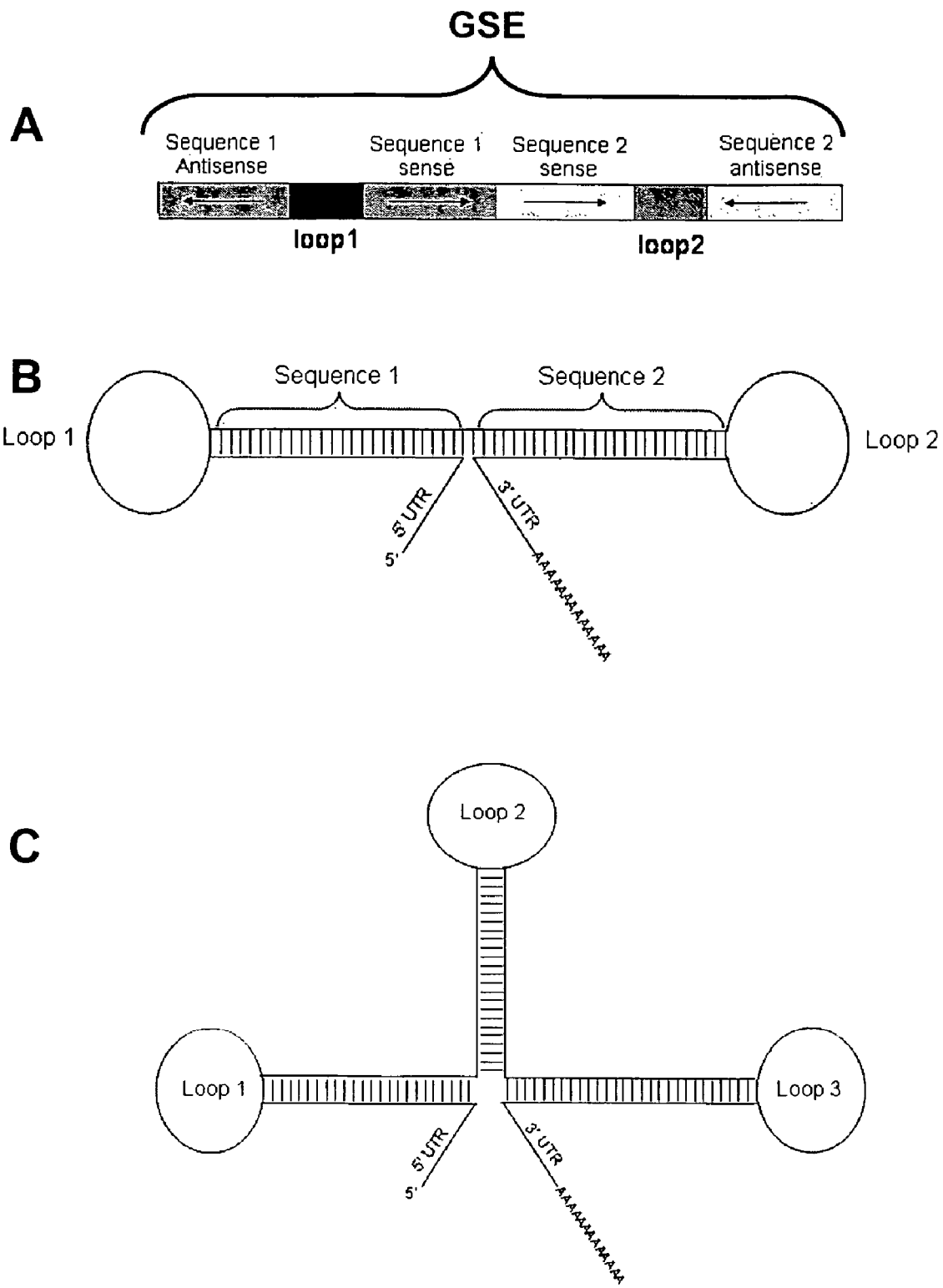
FIG. 10A depicts a non-limiting gene suppression element ("GSE") useful in recombinant DNA constructs of the invention, as described in Example 10.
FIG. 10B depicts a representation of the type of RNA double hairpin molecule that it would be expected to produce. In this example, orientations of the sequences are anti-sense followed by sense for sequence 1, then sense followed by anti-sense for sequence 2 (FIG. 10A). Analogous recombinant DNA constructs could be designed to provide RNA molecules containing more than 2 double-stranded "stems", as shown in FIG. 10C, which depicts an RNA molecule containing 3 "stems".

A specific, non-limiting example of this configuration of sequences is shown in FIG. 10, which depicts a gene suppression element ("GSE", FIG. 10A) useful in recombinant DNA constructs of the invention, and a representation of the type of RNA double hairpin molecule that it would be expected to produce (FIG. 10B). The double hairpin molecule is depicted with a 3' untranslated region including a polyadenylated tail; however, embodiments of the invention also include analogous constructs that produce a double hairpin molecule lacking a polyadenylated tail or a 3' untranslated region. In this example, orientations of the sequences are anti-sense followed by sense for sequence 1, then sense followed by anti-sense for sequence 2 (FIG. 10A). This arrangement may be convenient, e.g., when both sequence 1 and 2 are derived from the same target gene, in which cases the sense sequences can represent sequences that are contiguous in the native target gene. However, any order of sense and anti-sense sequences can be used in the recombinant DNA construct, as long as the transcribed RNA is capable of forming two separate double-stranded RNA "stems". Analogous recombinant DNA constructs could be designed to provide RNA molecules containing more than 2 double-stranded "stems", as shown in FIG. 10C, which depicts an RNA molecule containing 3 "stems".

Example 11

This example describes a non-limiting embodiment of the recombinant DNA construct of the invention, and methods for its use. More particularly, this example describes a recombinant DNA construct containing a gene suppression construct that transcribes to RNA capable of forming multiple double-stranded "stems" and that suppresses a first target gene, wherein the recombinant DNA construct can be transcribed in a transgenic plant, and the first target gene is a gene native to a pest or pathogen of the transgenic plant.

In this non-limiting example, an RNA molecule that is capable of generating a double hairpin structure is designed to be transcribed from a recombinant DNA construct containing a gene suppression element similar to that shown in FIG. 10A. In this specific example, the gene suppression element ("GSE") contains a first sense sequence and second sense sequence (as depicted in FIG. 10A), which are contiguous sequences from SEQ ID NO. 2 (a 872 nucleotide segment of the cDNA sequence of the corn root worm vacuolar ATPase gene). However, this method can be used for noncontiguous sequences, including sequences from different genes. The complete gene suppression element given as SEQ ID NO. 3 contains DNA sequences of SEQ ID NO. 2 arranged as follows: the reverse complement of the DNA segment starting at nucleotide 1 and ending at nucleotide 300 of SEQ ID NO. 2, followed by the DNA segment starting at nucleotide 100 and ending at nucleotide 600 of SEQ ID NO. 2, followed by the reverse complement of the DNA segment staring at nucleotide 300 and ending at nucleotide 500 of SEQ ID NO. 2. This gene suppression element (SEQ ID NO. 3) is embedded in a suitable intron (as described above under the heading "Introns") that is operably linked to a suitable promoter element (as described above under the heading "Promoter Elements"). Where it is desirable to transcribe RNA that is transported out of the nucleus, a terminator element can be included either embedded in the intron containing the GSE and operably linked to (5' to) the gene suppression element, or outside of and 5' to the intron containing the GSE.

Example 12

This example describes a non-limiting embodiment of the recombinant DNA construct of the invention, and methods for its use. More particularly, this example describes a recombinant DNA construct containing a gene suppression construct that suppresses a miRNA precursor molecule, e.g., a pri-miRNA.

The primary transcript of a miRNA gene (MIR gene), termed a pri-miRNA, is believed to be hundreds to thousands nucleotides in length and largely processed in the nucleus into a smaller (generally less than 100 nucleotides) stem-loop structure, which is then exported to the cytoplasm for further processing into a mature miRNA. By embedding a gene suppression element for suppressing a miRNA precursor molecule (for example, DNA that transcribes to RNA for suppressing a pri-miRNA by forming double-stranded RNA, preferably double-stranded RNA that lacks polyadenylation) into a spliceable intron, the resulting double-stranded RNA is expected to remain in the nucleus due to the absence of cis-acting nuclear export signals, resulting in suppression of the miRNA that is more efficient than that achieved by constructs that produce cytoplasmic dsRNA. Another potential advantage of this approach is that the miRNA precursors offer larger target sequences for suppression than does a mature miRNA. Alternatively, an intron-embedded gene suppression element can be designed to target the promoter sequences of the miRNA precursor, resulting in transcriptional gene silencing. See, for example, Matzke and Birchler (2005) *Nat. Rev. Genet.*, 6:24-35, Matzke et al. (2004), *Biochim. Biophys. Acta,* 1677:129-141, and Papp et al. (2003) *Plant Physiol.,* 132:1382-1390, all of which are incorporated by reference herein.

One general, non-limiting design for a recombinant DNA construct includes a suppression element for suppressing production of a mature miRNA and preferably designed to target the pri-miRNA sequence of a targeted MIR gene, wherein the gene suppression element is embedded in an intron (e.g., a heat shock 70, actin 1, or alcohol dehydrogenase intron) flanked on one or on both sides by non-protein-coding DNA, which is fused to a reporter gene (e.g., beta-glucuronidase GUS, or green fluorescent protein GFP) and driven by a constitutive (e.g., 35S) or tissue specific (e.g., B32) promoter. Such a construct generally resembles that shown in FIG. 7A, where the reporter gene can be upstream or downstream of the intron. The recombinant DNA construct can be transformed into *Arabidopsis* by standard techniques. Expression of the optional reporter gene confirms the proper processing of the intron in the transgenic *Arabidopsis* in which the construct is transcribed.

In a non-limiting specific example of this approach, a recombinant DNA construct of the invention is designed to suppress a specific allele, MIR164c, of the *Arabidopsis thaliana* microRNA gene MIR164. Loss-of-function of this allele, eep1, caused by T-DNA insertion, has been shown to increase the number of petals of early flowers in *Arabidopsis* (see Baker et al. (2005) *Curr. Biol.,* 15:303-315, which is incorporated by reference herein). One specific, non-limiting construct includes a heat shock 70 intron, within which is embedded a suppression element including DNA that transcribes to a sense/anti-sense double-stranded RNA for suppressing the pri-miRNA of MIR164c sequence, fused to GFP and driven by a 35S promoter. GFP expression confirms transcription and proper splicing of the construct in *Arabidopsis* plants transformed with the construct. The "early extra petal" phenotype of eep1 is used to score for the miRNA164c suppression.

In another non-limiting, specific example of this approach, a recombinant DNA construct of the invention is designed to suppress the *Arabidopsis thaliana* microRNA gene MIR172, which regulates the mRNA of a floral homeotic gene, APETALA2 (X. Chen (2004) *Science,* 303:2022-2025). Elevated miRNA172 accumulation results in floral organ identity defects similar to those in loss-of-function apetala2 mutants. On the other hand, the expression of mutant APETALA2 mRNA resistant to miRNA172 causes different floral patterning defects. One specific, non-limiting construct includes a heat shock 70 intron, within which is embedded a suppression element (for example, DNA that transcribes to a sense/anti-sense double-stranded RNA for suppressing the pri-miRNA of MIR162 sequence), fused to GFP and driven by a 35S promoter. GFP expression confirms transcription and proper splicing of the construct in Arabidopsis plants transformed with the construct. The floral patterning defect phenotype is used to score for the miRNA172 suppression.

Example 13

This example describes a non-limiting embodiment of a recombinant DNA construct of the invention, and methods for its use. More particularly, this example describes identifying a MIR gene in maize and, further, making and using a recombinant DNA construct containing a gene suppression element that suppresses production of the mature miRNA transcribed from the identified MIR gene in maize.

A single small RNA was isolated and cloned using procedures based on published protocols (Llave et al. (2002) Plant Cell, 14:1605-1619, and Lau et al. (2001) Science, 294:858-862). Low molecular weight RNA was isolated from developing maize endosperm. Adaptors were ligated followed by RT-PCR for conversion of RNA to DNA. Additional PCR amplification followed by TA cloning and sequencing led to the identification of a highly abundant 22-mer in maize endosperm corresponding to the DNA sequence TGAAGCTGCCAGCATGATCTGG (SEQ ID NO. 4). Sequence alignment analysis showed that the isolated 22-mer sequence is homologous to a rice sequence annotated as "Oryza sativa precursor microRNA 167g gene, complete sequence" (GenBank accession number AY551238, gi:45593912) and having the sequence, GAAGATATTAGTTCTTGCTGGTGTGAGAGGCTGAAGCTGCCAGCATGATCTGG TCCATGAGTTGCACT GCTGAATATATTGAATTCAGCCAGGAGCTGCTACTGCAGTTCTGATCTCGATCTGCATTC GTTGTTCTGA GCTATGTATGGATAATGATCGGTTTGAAGGCATCCATGTCTTTAATTTCATCGATCAGATCATGTTGCAGC TTCACTCTCTCACTACCAGCAAAACCATCTCA (SEQ ID NO. 5, with the homologous nucleotides indicated by bold, underlined text). A proprietary maize genomic DNA sequence database was searched for sequences containing 22-mer segments identical to SEQ ID NO. 4 or to its complement. The sequences thus identified included overlapping SEQ ID NO. 6, SEQ ID NO. 7, and SEQ ID NO. 8, as given in Table 3, with the location of the 22-mer indicated by underlined text.

TABLE 3

| SEQ ID NO. | Sequence |
|---|---|
| 6 | GTTTTGGCTTGTTCACCCCTCATGTGCACATGCTGTTACTCCGAAGCTTG CGCTTTTGTATTCGTTGTTGCATTGCAACCATCCCCGCCGAAGGTGAGCC GAAGGTAATCTTGGGTATTCTACCTGCAACACTTATTAATTCAAGCTACA AAACAGTTGTCGAGTTAGTTTTTTTTTTACCTTCGAAAAGAAGACTTCCG GCAATGCACAACTTCCCATCTGCATTATCGTGAGCAGGATTGTAGGCACA CAGTGATGACGAAGACAGAGACAGCAATATACACAACCGAACCAAGAGAG AAGCAAAGGCATAATAATAAAAAAAGAGAGAGGAAACTAGATCGACAAGG CCATTATTATCACGGATAATTAATCAACGTCGTCAACGGCGGAAATAAGC TAGCTTGACTGGTGGTCTCTGGCGAGTGCAGCATGGATATGAATTGCAGG AGGGTGAGCTAGCTAGGGTTTTCGATGTGCGGCCACCAGCAGATGAAACT ACAGCATGACCTGGTCCTGGTGCTCATTAATTACCCTCTCTCTCTCTCCC TTCCCCTCTCATCTTGGATTCGTCGATCCATATATGACAGTCAGGGACGG GGGAGAGAGAGAGAGTGACAGGGGCCGGTAGTAGTATAGATTACATCCAT TTTACATATACCACCACCATCATAACCAGATCATGCTGGCAGCTTCACCA ACTCGTGGTGCACCACTACATACCCTCTCGTCTGATCCAAACGGAGGAAG GAGGAAGAA |
| 7 | TTGGCTTGTTCACCCCTCATGTGCACATGCTGTTACTCCGAAGCTTGCGC TTTTGTATTCGTTGTTGCATTGCAACCATCCCCGCCGAAGGTGAGCCGAA GGTAATCTTGGGTATTCTACCTGCAACACTTATTAATTCAAGCTACAAAA CAGTTGTCGAGTTAGTTTTTTTTTACCTTCGAAAAGAAGACTTCCGGCA ATGCACAACTTCCCATCTGCATTATCGTGAGCAGGATTGTAGGCACACAG TGATGACGAAGACAGAGACAGCAATATACACAACCGAACCAAGAGAGAAG CAAAGGCATAATAATAAAAAAAGAGAGAGGAAACTAGATCGACAAGGCCA |

TABLE 3-continued

| SEQ ID NO. | Sequence |
|---|---|
| | TTATTATCACGGATAATTAATCAACGTCGTCAACGGCGGAAATAAGCTAG |
| | CTTGACTGGTGGTCTCTGGCGAGTGCAGCATGGATATGAATTGCAGGAGG |
| | GTGAGCTAGCTAGGGTTTTCGATGTGCGGCCACCAGCAGATGAAACTACA |
| | GCATGACCTGGTCCTGGTGCTCATTAATTACCCTCTCTCTCTCTCCCTTC |
| | CCCTCTCATCTTGGATTCGTCGATCCATATATGACAGTCAGGGACGGGGG |
| | AGAGAGAGAGAGTGACAGGGGCCGGTAGTAGTATAGATTACATCCATCTT |
| | ACATATACCACCACCATCATAACCAGATCATGCTGGCAGCTTCACCAACT |
| | CGTGGTGCACCACTACATACCCTCTCGTCTGATCCAAACGGAGGAAGGAG |
| | GAAGAAGAGCTAGCTATCCGAGAGAGAGGGAGAGGGTAGAGAGATGGAGA |
| | GAGCGAGGAATGAATTGAAGAACCGAGGGATAGCTATAGCTATATATATA |
| | TGGGGATGGGGAGGCCAACGTCTCGCTCACTCGC |
| 8 | TATTCTACCTGCAACACTTATTAATTCAAGCTACAAAACAGTTGTCGAGT |
| | TAGTTTTTTTTTTACCTTCGAAAAGAAGACTTCCGGCAATGCACAACTTC |
| | CCATCTGCATTATCGTGAGCAGGATTGTAGGCACACAGTGATGACGAAGA |
| | CAGAGACAGCAATATACACAACCGAACCAAGAGAGAAGCAAAGGCATAAT |
| | AATAAAAAAGAGAGAGGAAACTAGATCGACAAGGCCATTATTATCACGG |
| | ATAATTAATCAACGTCGTCAACGGCGGAAATAAGCTAGCTTGACTGGTGG |
| | TCTCTGGCGAGTGCAGCATGGATATGAATTGCAGGAGGGTGAGCTAGCTA |
| | GGGTTTTCGATGTGCGGCCACCAGCAGATGAAACTACAGCATGACCTGGT |
| | CCTGGTGCTCATTAATTACCCTCTCTCTCTCTCCCTTCCCCTCTCATCTT |
| | GGATTCGTCGATCCATATATGACAGTCAGGGACGGGGGAGAGAGAGAGAG |
| | TGACAGGGGCCGGTAGTAGTATAGATTACATCCATCTTACATATACCACC |
| | ACCATCATAACCAGATCATGCTGGCAGCTTCACCAACTCGTGGTGCACCA |
| | CTACATACCCTCTCGTCTGATCCAAACGGAGGAAGGAGGAAGAAGAGCTA |
| | GCTATCCGAGAGAGAGGGAGAGGGTAGAGAGATGGAGAGAGCGAGGAATG |
| | AATTGAAGAACCGAGGGATAGCTATAGCTATATATATATGGGATGGGGA |
| | GGCCAACGTCTCGCTCACTCGCAGCGTATTTTGATGCCCTTTTTTATTTG |
| | TTGCATTTCGATCCATTTTCTTTTGTCCTGCGCTTTTTTCGTACGATGTT |
| | TGTTGCAAGGATAAGCCTTTCGG |

These three sequences (SEQ ID NO. 6, SEQ ID NO. 7, and SEQ ID NO. 8) overlapped to give a single contiguous sequence SEQ ID NO. 9, GTTTTGGCTTGTTCACCCCT-CATGTGCACATGCTGTTACTCCGAAGCT-TGCGCTTTTGTATTCGTTGTTGC ATTGCAACCATC-CCCGCCGAAGGTGAGCCGAAGGTAATCTTGGGTAT TCTACCTGCAACACTTATTAATT CAAGCTACAAAA-CAGTTGTCGAGTTAGTTTTTTTTTTAC-CTTCGAAAAGAAGACTTCCGGCAATGCACAA CTTCCCATCTGCATTATCGTGAGCAG-GATTGTAGGCACACAGTGATGACGAAGA-CAGAGACAGCAATAT ACACAACCGAACCAA-GAGAGAAGCAAAGGCATAATAATAAAAAAAGAGAG AGGAAACTAGATCGACA AGGCCATTATTATCACG-GATAATTAATCAACGTCGTCAACGGCG-GAAATAAGCTAGCTTGACTGGTGGT CTCTGGC-GAGTGCAGCATGGATATGAATTGCAGGAGGGTGAG CTAGCTAGGGTTTTCGATGTGCGGCCA CCAGCA-GATGAAACTACAGCATGACCTGGTCCTG-GTGCTCATTAATTACCCTCTCTCTCTCTCCCTTCCC CTCTCATCTTGGATTCGTCGATC-CATATATGACAGTCAGGGACGGGG-GAGAGAGAGAGAGTGACAGGG GCCGGTAGTAG-TATAGATTACATCCATCTTACATATACCACCACCATC ATAA<u>CCAGATCATGCTGGCAGCTTCA</u>CCAA CTCGTGGTGCACCACTACATAC- CCTCTCGTCTGATCCAAACGGAGGAAG-GAGGAAGAA GAGCTAGCTATCCGAGAGAGAGG-GAGAGGGTAGAGAGATGGAGAGAGCGAGGAATGA ATTGAAGAAC CGAGGGATAGCTATAGC-TATATATATATGGGGATGGGGAGGC-CAACGTCTCGCTCACTCGCAGCGTATT TTGATGC-CCTTTTTTATTTGTTGCATTTCGATCCATTTTCTTTT GTCCTGCGCTTTTTTCGTACGATGTTTGT TGCAAG-GATAAGCCTTTCGG (with the location of the 22-mer indicated by bold, underlined text). This was identified as a maize MIR167 sequence which transcribes to a pri-miRNA. Recombinant DNA constructs of the invention, containing one or more suppression elements for suppressing the identified MIR167 pri-miRNA (or a pre-miRNA) are designed and transformed into maize plants by procedures such as those described above under the heading "Recombinant DNA Constructs for Suppressing Production of Mature miRNA and Methods of Use Thereof" and elsewhere in this disclosure (e.g., by *Agrobacterium*-mediated transformation). One non-limiting suppression element is an inverted repeat containing one or more sense and anti-sense pairs of SEQ ID NO. 4, embedded in an intron. Suppression of production of the mature miRNA corresponding to the identified MIR gene is detected by analysis of low molecular weight RNA from resulting transgenic maize endosperm and other tissues (e.g., embryo, leaf, root, flower) for example, by using a labelled oligoprobe corresponding to the 22-mer (SEQ ID NO. 4 or its complement). Transgenic suppression of production of the mature miRNA encoded by a MIR167 gene, is useful, for example, for identifying related genetic elements or to manipulate the pathways that are controlled by MIR167, e.g., by identifying target genes suppressed by a mature miRNA encoded by a MIR167 gene. Thus, the transgenic tissues are also analyzed for morphological and compositional changes (such as, but not limited to, changes in primary metabolite, secondary metabolite, trace element, carotenoid, or vitamin composition or modified responses to biotic or abiotic stress, or modified yield) to assess the function of the maize MIR167.

Example 14

This example describes novel mature miRNAs and MIR genes identified in crop plants (maize and soy). Novel MIR sequences were identified in proprietary expressed sequence tag (EST) sequence databases from crop plants. The criteria that were used for identifying MIR genes included a conserved miRNA sequence of at least 19 nucleotides, a stable predicted fold-back structure encompassing the miRNA in one arm, and the absence of a significant open reading frame (ORF). Seven MIR sequences were identified in maize (*Zea mays*): SEQ ID NO. 10 (Zm-MIR164e, including the DNA sequence SEQ ID NO. 11 corresponding to the conserved mature miRNA miR164e), SEQ ID NO. 12 (Zm-MIR319-like, including the DNA sequence SEQ ID NO. 13 corresponding to the conserved mature miRNA miR319-like), SEQ ID NO. 14 (Zm-MIR393b, including the DNA sequence SEQ ID NO. 15 corresponding to the conserved mature miRNA miR393b), SEQ ID NO. 16 (Zm-MIR399g, including the DNA sequence SEQ ID NO. 17 corresponding to the conserved mature miRNA miR399g), SEQ ID NO. 18 (Zm-MIR408b, including the DNA sequence SEQ ID NO. 19 corresponding to the conserved mature miRNA miR408b), SEQ ID NO. 20 (Zm-MIR398, including the DNA sequence SEQ ID NO. 21 corresponding to the conserved mature miRNA miR398), and SEQ ID NO. 22 (Zm-MIR397, including the DNA sequence SEQ ID NO. 23 corresponding to the conserved mature miRNA miR397). Six MIR sequences were identified in soybean (*Glycine max*): SEQ ID NO. 24 (Gm-MIR393a, including the DNA sequence SEQ ID NO. 25 corresponding to the conserved mature miRNA miR393a), SEQ ID NO. 26 (Gm-MIR393b, including the DNA sequence SEQ ID NO. 27 corresponding to the conserved mature miRNA miR393b), SEQ ID NO. 28 (Gm-MIR399, including the DNA sequence SEQ ID NO. 29 corresponding to the conserved mature miRNA miR399), SEQ ID NO. 30 (Gm-MIR164a, including the DNA sequence SEQ ID NO. 31 corresponding to the conserved mature miRNA miR164a), SEQ ID NO. 32 (Gm-MIR164b, including the DNA sequence SEQ ID NO. 33 corresponding to the conserved mature miRNA miR164b), and SEQ ID NO. 34 (Gm-MIR164c, including the DNA sequence SEQ ID NO. 35 corresponding to the conserved mature miRNA miR164c). The novel MIR sequences are given in Table 4, with the location of nucleotides corresponding to the mature miRNA indicated by underlined text.

TABLE 4

| SEQ ID NO. | Sequence |
|---|---|
| 10 | GTATGTTCTCCGCTCACTCCCCCATTCCACTCTCATCCATCTCTCAAGCTACACACA |
| | TATAAAAAAAAAAGAGTAGAGAAGGACCGCCGTTAGAGCACTTGATGCATGCGTA |
| | CGTCGATCCGGCGGACCGATCTGCTTTTGCTTGTGTGCTTGGTGAGAAGGTCCCTGT |
| | TGGAGAAGCAGGGCACGTGCAGAGACACGCCGGAGCACGGCCGCCGCCGATCTA |
| | CCGACCTCCCACACCTGCCTTGTGGTGTGGGGGTGGAGGTCNNNNNNCGNAGCGAG |
| | AGCTGNCGNTGNTGNTTNGATGCTGNTNGCTCCTCCTGCNCGTGCTCCCCTTCTCCA |
| | CCACGCCTTCTCACCACCCTCCTCCCCCGGCGGCGGCGGCGGCGGACCGCCCTTGC |
| | CGCGATCAATAATGAAACCAAAAGCCGACAGTGTTTGAGCAGGAAACACAAAAGG |
| | CGGATATCCCACTGNTAGCACTTCTGCGTTGATCATGGTCATCTGGAACAAAATAA |
| | TACTTGGGGACTTTACAGCGAGTGCAGCATGCTTAAGCTAGTTC |

TABLE 4-continued

| SEQ ID NO. | Sequence |
|---|---|
| 12 | TTCGGTCCAAGTAGTGGTGGTCATAATATGCTCCAAATAAAAGAAAGGTGGAGGAG |
| | CATCTCACAGACGACACAGCTGCTATGCTAGCACACGTCGAATCAATAGCTAGTTG |
| | CATGCAAAGTTCCAAAGCAAATAAACAGTGAGATCGAAAGACGTTTCGCTGTTGCA |
| | CGACACGACGAATCGATCGAACGAAAGTGTGTTTTTATGATTCCACAGATTCTCGTT |
| | TATATATAATCCTAGCTAGCTAATCTAGAACGTACAGTGCACACCATCTTCTTCCAC |
| | AGATCACAGAAAGACAGCAGAAACCTGCATGGATCGGATCCGGTCCTGTCCTGTAA |
| | GATCTACACACATGCAAAGCAAATCAATTTCTTCCTTTTCTTTTCTTCAGAAACTGGG |
| | ATAACTTTTTGGAAGAGATCGAACAGTATATAGATTCAGGGAGCAGATCAAGGATT |
| | ATATATATAGCTAGTATGTGTACATATCAAAAGGGCAAGAAAAGTACAAAAAAGCA |
| | TCGGATCTCCATTATATATATACAACAGCTATATAACAACCACAGAAGAACAGTAAG |
| | CACGCACATGGTAAAATTAAAATAGCCTGGCAGCTGCTATGGATGTATGCATCAGAT |
| | GCCTAATATATATGCAAGATAATAATTAATAAGCAGCTCAAGCAAAGACAGATCAA |
| | GAGTTCGAGACAGCAGGTTGGAAAATAAAATACAGATCATATGAAGTAAAACCTTG |
| | ACTTGAGATACGAATGATGAAGCTGCATGGGTAAAGTAAACAAGGAAAGGATCGGA |
| | GGGAGCACCCTTCAGTCCAAGCAAAGACGGTGCGAGATCGAAGCTTTTACCTCCCGC |
| | TTCATTCACTCATCTGCGAAGCTCGTTTCCATGGCCGTTTGCTTGGCATGTGGGTGAA |
| | TGAGTCGGCAGCTAATCCGACCCTAGCACCGCCCCTGAGTGGACTGAAGGACGCT |
| | CTCTTCCATCCGGCCGGCGACCATCGATCACAACCATGACGCCGCGCCCGGCGGCA |
| | AATATATTAACAAGAAATGAAATCAAAAGAGAGAGGAAGAACAAACATGATGCGC |
| | AGCTGCGCTAGCTAGTGCTTGATCTGTCTGACCACCTCATGGCGCGCAGTGTTTAGT |
| | TTTCTCCCTGGATCTTGCGAAGAAGGCGATGGATTTTCGATGGTTGCAAGGAGGAG |
| | CGACCGACAAAGGGTTTATATAATATGTAGACGGC |
| 14 | GCCGGCCGGGTCGGGATGCCGCCTACTAGCAGGAAGCTAGTGGAGGACTCCAAAG |
| | GGATCGCATTGATCTAACCTGCCGATCGACGCCGACGTACGTACGTGCCCGAGGA |
| | CAAGCAGATCAGTCAGTGCAATCCCTTTGGAATTCTCCACTTAGCGCCTCCATCCCC |
| | GCGCCGCCCTCCAGGTTTCGCTTCGATCCATCCATGTTTCCTTCGTTTAAATTAGTTC |
| | GTTTGTTTTTTTTTATTATTTATTTGATTCGCCGCCGCCGGTCTATCTACTCTGTTTG |
| | CAACGCCTTTCGATCCATCGGCTTCTACTGTATGCTATAATTAAGGGTTTTTTTACAT |
| | TGGTCCGATGCATGAGAGGAGCTGTGCAGACCAACATGGCAACCAATTACATCGAT |
| | CTTGAGGACTCTTATGGACCAACATGCCAAGTTCTTCATTGCTTGTACTACCATTCA |
| | AGTTGTCAAACAATTACCAATTAACTCAAGTATTCGAGAGAAGCATATATGTTAGTC |
| | AAATAGCAAATTCTTTACTAACTGATCTATGTACCGACATGTCAACTTCTTGCATAC |
| | CAACGTGGCAAGAAGGTAATCATTGTTCATGAATAAGATTATCACTA |
| 16 | CTAGGAATGGTACGGTGCTGGCTAAGCTAGCTAGATCATCGTCCTGGAGCTGAGAG |
| | CAGCAGCTACCTATATATCTAGCTGGTTTTCTAACGACGATGACGAACGACCGCGG |
| | GACTAGCATGATGCAGCTAGCTGAAGACAGTTGTAGGCAGCTCTCCTCTGGCAGGC |
| | AGGCGCGCGGTCATCGTCGCCATCGACGACGGTTGCTTGGCTCTGCTATGCTGTGT |
| | TCGTTCGGCCATGGTGTGCTAGCTAGCCGTGCATGCGTTGCAGTGTAACATGCGTG |

TABLE 4-continued

| SEQ ID NO. | Sequence |
|---|---|
| | CATGCACGCGCGTACGTCCTGCCAAAGGAGAGTTGCCCTGCGACTGTCTTCAGCT |
| | CGAACAAGATCGACCGGCCCGGACAGGAATGTTGGGCGTACGTTGTCATCAGGGT |
| | TTAAGCTCCACGATTCCAAATATTCACCACTTCTGGGAGGAGTTTTGAAGCTGCTC |
| | GAAAGCATATTGTGTCTGAGTGTAATAAATCGGCGGGGAATCATATGTTCATGTTC |
| | TCACTGCAAGAATAAGCTTGTCAAAGAGGGTGGTGAAGTAAAATCTCACCTGATC |
| | AGCGGCACAGGTGCTCCTAGCGACGGGTGTAAGTCATGGAGGACAAGCAACAGG |
| | AAGTCCACTGCCAAGTGCTTCCATCGTCGTCAAATCACAGGTCAGGGGTTAATTA |
| | TATGGGGAAGAGGCCATTATCATCAGGTACGCGTGGTTCTCACACAGTCGGGGC |
| | CACGTTCGTTGATGATCTGCCTCTTAATCGGCATCTCAAACTCTTGTTGTGCTCTCT |
| | ACATCAGTAGAGAAGGTGTGTTCACAAGTCGTTTCTTCTTAAGACTATGTTTTGGT |
| | TGATCTTGATCTATAGAACTATTTTATTGTAGAACTACTGAACCCTTTCGAAGTGT |
| | TGTACTCAATTTGTGTAGAACAATGCATGATTAATTTCTACCAATAGTCTACGGTA |
| | GCCGGTAGTTGTTTTATCCTACTAGAAATTGTTGCATGGTTAATTGGTTAATTTGT |
| | GTAGGATGTGCCAAAAGAAGAGGAAGAGAACACCATCAATATGAATGGTGAATT |
| | ATTCGTAAGCTTATCTTCCACTAATGGTGCTGGAAGCCAGAAGGAGAAAGAGGA |
| | GGATGGAGATCATGTGTCAAGGCTCAGGAGATAAATCGAGGAAGAAAAAGATCG |
| | AAGGGTGGTGTTTAGTTGTATCCTTCCAAGTTCCAAGTTCACGGTAAAGAGAGGA |
| | AAGTGTGCTAGTTCAAGAGAGTATGGGATGGAGATAGGCACCATTGGACTTGGAG |
| | TGGAGGACAAGATGTTACCATTTTGCATTTCCATGGAGCGTGGAGACTTCTGAGTG |
| | CTTCAATCTTTTTATTAAAAATCAGTCTGAGCGATGATGAGTCTAAAGAGACTAAG |
| | ACTATATCATAATCTACGATGGATTTAATCTATAAGGTGGATATATCACATATGGT |
| | TGCCAATCTTGTATATTTCATATTTGCATGGTTGGTAGTTGCACTGTTGCAATCTTA |
| | AGACCTGTATAGTTGCATATTTGATTGTGTTTTTAGAATGTTGATTTGTGGTTGTGC |
| | TCGCTTCTTTCT |
| 18 | GGTACCTTTAGCGTTAGCACAGACACACACAGGTAAGGAGAGCGAGAGGTGGGTT |
| | GGGTTTGATCGGAGACAGGGACGAGGCAGAGCATGGGTAGGGGGCCATCAACAG |
| | AATTCCAAATTTGATTTCTGTTTGCTCGCTCACAAAATGGAGGGACTCACCACAAA |
| | CACACTCAGGCGTTGTTGCTCCCTCCCCTGCACTGCCTCTTCCCTGGCTCCTCAC |
| | CGTCTCCCATCCACCTATCCTCTCTCTTTCTCTCTCTCGTTATGGTTTTGTATAATTT |
| | TTTTTCCTGCATTCTTTTCTCAGTACAAGTCCTACACTAATTTGGCTGTCTTTGCACC |
| | AGTACTAATAAACACCGCAGGTCCCTGCAATAGGGTTTACAACAATTCTATTGTAA |
| | TGACTGCTGTAAAACATCCGCATCATTTAATTCAACTTTCCGGTTTCAGTCAGCCCT |
| | GCAAAAGTGCTCCTCCGTTCGTCCGCGTTTGGTGTTGGCTTCTGCGGCTCCGGTGCC |
| | CAGAGTTGCTGCCGGCGGAGGCCGAGCAGGAGCGCAACTAACAAGAGCGGCCAA |
| | GGCGCCAGTGATCCTCACCATGGACAGGAGATCGATGGAGATGAGCGTGAGCTTC |
| | CGATGCTTCGGTACCCGAAGAAAAGAACGGGAACAAAGGCGAGAAACATGATCC |
| | ACCTCTATGCTTTTTTGGCAACATATCCTATGCTTAAACAGTTATGGTGTTCAAAT |

TABLE 4-continued

| SEQ ID NO. | Sequence |
|---|---|
|  | GTACACATTAATAGAGCGTTTGGTTTGAAGAATCACACCATCTAAATTGAGGTGG |
|  | TGCATCATGAATTTATTCCTTAAAAAAAAAAAAAAAAAAAAAAAA |
| 20 | GCCGGCCGGGTCGGGTGTGTTCTCAGGTCGCCCCCGATCACAGCCAACGCGGG |
|  | CGACCGCGCGCCATTATAGCACACGGGGCACGGCACGCCTTCGGCCTCCCACTAA |
|  | CTGCACAAGAGGACGACGCGGCAGCGAGGAGGGAGCAAAGGAAAGGGGATATG |
|  | TCGAGGCCGCCCAACAGGAGCGACGCGCACCTCTCCGCCGAGGACGAGGCGGCG |
|  | CTGGAGGCCGAGGTGCGGGAGTACTACGACGACGCGGCGCCAAAGCGCCACACC |
|  | AAGCCCTCCCGCAGCGAGCACTCCGCCGTGTACGTCGACGCGCTCGTCCCGGACG |
|  | TCGGCGGCAACTCCCACCCGGAGCTGGACAAGTTCCAAGAGCTGGAAGCCCACA |
|  | CCGAGAGGTTGGTGTACGAGGGCGCCAATGTGGGAGATGAGTTCGTAGAGACGG |
|  | AGTACTACAAGGACCTCGGCGGCGTCGGCGAGCAGCACCACACGACCGGAACGG |
|  | GCTTCATCAAGATGGACAAAGCTAAAGGCGCCCCCTTCAAACTGTCTGAAGATCC |
|  | CAATGCAGAGGAGCGACATGCTTCTTGCAGGGGAAACCCTGCTACCAACGAGTG |
|  | GATCCCGTCAGCTGACACGGTAAGACTGGGGGAGCACAGTCCAGTTTATCCTATG |
|  | CAGGTGCAGGGTCGGCTCCAATCGGCGTCTCTACTGACGAACGCATCGTTAGCTT |
|  | GTACCCAGCGTCAGACAAGCCAAGCAGAAGCGACAGCTGAGGGACTGTATATCT |
|  | CAAGCCATGAGAATTCAGACGAGTGCTTTCCGCCATTAGAATAAGGAACCACAC |
|  | TGGTTGTCCACCGTATCTTCACTGTTCTGCGTCGAGATTCTTGTGATTCTTACGTG |
|  | GAACAAATTAAGCGTGCTACGAGTTAGACCTCTGTGTTCTGGCTGTAAATGGCA |
|  | AGGAATGAAGTTCTAATCGTGGTTCAGCAGTCAATCAATTACTGTGTTTCTGATC |
|  | CTAAGGCTCTAGAAACAATCGGACCTTCAAAATAAACTAGGCGAAAATTCTATG |
|  | TCGTTTCG |
| 22 | GAGCGGGGTCTTGAAACTGGCTGCGCAGAAGGAAGGGATGAAGGGGTTCCTGGA |
|  | GCTCGACGCCGAGGTTTTCGAGCTTGCCCCTTCGTTCTTTCTGGTCGAGCTGAAGA |
|  | AGGCCAGCGGTGACACCATTGAGTACCAAAGGCTCGTGAGGGAAGAAGTGCGGC |
|  | CTGCGCTGAAGGATATGGTCTGGGCTTGGCAGAGCGACCGGCACCAGCAGCAGC |
|  | AGCAGCGGTGCGAGCAGTCTGTGCAAGGAGAGGACCAGCAGCAGCCGTTGTCGT |
|  | CTTTGCCGACGCAGCAGTAGTCACTGCACCACCAGTTGCGACCGCCATAACCAGA |
|  | TCACGTCAAAACTGCACCAAGCCGCACAGGACTAGTAACTCCCACTTGCATCGA |
|  | CGCTTATGTGATTGCGGAATTGTGTTTCAGGTTACCTGCCTGCTGCGGTAGGACCT |
|  | AAAACGCCTACCTGCCTACCATTTGGCATTTTTTTGTATACTGTACGTACATTAGA |
|  | GTAATAAACAAACATGCTTAACTTTTCAGCTTTCGATTGGAATGTGCTTTTCGATG |
|  | TAACTCTGTAACCAGTGTAGGTACGAAGTCGATTAGCCACAGGGTCTGGCCATGT |
|  | TGACCTCACGTAGCCCTGGTTCATTGGTGTAACAGTTTGTTGGCTGCGGCTTTACA |
|  | TTATTTTGTCTCTATGGATTACGGCTGCGACTATGTGTAGCTGAACAAGCTGGTAT |
|  | ATGATGAGCCCTGGAAACGTGTGTTTACTGCAGCTATTTGCAGCCAGTGACTGTT |
|  | GATACAAACGACGAAGTAGAGTTGGTTGTTTATGTAGGCACGCAGCATGACCATA |
|  | ATTATCCATGAATCATGGATAGATGCACAATGTTTAGGAAACAGGTGTGTGTGGC |

TABLE 4-continued

| SEQ ID NO. | Sequence |
|---|---|
| | TGGCTGGTGGTGCGAGAAGAGATGCGCTGCCTTGATGTACTGTACTGGGACTGGG |
| | AGGGATGCGTCTCGCAGTACAGTCTGTACTATCATCTCTACACGCACGCACGCAG |
| | GCTCGACGTGTCGGCGGCGGCGGTCCAGACTCCATATGGATCCGTAGTAGTACAA |
| | CCTGTTGGCGGGTAGTACAGGTTGGAGCACGCCTCTTCTTCAGTCTTCCTTCCTGA |
| | GATGAGGAGTCACTCACCAGCAAAACGCTTGCAGTACACCCCGCTCGCGGGCGTT |
| | GTTTATAGTGATCGGTAGCGTGAGCACAGAGCGCCATCAGAAGATGCAAAGAGA |
| | AAGAGAAGCAAAGGCATCATTGAGCGCAGCGTTGATGAGCCAGCCGCCGTGCC |
| | TCCCCTGTCGGCTGCGGCGGCTCACCAGCGCTGCACTCAATTACGCCTTTGCTTTC |
| | TCCCGCTGGCCGCGTGTGTGCAGAGCGGGCGGGCGTTCGGCATCATTCATCAGGT |
| | TTGCTTCATTTATTATGCACTCATCGAAGGCTTCTCCTTCGACACTGTCTAGGTGG |
| | CGCAGGATCTGAATCAGATGGGTGTCGTCTTCTTCCTCCATCTGCACTCCTGCCCC |
| | GTATGATGTCGGTGTCCTAGGACGGCCAGTTGTCTGCGTTCTGGCTTAACCCAATTA |
| | CCTGACGGGGCGGACGACGCTGATAATGATCAGAGAGAGCATGAGGCCATATGCA |
| | AGCCTAGACCTAGCTCCCAAACTATTAAAGGTTGCTTCGAGCCCTGGCTGTCATAT |
| | CAACTACCAACCAGTTTATGTCGATTATCAGTTCCTATCTATCACAACGCTCCACTG |
| | CACAACCTTAACCTTTACTGTAAACCTATAGTCACCTCATCGCTTACATCGGGTTTT |
| | TCCCCCTCTTTCGTAGACTTTTAGTTAACATCAAACAATGCATTTTATTGAAATCCA |
| | AAATACATCTGACTGCGTAATTGAGTAGATTTATCCCAAAATTTAATTAGCATGCC |
| | GCTGTGAGCTAGGAGAGCGACACTAGTTTACAATATGACAGTGTTTGTGTTCGGC |
| | CAAACCATTTTTGTTGATGGGTAAGGGGACACGACCCCCAAATAGACGCTCTCATT |
| | TTAATGAAGAATTAGTTGTGGACTAATTGATAATTCCCATTACAAATCGGATTGCAC |
| | GCATTAAATCTTAGTGCTAAGGAGGTGTTACAAATGAACCTAAAAAAGAAAAGAT |
| | AATTGTTGAWTTAATGTGGGTCTGGTCCATATTAATATTCAATAATTGTCAATGCT |
| | AGTTGTCACTTTATGCTACGGTGTACTAGTACTTACCAAACTAGAAGTTTAAGGGA |
| | CAATTCACTYAACTTAAATAGGTGGACTATTGGTGCATCTATTGAGAAGCTGAGAA |
| | AAGGATGAAGGACTGTCACGCGTGCGCGCACCCTGATCTGTTGAGAAGCTGAGAT |
| | CGTAGGAACAAGAATCACTAAATTCGGAGTTACAGATTTCAAGTTATGATTTTTCG |
| | AAGGTTTTATGTGTTTGGTACGGAATTGATTAAGTGATCAATTTTAATATGGGTTTC |
| | ATGCTAAAACTGAGGTACTAAGTGGTAAACAAAATTATAGAAATTGGAATGGGTTA |
| | AAAAGGAGTTTGCATGATTTTCCTATGAATTATACAAGATTATGGATTTATTTTAAT |
| | ACCAAAATCACTTTTTATATTTATTTTACCCTGGTTTTCTATCCACTAGACTGCGCCC |
| | AAGATTATACTAAAGTTTAGGGGCAACTGCATAAAAAAACTAAGACTTAGGGCCCG |
| | TTTGTGATGGACTGCGGGTTGATAACTTAGAAACAGAGGGTCTCTTATGTAAACTGT |
| | ATGTGCTGAAGGGGTATGAAGCATCTACGATCGTCAGATTACAATTCCACGGCCAA |
| | GATTAAATCGCCAGTGCGATGAACCGTTACGTAACAGCCATCATCCGATCTGAGAT |
| | CTACGACCCTGATTCTAAATGCCCTAAAACCTCCCAGATCCACTCCCTTTGTCCGAA |
| | TCGGTACGCATCGGATTAAATCGCAGCCGCACTCTGATGGATCTACGGCCCACGCAG |
| | ATCATCCCCCATACCAACGGCGAACGGGCGCCGCCGCCCGTAAACACGGCGGTGGC |

TABLE 4-continued

| SEQ ID NO. | Sequence |
|---|---|
|  | CATGGCCGTGGATGGCCAACTCGACTTCGAGGCCGTAATCCTCTAGTCTAAGACGTG |
|  | CTACGTGGTAAGTGGATGAAGACGATTTCCATGGGTTCAGTACTTACCGAGGGCAAG |
|  | GTCGTGCACAAGCTGTTCACGGCGAAGCGCGGCCGTAGCAAAAATTGAAAGGGAAA |
|  | TGTGACTTTGGGCTATTTCTATAAATGTTTTGGTGATTAGATGCCCAACACATATTGT |
|  | TTTAGTTCATATGTGCTAAGTGATTGAGAAGTGCAAATCAAGAATCAAGGTATATTT |
|  | CTAGCCCTAGTAAATTTCTTTTGGATACTAACATATCTCTCTAAGTGCTAGGGACACT |
|  | ACCAAGAAAAGTGGAAATGAACTGGAGAAGTTTGGCAGAGT |
| 24 | ACCATTACACTCTTAGTGAATATTTCATAAAATATAAAGTTCCTCCTGGGCGAGAAA |
|  | CATCTCCATGTTTAAGGAAACAGTGCGAAGAATTATTACACCAGACATATTCAAGGC |
|  | AACTAGTGGAATCCAATAAGGAATGCTGGCCCACTGCGGAAAATATTTCGGGTTGAA |
|  | TGATAGGGAAGGGGCTCATTCAACAAAAATCTTAATTTTCTCGGAGATTGGCAAATC |
|  | TACATTGACAAGATAAATAAATAATTTATGAAAACAATAAAAAAATGATAATGGAA |
|  | ACAGGGCTTATAATATAAGCACTACTAAGCTAGTTTGTTTCTCCTACGCTAAAAGCCT |
|  | AATCTCAAACCTACCCACTTCCTACAAGAGAGAAAGGGGGGGATAGTGTATAATACC |
|  | CTCAACTTCGAACCAATATTCATCAGAAGTAGAGGTGTGGGTATTCTTCCACTGCAAC |
|  | TGGAGGAGGCATCCAAAGGGATCGCATTGATCCCAAATCCAAGCTTTAATATTTTT |
|  | CTCTCTTCTCACTCAATAATATTAATTTATTTGGGATCATGCTATCCCTTTGGATTTCT |
|  | CCTTTAATGGCTTCTATAATGATGGCTCTCTCATGGATTCTGCTTGCTGCACCACAACA |
|  | CAAACACTTTCATATACGCCTCTAATGCT |
| 26 | CACAATACAATTAAGCTCATCATACTGGTCCTGAAATTGGTGAATAAAGTTGTTTGT |
|  | GGTGGATGAGTACTGAGTAGTGGTGCCTTATTGTGGGTGGAGAGTTCCAAAGGGAT |
|  | CGCATTGATCTAATTCTTGTAGATGTTTACACTTGCAAGCTTTGCATGCAATTCCTGG |
|  | ATTCAGATGTTATTCAGTGGTTCACTTATTGGATCATGCGATCCCTTAGGAACTTTCCA |
|  | TCAACTCTAAACATCTTGTTGATCCATTTGAGGAATTAATTTCATAGGTTCATATAATG |
|  | GCGACTGATTCTTCTAATGGTAATGGACATCACCAAACAACAACAAAGCAACCTTCTT |
|  | TGTCGTCTACACTGCGCTTATCCAAATTTTTTCAGTCCAACATGAGAATCTTGGTTACT |
|  | GGAGGAGCTGGATTCATTGCGTCTTACTTAGTTGACAGATTGATGGAAAATGAAAAAA |
|  | ATGAGGTTATTGTCGTTGCATAGGTGCTTTCATTTTACGTTCTTCAACATTCCGAATTGA |
|  | ACTTCAGTGGTCCTTGCAATGGCAACGAATTCTTCTGATGTACTATCGCCGAAGCAACC |
|  | TCCCTTGCCATCTCCCTTGCGTTTCTCCAAATTCTATCAGTCTAACATGAGAATCTTGAT |
|  | TACGGAGGAGCTGGATTCATTGGTTCTCACCTAGTTGATAGATTGATGGAAAATGAA |
|  | AAAAATGAGGTCATTGTTGCTGACAACTACTTCACTGGATCAAAGGACAACCTCAAAA |
|  | AATGGATTGGTCATCCAAGATTTGAGCTTATCCGTCATGATGTCACTGAACCTTTGACG |
|  | ATTGAGGTTGATCAGATCTACCATCTTGCATGCCCCGCATCTCCTATTTTCTACAAATA |
|  | TAATCCTGTGAAGACAATAAAGACAAATGTGATTGGCACACTGAACATGCTTGGGCTT |
|  | GCAAAACGAGTTGGGGCAAGGATTTTACTCACATCAACATCTGAGGTATATGGGGATC |
|  | CTCTTGTGCATCCCCAACCTGAAGGCTATTGGGGCAATGTGAACCCTATTGGAGTTCGT |
|  | AGTTGCTATGATGAGGGGAAACGTGTGGCTGAAACTTTGATGTTTGATTATCATAGGCA |

TABLE 4-continued

| SEQ ID NO. | Sequence |
|---|---|
| | GCATGGAATAGAAATACGTGTTGCAAGAATCTTTAACACATATGGGCCGCGCATGAAT |
| | ATTGATGATGGACGTGTTGTCAGCAACTTCATTGCTCAAGCAATTCGTGGTGAACCCTT |
| | GACAGTCCAGTCTCCAGGAACACAAACTCGCAGTTTCTGCTATGTCTCTGATCTGGTTG |
| | ATGGACTTATCCGTCTCATGGAAGGATCCGACACTGGACCAATCAACCTTGGAAATCCA |
| | GGTGAATTTACAATGCTAGAACTTGCTGAGACAGTGAAGGAGCTTATTAATCCAGATGT |
| | GGAGATAAAGGTAGTGGAGAACACTCCTGATGATCCGCGACAGAGAAAACCAATCATA |
| | ACAAAAGCAATGGAATTGCTTGGCTGGGAACCAAAGGTTAAGCTGCGAGATGGGCTTC |
| | CTCTTATGGAAGAGGATTTTCGTTTGAGGCTTGGATTTGACAAAAAAAATTAACTTATTT |
| | TCGCTCCTTTTATATCTAGTCAAAATATTCAGATAATAAGTGGGATGGATTATTCTATTA |
| | AGTTTTCCTATTTTTCCTTTTCATAATTATGATACTTAGGAAGTAGGGGTGCCTGTATTTT |
| | GGCTTCCTCAATCAAGATCGTACTCTTGTTTCACAAAGCACTGCAGCAATCATGCCTTTG |
| | CAAATTTTGCCGGTAAAATTACTACTGAGTTAAAATTTTCCTATAG |
| 28 | TGAAAATTACGTTTTCCCTTTTCCTTTGTTGCCGGTTAGCACTTCAATGTAAAAATTAA |
| | TTCACCATAAAGGATGGTTCGCATACAAAAGAATAAAACCTTATGAAAGGACACATGC |
| | AACGCAAAATAAAGGCATCGTTCCATAGGATATGCCGATCCTAGTGAGCCATAAATAA |
| | CGTTCCCAAAGGCATTTCCTCTATGTGTGTGGATCTTCCCAGTTGCAGCTGCATTACAGG |
| | GCAAGTTCTCCATTGGCAGGTAGCCACTATGATATGCATCTCATAAATATTTGCAACTT |
| | TCTTAATGTGCAATCTGCCAAAGGAGATTTGCCCAGCGATTCTCCTGCAACATCTGCT |
| | TCATGAAAACAGTATTCGTTAGTTTCTTCAATCATTCATTAGAAACATTTCTTGTACTGG |
| | TTGAAATGTTGCATCTCGAACCATTCATATGCCATATTTCCCTTGTTTTGTATTTTGGTA |
| | AAAACCATTTTTCC |
| 30 | CTGCAGAGTAAGACCTGAATTTCACTCATTGTTCCTGCCAATGTCCTTAGTTAGATAAA |
| | TGTAATTTTTTCTCTCTCTAAAGTTGCATCTATAAATATGAGCCTTTCCCTTGGTGCAGA |
| | TCAATTTGAGCTTTCATTACCGTTCTCATGAAGCTTAGGGTGCATGCAACGGTCTCTAC |
| | TTACTACTGGTTGAGAAGCTCCTTGTTGGAGAAGCAGGGCACGTGCAAGTCTCTTGG |
| | ATCTCAAATGCCACTGAACCCTTTGCACGTGCTCCCCTTCTCCAACACGGGTTTCTCCCC |
| | TTGCTTTTCTCCTAACCAATTGTGTCCAGCACTTATGAGGTAATCGCTTTCCTCCTATGT |
| | CTTAATTTGGTCCTACGTAAAGATCTACAATATGCATCTTCTTTGAGATACGGGCTGAA |
| | GCATGGTACTTTTAAATTGAAGGCTTCAATAACTATATTTAGAGGGAAAATTCAACATA |
| | CAAAGAAGGAAGAAGTGTTATGCATACAATATTTTACCGATGTTCTATGCGTATCAAAC |
| | ATA |
| 32 | TCTATATAATTTTTTTCCTATTTTATTTTTATTTTATTTTGTATCATATCCTTATACATC |
| | TTTTACTTTCACTCATACACTAAATTTTCGGGTGTAGGAATACTCCGGCAAAGAGAGAA |
| | TAGGTTTGCTTATTTCCTAATTCTGAAGTTAGGGTACGTGCGTAATTTACTGTGTGTTCT |
| | GTGATGATGAGTTAAGTGGTCCTATTTTACATGTAACTTTTGACAATCTGTTTGGGTTGA |
| | GAATACAAATTAAGGCCCCACACCCAACTAAGCTTAGCTCTCTCCCATTTTTAGCACCC |
| | ATCCCGCACCCAACTTTAAAAGCACCCTCAATTGCCTCTTCTATTATAGGAGAGTAGGC |
| | TTCAAAGCACACAAGAATATGATAAGATGAAGAAGTTCAGTGTCTCAAAATTCACCAC |

TABLE 4-continued

| SEQ ID NO. | Sequence |
|---|---|
|  | TTCTCTTAAAACCTCCCTCATTTGTTTTTTCACACTTTCCTTTCCCTCACCACTCTCTCTA |
|  | TTACCTCTTGTTTGTTGTTAAGAGTACTCAGAAGAATAACTCCTCCAACCCACTTAGCA |
|  | TGTGGCAAAGGTGCATGCTGAGCAAGATGGAGAAGCAGGGCACGTGCAATTCTAAC |
|  | TCATGAAACCATAGAATCATCTTGTTTTTTCTTCTTTTCACTCTAACCAAATAGATTCCT |
|  | CTACCTGCAG |
| 34 | ACTCAAGCTTGAAGCACCAAAGTTGCAGTCGGAGGAGTCACAGATTAAATTCTTCGCT |
|  | TCTTTAACCTTTGTGTTTCTCTTTTCATACCATTGTTTCTTTCCCTATAGCTGCTTTAATT |
|  | TTCTTGTGAGAGTCAGAAAAGTATCACTATATCAAGTGACATGATCATCAGAATTGAA |
|  | TTATGTGCATGTTGTGCAAGATGGAGAAGCAGGGCACGTGCAATACTAACTCATGAA |
|  | CACTACACGGNGCGTGAACTCGGAGAATCATATTCTCTTCTGCTTCATTTCACCAACAA |
|  | GAGAGATCCTATTAGTTAGTTCTTCATGTGCCCCTCTTTCCCATCATGACAACAGCACCT |
|  | TATATATATTGCATTTGGAAATGTTGAACGATGAAGTTCGCTTGGCTTCTGCTCATAAA |
|  | TCAGCACCGAGNTTTATAGGTTATGCTCCAT |

The fold-back structure of the pri-miRNA was identified in each of these crop plant MIR sequences using the program EINVERTED (Rice et al (2000) *Trends Genet.*, 16:276-277), and the results depicted in FIG. 11, which shows the fold-back portion of the sequences, with the nucleotide positions indicated by numbers. The fold-back portion of the MIR sequences is included in the pre-miRNA precursors processed from these MIR genes.

The MIR sequences, the complete MIR genes which include these, and the miRNA precursors (i.e., pri-miRNAs and pre-miRNAs) processed from these, are useful as target sequences for gene suppression (e.g., for nuclear suppression of the production of mature miRNAs encoded by these MIR genes) and as a source of primer or probe sequences (e.g., for primer sequences for cloning and sequencing the promoters of these MIR genes). The fold-back portion of the sequences has been proposed to be sufficient for miRNA processing (Parizotto et al. (2004) *Genes Dev.*, 18:2237-2242), and thus in many embodiments the region of the sequence that contains the fold-back portion is preferably targeted for suppression, or, alternatively, serves as the source of a sequence for suppressing a target gene.

The mature miRNAs produced from these miRNA precursors may be engineered for use in suppression of a target gene, e.g., in transcriptional suppression by the miRNA, or to direct in-phase production of siRNAs in a trans-acting siRNA suppression mechanism (see Allen et al. (2005) *Cell*, 121:207-221, Vaucheret (2005) *Science STKE*, 2005:pe43, and Yoshikawa et al. (2005) *Genes Dev.*, 19:2164-2175, all of which are incorporated by reference herein). Plant miRNAs generally have near-perfect complementarity to their target sequences (see, for example, Llave et al. (2002) *Science*, 297:2053-2056, Rhoades et al. (2002) *Cell*, 110:513-520, Jones-Rhoades and Bartel (2004) *Mol. Cell*, 14:787-799, all of which are incorporated by reference herein). Thus, the mature miRNAs can be engineered to serve as sequences useful for gene suppression of a target sequence, by replacing nucleotides of the mature miRNA sequence with nucleotides of the sequence that is targeted for suppression; see, e.g, methods disclosed by Parizotto et al. (2004) *Genes Dev.*, 18:2237-2242 and especially U.S. Patent Application Publications 2004/0053411A1, 2004/0268441A1, 2005/0144669, and 2005/0037988 all of which are incorporated by reference herein. When engineering a novel miRNA to target a specific sequence, one strategy is to select within the target sequence a region with sequence that is as similar as possible to the native miRNA sequence. Alternatively, the native miRNA sequence can be replaced with a region of the target sequence, preferably a region that meets structural and thermodynamic criteria believed to be important for miRNA function (see, e.g., U.S. Patent Application Publication 2005/0037988). Sequences are preferably engineered such that the number and placement of mismatches in the stem structure of the fold-back region or pre-miRNA is preserved. Thus, an engineered miRNA or engineered miRNA precursor can be derived from any of the mature miRNA sequences, or their corresponding miRNA precursors (including the fold-back portions of the corresponding MIR genes) disclosed herein.

An engineered miRNA precursor based on a mature miRNA (e.g., a mature miRNA corresponding to SEQ ID NO. 11, 13, 15, 17, 19, 21, 23, 25, 27, 29, 31, 33, or 35), preferably including the fold-back portion (e.g. as depicted in FIG. 11) of the corresponding MIR sequences (e.g., SEQ ID NO. 10, 12, 14, 16, 18, 22, 24, 26, 28, 30, or 34), is cloned and used to evaluate engineered miRNAs in transient plant (e.g., tobacco, maize, soy, potato, and *Arabidopsis*) assays. Successful constructs are moved to stable transformation into a plant of interest, including maize, soybean, or potato. The sequence targeted for suppression can be endogenous or exogenous to the plant cell in which the engineered miRNA construct is expressed.

In a non-limiting example, engineered miRNA sequences based on the fold-back portion of SEQ ID NO. 10, 12, 14, 16, 18, 22, 24, 26, 28, 30, or 34 are engineered to target green fluorescent protein (GFP), with nucleotides of the native sequence replaced with nucleotides to match a targeted portion of the GFP sequence, while maintaining the position and number of mismatches in the stem portion of the fold-back structure, by altering as needed the opposite strand of the stem of the fold-back structure or pre-miRNA. The engineered miRNA sequence is placed in an expression cassette including a suitable promoter (e.g., e35S) and terminator (e.g., Nos 3' transcriptional terminator). As a control, a similar gene cassette that expresses the native (non-engineered fold-back portion of SEQ ID NO. 10, 12, 14, 16, 18, 22, 24, 26, 28, 30, or 34) is used. A third cassette is designed to express the target sequence (GFP) and used for co-transformation with either of the miRNA cassettes. These three cassettes are inserted into binary vectors for use in *Agrobacterium*-mediated transformation. Constructs are tested for their ability to suppress the expression of GFP in a transient co-transformation experiment in which leaves are transformed in planta on wild-type maize, soybean, potato, *Arabidopsis*, or *Nicotiana* spp. plants. After four days, leaf punches corresponding to the regions infiltrated with *Agrobacterium* containing the plasmids are assayed for GFP fluorescence, which is normalized to total protein content. Constructs that express a miRNA that has been engineered to suppress the GFP gene have lower GFP expressed than the unengineered control.

Example 15

This example describes identifying novel mature miRNAs and the corresponding MIR sequences in soy. A single small RNA was isolated and cloned using procedures based on published protocols (Llave et al. (2002) *Plant Cell*, 14:1605-1619, and Lau et al. (2001) *Science*, 294:858-862). In summary, low molecular weight RNA was isolated from soy (*Glycine max*) leaf tissue. Adaptors were ligated followed by RT-PCR for conversion of RNA to DNA. Additional PCR amplification followed by TA cloning and sequencing led to the identification of novel mature miRNA 21-mers corresponding to the DNA sequence TGAGACCAAATGAGCAGCTGA (SEQ ID NO. 36) or ATGCACTGCCTCTTCCCTGGC (SEQ ID NO. 37).

A soy cDNA contig sequence database was searched for sequences containing 21-mer segments identical to SEQ ID NO. 36 or SEQ ID NO. 37 or to their respective complements. The sequences thus identified included SEQ ID NO. 38 (including the DNA sequence SEQ ID NO. 36 corresponding to a non-conserved mature miRNA) and SEQ ID NO. 39 (Gm-MIR408, including the DNA sequence SEQ ID NO. 37 corresponding to the conserved mature miRNA miR408). The novel MIR sequences are given in Table 5, with the location of nucleotides corresponding to the mature miRNA indicated by underlined text.

TABLE 5

| SEQ ID NO. | Sequence |
| --- | --- |
| 38 | AAAATTCATTACATTGATAAAACACAATTCAAAAGATCAATGTTCCACTTCATGCAAAGACATTTCCAAAATATGTGTAGGTAGAGGGGTTTTACAGGATCGTCCTGAGACCAAATGAGCAGCTGACCACATGATGCAGCTATGTTTGCTATTCAGCTGCTCATCTGTTCTCAGGTCGCCCTTGTTGGACTGTCCAACTCCTACTGATTGCGGATGCACTTGCCACAAATGAAAATCAAAGCGAGGGGAAAAGAATGTAGAGTGTGACTACGATTGCATGCATGTGATTTAGGTAATTAAGTTACATGATTGTCTAATTGTGTTTATGGAATTGTATATTTTCAGACCAGGCACCTGTAACTAATTATAGGTACCATACCTTAAAATAAGTCCAACTAAGTCCATGTCTGTGATTTTTTAGTGTCACAAATCACAATCCATTGCCATTGGTTTTTTAATTTTTCATTGTCTGTTGTTTAACTAACTCTAGCTTTTTAGCTGCTTCAAGTACAGATTCCTCAAAGTGGAAAATGTTCTTTGAAGTCAATAAAAAGAGCTTTGATGATCATCTGCATTGTCTAAGTTGGATAAACTAATTAGAGAGAACTTTTGAACTTTGTCTACCAAATATCTGTCAGTGTCATCTGTCAGTTCTGCAAGCTGAAGTGTTGAATCCACGAGGTGCTTGTTGCAAAGTTGTGATATTAAAAGACATCTACGAAGAAGTTCAAGCAAAACTCTTTTTGGC |
| 39 | CCGTGGTGGGCGAAGGGAATTAACGCCTATCGCGTGGCGAGAGAAGGAGCAGAACGGCAGGGGGGGCCGGCTCCGGGGGGCGCCCCGGTACGCACCGCGCTCTCCGAGTCCCTGGGGTCCCCCCCCAGAACATCCTAATCGAAAAATTCAAGAGTGCATTTTGTGCGTAATGTAGTTAATTAGACAAATTTCTAATGTGAGAATCTTTCTGAGAATGAGATGTTGCTAAATATTTCGGATGTTGTCGACAAGGATGAGGTAATAATAGTTAGAGACAGGACAAAGCAGGGGAACAGGCAGAGCATGGATGGAGCTATCAACACAATATTGTCAAGAAACTGAGAGTGAGAGGAGAAATATGTTGTGGTTCTGCTCATGCACTGCCTCTTCCCTGGCTCTGTCTCCATTTCTCCTTCCCTTATTTATTTTTTGATTTATTGAGTATGATCTGTTTTCAAATGTGTTCATAGGTTCAACTTATTAAGGTACGAACATACTCTGGGCATTGAAAACTGGTTTGACTCTTGAACATATTCCGCACCACTAATCTTTCTTGTAATCCAGGCTCACGCACGATCACTATAAGGTCCCACATTCTTAGTGGCCTAATCGTTGGAAAATGCTACTTTG |

TABLE 5-continued

| SEQ ID NO. | Sequence |
|---|---|
| | GCACTACTTGATGAATTGTATGGCTGGGATTTTTTTCCCCTTGCTTGTAGAATCCTCTC |
| | AATTTATGTAACCATCGTGTACTCATTTACATGTCATCATTTTTGAATGAGATGTGATA |
| | TACATAGAGCAAAAAAAAAAAAAAAATTGTATGACCTCATTTTCTGTGTTTATTTCTC |
| | TCCATCAATATCATTTTCTAAATCTCAAAATTCTCTCTTTTTTCTTAGTTGTAGAAGTT |
| | ATTGTTTACTCGACTCCTCGCCTCACATCCCTCTCACCCCTCTCCCCACTACTGCCCCG |
| | CCAGCGTCACCGATGCTCTCCTTTGTGGCCGGT |

The fold-back structure of the pri-miRNA was identified in these MIR sequences using the program EINVERTED (Rice et al. (2000) *Trends Genet.*, 16:276-277), and the results shown in FIG. 12, with nucleotide positions indicated by numbers in the fold-back portion of the sequences. The fold-back portion of the MIR sequences is included in the pre-miRNA precursors processed from these MIR genes.

(mfold) and putative miRNAs identified. Two microRNA precursors in the miR66 family were thus identified, and are listed in Table 6. These novel MIR sequences contained the consensus fold-back structure indicated by the shaded nucleotides depicted in FIG. 13 (Griffiths-Jones (2004) *Nucleic Acids Res.*, 32, Database Issue, D109-D111, which is incorporated by reference herein).

TABLE 6

| MIR gene | Sequence |
|---|---|
| SEQ ID NO. 43 | GTTAAGGGGTCTGTTGTCTGGTTCAAGGTCGCCACAGCAGGCAAATAAAGC |
| | CCATTTCGCGCTTAGCATGCACCATGCATGATGGGTGTACCTGTTGGTGATC |
| | TCGGACCAGGCTTCAATCCCTTTAAC |
| SEQ ID NO. 44 | GTCGAGGGGAATGACGTCCGGTCCGAACGAGCCACGGCTGCTGCTGCGCCG |
| | CCGCGGGCTTCGGACCAGGCTTCATTCCCCGTGAC |

A family of related miRNAs was cloned from the soy leaf tissue, including the abundant miRNA described above and corresponding to the DNA sequence TGAGACCAAAT-GAGCAGCTGA (SEQ ID NO. 36), and in lower abundances mature miRNA 21-mers corresponding to the DNA sequence TGAGATCAAATGAGCAGCTGA (SEQ ID NO. 40), TGAGACCAAATGAGCAGCTGT (SEQ ID NO. 41), and TGAGACCAAATGACCAGCTGA (SEQ ID NO. 42), respectively, each of which differs from SEQ ID NO. 36 at only one nucleotide position.

The MIR sequences, the complete MIR genes which include these, and the miRNA precursors (i.e., pri-miRNAs and pre-miRNAs) processed from these, the mature miRNAs transcribed from these, and miRNA recognition sites of the mature miRNAs have various utilities as described above in Examples 12, 13, and 14 and elsewhere in this disclosure.

Example 16

This example describes identifying novel MIR sequences in maize. Public and proprietary maize (*Zea mays*) genomic datasets were searched for novel microRNA precursor sequences, starting with all pre-miRNA sequences known at the time (April 2004) using blastn and a very permissive cutoff (e<=10,000). Hits matching a minimum length criteria were extracted and tested (cmsearch) against all known miRNA covariance models (Rfam v5.1). Sequences showing significant similarity (>15 bits) to Rfam models were folded The MIR sequences, the complete MIR genes which include these, the miRNA precursors (i.e., pri-miRNAs and pre-miRNAs) processed from these, and the mature miRNAs transcribed from these, and miRNA recognition sites of the mature miRNAs have various utilities as described above in Examples 12, 13, and 14 and elsewhere in this disclosure.

Example 17

This non-limiting example describes the distribution of miRNAs in specific cells or tissues of a multicellular eukaryote (a plant). Knowledge of the spatial or temporal distribution of a given miRNA's expression is useful, e.g., in designing recombinant constructs to be expressed in a spatially or temporally specific manner. This example discloses mature miRNA expression patterns in maize and provides sequences of recognition sites for these miRNAs that are suitable for inclusion in recombinant DNA constructs useful in maize and other plants.

Total RNA was isolated from LH244 maize plants using Trizol (Invitrogen, Carlsbad, Calif.). Seven developmental stages were used, including roots and shoot meristems from germinating seedlings, juvenile (V1 to V2) and adult leaves (V7 to V8), stalk internode, tassel before shedding, and immature (approximately 1") ears. Five micrograms total RNA was resolved on 17% PAGE-Urea as described by Allen et al. (2004) *Nat. Genet.*, 36:1282-1290, which is incorporated by reference herein. Blots were probed with DNA oligonucleotides that were antisense to the small RNA sequence and end-labelled with gamma $^{32}$P-ATP using Optikinase (USB). The probes used, and their respective sequences, are given in Table 7.

TABLE 7

| SEQ ID NO. | Sequence | miRNA |
|---|---|---|
| 45 | GTGCTCACTCTCTTCTGTCA | miR156 |
| 46 | TAGAGCTCCCTTCAATCCAAA | miR159 |
| 47 | TGGCATCCAGGGAGCCAGGCA | miR160 |
| 48 | CTGGATGCAGAGGTTTATCGA | miR162 |
| 49 | TGCACGTGCCCTGCTTCTCCA | miR164 |
| 50 | GGGGAATGAAGCCTGGTCCGA | miR166 |
| 51 | TAGATCATGCTGGCAGCTTCA | miR167 |
| 52 | TTCCCGACCTGCACCAAGCGA | miR168 |
| 53 | TCGGCAAGTCATCCTTGGCTG | miR169 |
| 54 | GATATTGGCGCGGCTCAATCA | miR171 |
| 55 | CTGCAGCATCATCAAGATTCT | miR172 |
| 56 | GGCGCTATCCCTCCTGAGCTT | miR390 |
| 57 | GATCAATGCGATCCCTTTGGA | miR393 |
| 58 | TGGGGTCCTTACAAGGTCAAGA | TAS3 5'D7(+) |
| 59 | GGAGGTGGACAGAATGCCAA | miR394 |
| 60 | GAGTTCCCCCAAACACTTCAC | miR395 |
| 61 | CATCAACGCTGCGCTCAATGA | miR397 |
| 62 | CGGGGGCGACCTGAGAACACA | miR398 |
| 63 | AGCCAGGGAAGAGGCAGTGCA | miR408 |

Figure 14:
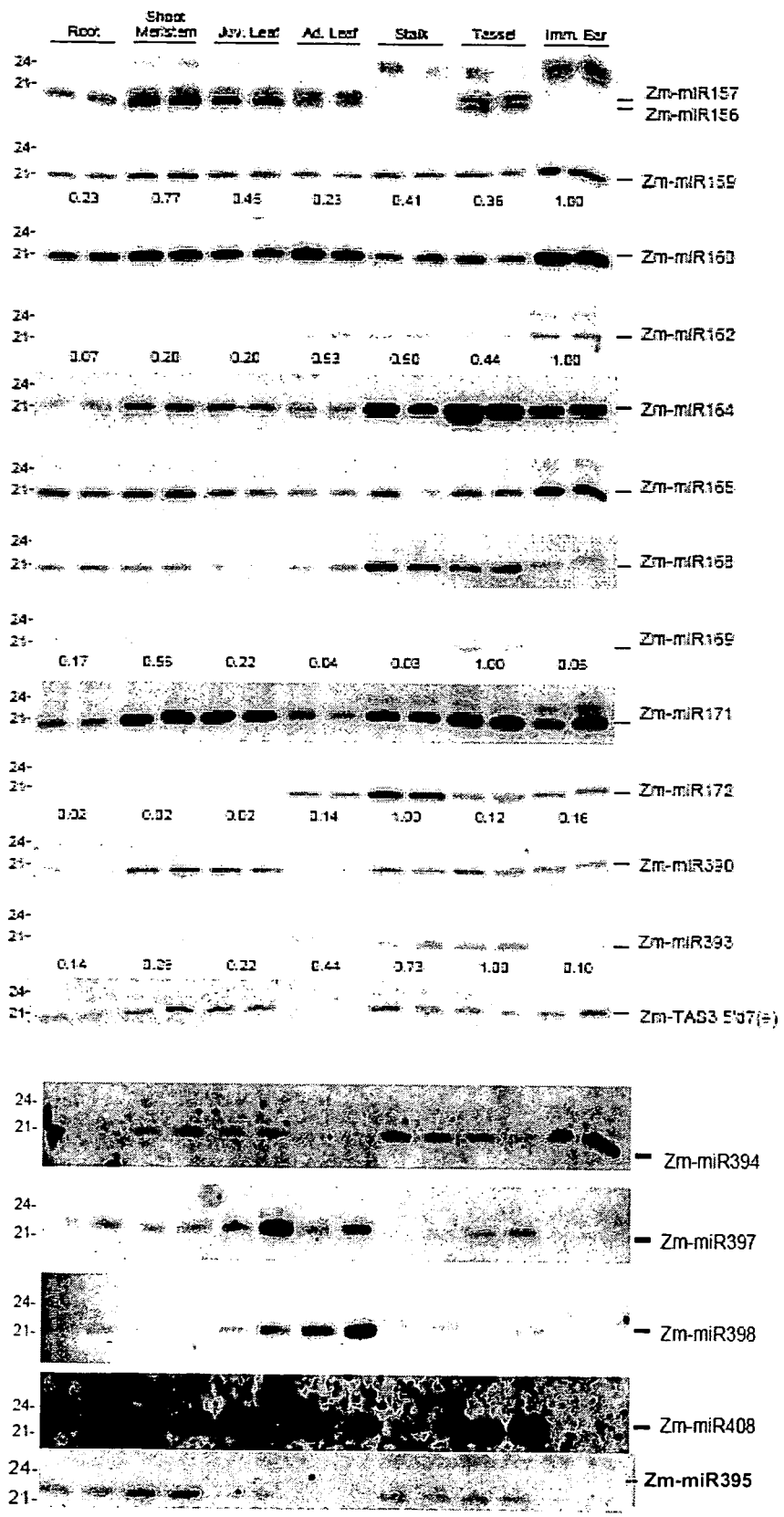
FIG. 14 depicts expression levels of the indicated mature miRNAs in various tissues from maize, as described in detail in Example 17.
Figure 18:
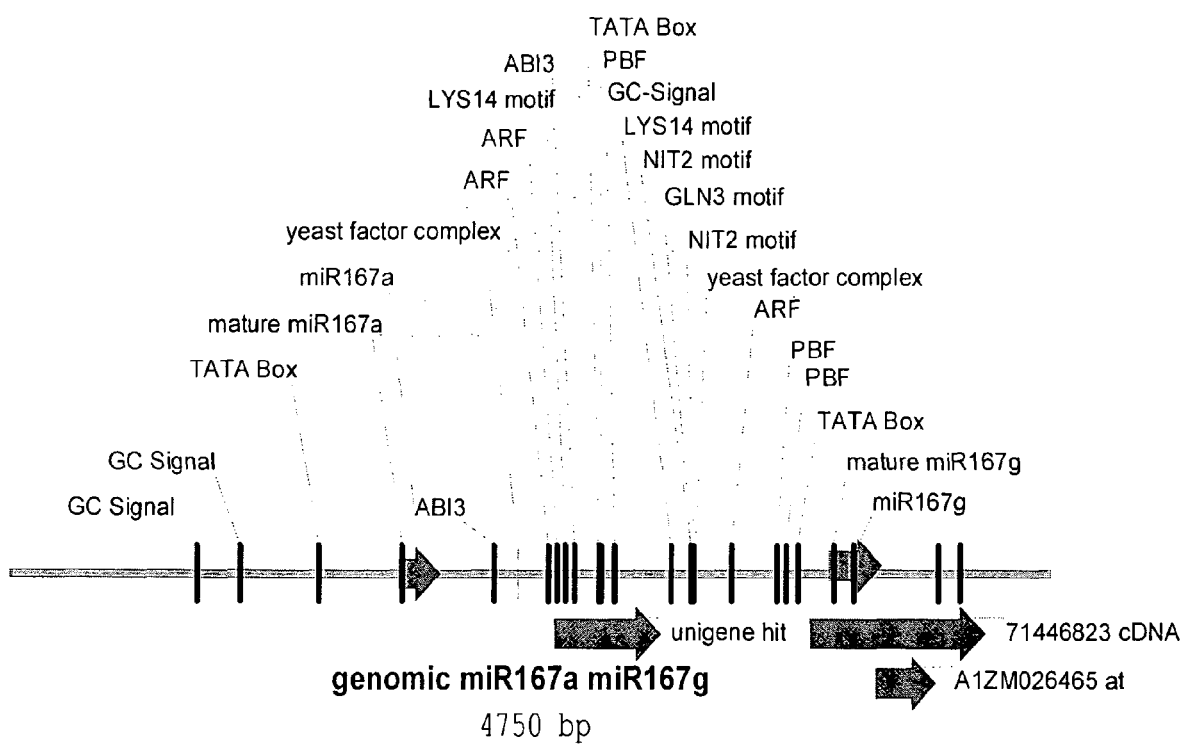
FIG. 18 depicts a partial annotation map, including locations of the miR167a and miR167g genes and mature miR-NAs, and promoter elements (e.g., TATA boxes), of the genomic cluster within which was identified the miR167g promoter sequences as described in detail in Example 19. Abbreviations: "PBF", prolamin box binding factor; "ARF" auxin-responsive (auxin binding) factor; "NIT2", activator of nitrogen-related genes; "LYS14", element that binds to UASLYS, an upstream activating element conferring Lys14- and adipate semialdehyde-dependent activation and apparent repression; "GLN3", element that binds the nitrogen upstream activation sequence of glutamine synthetase.

The results are shown in FIG. 14. Individual mature miR-NAs were expressed at differing levels in specific cells or tissues. For example, Zm-miR390 was not expressed, or expressed only at low levels, in root and adult leaf.

Example 18

This example describes recombinant DNA constructs of the invention, useful for suppressing expression of a target RNA in a specific cell of or derived from a multicellular eukaryote such as a plant cell or an animal cell, and methods for their use. The constructs include a promoter operably linked to DNA that transcribes to RNA including at least one exogenous miRNA recognition site recognizable by a mature miRNA expressed in a specific cell of a multicellular eukaryote, and target RNA to be suppressed in the specific cell, wherein said target RNA is to be expressed in cells of the multicellular eukaryote other than the specific cell.

Strong constitutive promoters that are expressed in nearly all plant cells have been identified (e.g., CaMC 35S, OsAct), but strong spatially specific (cell- or tissue-specific) and temporally specific promoters have been less well characterized. To limit target RNA or transgene expression to a specific cell or tissue type in the absence of a strong cell- or tissue-specific promoter, it may be desirable to suppress in selected cells or tissues the expression of a transcript under the control of a constitutive promoter. The invention provides methods that use recognition sequences of endogenous miRNAs to suppress expression of a constitutively expressed target RNA in specific cells.

Methods of the invention allow spatially or temporally specific post-transcriptional control of expression of a target RNA wherein transcription is driven by a non-specific (e.g., constitutive) promoter. The methods of the invention allow, for example, the restricted expression of a gene transcribed by a constitutive promoter or a promoter with expression beyond the desired cell or tissue type(s). Restricted expression may be spatially or temporally restricted, e.g., restricted to specific tissues or cell types or files, or to specific developmental, reproductive, growth, or seasonal stages. Where a miRNA is expressed under particular conditions (e.g., under biotic stress such as crowding, allelopathic interactions or pest or pathogen infestation, or abiotic stress such as heat or cold stress, drought stress, nutrient stress, heavy metal or salt stress), the corresponding miRNA recognition site can be used for conditionally specific suppression, i.e., to suppress a target RNA under the particular condition.

For example, Zm-miR162 is poorly expressed in maize roots (see Example 17 and FIG. 14), therefore, designing an expression construct to include an exogenous miRNA162 recognition site adjacent to, or within, a constitutively expressed target RNA, may limit target RNA transcript accumulation in all cells of a maize plant with the exception of roots. This method has utility for all gene expression applications in multicellular eukaryotes (plants and animals), where restricted expression is desired in cells wherein the given mature miRNA is expressed.

In multicellular eukaryotes, including plants, microRNAs (miRNAs) regulate endogenous genes by a post-transcriptional cleavage mechanism, which can spatially or temporally specific. The present invention provides methods by which the addition of a miRNA recognition site to a constitutively expressed transgene could be used to limit expression of the transgene to cells lacking, or distant to those expressing, the complementary mature miRNA either spatially or temporally (including conditionally). Manipulation of these miRNA recognition sites in new transcripts introduced into transgenic plant cells and transgenic plants derived from these cells, is useful for altering expression patterns for the new transgene.

In an alternative approach, an existing (native or endogenous) miRNA recognition site is mutated (e.g., by chemical mutagenesis) sufficiently to reduce or prevent cleavage (see Mallory et al. (2004) Curr. Biol., 14:1035-1046, incorporated by reference herein). In this way a target RNA sequence with desirable effects, e.g., increased leaf or seed size, can be expressed at levels higher than when the native or endogeous miRNA recognition site was present. One embodiment is to replace a native gene with an engineered homologue, wherein a native miRNA has been mutated or even deleted, that is less susceptible to cleavage by a given miRNA.

One embodiment of the method is the introduction of at least one exogenous miRNA recognition site (typically a 21 nucleotide sequence) into the 5' or into the 3' untranslated regions of a target RNA, or within the target RNA. Where the target RNA includes coding sequence, the at least one exogenous miRNA recognition site can be introduced into the coding region of the target RNA. This results in the reduced expression of the target RNA in tissues or cell types that express the corresponding mature miRNA. By including a recognition site corresponding to a mature miRNA in a target RNA transcript, it is possible to modulate the target RNA's expression in such a way that even under the control of a constitutive promoter, the target RNA is expressed only in selected cells or tissues or during selected temporal periods.

This allows both the high levels of expression obtainable with strong constitutive promoters, and spatial or temporal limiting of such expression.

Any miRNA recognition site may be used, preferably where the expression of the corresponding mature miRNA has been determined to suit the desired expression or suppression of the target RNA. Numerous miRNA recognition sequences are known. See, for example, Jones-Rhoades and Bartel (2004). *Mol. Cell,* 14:787-799, Rhoades et al. (2002) *Cell,* 110:513-520, Allen et al. (2004) *Nat. Genet.,* 36:1282-1290, which are incorporated by reference herein). Also see the ASRP database online (Gustafson et al. (2005) *Nucleic Acids Res.,* 33:D6379-D640). Non-limiting examples of miRNA recognition sites useful in constructs and methods of the invention include those provided in Table 8, which gives the recognition site sequences for the indicated miRNA family and indicates the distribution among "all plants" (i.e., lower plants, monocots, and dicots), monocots and/or dicots. The plant species from which the miRNA was identified and the abbreviations used were: *Arabidopsis thaliana* (At), *Glycine max* (Gm), *Gossypium hirsutum* (Gh), *Hordeum vulgare* (Hv), *Lycopersicum esculentum* (Le), *Lotus corniculatus* var. *japonicus* (synonymous with "*Lotus japonicus*") (Lj), *Medicago truncatula* (Mt), *Mesembryanthemum crystallinum* (Mc), *Oryza sativa* (Os), *Pennisetum glaucum* (Pg), *Phaseolus vulgaris* (Pv), *Populus tremula* (Pt), *Saccharum officinarum* (So), *Sorghum bicolor* (Sb), *Theobroma cacao* (Tc), *Triticum aestivum* (Ta), *Vitis vinifera* (Vv), and *Zea mays* (Zm).

TABLE 8

| SEQ ID NO. | miRNA Recognition Site | Recognition Site Sequence |
|---|---|---|
| miR156 family recognition sequence - all plants | | |
| 64 | At1g27370 | GUGCUCUCUCUCUUCUGUCA |
| 65 | At1g53160 | CUGCUCUCUCUCUUCUGUCA |
| 66 | At2g33810 | UUGCUUACUCUCUUCUGUCA |
| 67 | At3g15270 | CCGCUCUCUCUCUUCUGUCA |
| miR159 family recognition sequence - all plants | | |
| 68 | At5g06100 | UGGAGCUCCCUUCAUUCCAAU |
| 69 | At2g26960 | UCGAGUUCCCUUCAUUCCAAU |
| 70 | At4g26930 | AUGAGCUCUCUUCAAACCAAA |
| 71 | At2g26950 | UGGAGCUCCCUUCAUUCCAAG |
| 72 | At2g32460 | UAGAGCUUCCUUCAAACCAAA |
| 73 | At3g60460 | UGGAGCUCCAUUCGAUCCAAA |
| 74 | At5g55020 | AGCAGCUCCCUUCAAACCAAA |
| 75 | PvMYB | CAGAGCUCCCUUCACUCCAAU |
| 76 | VvMYB | UGGAGCUCCCUUCACUCCAAU |
| 77 | HvMYB33 | UGGAGCUCCCUUCACUCCAAG |
| 78 | OsMYB33 | UGGAGCUCCCUUUAAUCCAAU |
| miR160 family target sequences - all plants | | |
| 79 | At1g77850 | UGGCAUGCAGGGAGCCAGGCA |
| 80 | At2g28350 | AGGAAUACAGGGAGCCAGGCA |
| 81 | At4g30080 | GGGUUUACAGGGAGCCAGGCA |

TABLE 8-continued

| SEQ ID NO. | miRNA Recognition Site | Recognition Site Sequence |
|---|---|---|
| 82 | OsARF | AGGCAUACAGGGAGCCAGGCA |
| 83 | LjARF | AAGCAUACAGGGAGCCAGGCA |
| miR161 family target sequences - *Arabidopsis* | | |
| 84 | At5g41170 | ACCUGAUGUAAUCACUUUCAA |
| 85 | At1g06580 | CCCGGAUGUAAUCACUUUCAG |
| 86 | At1g63150 | UUGUUACUUUCAAUGCAUUGA |
| 87 | At5g16640 | CCCUGAUGUAUUUACUUUCAA |
| 88 | At1g62590 | UAGUCACGUUCAAUGCAUUGA |
| 89 | At1g62670 | CCCUGAUGUAUUCACUUUCAG |
| 90 | At1g62860 | CCCUGAUGUUGUUACUUUCAG |
| 91 | At1g62910 | UAGUCACUUUCAGCGCAUUGA |
| 92 | At1g62930 | UCCAAAUGUAGUCACUUUCAG |
| 93 | At1g63080 | UCCAAAUGUAGUCACUUUCAA |
| 94 | At1g63130 | UCCAAAUGUAGUCACUUUCAG |
| 95 | At1g63400 | UCCAAAUGUAGUCACUUUCAA |
| 96 | At1g63230 | UUGUAACUUUCAGUGCAUUGA |
| 97 | At1g63330 | UAGUCACGUUCAAUGCAUUGA |
| 98 | At1g63630 | UUGUUACUUUCAGUGCAUUGA |
| 99 | At1g64580 | CCCUGAUGUUGUCACUUUCAC |
| 100 | At2g41720 | UUGUUACUUACAAUGCAUUGA |
| 101 | At1g63070 | UAGUCUUUUUCAACGCAUUGA |
| miR162 family target sequences - monocots and dicots | | |
| 102 | At1g01040 | CUGGAUGCAGAGGUAUUAUCGA |
| 103 | PtDCL1 | CUGGAUGCAGAGGUCUUAUCGA |
| 104 | OsDCL1 | CUGGAUGCAGAGGUUUUAUCGA |
| miR163 family target sequences - *Arabidopsis* | | |
| 105 | At1g66700 | AUCGAGUUCCAAGUCCUCUUCAA |
| 106 | At1g66720 | AUCGAGUUCCAGGUCCUCUUCAA |
| 107 | At3g44860 | AUCGAGUUCCAAGUUUUCUUCAA |
| miR164 family target sequences - monocots and dicots | | |
| 108 | At1g56010 | AGCACGUACCCUGCUUCUCCA |
| 109 | At5g07680 | UUUACGUGCCCUGCUUCUCCA |
| 110 | At5g53950 | AGCACGUGUCCUGUUUCUCCA |
| 111 | At5g61430 | UCUACGUGCCCUGCUUCUCCA |
| 112 | At5g39610 | CUCACGUGACCUGCUUCUCCG |
| 113 | OsNAC1 | CGCACGUGACCUGCUUCUCCA |
| 114 | MtNAC | CUUACGUGUCCUGCUUCUCCA |

TABLE 8-continued

| SEQ ID NO. | miRNA Recognition Site | Recognition Site Sequence |
|---|---|---|
| 115 | GmNAC | CUUACGUGCCCUGCUUCUCCA |
| 116 | LeNAC | GCCACGUGCACUGCUUCUCCA |
| miR165/166 family target sequences - all plants | | |
| 117 | At1g30490 | UUGGGAUGAAGCCUGGUCCGG |
| 118 | At5g60690 | CUGGGAUGAAGCCUGGUCCGG |
| 119 | At1g52150 | CUGGAAUGAAGCCUGGUCCGG |
| 120 | PtHDZIPIII | CCGGGAUGAAGCCUGGUCCGG |
| miR167 family target sequences - monocots and dicots | | |
| 121 | At1g30330 | GAGAUCAGGCUGGCAGCUUGU |
| 122 | At5g37020 | UAGAUCAGGCUGGCAGCUUGU |
| 123 | OsARF6 | AAGAUCAGGCUGGCAGCUUGU |
| miR168 family target sequences - all plants | | |
| 124 | At1g48410 | UUCCCGAGCUGCAUCAAGCUA |
| miR169 family target sequences - all plants | | |
| 125 | At1g17590 | AAGGGAAGUCAUCCUUGGCUG |
| 126 | At1g54160 | ACGGGAAGUCAUCCUUGGCUA |
| 127 | At1g72830 | AGGGGAAGUCAUCCUUGGCUA |
| 128 | At3g05690 | AGGCAAAUCAUCUUUGGCUCA |
| 129 | At3g20910 | GCGGCAAUUCAUUCUUGGCUU |
| 130 | At5g12840 | CCGGCAAAUCAUUCUUGGCUU |
| 131 | At3g14020 | AAGGGAAGUCAUCCUUGGCUA |
| 132 | ZmHAP2 | GUGGCAACUCAUCCUUGGCUC |
| 133 | VvHAP2 | UGGGCAAUUCAUCCUUGGCUU |
| 134 | OsHAP2 | AUGGCAAAUCAUCCUUGGCUU |
| 135 | GmHAP2 | UAGGGAAGUCAUCCUUGGCUC |
| 136 | GhHAP2 | CUGGGAAGUCAUCCUUGGCUC |
| miR170/171 family target sequences - all plants | | |
| 137 | At2g45160 | GAUAUUGGCGCGGCUCAAUCA |
| miR272 family target sequences - all plants | | |
| 138 | At4g36920 | CUGCAGCAUCAUCAGGAUUCU |
| 139 | At2g28550 | CAGCAGCAUCAUCAGGAUUCU |
| 140 | At5g60120 | AUGCAGCAUCAUCAGGAUUCU |
| 141 | At5g67180 | UGGCAGCAUCAUCAGGAUUCU |
| 142 | At2g39250 | UUGUAGCAUCAUCAGGAUUCC |
| 143 | At3g54990 | UUGCAGCAUCAUCAGGAUUCC |
| miR319 family target sequences - all plants | | |
| 144 | At4g18390 | CAGGGGGACCCUUCAGUCCAA |
| 145 | At1g53230 | GAGGGGUCCCCUUCAGUCCAU |
| 146 | At3g15030 | GAGGGGUCCCCUUCAGUCCAG |
| 147 | At2g31070 | AAGGGGUACCCUUCAGUCCAG |
| 148 | At1g30210 | UAGGGGGACCCUUCAGUCCAA |
| 149 | OsPCF5 | GAGGGGACCCCUUCAGUCCAG |
| 150 | OsPCF8 | UCGGGGCACACUUCAGUCCAA |
| miR393 family target sequences - monocots and dicots | | |
| 151 | At1g12820 | AAACAAUGCGAUCCCUUUGGA |
| 152 | At4g03190 | AGACCAUGCGAUCCCUUUGGA |
| 153 | At3g23690 | GGUCAGAGCGAUCCCUUUGGC |
| 154 | At3g62980 | AGACAAUGCGAUCCCUUUGGA |
| miR394 family target sequences - monocots and dicots | | |
| 155 | At1g27340 | GGAGGUUGACAGAAUGCCAAA |
| miR395 family target sequences - monocots and dicots | | |
| 156 | At5g43780 | GAGUUCCUCCAAACACUUCAU |
| 157 | At3g22890 | GAGUUCCUCCAAACUCUUCAU |
| 158 | At5g10180 | AAGUUCUCCCAAACACUUCAA |
| miR396 family target sequences - monocots and dicots | | |
| 159 | At2g22840 | UCGUUCAAGAAAGCCUGUGGAA |
| 160 | At2g36400 | CCGUUCAAGAAAGCCUGUGGAA |
| 161 | At4g24150 | UCGUUCAAGAAAGCAUGUGGAA |
| 162 | At2g45480 | ACGUUCAAGAAAGCUUGUGGAA |
| 163 | At3g52910 | CCGUUCAAGAAAGCCUGUGGAA |
| miR397 family target sequences - monocots and dicots | | |
| 164 | At2g29130 | AAUCAAUGCUGCACUCAAUGA |
| 165 | At2g38080 | AGUCAACGCUGCACUUAAUGA |
| 166 | At2g60020 | AAUCAAUGCUGCACUUAAUGA |
| miR398 family target sequences - monocots and dicots | | |
| 167 | At1g08830 | AAGGGGUUUCCUGAGAUCACA |
| 168 | At2g28190 | UGCGGGUGACCUGGGAAACAUA |
| 169 | At3g15640 | AAGGUGUGACCUGAGAAUCACA |
| miR173 family target sequences - *Arabidopsis* | | |
| 170 | AtTAS1a | GUGAUUUUUCUCAACAAGCGAA |
| 171 | AtTAS1c | GUGAUUUUUCUCUACAAGCGAA |
| 172 | AtTAS2 | GUGAUUUUUCUCUCCAAGCGAA |

TABLE 8-continued

| SEQ ID NO. | miRNA Recognition Site | Recognition Site Sequence |
|---|---|---|
| miR399 family target sequences - monocots and dicots | | |
| 173 | At2g33770 | UAGGGCAUAUCUCCUUUGGCA |
| 174 | At2g33770 | UUGGGCAAAUCUCCUUUGGCA |
| 175 | At2g33770 | UCGAGCAAAUCUCCUUUGGCA |
| 176 | At2g33770 | UAGAGCAAAUCUCCUUUGGCA |
| 177 | At2g33770 | UAGGGCAAAUCUUCUUUGGCA |
| 178 | OsE2UBC | UAGGGCAAAUCUCCUUUGGCA |
| 179 | OsE2UBC | CUGGGCAAAUCUCCUUUGGCA |
| 180 | OsE2UBC | UCGGGCAAAUCUCCUUUGGCA |
| 181 | OsE2UBC | CCGGGCAAAUCUCCUUUGGCA |
| 182 | PtE2UBC | GCGGGCAAAUCUUCUUUGGCA |
| 183 | MtE2UBC | AAGGGCAAAUCUCCUUUGGCA |
| 184 | TaE2UBC | UAGGGCAAAUCUCCUUUGGCG |
| 185 | TaE2UBC | CUGGGCAAAUCUCCUUUGGCG |
| 186 | TaE2UBC | UUCGGCAAAUCUCCUUUGGCA |
| miR403 family target sequences - dicots | | |
| 187 | At1g31280 | GGAGUUUGUGCGUGAAUCUAAU |
| miR390 family target sequences - all plants | | |
| 188 | At3g17185 | CUUGUCUAUCCCUCCUGAGCUA |
| 189 | SbTAS3 | UAUGUCUAUCCCUUCUGAGCUG |
| 190 | SoTAS3 | UAUGUCUAUCCCUUCUGAGCUA |
| 191 | ZmTAS3 | UAUGUCUAUCCCUUCUGAGCUG |
| 192 | OsTAS3 | UCGGUCUAUCCCUCCUGAGCUG |
| 193 | PgTAS3 | UUAGUCUAUCCCUCGUGAGCUA |
| 194 | VvTAS3 | AUUGCCUAUCCCUCCUGAGCUG |
| 195 | TcTAS3 | CCUUGGUAUCCCUCCUGAGCUG |
| 196 | LeASR | CUUGUCUAUCCCUCCUGAGCUG |
| 197 | ZmTAS3 | CCCUUCUAUCCCUCCUGAGCUA |
| 198 | PtTAS3 | CUUGUCUAUCCCUCCUGAGCUA |
| 199 | OsTAS3 | CCCUUCUAUCCCUCCUGAGCUA |
| 200 | TaTAS3 | CCCUUCUAUCCCUCCUGAGCUA |
| 201 | HvTAS3 | CCUUUCUAUCCCUCCUGAGCUA |
| 202 | PtTAS3 | CCUGUCUAUGCCUCCUGAGCUA |
| 203 | McTAS3 | UGUGUCUAUCCCUCCUGAGCUA |
| miR447 family target sequences - Arabidopsis | | |
| 204 | At5g60760 | UGACAAACAUCUCGUCCCCAA |
| 205 | At3g45090 | UGACAAACAUCUCGUUCCUAA |

TABLE 8-continued

| SEQ ID NO. | miRNA Recognition Site | Recognition Site Sequence |
|---|---|---|
| miR408 family target sequences - monocots and dicots | | |
| 206 | At2g02850 | CCAAGGGAAGAGGCAGUGCAU |
| 207 | At2g30210 | ACCAGUGAAGAGGCUGUGCAG |
| 208 | At2g47020 | GCCAGGGAAGAGGCAGUGCAU |
| 209 | At5g05390 | GCCGGUGAAGAGGCUGUGCAA |
| 210 | At5g07130 | GCCGGUGAAGAGGCUGUGCAG |
| TAS3 ta-siRNA target sequences - monocots and dicots | | |
| 211 | At2g33860a | AGGGUCUUGCAAGGUCAAGAA |
| 212 | At5g60450a | AAGGUCUUGCAAGGUCAAGAA |
| 213 | OsARF3-like | GAGGUCUUGCAAGGUCAAGAA |
| 214 | OsARF2-like | ACGGUCUUGCAAGGUCAAGAA |
| TAS1/TAS2 target sequences - *Arabidopsis thaliana* | | |
| 215 | Atg12770 | AGAACUAGAGAAAGCAUUGGA |
| 216 | Atg12770 | AGAGUAAGAUGGAGCUUGAUA |
| 217 | At1g63130 | AGAUGGUGGAAAUGGGAUAUC |
| 218 | At1g63230 | UUGUUGAUCGUAUGGUAGAAG |
| 219 | At1g62930 | GGUAUUCGAGUAUCUGCAAAA |

Thus, a transgenic plant expressing a recombinant DNA construct that, under the control of a constitutive promoter (e.g., a 35S promoter) transcribes to RNA containing a Zm-miR390 recognition site and a target RNA would be expected to show suppression of the target RNA expression in root and adult leaf, relative to expression in other tissues.

In another example, Zm-miR172 was expressed at high levels in stalk, and not expressed, or expressed only at low levels, in other tissues. A transgenic plant expressing a construct that, under the control of a strong constitutive promoter (e.g., a CaMV 35S promoter) transcribes to RNA containing a Zm-miR172 recognition site and a target RNA would be expected to express that target RNA at higher levels in tissues other than stalk (where expression of the target RNA would be suppressed).

To illustrate use of the constructs and methods of the invention to control expression of a gene of interest, a reporter gene is used as the gene of interest itself, or as a surrogate for the gene of interest. For example, where expression of a reporter gene (e.g., green fluorescent protein, GFP) is desired in maize stalk and immature ear tissue, a miR156 target site is included in a GFP expression cassette and expressed in a stably transgenic maize plant under the control of the CaMV 35S promoter. In other tissues (e.g., roots, leaves, and tassel), GFP expression is suppressed. The suppression phenotype may be limited to very specific cell types within the suppressed tissues, with neighboring cells showing expression or a gradient of expression of GFP adjacent to those cells expressing the mature miR156.

In another example, a strong constitutive promoter is used to drive expression of a *Bacillus thuringiensis* insecticidal protein or protein fragment ("Bt"), where a recognition site for a miRNA expressed in pollen is included in the construct, resulting in strong expression in tissues of the plant except for the pollen.

One specific, non-limiting example of the method is the inclusion of the recognition site for a miRNA that is not expressed in roots to a recombinant DNA construct including a target RNA of which expression is desired only in the roots. A strong constitutive promoter (e.g., enhanced 35S) can still be used, but the target RNA's expression is now restricted to the cells that that do not express the corresponding mature miRNA. A specific example of this approach is the inclusion of a maize miRNA162, maize miRNA164, or maize miRNA390 recognition site in a recombinant DNA construct for the expression of a *Bacillus thuringiensis* insecticidal protein or protein fragment ("Bt", see, for example, the *Bacillus thuringiensis* insecticidal sequences and methods of use thereof disclosed in U.S. Pat. No. 6,953,835 and in U.S. Provisional Patent Application No. 60/713,111, filed on 31 Aug. 2005, which are incorporated by reference herein) as the target RNA, e.g., in a construct including the expression cassette e35S/Bt/hsp17. These miRNAs (e.g., miRNA162, miRNA164, or miRNA390) are not substantially expressed in maize roots but are expressed in most other tissues. Including one or more of these recognition sites within the expression cassette reduces the expression of transcripts in most tissues other than root, but maintains high Bt target RNA expression levels in roots, such as is desirable for control of pests such as corn rootworm. In one embodiment, combinations of different miRNA recognition sites are included in the construct in order to achieve the desired expression pattern.

Non-limiting specific examples of transcribable DNA sequence including an exogenous miRNA recognition site are depicted in FIG. 15 and FIG. 16. FIG. 15 depicts chloroplast-targeted TIC809 with a miRNA162 recognition site (in bold text) located in the 3' untranslated region (SEQ ID NO. 220). FIG. 16 depicts non-targeted TIC809 with a miRNA164 recognition site (in bold text) located in the 3' untranslated region (SEQ ID NO. 221).

Example 19

This example describes a crop plant miRNA gene with tissue-specific expression, and identification of the miR gene promoter. More particularly, this example describes identification of a maize miR167 promoter sequence with endosperm-specific expression. A member of the miR167 family (SEQ ID NO. 4) was found to represent about a quarter of the small RNA population cloned from developing maize endosperm as described in Example 13. To determine whether a single miR167 gene family member is responsible for the observed strong endosperm expression, several miR167 genes were analyzed by RT-PCR. Nine *Zea mays* miR167 stem-loop sequences were found in the public miRNA registry ("miRBase", available on line at microrna.sanger.ac.uk/sequences), listed as miR167a through miR167i. Tissue-specific RT-PCR was performed for several of the *Z. mays* miR167 sequences using gene-specific primers for first strand cDNA synthesis followed by PCR with gene-specific primer pairs. Expression of miR167g was strong and tissue-specific for endosperm (15, 20 days after pollination).

To determine whether miR167g is abundantly expressed in endosperm, Northern blots of maize (LH59) were prepared. The blot was probed with an end-labeled mature miR167 22-mer LNA probe (FIG. 17A), stripped, and re-probed with a ~400 bp miR167g gene-specific probe (FIG. 17B). The strong endosperm signal observed indicated that miR167g is largely responsible for endosperm-enhanced expression. Transcription profiling of maize tissues corroborated the Northern blot results (FIG. 17C); the transcript corresponding to miR167g was abundantly and specifically expressed in endosperm tissue.

A GenBank publicly available 804 base pair cDNA sequence (annotated as "ZM_BFb0071I20.r ZM_BFb *Zea mays* cDNA 5', mRNA sequence") and having the accession number DR827873.1 (GI:71446823) is incorporated here by reference. This sequence includes a segment corresponding to the mature miR167g (SEQ ID NO. 4). Using the public sequence, bioinformatic analysis was performed on proprietary maize genomic sequence. A 4.75 kilobase genomic cluster including sequence from maize inbred line B73 was identified as containing predicted gene sequences for miR167a and miR167g. A 486 base pair region between the two miR167 genes was identified as having homology to an expressed sequence tag (EST) sequence. Promoter motifs were identified in the upstream sequences of both (miR167a and miR167g) predicted transcripts. A region of 1682 base pairs (SEQ ID NO. 222) between the predicted miR167a and miR167g transcripts, and a smaller region of 674 base pairs (SEQ ID NO. 223) between the EST and the predicted miR167g transcript was identified as miR167g promoter sequences. Subsets of these sequences (e.g., at least about 50, about 100, about 150, about 200, about 250, or about 300 nucleotides of SEQ ID NO. 222 or SEQ ID NO. 223, or fragments of at least about 50, about 100, about 150, and about 200 contiguous nucleotides having at least 85%, at least 90%, or at least 95% identity to a segment of SEQ ID NO. 222 or SEQ ID NO. 223) are also useful as promoters; their promoter effects are demonstrable by procedures well known in the art (e.g., to drive expression of a reporter gene such as luciferase or green fluorescent protein). The annotation map, including locations of the miR167a and miR167g genes and mature miRNAs, and promoter elements (e.g., TATA boxes), of this genomic cluster is shown in FIG. 18. The annotation map also shows the location of auxin-responsive factor (ARF) motifs or auxin response elements with the sequence TGTCTC (SEQ ID NO. 224), which indicates that auxin may regulate expression of miR167g. Mature miR167 miRNAs are complementary to ARF6 and ARF8 (which encode activating ARFs) and have been proposed to regulate auxin homeostasis; see, for example, Rhoades et al. (2002) *Cell,* 110:513-520, Bartel and Bartel (2003) *Plant Physiol.,* 132: 709-717, Ulmasov et al. (1999) *Proc. Natl. Acad. Sci. USA,* 96:5844-5849, and Mallory et al. (2005) *Plant Cell,* 17:1360-1375, all of which are incorporated by reference herein.

In addition to the miR167g promoter sequences (SEQ ID NO. 222 and SEQ ID NO. 223) identified from maize inbred line B73, two additional miR167g promoter sequences (SEQ ID NO. 225 and SEQ ID NO. 226) were amplified from the maize inbred line LH244. The 3' ends of SEQ ID NO. 225 and SEQ ID NO. 226 were determined experimentally by 5' RACE (rapid amplification of cDNA ends, Invitrogen Corporation, Carlsbad, Calif.) of miR167g. The 5' end of the 768 base pairs sequence (SEQ ID NO. 225) corresponds to the end of a GenBank publicly available 481 base pair cDNA sequence (annotated as "QCG17c03.yg QCG *Zea mays* cDNA clone QCG17c03, mRNA sequence") and having the accession number CF035345.1 (GI:32930533). The 5' end of the 407 base pairs sequence (SEQ ID NO. 226) corresponds to the end of a GenBank publicly available 746 base pair cDNA sequence (annotated as "MEST991_A06.T7-1 UGA-ZmSAM-XZ2 *Zea mays* cDNA, mRNA sequence") and having the accession number DN214085.1 (GI:60347112).

The miR167g promoter sequences, miR167g gene, mature miR167g microRNA, and miR167g recognition site described herein have various utilities as described in Examples 12, 13, 14, and 18, and elsewhere in this disclosure. In particular, a miR167g promoter is useful as an endosperm-specific promoter, and can be used, for example to replace the maize B32 promoter used in the recombinant DNA construct described in Example 4 (also see FIG. 5B). In another utility, the miR167g sequence or mature miR167g (or a precursor thereof) is engineered to suppress a target gene, especially where suppression is to be endosperm-specific. The miR167g recognition site is useful, e.g., in constructs for gene expression where the gene is to be expressed in tissues other than endosperm.

MicroRNA genes were cloned essentially as described in Example 15 from maize. These included a ZmMIR159a sequence (SEQ ID NO. 227) and a ZmMIR164e (SEQ ID NO. 228); the sequences are provided in Table 9, with the location of nucleotides corresponding to the mature miRNA indicated by underlined text.

TABLE 9

| Zea mays MIR sequence | |
|---|---|
| MIR159a | GCATCTGCTGTTCTTTATTTCTATACATACATATATACTATCAC |
| (SEQ ID NO. 227) | CGGTTATTTGCTTCTCTATTCTGTCCGAGTACTTTACGGTGTTC |
| | CGCACATAGATCTCGTGGCCGGCGGTTTTGCGCTTTCGCTTGC |
| | GTTTCTTGGCCCTGCTGGTGTTTGACCGGACCGAACGGGGGCA |
| | GATCGATGCTTTGGGTTTGAAGCGGAGCTCCTATCATTCCAATGA |
| | AGGGTCGTTCCGAAGGGCTGGTTCCGCTGCTCGTTCATGGTTCCC |
| | ACTATCCTATCTCATCATGTGTATATATGTATTCCATGGGGAGGGT |
| | TTCTCTCGTCTTTGAGATAGGCTTGTGGTTTGCATGACCGAGGAGC |
| | TGCACCGCCCCCTTGCTGGCCGCTCTTTGGATTGAAGGGAGCTCTG |
| | CATCCTGATCCACCCCTCCATTTTTTTTGCTTGTTGTGTCCTTCC |
| | TGGGACCTGAGATCTGAGGCTCGTGGTGGCTCACTG |
| MIR164e | CCTTGTATGTTCTCCGCTCACTCCCCCATTCCACTCTCATCCATCTCTC |
| (SEQ ID NO. 228) | AAGCTACACACATATAAAAAAAAAAGAGTAGAGAAGGACCGCCGT |
| | TAGAGCACTTGATGCATGCGTACGTCGATCCGGCGGACCGATCTGC |
| | TTTTGCTTGTGTGCTTGGTGAGAAGGTCCCTGTTGGAGAAGCAGGGC |
| | ACGTGCAGAGACACGCCGGAGCACGGCCGCCGCCGATCTACCGAC |
| | CTCCCACACCTGCCTTGTGGTGTGGGGGTGGAGGTCGTCGGTGGAA |
| | GCGATAGCTGTCGTTGTTGCTTCGATGTTGTTAGCTCCTCCTGCACG |
| | TGCTCCCCTTCTCCACCACGGCCTTCTCACCACCCTCCTCCCCCGGC |
| | GGCGGCGGCGGCGGACCGCCCTTGCCGCGATCAATAATGAAACCA |
| | AAAGCCGACAGTATTTGAGCAGGAAATACAAAGAGGCGGATATCCCAC |
| | TGCTAGCACTTCTGCGTTGATCATGtTCATCTGGAACAAAATAATACT |
| | CGGCGACTTTACAGCGAGTGCAGCATG |

Example 20

This example describes a recombinant DNA construct including a transcribable engineered miRNA precursor designed to suppress a target sequence, wherein the transcribable engineered miRNA precursor is derived from the fold-back structure of a MIR gene, preferably a maize or soybean MIR sequence.

An engineered miRNA, "MIR159a-CPB.miR1", based on cloned SEQ ID NO. 227, was designed to target a vacuolar ATPase sequence from Colorado potato beetle and had the sequence GCATCTGCTGTTCTTTATTTCTATA-CATACATATATACTATCACCGGT-TATTTGCTTCTCTATTCTGTCCGA GTACTTTACGGT-GTTCCGCACATAGATCTCGTGGCCGGCGGTTTTGC GCTTTCGCTTGCGTTTCTTGGCCC TGCTGGTGM-GACCGGACCGAACGGGGGCAGATCGAT-GCTTTGGGTTTGAAGatacGtggCaAaacTaggAAT GAAGGGTCGTTCCGAAGGGCTGGTTC-CGCTGCTCGTTCATGGTTCCCACTATC-CTATCTCATCATGTGTA TATATGTATTCCATGGGG-GAGGGTTTCTCTCGTCTTTGAGATAGGCTTGTGGTT TGCATGACCGAGGAGC TGCACCGCCCCCTTGCTG-GCCGCTC<u>TTTCCTGGTTCTGCCACGTAT</u>CAT CCT- GATCCACCCCTCCATTTT TTTTTGCTTGTTGTGTC-CTTCCTGGGACCTGAGATCTGAGGCTCGTGGTGGCTCACTG (SEQ ID NO. 229, where the nucleotides corresponding to the engineered mature miRNA are indicated by bold underlined text, and the nucleotides included in the complementary strand of the miRNA hairpin are indicated by lower-case text). A recombinant DNA construct containing this engineered miRNA (SEQ ID NO. 229), was made and expressed in tobacco (*N. benthamiana*) using a transient in planta expression assay as in Llave et al. (2002) *Plant Cell*, 14:1605-1619 and Palatnik et al. (2003) *Nature*, 425:257-263, which are incorporated by reference herein. Briefly, *Agrobacterium tumefaciens* containing a binary expression vector was grown to late log phase, VIR genes induced, and all desired combinations of expression vectors mixed to a final optical density (600 nanometers) of 0.5. A GFP expression vector was used to equalize all mixes to the same optical density. *Agrobacterium* mixes were infiltrated into *N. benthamiana* using a syringe applied with slight pressure to the bottom surface of two to three leaves per plant leaf. Inoculated leaves were harvested 48 hours after infiltration. All assays were performed in triplicate, with a single plant per replicate. The predicted mature engineered miRNA processed from the precursor sequence SEQ ID NO. 229 has the sequence UUUCCUGGUUCUGCCACGUAU (SEQ ID NO. 230), which has a Reynolds score of 4 (where values range from −1 to 10 and a higher score is predictive of efficacy; see Reynolds et al. (2004) *Nature Biotechnol.*, 22:326-330, which is incorporated by reference in its entirety herein), a functional asymmetry score of −1.1 (where a negative value predicts incorporation into the RISC complex, see Khvorova et al. (2003) *Cell*, 115:209-216, which is incorporated by reference herein), and was observed to be efficiently processed (FIG. 19B).

This approach is useful with other plant mature miRNA and miRNA precursor sequences, which can be engineered to silence various target genes of the plant or of a pest or pathogen of the plant. Thus, another engineered miRNA, "MIR159a-CRW.miR1", also based on cloned SEQ ID NO. 227, is designed to target a vacuolar ATPase sequence from corn rootworm and had the sequence GCATCTGCTGT-TCTTTATTTCTATACATACATATATAC-TATCACCGGTTATTTGCTTCTCTATTCTGTCCGA GTACTTTACGGTGTTCCGCACATA-GATCTCGTGGCCGGCGGTTTTGCGC TTTCGCT-TGCGTTTCTTGGCCC TGCTGGTGTTTGACCGGAC-CGAACGGGGGCAGATCGATGCTTTGGGTTTGAAG TCTCTGGCAGTAACTG ACAATGAAGGGTCGTTC-CGAAGGGCTGGTTCCGCTGCTCGTTCATGGTT CCCACTATCCTATCTCATCAT GTGTATATATGTATTC-CATGGGGGAGGGTTTCTCTCGTCTTTGAGATAGGC TTGTGGTTTGCATGACCGA GGAGCTGCACCGCCC CCTTGCTGGCCGCT<u>CTTTGTCCGTTTCTGCCAGAGA</u> CATCCTGATCCACCCCTC CATTTTTTTTGCTTGT-TGTGTCCTTCCTGGGACCTGAGATCT-GAGGCTCGTGGTGGCTCACTG (SEQ ID NO. 231, where the nucleotides corresponding to the engineered mature miRNA are indicated by bold underlined text). The Western corn rootworm (*Diabrotica virgifera*) vacuolar ATPase sequence selected for suppression has the sequence AGAAGCCTGGCAATTTCCAAGGT-GATTTTGTCCGTTTCTGCCAGAGAT-GCTTTACCTACCAGCTGCACAA TTTCGGCTAGAT-CATCTTCTTCCTGAAGAATTTCCTTAACTTGGTTCTA AGAGGAATAAACTCTTGGAA GTTTTTGTCAT-AAAAGTCGTCCAATGCTCT-TAAATATTTGGAATATGATCCAAGC-CAGTCTACTGAAGGG AAGTGCTTACGTTGGGCAAG (SEQ ID NO. 232). The predicted mature engineered miRNA processed from the precursor sequence SEQ ID NO. 229 has the sequence UUUGUCCGUUUCUGCCAGAGA (SEQ ID NO. 233), which has a Reynolds score of 6 and a functional asymmetry score of −3.2. This gene suppression element is tested in *Agrobacterium*-mediated transient assays in tobacco for expression of the engineered miRNA, and then stably transformed into maize to test for efficacy in controlling corn rootworm. These engineered miRNAs or miRNA precursors can be included in various recombinant DNA constructs of the invention, e.g., in a construct including the engineered miRNA or miRNA precursor embedded within an intron flanked on one or on both sides by non-protein-coding DNA, or in combination with a miRNA recognition site, or with an aptamer.

Example 21

Current criteria for miRNA identification have emphasized phylogenetic conservation of miRNAs across species, and thus few non-conserved or species-specific miRNAs in plants have been characterized in plants. This example describes identifying five novel non-conserved miRNAs and the corresponding MIR sequences from a size-fractionized cDNA library constructed from soybean leaves. Criteria for miRNA identification included: (1) a cloned 21-nt small RNA, and possible miRNA* (strand corresponding to the miRNA) at a lower abundance, (2) containment of the miRNA/miRNA* duplex wholly within a short, imperfect foldback structure, (3) derivation of the miRNA from an RNA Pol II non-protein-coding transcript, and (4) presence of a complementary target site in a coding gene; see Ambros et al. (2003) *RNA*, 9: 277-279, which is incorporated by reference herein.

Small RNAs were extracted from adaptor-containing raw sequences and their strands were determined. This sequence set was filtered to remove small RNA sequences that were virus, tRNA, rRNA, chloroplast and mitochondria RNAs, and transgene, resulting in a filtered set of 381,633 putative miRNA sequences. Small RNAs not originating from the above sources and not homologous to known miRNAs were mapped to reference soybean cDNA sequences. For the mapped cDNA sequences with low protein-coding content, a cDNA sequence fragment of about 250 nucleotides, containing the putative miRNA, was folded using RNA Folder. The foldback structure was examined to check if the small RNA was located in the stem, and if an extensively (but not perfectly) complementary small RNA with lower abundance was located in the opposite side of the stem. The potential targets of the small RNA are predicted based on rules modified from Jones-Rhoades and Bartel (2004) *Mol. Cell*, 14:787-799, and Zhang (2005) *Nucleic Acids Res.*, 33:W701-704, which are incorporated by reference herein. Table 10 lists the five novel non-conserved miRNAs cloned from soy leaf tissue, and for each the corresponding miRNA* and precursor pri-miRNA(s); abundance ("abund") is given as the number of times the sequence occurred in a total of 381,633 sequences.

TABLE 10

| miRNA SEQ ID NO. | sequence | abund | miRNA* SEQ ID NO. | sequence | abund | miRNA precursor SEQ ID NO. |
|---|---|---|---|---|---|---|
| 234 | UGAGACCAAAUGAGCAGCUGA | 94123 | 235 | GCUGCUCAUCUGUUCUCAGG | 26 | 236 |
| 237 | UAGAAGCUCCCCAUGUUCUCA | 7259 | 238 | GAGCAUGGGUAACUUCUAU | 24 | 239 |
| 240 | UGUUGCGGGUAUCUUUGCCUC | 4127 | 241 | GGCGUAGAUCCCCACAACAG | 9 | 242 |
| 243 | UGCGAGUGUCUUCGCCUCUGA | 3778 | 244 | GGAGGCGUAGAUACUCACACC | 70 | 245 |
| 246 | UUGCCGAUUCCACCCAUUCCUA | 3733 | 247 | GCUGCUCAUCUGUUCUCAGG | 93 | 248, 249 |

For each novel soy miRNA, the fold-back structure of the miRNA precursor sequence(s) was predicted by an algorithm ("RNAFolder", based on RNAfold, publicly available at www.tbi.univie.ac.at/~ivo/RNA/RNAfold.html), and the miRNA precursor transcription profile obtained when available, as listed in Table 11. Examples of predicted targets (recognition sites) in soybean and their expression pattern identified were identified for two of the miRNAs (SEQ ID NO: 234 and SEQ ID NO. 237).

TABLE 11

Figure 22:
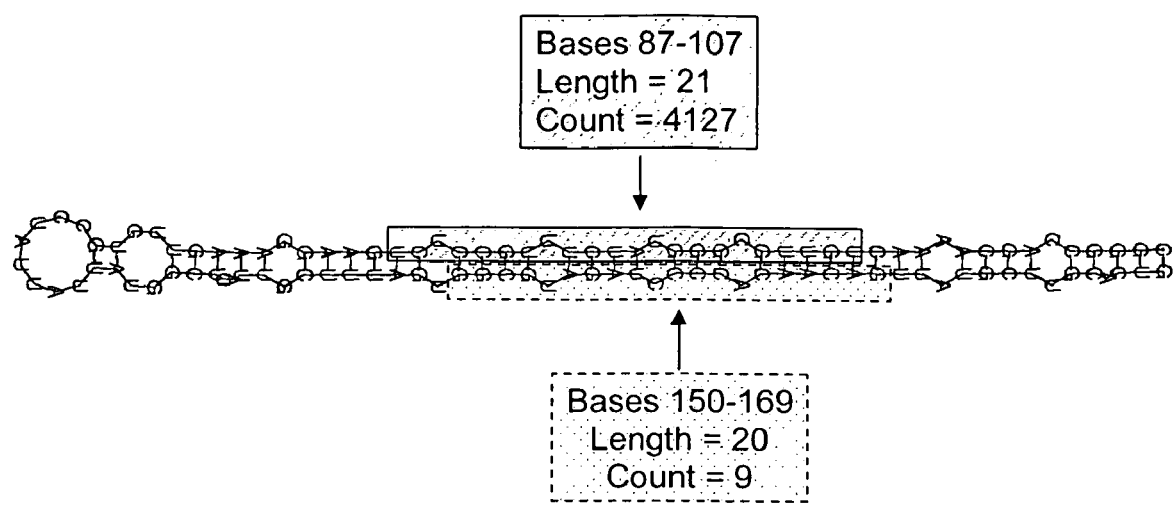
FIG. 22 depicts results described in detail in Example 21.
Figure 23:
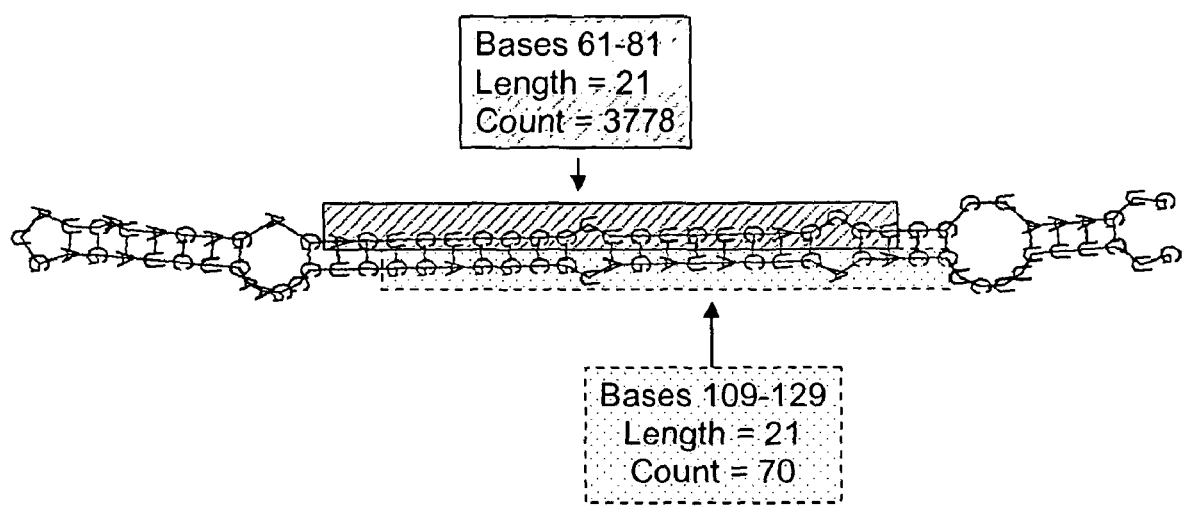
FIG. 23 depicts results described in detail in Example 21.

| miRNA SEQ ID NO. | miRNA precursor | miRNA precursor fold-back | miRNA precursor transcription profile | predicted G. max target (recognition site) sequence | predicted target expression pattern |
|---|---|---|---|---|---|
| 234 | 236 | see FIG. 20A | see FIG. 20B | polyphenol oxidase (SEQ ID NO. 250) | see FIG. 20C |
| 237 | 239 | see FIG. 21A | — | polyphenol oxidase (SEQ ID NO. 251) | see FIG. 21B |
| 240 | 242 | see FIG. 22 | — | — | — |
| 243 | 245 | see FIG. 23 | — | — | — |
| 246 | 248, 249 | see FIG. 24A | see FIG. 24B | — | — |

In addition, target (recognition site) sequences for each novel soy miRNA were identified from in-house ("MRTC") soy databases, as listed in Table 12.

TABLE 12

| Glycine max target (recognition site) SEQ ID NO. | MRTC designation | Location of target (recognition site) | target (recognition site) sequence | score | mismatch |
|---|---|---|---|---|---|
| | miRNA SEQ ID NO. 234 | | miRNA sequence (3'→5') AGUCGACGAGUAAACCAGAGU | | |
| 252 | MRT3847_253879C.2 | 153–173 | ucagcugcucaucuguucuca | 2.5 | 2 |
| 253 | MRT3847_54392C.5 | 402–422 | ccagcugcucauuuggucacu | 2.5 | 3 |
| 254 | MRT3847_41382C.3 | 118–138 | ucagcucuucuuuggucucu | 2.5 | 4 |
| 255 | MRT3847_319840C.1 | 408–428 | ucagcuacugaucuggucuca | 3 | 3 |
| 256 | MRT3847_326146C.1 | 117–137 | ucagcuguccuuuggucucu | 3 | 4 |
| 257 | MRT3847_39543C.6 | 768–788 | ucagcuguccuuuguucucu | 3 | 4 |
| 258 | MRT3847_253942C.4 | 1837–1857 | guagcuucucacuuggucuua | 3 | 5 |
| 259 | MRT3847_260486C.4 | 124–144 | uuagcugcuucuucggucucu | 3 | 5 |
| 260 | MRT3847_210520C.2 | 357–377 | uuagaugcuuguuuggucuuu | 3 | 6 |
| | miRNA SEQ ID NO. 237 | | miRNA sequence (3'→5') ACUCUUGUACCCCUCGAAGAU | | |
| 261 | MRT3847_303349C.1 | 435–455 | ugagaacauggggagccucua | 1.5 | 1 |
| 262 | MRT3847_14593C.6 | 1133–1153 | agaggacauggggagauucua | 2 | 3 |
| 263 | MRT3847_241913C.3 | 1111–1131 | agaggacauggggagguucua | 2 | 3 |
| 264 | MRT3847_32439C.4 | 1142–1162 | ugagaacaugggaaucuucua | 2.5 | 2 |
| 265 | MRT3847_187197C.5 | 689–709 | aaagaacauggggagccucua | 2.5 | 3 |

TABLE 12-continued

| Glycine max target (recognition site) SEQ ID NO. | MRTC designation | Location of target (recognition site) | target (recognition site) sequence | score | mismatch |
|---|---|---|---|---|---|
| 266 | MRT3847_33448C.5 | 1047-1067 | ugagaacaugggggauuucua | 2.5 | 3 |
| 267 | MRT3847_39693C.6 | 305-325 | ugugaaggugggagcuucuu | 2.5 | 4 |
| 268 | MRT3847_50432C.5 | 89-109 | ggagaacaugcagagcuucug | 2.5 | 4 |
| 269 | MRT3847_95417C.1 | 308-328 | ugagaaacugggggagcuuuuc | 2.5 | 4 |
| 270 | MRT3847_115705C.2 | 82-101 | ugagaac-uggugagcuucug | 3 | 3 | miRNA SEQ ID NO. 237 miRNA sequence (3'→5') ACUCUUGUACCCCUCGAAGAU

| 271 | MRT3847_182667C.1 | 143-162 | ugaguac-uggggagcuucuc | 3 | 3 |
| 272 | MRT3847_184995C.1 | 16-36 | ugagagcaugggguaacuucua | 3 | 3 |
| 273 | MRT3847_253437C.4 | 141-160 | ugagcac-uggggagcuucuc | 3 | 3 |
| 274 | MRT3847_293395C.2 | 294-313 | ugagcac-uggggagcuucuc | 3 | 3 |
| 275 | MRT3847_63512C.6 | 321-340 | ugagcac-ugggagcuucuc | 3 | 3 |
| 276 | MRT3847_64829C.6 | 1087-1107 | ugagaacaugggagacuuucua | 3 | 3 |
| 277 | MRT3847_80470C.3 | 15-35 | ugagagcaugggguaacuucua | 3 | 3 |
| 278 | MRT3847_136444C.5 | 312-332 | ugagaaccuguaagcuucug | 3 | 4 |
| 279 | MRT3847_231576C.1 | 360-380 | ugagaacaucgaaagcuucuu | 3 | 4 |
| 280 | MRT3847_263317C.1 | 90-110 | ugaggcaaggggagcuuuaug | 3 | 4 |
| 281 | MRT3847_304409C.1 | 217-237 | cuaaaacaugggggagcuucuu | 3 | 4 |
| 282 | MRT3847_247682C.3 | 1287-1307 | ugaggaaauagggagguucug | 3 | 5 |
| 283 | MRT3847_251048C.2 | 280-300 | ugagaacauagugaguuuuu | 3 | 5 |
| 284 | MRT3847_270705C.2 | 575-595 | uaggacguggggagcuucuc | 3 | 5 |
| 285 | MRT3847_304509C.2 | 592-612 | uaggaucgugggagcuucuc | 3 | 5 |
| 286 | MRT3847_62576C.4 | 540-560 | uaggaucgugggagcuucuc | 3 | 5 |
| 287 | MRT3847_67153C.3 | 661-681 | gaugaauaugggagguucua | 3 | 5 | miRNA SEQ ID NO. 240 miRNA sequence (3'→5') CUCCGUUUCUAUGGGCGUUGU

| 288 | MRT3847_106868C.2 | 318-338 | ggggcaaggacauccgcaacg | 2.5 | 5 |
| 289 | MRT3847_307036C.1 | 171-191 | aaggcaaaguugcccgcgacg | 2.5 | 5 |
| 290 | MRT3847_308816C.2 | 719-739 | gaggcaaaagaugcgagcaacg | 3 | 4 |
| 291 | MRT3847_6248C.3 | 584-604 | gcggcaaagauacucacaacc | 3 | 4 |
| 292 | MRT3847_104943C.2 | 177-197 | aacgcaaagagaccuguaaca | 3 | 5 |
| 293 | MRT3847_290510C.2 | 181-201 | aaggcaaaagaugccagcgacg | 3 | 5 |
| 294 | MRT3847_294184C.2 | 1090-1110 | gagccaaaagagacccgugacg | 3 | 5 |
| 295 | MRT3847_321797C.1 | 847-867 | aaggcauagauagucgcagca | 3 | 5 |
| 296 | MRT3847_63653C.5 | 1096-1116 | aaggcaaaagaugccagcaaug | 3 | 5 |
| 297 | MRT3847_9362C.2 | 481-501 | uagggaaagauacaguaaca | 3 | 5 |
| 298 | MRT3847_112761C.3 | 331-351 | gaggcaaaaguugguccaaug | 3 | 6 |
| 299 | MRT3847_249731C.3 | 515-535 | caggcaaaagaugucugcaauu | 3 | 6 |
| 300 | MRT3847_313052C.1 | 253-273 | uagguauggauacuugcaaca | 3 | 6 |
| 301 | MRT3847_318082C.1 | 123-143 | aaggcaaagcugcccgcgaug | 3 | 6 | miRNA SEQ ID NO. 243 miRNA sequence (3'→5') AGUCUCCGCUUCUGUGAGCGU

| 302 | MRT3847_160536C.3 | 182-202 | ucaggggaggagacacucgca | 2 | 3 |
| 303 | MRT3847_290017C.2 | 304-324 | uuagaggcaaagacacucguc | 2 | 4 |
| 304 | MRT3847_97323C.1 | 55-75 | ucagaggagaagauacucgug | 2 | 4 |
| 305 | MRT3847_182887C.1 | 43-63 | ucagaggagaagacacgcgca | 2.5 | 2 |
| 306 | MRT3847_290275C.2 | 177-197 | ucagaggggaagacacacgcu | 2.5 | 3 |
| 307 | MRT3847_296312C.2 | 155-175 | ucagaggggaagacacacgcu | 2.5 | 3 |
| 308 | MRT3847_292252C.2 | 171-191 | ucagaggugaggacacacgcu | 2.5 | 4 |
| 309 | MRT3847_206250C.1 | 306-326 | ccagaggcggaugcauucgca | 2.5 | 5 |
| 310 | MRT3847_240825C.3 | 436-456 | acagaggcagggacacucgca | 2.5 | 5 |
| 311 | MRT3847_250458C.2 | 776-796 | gcagaggugaaagcuucgca | 2.5 | 5 |
| 312 | MRT3847_36461C.4 | 87-107 | uuagaggagaggauacucgcg | 2.5 | 5 |
| 313 | MRT3847_48749C.4 | 715-735 | gcagaggugaaagcuugca | 2.5 | 5 |
| 314 | MRT3847_97362C.3 | 566-586 | ucagaggcaaagauacccgca | 3 | 3 |
| 315 | MRT3847_20647C.2 | 143-163 | uuagaggggaagacacgcgcu | 3 | 4 |
| 316 | MRT3847_219382C.1 | 147-167 | ucagaggggaagacacccgug | 3 | 4 |
| 317 | MRT3847_243196C.3 | 73-93 | ucagaggcuaagagacuugca | 3 | 4 |
| 318 | MRT3847_248880C.3 | 760-780 | ucagaggggaagacacacgug | 3 | 4 |
| 319 | MRT3847_25201C.4 | 173-193 | ucagaggggaagacacccgug | 3 | 4 |
| 320 | MRT3847_264555C.4 | 212-232 | ucagaggggaagacacacguu | 3 | 4 |
| 321 | MRT3847_28447C.6 | 142-162 | ucagaggggaagacacacguu | 3 | 4 |
| 322 | MRT3847_32431C.4 | 59-79 | ucagaggugaagacacacgua | 3 | 4 |
| 323 | MRT3847_99342C.1 | 116-136 | ucagaggggaagacacccgug | 3 | 4 |
| 324 | MRT3847_210811C.2 | 273-293 | ucagaaacgaagacgcucguu | 3 | 5 |
| 325 | MRT3847_240622C.2 | 92-112 | uccgaggggaagauacucguu | 3 | 5 |
| 326 | MRT3847_254863C.2 | 175-195 | uccgaggggaagauacucguc | 3 | 5 |

TABLE 12-continued

| Glycine max target (recognition site) SEQ ID NO. | MRTC designation | Location of target (recognition site) | target (recognition site) sequence | score | mismatch |
|---|---|---|---|---|---|
| 327 | MRT3847_255345C.3 | 113-133 | uccgagggaagauacucguc | 3 | 5 |
| 328 | MRT3847_257424C.1 | 378-398 | gcagaggcuguggcacucgca | 3 | 5 |
| 329 | MRT3847_38012C.4 | 56-76 | uuagaggcgaggacacacguu | 3 | 5 |
| 330 | MRT3847_695IC.6 | 306-326 | uccgaggagaagauacucguu | 3 | 5 |
| 331 | MRT3847_263266C.4 | 163-183 | ucaguggcgaaggcguucguc | 3 | 6 |
| 332 | MRT3847_272810C.2 | 502-522 | uuagaggugauggcacucgug | 3 | 6 |

| miRNA SEQ ID NO. 246 | | | miRNA sequence (3'→5') AUCCUUACCCACCUUAGCCGUU | | |
|---|---|---|---|---|---|
| 333 | MRT3847_302750C.1 | 259-280 | ggggaaugggguggaaacggcaa | 1.5 | 3 |
| 334 | MRT3847_136115C.3 | 661-682 | ugggaaugggguggauggguaa | 2.5 | 4 |
| 335 | MRT3847_235247C.2 | 694-715 | ugggaaugggguggauggguaa | 2.5 | 4 |
| 336 | MRT3847_21031C.3 | 1364-1385 | auggaacugguggaauuggcaa | 2.5 | 5 |
| 337 | MRT3847_297070C.2 | 280-301 | cgggaaagguuggaauuggcaa | 2.5 | 5 |
| 338 | MRT3847_248343C.3 | 392-413 | uagagaaugggguggauuuugcaa | 3 | 3 |
| 339 | MRT3847_207469C.2 | 1-20 | ggaaugggguggcgugggcaa | 3 | 5 |
| 340 | MRT3847_216295C.4 | 537-558 | caggaaaggggggaguuggcaa | 3 | |
| 341 | MRT3847_287795C.2 | 141-162 | uagcaauggguuggaucgguga | 3 | 5 |
| 342 | MRT3847_302511C.2 | 35-56 | guugaaugggguggaauuggaaa | 3 | 5 |
| 343 | MRT3847_312620C.1 | 46-67 | guugaaugggguggaauuggaaa | 3 | 5 |
| 344 | MRT3847_20416C.2 | 679-700 | aaggaauugggggaauugguac | 3 | 6 |
| 345 | MRT3847_297209C.1 | 289-310 | cacgaguggggggaaucggcgg | 3 | 6 |
| 346 | MRT3847_6639C.4 | 195-216 | guggaaugggugggucuugguaa | 3 | 6 |

Example 22

This example describes a recombinant DNA construct of the invention, including a promoter, a terminator, transcribable sequence between the promoter and the terminator, and at least one gene suppression element that is 3' to the terminator. More specifically, this example demonstrates that a gene suppression element 3' to a terminator was transcribed and silenced a target gene in a plant cell.

Most expression cassettes include both a promoter and a terminator (i.e., a genetic element containing sequences necessary for polyadenylation of the primary transcript), between which is contained the sequence(s) to be expressed in a cell. Nonetheless, it is likely that the primary transcript extends beyond the terminator element. In plants, it is believed that transcription continues some distance beyond the polyadenylation signal and site. In one of the few studies to examine transcription termination in plants, transcripts terminated downstream of the polyA site by as much as 300 bp; no single transcriptional termination sites were found, but rather a series of potential termination sites that corresponded with T-rich sequences; see Hasegawa et al (2003) *Plant J*, 33:1063-1072. It is believed that polyadenylation pathway genes are conserved from animals to plants; see Yao et al. (2002) *J. Exp. Bot.*, 53:2277-2278. Plant mRNAs analogous sequences are found in positions similar to those of animal AAUAAA and U-rich sequences, suggesting an equivalent regulatory mechanisms in plants; see Graber et al. (1999) *Proc. Natl. Acad. Sci. USA*, 96:14055-14060. In yeast and animals, transcripts have been shown to extend over 1 kilobase downstream of the polyadenylation signal and site; see Proudfoot (2004) *Curr. Opin. Cell Biol.*, 16:272-278. The 3' end of a mature RNA transcript is formed by cleavage and polyadenylation at the polyA site. Although the primary transcript extends well beyond the polyA site, most current models for transcriptional termination invoke a coupling between polyadenylation and termination; see Proudfoot (2004) *Curr. Opin. Cell Biol.*, 16:272-278. For example, some evidence indicates that the presence of PolII "pause sites" downstream of the polyadenylation site. Removal of such pause sites is expected to allow transcription to extend even further downstream of the polyadenylation site. Thus, a single RNA transcript can be used to both express a gene (with sequence upstream of the terminator) and suppress a gene (with RNA downstream of the terminator), and furthermore allows the expression and suppression to be temporally and spatially coupled. In one non-limiting example, the coordinated expression of a bacterial cordapA gene and suppression of the endogenous LKR-SDH gene has been shown to result in elevation of lysine levels in the maize kernel. Another example is the expression in a transgenic plant of a gene encoding a *Bacillus thuringiensis* insecticidal protein and the production of dsRNA targeting an essential corn rootworm (CRW) gene, the combination of which provides enhanced control of CRW.

Various non-limiting embodiments are depicted in FIG. 25, where gene suppression elements can be any of those disclosed herein, e.g., the gene suppression elements depicted in FIG. 8, as well as aptamers or riboswitches. In one embodiment, an inverted repeat of at least 21 base pairs is positioned 3' to a terminator, e.g., downstream of a typical gene expression cassette that includes a promoter, a sequence to be expressed, and a terminator. In other embodiments, tandem repeats of anti-sense or sense sequence of the target gene are used as the gene suppression element. In some embodiments, the gene suppression element is embedded in an intron directly or substantially directly 3' to the terminator. The downstream sequence can contain a gene suppression element designed to be processed by a trans-acting siRNA mechanism, e.g., sequences corresponding to a target gene fused to a miRNA target sequence, such that miRNA-triggered dsRNA production occurs resulting in silencing of a target gene. A second terminator can be included as shown in FIG. 26A, or can be omitted, as the absence of a polyadenylation signal downstream of a gene suppression element does not reduce suppression efficiency (see Example 1) and can enhance it. Where two terminators are included, it is preferable that the two terminators be unrelated to reduce the possibility of recombination between them.

The constructs depicted in FIG. 26A (suppression construct) and FIG. 26B (control construct) were tested in a maize protoplast assay as described in Examples 1 and 2. Firefly luciferase suppression experiments were performed, and the target gene, firefly luciferase, was suppressed by an inverted repeat 3' to the terminator, as indicated by the logarithm of the ratio of firefly luciferase to Renilla luciferase, "log(Fluc/Rluc)", as depicted in FIG. 26C.

Example 23

This non-limiting example illustrates the transgenic plants of the invention, which have in their genome recombinant DNA including transcribable DNA including DNA that transcribes to an RNA aptamer capable of binding to a ligand. One application of the invention is to provide a ligand-activated, herbicide-resistant system for gene identity preservation ("gene lock") as well as to maintain herbicide-resistant volunteer control.

In one embodiment, the DNA sequence encoding an "on" riboswitch is inserted into an expression cassette containing as the target sequence "CP4", a selectable marker conferring glyphosate resistance, epsps-cp4 (5-enolpyruvylshikimate-3-phosphate synthase from Agrobacterium tumefaciens strain CP4), to conditionally express CP4 in transgenic plants. See the construct depicted in FIG. 28A, where CP4 is the target sequence ("TS"), and FIG. 28F, which depicts a non-limiting example of a CP4 expression cassette useful for Agrobacterium-mediated transformation of maize and other crop plants, and the expected "ligand A"-controlled CP4 expression. Transgenic plants harboring the riboswitch-controlled CP4 cassette express CP4 only in the presence of the ligand, which is applied (e.g., by a foliar spray) to the plant by means of a proprietary glyphosate formulation containing the ligand. Upon application, the formulated glyphosate herbicide activates CP4 transcription/translation and renders the transgenic plant resistant to glyphosate. Transgenic plants are susceptible to generic glyphosate formulations that do not contain the ligand. Similarly, this approach can be applied to any other herbicide-resistance gene/herbicide combinations, for example, dicamba-degrading-oxygenase/dicamba, or antibiotic-resistance gene/antibiotic combination.

Ligand-activated herbicide resistance riboswitches allow formulation of crop-specific herbicides, by using a riboswitch that binds to a different ligand for selected plant species. For example, where an adenine-binding riboswitch is used for soybeans and a lysine-binding riboswitch is used for corn, a lysine-containing glyphosate formulation will control non-transgenic weeds as well as glyphosate-resistant soybean volunteers (e.g., from a previous crop).

In another embodiment, an autoinduced riboswitch is used to treat seeds. If the residual herbicide lasts longer than the ligand in plant tissues after the ligand-containing herbicide formulation is applied, it could cause crop damage due to the shut down of the herbicide resistance gene. One approach to prevent this is to choose a ligand that is an endogenously produced metabolite and to include a mechanism for the ligand's production with the riboswitch. This makes it possible to engineer an autoinduced riboswitch to maintain expression of the herbicide resistance gene. Using a lysine-autoinduced riboswitch for glyphosate resistance as an example (FIG. 28C), the addition of a second gene, Coryne-bacterium DHDPS or cordapA ("dapA") (see U.S. Pat. Nos. 6,459,019 and 5,773,691 and U.S. Patent Application Publication No. 2003/0056242, which are incorporated by reference), maintains a persistent lysine level sufficient to maintain expression of both CP4 and dapA. This autoinduced system also allows the ligand to be applied by seed treatment as an alternative to including the ligand in the glyphosate formulation. Untreated seeds are viable but require treatment with the appropriate ligand prior to planting in order for the resulting plants to be resistant to the herbicide.

Example 24

This non-limiting example further illustrates the transgenic plants of the invention. One embodiment of the invention is to use an herbicide such as glyphosate as a chemical hybridization agent. This embodiment entails transgenic plants having lower CP4 expression in male tissues relative to the rest of plants, whereby, when the transgenic plants are exposed to glyphosate, male sterility ensues. One approach is to combine a transcriptional control riboswitch with tissue specific control of expression of that riboswitch. An example is depicted in FIG. 28E, where "Promoter1" is a constitutive promoter driving expression of the target gene ("TS") CP4, and "Promoter 2" is a male-specific promoter driving lysine-induced, riboswitch controlled expression of a gene suppression construct for suppressing CP4 ("$TS_{sup}$"). Application of lysine and glyphosate (e.g. as a spray) results in male sterility. Alternatively, using the construct shown in FIG. 28D, where "Promoter 1" is constitutive, "Promoter 2" is male-specific, and the target gene ("TS") is CP4, initial lysine application reduces overall CP4 expression, but CP4 expression is enhanced in male tissues, thereby causing male tissues to be more susceptible to glyphosate.

Example 25

This non-limiting example further illustrates the transgenic plants of the invention. One embodiment of the invention is induced expression of a trait gene under the control of a constitutive promoter. The insertion of a riboswitch allows the trait genes, though under the control of a constitutive promoter, to be expressed only upon selected conditions. This makes it possible to avoid yield penalty (e.g., loss of yield due to non-selective expression of the trait gene), transgene silencing, or other concerns caused by constitutive expression of the transgenes. Non-limiting examples of such riboswitches include a glyphosate "on" riboswitch for CP4 expression, a salicylic acid "on" riboswitch for disease resistance genes, a jasmonic acid "on" riboswitch for insect resistance genes, an ascorbate "on" riboswitch for oxidative stress tolerance genes, and a proline or glycine betaine or mannitol riboswitch for drought tolerance genes.

Example 26

This example further illustrates the transgenic plants of the invention. One embodiment is chemically inducible or suppressible male sterility or fertility for hybridization. Preferred examples use a riboswitch containing an aptamer that binds a ligand that is an already registered substance, e.g., an approved herbicide. In a non-limiting example, a transgenic plant harboring a male sterility gene under the control of a male-specific promoter and a glyphosate "off" riboswitch is male-sterile unless glyphosate is applied. In contrast, a transgenic plant harboring a male sterility gene under the control of a male-specific promoter and a glyphosate "on" riboswitch is male-sterile only when glyphosate is applied.

Example 27

This non-limiting example further illustrates the transgenic plants of the invention. One embodiment of the invention includes artificial riboswitches that are engineered in vitro to permit expression (or suppression) of a target sequence under inducible conditions or in response to biotic or abiotic stress. Such riboswitches use novel aptamers designed for a specific ligand by means well known in the art. See, for example, the detailed discussion above under the heading "Aptamers". Especially useful riboswitches are designed to be triggered by registered agricultural chemicals (e.g., glyphosate, dicamba), disease-induced compounds (e.g., salicylic acid), invertebrate pest-induced or wounding-induced compounds (e.g., jasmonic acid), water stress-induced compounds (e.g., proline, glycine betaine, mannitol) and oxidative stress-induced compounds (e.g., ascorbate).

Example 28

This non-limiting example further illustrates the transgenic plants of the invention. Riboswitches useful in transgenic plants of the invention are designed to function at a given concentration of the ligand. One embodiment is a lysine riboswitch engineered to function in a transgenic plant.

Naturally occurring bacterial lysine riboswitches exist as both "on" and "off" riboswitches, and have a $K_d$~1 millimolar (128 ppm) in vitro (see Sudarsan et al. (2003) Genes Dev., 17:2688-2697, which provides individual and consensus sequences of prokaryotic lysine-responsive riboswitches, and is incorporated by reference). However, maize tissues generally have a lysine content of less than 50 ppm, which is thus a concentration useful as the default state for novel lysine riboswitches. Using bacterial lysine riboswitches as an example, a series of constructs (FIG. 28) is transformed into maize callus, producing transgenic maize callus lines or transgenic maize plants useful for studying riboswitch efficacy in plants and plant cells. In some embodiments, a non-lysine-feedback-inhibited lysine biosynthetic gene, cordapA, is co-expressed in order to obtain autoinducible control of gene expression. As shown in FIG. 28A and FIG. 28B, transcribable DNA fragments of ~150 base pairs, encoding lysine "on" (or "off") riboswitches, are inserted between the promoter and the target sequence ("TS"), in this example a green fluorescent protein (GFP) reporter gene. Other reporter genes or marker genes, as well as any gene of interest, can be used as the target sequence. The callus lines transformed with these constructs display a lysine inducible (or lysine-suppressible) GFP expression phenotype (FIG. 29, top panel, A and B). In some embodiments, a second cassette containing cordapA ("dapA") under the control of a lysine "on" riboswitch, is added (FIG. 28C and FIG. 28D); these callus lines or transgenic plants become autoinducible or autosupressible (FIG. 29, top panel, C and D). FIG. 29, lower panel, schematically depicts an expression cassette, useful in *Agrobacterium*-mediated transformation of maize and other plants, containing a lysine "on" riboswitch, whereby binding of lysine to the aptamer of the riboswitch induces expression of CP4 (for glyphosate resistance) as well as expression of *Corynebacterium* DHDPS or cordapA ("DHDPS"). The resulting endogenous synthesis of additional lysine maintains expression of the transgenes.

Example 29

This example further illustrates the transgenic plants of the invention. One preferred embodiment is a transgenic plant including in its genome transcribable DNA that transcribes to a "trans"-acting riboswitch, i.e., a riboswitch that affects expression of a target sequence to which it is not operably linked.

In some embodiments, the "trans" riboswitch is flanked by ribozymes (e.g., self-splicing or hammerhead ribozymes) and is transcribed under the control of a pol II promoter (FIG. 27A); see, for example, Bayer and Smolke (2005) Nature Biotechnol., 23:337-343, which is incorporated by reference. In other embodiments, the "trans" riboswitch is transcribed under the control of a pol III promoter (FIG. 27B), whereby transcription is terminated at a poly-T region. In other embodiments, the "trans" riboswitch is flanked by intron-splicing junctions (FIG. 27C), whereby the riboswitch is spliced out after transcription; such embodiments can optionally include DNA that transcribes to a microRNA recognition site or DNA that transcribes to RNA capable of forming double-stranded RNA (dsRNA) (FIG. 27D). Embodiments containing intron-embedded transcribable DNA can optionally include one or more gene expression (or suppression) elements ("GOI" in FIG. 27C and FIG. 27D). Alternatively, the transcribed riboswitch can be flanked by double-stranded RNA that can be cleaved through an RNAi (siRNA or miRNA) processing mechanism (FIG. 27E). In yet other embodiments, the "trans" riboswitch is flanked by DNA that transcribes to a microRNA recognition site (FIG. 27E), whereby cleavage of the transcribed riboswitch occurs after binding of the corresponding mature miRNA to the miRNA recognition site. These approaches enable the creation of noncoding riboregulators with defined 5' and 3' ends that are free of potentially interfering flanking sequences. In still other embodiments, the "trans" riboswitch is flanked by DNA that transcribes to RNA capable of forming double-stranded RNA (dsRNA) (FIG. 27E). In some of these cases, the dsRNA is processed by an RNAi (siRNA or miRNA) mechanism, whereby the transcribed riboswitch is cleaved from the rest of the transcript. In other cases, the two transcribed RNA regions flanking the "trans" riboswitch form at least partially double-stranded RNA "stem" between themselves, wherein the "trans" riboswitch serves as a "spacer" or "loop" in a stem-loop structure.

In one example, the transgenic plant has in its genome an expression cassette using pol II promoters to express a "trans" riboswitch flanked by self-cleaving hammerhead ribozyme sequences, resulting in a riboswitch with defined 5' and 3' ends, free of potentially interfering flanking sequences (FIG. 27A; also see Bayer and Smolke (2005) Nature Biotechnol., 23:337-343). An alternative approach uses expression cassettes under the control of pol III promoters to produce noncoding RNAs with minimal 5' and 3' flanking sequences; RNA polymerase II transcribes structural or catalytic RNAs that are usually shorter than 400 nucleotides in length, and recognizes a simple run of T residues as a termination signal; it has been used to transcribe siRNA duplexes (Lu et al. (2004) Nucleic Acids Res., 32:e171, which is incorporated by reference). Riboregulators expressed by Pol III are expected to generate transcripts with relatively defined 5' and 3' ends (FIG. 27B). It has been used to transcribe siRNA duplexes. Alternatively, a "trans" riboswitch is fused to the minimal sequences required for splicing, and endogenous intron splicing mechanisms are used to release the riboregulator (FIG. 27C). This intron-embedded configuration provides the advantage of allowing concurrent expression of a gene of interest (GOI).

One specific application of "trans" riboswitch is their use in generating transgenic plants with inducible male sterility or fertility. Hybrid plant varieties have a significant yield advantage over their inbred counterparts, but can be more costly to produce. Reversible male sterility/fertility is one of the most cost-effective ways to produce hybrids. In this application, "trans" riboswitches are designed to target endogenous genes required for male development. Suppression of any of these genes results in male sterility. "Trans" riboswitches driven by male-specific pol II promoters (FIG. 27A) can be used to control the expression of any target sequence or gene that leads to cell death (apoptosis) or growth arrest. Alternatively "trans" riboswitches transcribed under the control of pol III promoters (FIG. 27B), which are constitutive, are designed to be male specific to avoid undesirable phenotypes. In an inducible male fertility system, the "trans" riboswitch used is an "off" switch (where the riboswitch is bound to its target sequence by default and is released from the target sequence when bound by ligand), supply of the ligand (by endogenous biosynthesis or exogenous application, e.g., by spraying) restores fertility. In an inducible male sterility system, the "trans" riboswitch used is an "on" switch, and binding of the ligand results in the "trans" riboswitch binding to its target sequence and inducing male sterility.

Another specific application of "trans" riboswitches is their use in generating transgenic plants displaying "gene lock". Seeds containing an "off" "trans" riboswitch designed to target endogenous genes required for germination will not be able to germinate. When under the control of a pol II promoter (FIG. 1A), any gene functioning in cell death or growth arrest can be targeted. Alternatively Pol III driven "trans" riboswitches (FIG. 1B) would have to target genes that are specific to germination to avoid undesirable phenotypes. The germination restoration could be seed treatment and illegally copied seeds without seed treatment would not be able to germinated.

Figure 30:
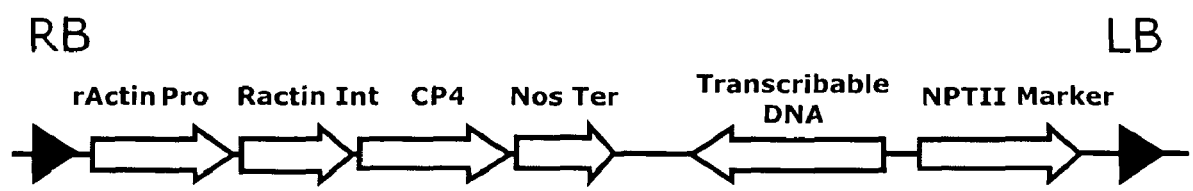
FIG. 30 depicts a non-limiting example of a riboswitch in a binary vector useful in making a transgenic plant of the invention, as described in Example 29. "RB", right T-DNA border element; "LB", left T-DNA border element; "Nos Ter", Nos terminator.

"Trans" riboswitches, similarly to the "cis" riboswitches described in Examples 23 through 2, are useful in regulating transgenes. In a specific example, a transgenic plant including a "trans" riboswitch designed to regulate the glyphosate-resistance transgene CP4 as the target sequence is particularly useful in "trans" riboswitch-controlled applications parallel to that described in Example 23 (glyphosate as a ligand for ligand-activated herbicide resistance, or for control of herbicide resistant volunteers) and Example 24 (glyphosate as a chemical hybridization agent). To illustrate this approach, CP4 expression is suppressed in stably transformed maize callus. A modified transcribable DNA encoding an "off" "trans" riboswitch with theophylline as its ligand (Bayer and Smolke (2005) Nature Biotechnol., 23:337-343) is designed to target CP4 as a target sequence. Transcription of the theophylline riboswitch can be driven either by a pol II promoter (e.g., FIG. 27A) or by pol III promoter (e.g., FIG. 27B). The transcribable DNA is inserted into a binary vector (FIG. 30) and co-transformed into maize callus under nptIII selection, generating stably transformed maize callus lines. CP4 expression is assayed in the transformed cells, where CP4 expression is observed to be suppressed in transformed cells that are treated with theophylline.

Similarly, a "trans" riboswitch is used to control expression of an endogenous target sequence (lysine ketoglutarate reductase/saccharopine dehydrogenase gene, LKR/SDH) in stably transformed maize plants. A modified transcribable DNA encoding an "off" "trans" riboswitch with theophylline as its ligand (Bayer and Smolke (2005) Nature Biotechnol., 23:337-343) is designed to target at least one region of the LKR/SDH sequence, and co-transformed into maize callus. LKR/SDH expression is assayed in the resulting transformed cells, where LKR/SDH expression is observed to be suppressed in transformed cells that are treated with theophylline.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A recombinant DNA construct comprising a promoter with maize endosperm-specific expression operably linked to heterologous DNA, wherein said construct is in a maize cell, and wherein said promoter is a maize miR167g promoter having the nucleotide sequence of SEQ ID NO:223 or a fragment thereof with at least 50 contiguous nucleotides of SEQ ID NO:223 and that is functional for transcribing said heterologous DNA in maize endosperm tissue.

2. The recombinant DNA construct of claim 1, wherein said heterologous DNA comprises one or more of:
   (a) at least one gene suppression element, and
   (b) at least one gene expression element.

3. A transgenic maize plant cell having in its genome the recombinant DNA construct of claim 1.

4. A transgenic maize plant regenerated from said transgenic maize plant cell of claim 3, or a progeny thereof comprising said recombinant DNA construct.

5. The transgenic maize plant of claim 4, wherein said transgenic maize plant has at least one altered trait, relative to a maize plant lacking said recombinant DNA construct, selected from the group of traits consisting of:
   (a) improved abiotic stress tolerance;
   (b) improved biotic stress tolerance;
   (c) improved resistance to a pest or pathogen of said maize plant;
   (d) modified primary metabolite composition;
   (e) modified secondary metabolite composition;
   (f) modified trace element, carotenoid, or vitamin composition;
   (g) improved yield;
   (h) improved ability to use nitrogen or other nutrients;
   (i) modified agronomic characteristics;
   (j) modified growth or reproductive characteristics, and
   (k) improved harvest, storage or processing quality.

6. A seed of the transgenic maize plant of claim 4, wherein said seed has modified primary metabolite, trace element, carotenoid, vitamin, or secondary metabolite composition, or improved storage or processing quality.

7. A method of providing at least one altered maize plant tissue, comprising:
   (a) providing a transgenic maize plant regenerated from said transgenic maize plant cell of claim 3, or a progeny thereof comprising said recombinant DNA construct; and
   (b) transcribing said recombinant DNA construct in at least one tissue of said transgenic maize plant, whereby an altered trait in said at least one tissue results, relative to tissue, wherein said recombinant DNA construct is not transcribed, said altered trait being selected from:
   (i) improved abiotic stress tolerance;
   (ii) improved biotic stress tolerance;
   (iii) improved resistance to a pest or pathogen of said maize plant;
   (iv) modified primary metabolite composition;
   (v) modified secondary metabolite composition;

(vi) modified trace element, carotenoid, or vitamin composition;
(vii) improved yield;
(viii) improved ability to use nitrogen or other nutrients;
(ix) modified agronomic characteristics;
(x) modified growth or reproductive characteristics, and
(xi) improved harvest, storage, or processing quality.

8. The recombinant DNA construct of claim 1, wherein said recombinant DNA construct further comprises:
(a) at least one gene suppression element comprising nucleotides derived from a plant miRNA, and
(b) at least one gene expression element.

* * * * *

SEQUENCE LISTING

<160> NUMBER OF SEQ ID NOS: 349

<210> SEQ ID NO 1
<211> LENGTH: 2767
<212> TYPE: DNA
<213> ORGANISM: Artificial sequence
<220> FEATURE:
<223> OTHER INFORMATION: Synthetic construct

<400> SEQUENCE: 1

```
ggtccgatgt gagactttc aacaaagggt aatatccgga aacctcctcg gattccattg      60
cccagctatc tgtcacttta ttgtgaagat agtggaaaag gaaggtggct cctacaaatg     120
ccatcattgc gataaaggaa aggccatcgt tgaagatgcc tctgccgaca gtggtcccaa     180
agatggaccc ccacccacga ggagcatcgt ggaaaaagaa gacgttccaa ccacgtcttc     240
aaagcaagtg gattgatgtg atggtccgat gtgagacttt tcaacaaagg gtaatatccg     300
gaaacctcct cggattccat tgcccagcta tctgtcactt tattgtgaag atagtggaaa     360
aggaaggtgg ctcctacaaa tgccatcatt gcgataaagg aaaggccatc gttgaagatg     420
```

```
cctctgccga cagtggtccc aaagatggac ccccacccac gaggagcatc gtggaaaaag     480
aagacgttcc aaccacgtct tcaaagcaag tggattgatg tgatatctcc actgacgtaa     540
gggatgacgc acaatcccac tatccttcgc aagacccttc ctctatataa ggaagttcat     600
ttcatttgga gaggacacgc tgacaagctg actctagcag atctaccgtc ttcggtacgc     660
gctcactccg ccctctgcct tgttactgc cacgtttctc tgaatgctct cttgtgtggt      720
gattgctgag agtggtttag ctggatctag aattacactc tgaaatcgtg ttctgcctgt     780
gctgattact tgccgtcctt tgtagcagca aaatataggg acatggtagt acgaaacgaa     840
gatagaacct acacagcaat acgagaaatg tgtaatttgg tgcttagcgg tatttattta     900
agcacatgtt ggtgttatag ggcacttgga ttcagaagtt tgctgttaat ttaggcacag     960
gcttcatact acatgggtca atagtatagg gattcatatt ataggcgata ctataataat    1020
ttgttcgtct gcagagctta ttatttgcca aaattagata ttcctattct gttttttgttt   1080 gtgtgctgtt aaattgttaa cgcctgaagg aataaatata aatgacgaaa ttttgatgtt    1140
tatctctgct cctttattgt gaccataagt caagatcaga tgcacttgtt ttaaatattg    1200
ttgtctgaag aaataagtac tgacagtatt ttgatgcatt gatctgcttg tttgttgtaa    1260
caaaatttaa aaataaagag tttccttttt gttgctctcc ttacctcctg atggtatcta    1320
gtatctacca actgacacta tattgcttct ctttacatac gtatcttgct cgatgccttc    1380
tccctagtgt tgaccagtgt tactcacata gtctttgctc atttcattgt aatgcagata    1440
ccaagcggcc atggcacacc cttaggtaac ccagtagatc cagaggaatt cattatcagt    1500
gcaattgttt tgtcacgatc aaaggactct ggtacaaaat cgtattcatt aaaaccggga    1560
ggtagatgag atgtgacgaa cgtgtacatc gactgaaatc cctggtaatc cgttttagaa    1620
tccatgataa taattttctg gattattggt aattttttt gcacgttcaa aatttttttgc    1680 aaccccttt tggaaacaaa cactacggta ggctgcgaaa tgttcatact gttgagcaat     1740
tcacgttcat tataaatgtc gttcgcgggc gcaactgcaa ctccgataaa taacgcgccc    1800
aacaccggca taagaattg aagagagttt tcactgcata cgacgattct gtgatttgta    1860
ttcagcccat atcgtttcat agcttctgcc aaccgaacgg acatttcgaa gtattccgcg    1920
tacgtgatgt tcacctcgat atgtgcatct gtaaaagcaa ttgttccagg aaccagggcg    1980
tatctcttca tagccttatg cagttgctct ccagcggttc catcctctag aggatagaat    2040
ggcgccgggc cttcttat gttttggcg tcttcacgcg tcgatatggg ctgaatacaa       2100
atcacagaat cgtcgtatgc agtgaaaact ctcttcaatt ctttatgccg gtgttgggcg    2160
cgttatttat cggagttgca gttgcgcccg cgaacgacat ttataatgaa cgtgaattgc    2220
tcaacagtat gaacatttcg cagcctaccg tagtgtttgt ttccaaaaag gggttgcaaa    2280
aaattttgaa cgtgcaaaaa aaattaccaa taatccagaa aattattatc atggattcta    2340
aaacggatta ccagggattt cagtcgatgt acacgttcgt cacatctcat ctacctcccg    2400
gttttaatga atacgatttt gtaccagagt cctttgatcg tgacaaaaca attgcactga    2460
taatgaattc ctctggatct actgggttac ctaagggtgt gggatccaat tcccgatcgt    2520
tcaaacattt ggcaataaag tttcttaaga ttgaatcctg ttgccggtct tgcgatgatt    2580
atcatataat ttctgttgaa ttcgttaag catgtaataa ttaacatgta atgcatgacg    2640
ttatttatga gatgggtttt tatgattaga gtcccgcaat tatacattta atacgcgata    2700
gaaaacaaaa tatagcgcgc aaactaggat aaattatcgc gcgcggtgtc atctatgtta    2760
ctagatc                                                              2767
```

<210> SEQ ID NO 2
<211> LENGTH: 872
<212> TYPE: DNA
<213> ORGANISM: Artificial sequence
<220> FEATURE:
<223> OTHER INFORMATION: Synthetic construct

<400> SEQUENCE: 2

| | | | | | |
|---|---|---|---|---|---|
| gcaagtatgg | cctgtacgtc | aagcaaggcc | agtcagtgaa | aaattacctg | ccaaccatcc | 60 |
| tctgcttaca | ggacagcgtg | tacttgatgc | tcttttccca | tgtgtacagg | gtggtactac | 120 |
| tgccattccc | ggagctttcg | gttgtggaaa | aactgtaatt | tcacaatctc | tttccaaata | 180 |
| ttccaactct | gatgtcatta | tctacgtcgg | ttgcggagaa | agaggtaacg | aaatgtctga | 240 |
| agtattgaga | gatttccctg | aattgactgt | tgaaattgac | gggcacactg | aatctattat | 300 |
| gaaacgtacc | gcattggtcg | ccaacacatc | taacatgcct | gtagctgctc | gtgaagcttc | 360 |
| tatctatact | ggtattactc | tttctgaata | cttccgtgat | atgggttaca | acgtatctat | 420 |
| gatggctgac | tcgacatcac | gttgggccga | agctttgaga | gaaatttcag | gtcgtttggc | 480 |
| tgaaatgcct | gccgattccg | gttatccggc | ttacttaggt | gcccgtttgg | cttccttcta | 540 |
| cgaacgtgct | ggtcgcgtta | aatgtttagg | taatccagac | agagaaggat | ccgtttcaat | 600 |
| tgtaggagcc | gtatcacctc | ctggtggtga | tttctcagat | cctgttacca | ctgctactct | 660 |
| tggtattgta | caggtgttct | ggggtttgga | caagaaactt | gcccaacgta | agcacttccc | 720 |
| ttcagtagac | tggcttggat | catattccaa | atatttaaga | gcattggacg | acttttatga | 780 |
| caaaaacttc | caagagttta | ttcctcttag | aaccaaagtt | aaggaaattc | ttcaggaaga | 840 |
| agatgatcta | gccgaaattg | tgcagctggt | ag | | | 872 |

<210> SEQ ID NO 3
<211> LENGTH: 1000
<212> TYPE: DNA
<213> ORGANISM: Artificial sequence
<220> FEATURE:
<223> OTHER INFORMATION: Synthetic construct

<400> SEQUENCE: 3

| | | | | | |
|---|---|---|---|---|---|
| ataatagatt | cagtgtgccc | gtcaatttca | acagtcaatt | cagggaaatc | tctcaatact | 60 |
| tcagacattt | cgttacctct | ttctccgcaa | ccgacgtaga | taatgacatc | agagttggaa | 120 |
| tatttggaaa | gagattgtga | aattacagtt | tttccacaac | cgaaagctcc | gggaatggca | 180 |
| gtagtaccac | cctgtacaca | tgggaaaaga | gcatcaagta | cacgctgtcc | tgtaagcaga | 240 |
| ggatggttgg | caggtaattt | ttcactgact | ggccttgctt | gacgtacagg | ccatacttgc | 300 |
| tgtgtacagg | gtggtactac | tgccattccc | ggagctttcg | gttgtggaaa | aactgtaatt | 360 |
| tcacaatctc | tttccaaata | ttccaactct | gatgtcatta | tctacgtcgg | ttgcggagaa | 420 |
| agaggtaacg | aaatgtctga | agtattgaga | gatttccctg | aattgactgt | tgaaattgac | 480 |
| gggcacactg | aatctattat | gaaacgtacc | gcattggtcg | ccaacacatc | taacatgcct | 540 |
| gtagctgctc | gtgaagcttc | tatctatact | ggtattactc | tttctgaata | cttccgtgat | 600 |
| atgggttaca | acgtatctat | gatggctgac | tcgacatcac | gttgggccga | agctttgaga | 660 |
| gaaatttcag | gtcgtttggc | tgaaatgcct | gccgattccg | gttatccggc | ttacttaggt | 720 |
| gcccgtttgg | cttccttcta | cgaacgtgct | ggtcgcgtta | aatgtttagg | taatccagac | 780 |
| agagaaggat | ccgtttcaat | cggaatcggc | aggcatttca | gccaaacgac | ctgaaatttc | 840 |

| | |
|---|---:|
| tctcaaagct tcggcccaac gtgatgtcga gtcagccatc atagatacgt tgtaacccat | 900 |
| atcacggaag tattcagaaa gagtaatacc agtatagata gaagcttcac gagcagctac | 960 |
| aggcatgtta gatgtgttgg cgaccaatgc ggtacgtttc | 1000 |

<210> SEQ ID NO 4
<211> LENGTH: 22
<212> TYPE: DNA
<213> ORGANISM: Zea mays

<400> SEQUENCE: 4

| | |
|---|---:|
| tgaagctgcc agcatgatct gg | 22 |

<210> SEQ ID NO 5
<211> LENGTH: 240
<212> TYPE: DNA
<213> ORGANISM: Oryza sativa

<400> SEQUENCE: 5

| | |
|---|---:|
| gaagatatta gttcttgctg gtgtgagagg ctgaagctgc cagcatgatc tggtccatga | 60 |
| gttgcactgc tgaatatatt gaattcagcc aggagctgct actgcagttc tgatctcgat | 120 |
| ctgcattcgt tgttctgagc tatgtatgga tttgatcggt ttgaaggcat ccatgtcttt | 180 |
| aatttcatcg atcagatcat gttgcagctt cactctctca ctaccagcaa aaccatctca | 240 |

<210> SEQ ID NO 6
<211> LENGTH: 759
<212> TYPE: DNA
<213> ORGANISM: Zea mays

<400> SEQUENCE: 6

| | |
|---|---:|
| gttttggctt gttcacccct catgtgcaca tgctgttact ccgaagcttg cgcttttgta | 60 |
| ttcgttgttg cattgcaacc atccccgccg aaggtgagcc gaaggtaatc ttgggtattc | 120 |
| tacctgcaac acttattaat tcaagctaca aaacagttgt cgagttagtt ttttttttac | 180 |
| cttcgaaaag aagacttccg gcaatgcaca acttcccatc tgcattatcg tgagcaggat | 240 |
| tgtaggcaca cagtgatgac gaagacagag acagcaatat acacaaccga accaagagag | 300 |
| aagcaaaggc ataataataa aaaaagagag aggaaactag atcgacaagg ccattattat | 360 |
| cacggataat taatcaacgt cgtcaacggc ggaaataagc tagcttgact ggtggtctct | 420 |
| ggcgagtgca gcatggatat gaattgcagg agggtgagct agctagggtt ttcgatgtgc | 480 |
| ggccaccagc agatgaaact acagcatgac ctggtcctgg tgctcattaa ttaccctctc | 540 |
| tctctctccc ttcccctctc atcttggatt cgtcgatcca tatatgacag tcagggacgg | 600 |
| gggagagaga gagagtgaca ggggccggta gtagtataga ttacatccat tttacatata | 660 |
| ccaccaccat cataaccaga tcatgctggc agcttcacca actcgtggtg caccactaca | 720 |
| taccctctcg tctgatccaa acggaggaag gaggaagaa | 759 |

<210> SEQ ID NO 7
<211> LENGTH: 884
<212> TYPE: DNA
<213> ORGANISM: Zea mays

<400> SEQUENCE: 7

| | |
|---|---:|
| ttggcttgtt caccsctcat gtgcacatgc tgttactccg aagcttgcgc ttttgtattc | 60 |
| gttgttgcat tgcaaccatc cccgccgaag gtgagccgaa ggtaatcttg ggtattctac | 120 |
| ctgcaacact tattaattca agctacaaaa cagttgtcga gttagttttt ttttaccctt | 180 |

```
cgaaaagaag acttccggca atgcacaact tcccatctgc attatcgtga gcaggattgt    240
aggcacacag tgatgacgaa gacagagaca gcaatataca caaccgaacc aagagagaag    300
caaaggcata ataataaaaa aagagagagg aaactagatc gacaaggcca ttattatcac    360
ggataattaa tcaacgtcgt caacggcgga aataagctag cttgactggt ggtctctggc    420
gagtgcagca tggatatgaa ttgcaggagg gtgagctagc tagggttttc gatgtgcggc    480
caccagcaga tgaaactaca gcatgacctg gtcctggtgc tcattaatta ccctctctct    540
ctctcccttc ccctctcatc ttggattcgt cgatccatat atgacagtca gggacggggg    600
agagagagag agtgacaggg gccggtagta gtatagatta catccatctt acatatacca    660
ccaccatcat aaccagatca tgctggcagc ttcaccaact cgtggtgcac cactacatac    720
cctctcgtct gatccaaacg gaggaaggag gaagaagagc tagctatccg agagagaggg    780
agagggtaga gagatggaga gagcgaggaa tgaattgaag aaccgaggga tagctatagc    840
tatatatata tggggatggg gaggccaacg tctcgctcac tcgc                    884

<210> SEQ ID NO 8
<211> LENGTH: 872
<212> TYPE: DNA
<213> ORGANISM: Zea mays

<400> SEQUENCE: 8
tattctacct gcaacactta ttaattcaag ctacaaaaca gttgtcgagt tagttttttt    60
tttaccttcg aaaagaagac ttccggcaat gcacaacttc ccatctgcat tatcgtgagc    120
aggattgtag gcacacagtg atgacgaaga cagagacagc aatatacaca accgaaccaa    180
gagagaagca aaggcataat aataaaaaaa gagagaggaa actagatcga caaggccatt    240
attatcacgg ataattaatc aacgtcgtca acggcggaaa taagctagct tgactggtgg    300
tctctggcga gtgcagcatg gatatgaatt gcaggagggt gagctagcta ggttttcga    360 tgtgcggcca ccagcagatg aaactacagc atgacctggt cctggtgctc attaattacc    420
ctctctctct ctcccttccc ctctcatctt ggattcgtcg atccatatat gacagtcagg    480
gacgggggag agagagagag tgacaggggc cggtagtagt atagattaca tccatcttac    540
ataccaccac catcataacc agatcatgct ggcagcttca ccaactcgtg gtgcacca    600 ctacataccc tctcgtctga tccaaacgga ggaaggagga agaagctagc tatccgag    660 agagagggag agggtagaga gatggagaga gcgaggaatg aattgaagaa ccgagggata    720
gctatagcta tatatatatg ggatggggag gccaacgtct cgctcactcg cagcgtattt    780
tgatgccctt ttttatttgt tgcatttcga tccatttttct tttgtcctgc gcttttttcg    840
tacgatgttt gttgcaagga taagcctttc gg                                 872

<210> SEQ ID NO 9
<211> LENGTH: 988
<212> TYPE: DNA
<213> ORGANISM: Zea mays

<400> SEQUENCE: 9
gttttggctt gttcaccccct catgtgcaca tgctgttact ccgaagcttg cgcttttgta    60
ttcgttgttg cattgcaacc atcccgccg aaggtgagcc gaaggtaatc ttgggtattc    120
tacctgcaac acttattaat tcaagctaca aaacagttgt cgagttagtt ttttttttac    180
cttcgaaaag aagacttccg gcaatgcaca acttcccatc tgcattatcg tgagcaggat    240
```

```
tgtaggcaca cagtgatgac gaagacagag acagcaatat acacaaccga accaagagag    300
aagcaaaggc ataataataa aaaagagag aggaaactag atcgacaagg ccattattat     360
cacggataat taatcaacgt cgtcaacggc ggaaataagc tagcttgact ggtggtctct    420
ggcgagtgca gcatggatat gaattgcagg agggtgagct agctagggtt ttcgatgtgc    480
ggccaccagc agatgaaact acagcatgac ctggtcctgg tgctcattaa ttaccctctc    540
tctctctccc ttccctctc atcttggatt cgtcgatcca tatatgacag tcagggacgg     600
gggagagaga gagagtgaca ggggccggta gtagtataga ttacatccat cttacatata    660
ccaccaccat cataaccaga tcatgctggc agcttcacca actcgtggtg caccactaca    720
taccctctcg tctgatccaa acggaggaag gaggaagaag agctagctat ccgagagaga    780
gggagagggt agagagatgg agagagcgag gaatgaattg aagaaccgag ggatagctat    840
agctatatat atatggggat ggggaggcca acgtctcgct cactcgcagc gtattttgat    900
gccctttttt atttgttgca tttcgatcca ttttcttttg tcctgcgctt ttttcgtacg    960
atgtttgttg caaggataag cctttcgg                                       988

<210> SEQ ID NO 10
<211> LENGTH: 548
<212> TYPE: DNA
<213> ORGANISM: Zea mays
<220> FEATURE:
<221> NAME/KEY: unsure
<222> LOCATION: (1)..(548)
<223> OTHER INFORMATION: unsure at all n locations

<400> SEQUENCE: 10
gtatgttctc cgctcactcc cccattccac tctcatccat ctctcaagct acacacatat    60
aaaaaaaaaa gagtagagaa ggaccgccgt tagagcactt gatgcatgcg tacgtcgatc    120
cggcggaccg atctgctttt gcttgtgtgc ttggtgagaa ggtccctgtt ggagaagcag    180
ggcacgtgca gagacacgcc ggagcacggc cgccgccgat ctaccgacct cccacacctg    240
ccttgtggtg tggggtgga ggtcnnnnnn cgnagcgaga gctgncgntg ntgnttngat     300
gctgntngct cctcctgcnc gtgctcccct tctccaccac ggccttctca ccaccctcct    360
cccccggcgg cggcggcggc ggaccgcccct tgccgcgatc aataatgaaa ccaaaagccg   420
acagtgtttg agcaggaaac acaaaaggcg gatatcccac tgntagcact tctgcgttga    480
tcatggtcat ctggaacaaa ataatacttg gggactttac agcgagtgca gcatgcttaa    540
gctagttc                                                             548

<210> SEQ ID NO 11
<211> LENGTH: 22
<212> TYPE: DNA
<213> ORGANISM: Zea mays

<400> SEQUENCE: 11
tggagaagca gggcacgtgc ag                                             22

<210> SEQ ID NO 12
<211> LENGTH: 1219
<212> TYPE: DNA
<213> ORGANISM: Zea mays

<400> SEQUENCE: 12
ttcggtccaa gtagtggtgg tcataatatg ctccaaataa agaaaggtg gaggagcatc     60 tcacagacga cacagctgct atgctagcac acgtcgaatc aatagctagt tgcatgcaaa    120
```

```
gttccaaagc aaataaacag tgagatcgaa agacgtttcg ctgttgcacg acacgacgaa      180
tcgatcgaac gaaagtgtgt ttttatgatt ccacagattc tcgtttatat ataatcctag      240
ctagctaatc tagaacgtac agtgcacacc atcttcttcc acagatcaca gaaagacagc      300
agaaacctgc atggatcgga tccggtcctg tcctgtaaga tctacacaca tgcaaagcaa      360
atcaatttct tccttttctt ttcttcagaa actgggataa cttttttggaa gagatcgaac      420 agtatataga ttcagggagc agatcaagga ttatatatat agctagtatg tgtacatatc      480
aaaagggcaa gaaaagtaca aaaaagcatc ggatctccat tatatatata caacagctat      540
ataacaacca cagaagaaca gtaagcacgc acatggtaaa attaaaatag cctggcagct      600
gctatggatg tatgcatcag atgcctaata tatatgcaag ataataatta ataagcagct      660
caagcaaaga cagatcaaga gttcgagaca gcaggttgga aaataaaata cagatcatat      720
gaagtaaaac cttgacttga gatacgaatg atgaagctgc atgggtaaag taaacaagga      780
aaggatcgga gggagcaccc ttcagtccaa gcaaagacgg tgcgagatcg aagcttttac      840
ctcccgcttc attcactcat ctgcgaagct cgtttccatg gccgtttgct tggcatgtgg      900
gtgaatgagt cggcagctaa tccgaccta gcaccgcccc tgagtggact gaaggacgct      960
ctcttccatc cggccggcga ccatcgatca caaccatgac gccgcgcccg gcggcaaata     1020
tattaacaag aaatgaaatc aaaagagaga ggaagaacaa acatgatgcg cagctgcgct     1080
agctagtgct tgatctgtct gaccacctca tggcgcgcag tgtttagttt ctccctgga     1140 tcttgcgaag aaggcgatgg attttcgatg gttgcaagga ggagcgaccg acaaagggtt     1200
tatataatat gtagacggc                                                  1219

<210> SEQ ID NO 13
<211> LENGTH: 23
<212> TYPE: DNA
<213> ORGANISM: Zea mays

<400> SEQUENCE: 13
gtggactgaa ggacgctctc ttc                                               23

<210> SEQ ID NO 14
<211> LENGTH: 616
<212> TYPE: DNA
<213> ORGANISM: Zea mays

<400> SEQUENCE: 14
gccggccggg tcgggatgcc gcctactagc aggaagctag tggaggactc caagggatc       60 gcattgatct aacctgccga tcgacgccga cgtacgtacg tgcccgagga caagcagatc      120
agtcagtgca atccctttgg aattctccac ttagcgcctc catccccgcg ccgccctcca      180
ggtttcgctt cgatccatcc atgtttcctt cgtttaaatt agttcgtttg ttttttttt      240 attatttatt tgattcgccg ccgccggtct atctactctg tttgcaacgc ctttcgatcc      300
atcggcttct actgtatgct ataattaagg gttttttttac attggtccga tgcatgagag      360
gagctgtgca gaccaacatg gcaaccaatt acatcgatct tgaggactct tatggaccaa      420
catgccaagt tcttcattgc ttgtactacc attcaagttg tcaaacaatt accaattaac      480
tcaagtattc gagagaagca tatatgttag tcaaatagca aattctttac taactgatct      540
atgtaccgac atgtcaactt cttgcatacc aacgtggcaa gaaggtaatc attgttcatg      600
aataagatta tcacta                                                     616
```

<210> SEQ ID NO 15
<211> LENGTH: 21
<212> TYPE: DNA
<213> ORGANISM: Zea mays

<400> SEQUENCE: 15
tccaaaggga tcgcattgat c                                           21

<210> SEQ ID NO 16
<211> LENGTH: 1568
<212> TYPE: DNA
<213> ORGANISM: Zea mays

<400> SEQUENCE: 16

```
ctaggaatgg tacggtgctg gctaagctag ctagatcatc gtcctggagc tgagagcagc    60
agctacctat atatctagct ggttttctaa cgacgatgac gaacgaccgc gggactagca   120
tgatgcagct agctgaagac agttgtaggc agctctcctc tggcaggcag gcgcgcggtc   180
atcgtcgcca tcgacgacgg ttgcttggct ctgctatgct gtgttcgttc ggccatggtg   240
tgctagctag ccgtgcatgc gttgcagtgt aacatgcgtg catgcacgcg cgtacgtcct   300
gccaaaggag agttgccctg cgactgtctt cagctcgaac aagatcgacc ggcccggaca   360
ggaatgttgg gcgtacgttg tcatcagggt ttaagctcca cgattccaaa tattcaccac   420
ttctgggagg agttttgaag ctgctcgaaa gcatattgtg tctgagtgta ataaatcggc   480
ggggaatcat atgttcatgt tctcactgca agaataagct tgtcaaagag ggtggtgaag   540
taaaatctca cctgatcagc ggcacaggtg ctcctagcga cgggtgtaag tcatggagga   600
caagcaacag gaagtccact gccaagtgct tccatcgtcg tcaaatcaca ggtcaggggt   660
taattatatg ggggaagagg ccattatcat caggtacgcg tggttctcac acagtcgggg   720
ccacgttcgt tgatgatctg cctcttaatc ggcatctcaa actcttgttg tgctctctac   780
atcagtagag aaggtgtgtt cacaagtcgt ttcttcttaa gactatgttt tggttgatct   840
tgatctatag aactatttta ttgtagaact actgaaccct ttcgaagtgt tgtactcaat   900
ttgtgtagaa caatgcatga ttaatttcta ccaatagtct acggtagccg gtagttgttt   960
tatcctacta gaaattgttg catggttaat tggttaattt gtgtaggatg tgccaaaaga  1020
agaggaagag aacaccatca atatgaatgg tgaattattc gtaagcttat cttccactaa  1080
tggtgctgga agccagaagg agaaagagga ggatggagat catgtgtcaa ggctcaggag  1140
ataaatcgag gaagaaaaag atcgaagggt ggtgtttagt tgtatccttc caagttccaa  1200
gttcacggta aagagaggaa agtgtgctag ttcaagagag tatgggatgg agataggcac  1260
cattggactt ggagtggagg acaagatgtt accattttgc atttccatgg agcgtggaga  1320
cttctgagtg cttcaatctt tttattaaaa atcagtctga gcgatgatga gtctaaagag  1380
actaagacta tatcataatc tacgatggat ttaatctata aggtggatat atcacatatg  1440
gttgccaatc ttgtatattt catatttgca tggttggtag ttgcactgtt gcaatcttaa  1500
gacctgtata gttgcatatt tgattgtgtt tttagaatgt tgatttgtgg ttgtgctcgc  1560
ttctttct                                                          1568
```

<210> SEQ ID NO 17
<211> LENGTH: 21
<212> TYPE: DNA
<213> ORGANISM: Zea mays

<400> SEQUENCE: 17

```
tgccaaagga gagttgccct g                                              21

<210> SEQ ID NO 18
<211> LENGTH: 825
<212> TYPE: DNA
<213> ORGANISM: Zea mays

<400> SEQUENCE: 18
ggtaccttta gcgttagcac agacacacac aggtaaggag agcgagaggt gggttgggtt    60
tgatcggaga cagggacgag gcagagcatg ggtaggggc catcaacaga attccaaatt   120
tgatttctgt ttgctcgctc acaaaatgga gggactcacc acaaacacac tcaggcgttg   180
ttgctccctc ccctgcactg cctcttccct ggctcctcac cgtctcccat ccacctatcc   240
tctctctttc tctctctcgt tatggttttg tataattttt tttcctgcat tcttttctca   300
gtacaagtcc tacactaatt tggctgtctt tgcaccagta ctaataaaca ccgcaggtcc   360
ctgcaatagg gtttacaaca attctattgt aatgactgct gtaaaacatc cgcatcattt   420
aattcaactt tccggtttca gtcagccctg caaaagtgct cctccgttcg tccgcgtttg   480
gtgttggctt ctgcggctcc ggtgcccaga gttgctgccg gcggaggccg agcaggagcg   540
caactaacaa gagcggccaa ggcgccagtg atcctcacca tggacaggag atcgatggag   600
atgagcgtga gcttccgatg cttcggtacc cgaagaaaag aacgggaaca aaggcgagaa   660
acatgatcca cctctatgct tttttggcaa catatcctat gcttaaacag ttatggtgtt   720
caaatgtaca cattaataga gcgtttggtt tgaagaatca caccatctaa attgaggtgg   780
tgcatcatga atttattcct taaaaaaaaa aaaaaaaaaa aaaaa                   825

<210> SEQ ID NO 19
<211> LENGTH: 20
<212> TYPE: DNA
<213> ORGANISM: Zea mays

<400> SEQUENCE: 19
tgcactgcct cttccctggc                                                20

<210> SEQ ID NO 20
<211> LENGTH: 1040
<212> TYPE: DNA
<213> ORGANISM: Zea mays

<400> SEQUENCE: 20
gccggccggg tcgggtgtgt tctcaggtcg cccccgatca cagccaacgc gggcgaccgc    60
gcgccattat agcacacggg gcacggcacg ccttcggcct cccactaact gcacaagagg   120
acgacgcggc agcgaggagg gagcaaagga aagggatat gtcgaggccg cccaacagga   180
gcgacgcgca cctctccgcc gaggacgagg cggcgctgga ggccgaggtg cgggagtact   240
acgacgacgc ggcgccaaag cgccacacca agccctcccg cagcgagcac tccgccgtgt   300
acgtcgacgc gctcgtcccg gacgtcggcg gcaactccca cccggagctg acaagttcc   360 aagagctgga agcccacacc gagaggttgg tgtacgaggg cgccaatgtg ggagatgagt   420
tcgtagagac ggagtactac aaggacctcg gcggcgtcgg cgagcagcac cacacgaccg   480
gaacgggctt catcaagatg gacaaagcta aaggcgcccc cttcaaactg tctgaagatc   540
ccaatgcaga ggagcgacat gcttcttgca ggggaaaccc tgctaccaac gagtggatcc   600
cgtcagctga cacggtaaga ctgggggagc acagtccagt ttatcctatg caggtgcagg   660
```

```
gtcggctcca atcggcgtct ctactgacga acgcatcgtt agcttgtacc cagcgtcaga      720
caagccaagc agaagcgaca gctgagggac tgtatatctc aagccatgag aattcagacg      780
agtgctttcc gccattagaa taaggaacca cactggttgt ccaccgtatc ttcactgttc      840
tgcgtcgaga ttcttgtgat tcttacgtgg aacaaattaa gcgtgctacg agttagacct      900
ctgtgttctg gctgtaaatg gcaaggaatg aagttctaat cgtggttcag cagtcaatca      960
attactgtgt ttctgatcct aaggctctag aaacaatcgg accttcaaaa taaactaggc     1020
gaaaattcta tgtcgtttcg                                                 1040

<210> SEQ ID NO 21
<211> LENGTH: 21
<212> TYPE: DNA
<213> ORGANISM: Zea mays

<400> SEQUENCE: 21
tgtgttctca ggtcgccccc g                                                21

<210> SEQ ID NO 22
<211> LENGTH: 3389
<212> TYPE: DNA
<213> ORGANISM: Zea mays

<400> SEQUENCE: 22
gagcggggtc ttgaaactgg ctgcgcagaa ggaagggatg aaggggttcc tggagctcga       60
cgccgaggtt ttcgagcttg ccccttcgtt ctttctggtc gagctgaaga aggccagcgg      120
tgacaccatt gagtaccaaa ggctcgtgag ggaagaagtg cggcctgcgc tgaaggatat      180
ggtctgggct tggcagagcg accggcacca gcagcagcag cagcggtgcg agcagtctgt      240
gcaaggagag gaccagcagc agccgttgtc gtctttgccg acgcagcagt agtcactgca      300
ccaccagttg cgaccgccat aaccagatca cgtcaaaact gcaccaagcc gcacaggact      360
agtaactccc acttgcatcg acgcttatgt gattgcggaa ttgtgtttca ggttacctgc      420
ctgctgcggt aggacctaaa acgcctacct gcctaccatt tggcattttt ttgtatactg      480
tacgtacatt agagtaataa acaaacatgc ttaacttttc agctttcgat tggaatgtgc      540
ttttcgatgt aactctgtaa ccagtgtagg tacgaagtcg attagccaca gggtctggcc      600
atgttgacct cacgtagccc tggttcattg gtgtaacagt ttgttggctg cggctttaca      660
ttattttgtc tctatggatt acggctgcga ctatgtgtag ctgaacaagc tggtatatga      720
tgagccctgg aaacgtgtgt ttactgcagc tatttgcagc cagtgactgt tgatacaaac      780
gacgaagtag agttggttgt ttatgtaggc acgcagcatg accataatta tccatgaatc      840
atggatagat gcacaatgtt taggaaacag gtgtgtgtgt ctggctggtg gtgcgagaag      900
agatgcgctg ccttgatgta ctgtactggg actgggaggg atgcgtctcg cagtacagtc      960
tgtactatca tctctacacg cacgcacgca ggctcgacgt gtcggcggcg gcggtccaga     1020
ctccatatgg atccgtagta gtacaacctg ttggcgggta gtacaggttg gagcacgcct     1080
cttcttcagt cttccttcct gagatgagga gtcactcacc agcaaaacgc ttgcagtaca     1140
ccccgctcgc gggcgttgtt tatagtgatc ggtagcgtga gcacagagcg ccatcagaag     1200
atgcaaagag aaagagaagc aaaggcatca ttgagcgcag cgttgatgag ccagccgccg     1260
tgcctcccct gtcggctgcg gcggctcacc agcgctgcac tcaattacgc ctttgctttc     1320
tcccgctggc cgcgtgtgtg cagagcgggc gggcgttcgg catcattcat caggtttgct     1380
tcatttatta tgcactcatc gaaggcttct ccttcgacac tgtctaggtg gcgcaggatc     1440
```

-continued

```
tgaatcagat gggtgtcgtc ttcttcctcc atctgcactc ctgccccgta tgatgtcggt    1500
gtcctaggac ggccagttgt ctgcgttctg gttaacccaa ttacctgacg gggcggacga    1560
cgctgataat gatcagagag agcatgaggc catatgcaag cctagaccta gctcccaaac    1620
tattaaaggt tgcttcgagc cctggctgtc atatcaacta ccaaccagtt tatgtcgatt    1680
atcagttcct atctatcaca acgctccact gcacaacctt aacctttact gtaaacctat    1740
agtcacctca tcgcttacat cgggttttc ccctctttc gtagactttt agttaacatc    1800
aaacaatgca ttttattgaa atccaaaata catctgactg cgtaattgag tagatttatc    1860
ccaaaattta attagcatgc cgctgtgagc taggagagcg acactagttt acaatatgac    1920
agtgtttgtg ttcggccaaa ccattttgt tgatgggtaa ggggacacga cccccaaata    1980
gacgctctca ttttaatgaa gaattagttg tggactaatt gataattccc attacaatcg    2040
gattgcacgc attaaatctt agtgctaagg aggtgttaca aatgaaccta aaaagaaaa    2100 gataattgtt gawttaatgt gggtctggtc catattaata ttcaataatt gtcaatgcta    2160
gttgtcactt tatgctacgg tgtactagta cttaccaaac tagaagttta agggacaatt    2220 cactyaacttaaataggtgg actattggtg catctattga gaagctgaga aaaggatgaa    2280
ggactgtcac gcgtgcgcgc accctgatct gttgagaagc tgagatcgta ggaacaagaa    2340
tcactaaatt cggagttaca gatttcaagt tatgattttt cgaaggtttt atgtgtttgg    2400
tacggaattg attaagtgat caatttaat atgggtttca tgctaaaact gaggtactaa    2460
gtggtaaaca aaattataga aattggaatg ggttaaaaag gagtttgcat gattttccta    2520
tgaattatac aagattatgg atttatttta ataccaaaat cacttttat atttatttta    2580 ccctggtttt ctatccacta gactgcgccc aagattatac taaagtttag gggcaactgc    2640
ataaaaaaac taagacttag ggcccgtttg tgatggactg cgggttgata acttagaaac    2700
agagggtctc ttatgtaaac tgtatgtgct gaagggtat gaagcatcta cgatcgtcag    2760
attacaattc cacggccaag attaaatcgc cagtgcgatg aaccgttacg taacagccat    2820
catccgatct gagatctacg accctgattc taaatgccct aaaacctccc agatccactc    2880
cctttgtccg aatcggtacg catcggatta atcgcagcc gcactctgat ggatctacgg    2940
cccacgcaga tcatccccca taccaacggc gaacgggcgc cgccgcccgt aaacacggcg    3000
gtggccatgg ccgtggatgg ccaactcgac ttcgaggccg taatcctcta gtctaagacg    3060
tgctacgtgg taagtggatg aagacgattt ccatgggttc agtacttacc gagggcaagg    3120
tcgtgcacaa gctgttcacg gcgaagcgcg gccgtagcaa aaattgaaag ggaaatgtga    3180
ctttgggcta tttctataaa tgttttggtg attagatgcc caacacatat tgttttagtt    3240
catatgtgct aagtgattga gaagtgcaaa tcaagaatca aggtatattt ctagccctag    3300
taaatttctt ttggatacta acatatctct ctaagtgcta gggacactac caagaaaagt    3360
ggaaatgaac tggagaagtt tggcagagt                                      3389
```

<210> SEQ ID NO 23
<211> LENGTH: 21
<212> TYPE: DNA
<213> ORGANISM: Zea mays

<400> SEQUENCE: 23
tcattgagcg cagcgttgat g    21

<210> SEQ ID NO 24

<211> LENGTH: 660
<212> TYPE: DNA
<213> ORGANISM: Glycine max

<400> SEQUENCE: 24

```
accattacac tcttagtgaa tatttcataa aatataaagt tcctcctggg cgagaaacat      60
ctccatgttt aaggaaacag tgcgaagaat tattacacca gacatattca aggcaactag     120
tggaatccaa taaggaatgc tggcccactg cggaaaatat ttcgggttga atgataggga     180
aggggctcat tcaacaaaaa tcttaatttt ctcggagatt ggcaaatcta cattgacaag     240
ataaataaat aatttatgaa acaataaaaa aaatgataat ggaaacaggg cttataatat     300
aagcactact aagctagttt gtttctccta cgctaaaagc ctaatctcaa acctacccac     360
ttcctacaag agaaaaggg ggggatagtg tataatacc tcaacttcga accaatattc     420
atcagaagta gaggtgtggg tattcttcca ctgcaactgg aggaggcatc caagggatc     480
gcattgatcc caaatccaag ctttaatatt tttctctctt ctcactcaat aatattaatt     540
tatttgggat catgctatcc ctttggattt ctcctttaat ggcttctata atgatggctc     600
tctcatggat tctgcttgct gcaccacaac acaaacactt tcatatacgc ctctaatgct     660
```

<210> SEQ ID NO 25
<211> LENGTH: 21
<212> TYPE: DNA
<213> ORGANISM: Glycine max

<400> SEQUENCE: 25

```
tccaaaggga tcgcattgat c                                                21
```

<210> SEQ ID NO 26
<211> LENGTH: 1809
<212> TYPE: DNA
<213> ORGANISM: Glycine max

<400> SEQUENCE: 26

```
cacaatacaa ttaagctcat catactggtc ctgaaattgg tgaataaagt tgttttgtgg      60
tggatgagta ctgagtagtg gtgccttatt gtgggtggag agttccaaag ggatcgcatt     120
gatctaattc ttgtagatgt ttacacttgc aagctttgca tgcaattcct ggattcagat     180
gttattcagt ggttcactta ttggatcatg cgatccctta ggaactttcc atcaactcta     240
aacatcttgt tgatccattt gaggaattaa tttcataggt tcatataatg gcgactgatt     300
cttctaatgg taatggacat caccaaacaa caacaaagca accttctttg tcgtctacac     360
tgcgcttatc caaattttttt cagtccaaca tgagaatctt ggttactgga ggagctggat     420
tcattgcgtc ttacttagtt gacagattga tggaaaatga aaaaaatgag gttattgtcg     480
ttgcataggt gctttcattt tacgttcttc aacattccga attgaacttc agtggtcctt     540
gcaatggcaa cgaattcttc tgatgtacta tcgccgaagc aacctccctt gccatctccc     600
ttgcgtttct ccaaattcta tcagtctaac atgagaatct tgattacggg aggagctgga     660
ttcattggtt ctcacctagt tgatagattg atggaaaatg aaaaaaatga ggtcattgtt     720
gctgacaact acttcactgg atcaaaggac aacctcaaaa aatggattgg tcatccaaga     780
tttgagctta tccgtcatga tgtcactgaa cctttgacga ttgaggttga tcagatctac     840
catcttgcat gccccgcatc tcctattttc tacaaatata atcctgtgaa gacaataaag     900
acaaatgtga ttggcacact gaacatgctt gggcttgcaa acgagttgg ggcaaggatt     960
ttactcacat caacatctga ggtatatggg gatcctcttg tgcatcccca acctgaaggc    1020
```

```
tattggggca atgtgaaccc tattggagtt cgtagttgct atgatgaggg gaaacgtgtg    1080
gctgaaactt tgatgtttga ttatcatagg cagcatggaa tagaaatacg tgttgcaaga    1140
atctttaaca catatgggcc gcgcatgaat attgatgatg acgtgttgt cagcaacttc     1200 attgctcaag caattcgtgg tgaacccttg acagtccagt ctccaggaac acaaactcgc    1260
agtttctgct atgtctctga tctggttgat ggacttatcc gtctcatgga aggatccgac    1320
actggaccaa tcaaccttgg aaatccaggt gaatttacaa tgctagaact tgctgagaca    1380
gtgaaggagc ttattaatcc agatgtggag ataaaggtag tggagaacac tcctgatgat    1440
ccgcgacaga gaaaaccaat cataacaaaa gcaatggaat tgcttggctg ggaaccaaag    1500
gttaagctgc gagatgggct tcctcttatg gaagaggatt tcgtttgag gcttggatt     1560 gacaaaaaaa attaacttat tttcgctcct tttatatcta gtcaaaatat tcagataata    1620
agtgggatgg attattctat taagttttcc tattttcct tttcataatt atgatactta     1680
ggaagtaggg gtgcctgtat tttggcttcc tcaatcaaga tcgtactctt gtttcacaaa    1740
gcactgcagc aatcatgcct ttgcaaattt tgccggtaaa attactactg agttaaaatt    1800
ttcctatag                                                            1809

<210> SEQ ID NO 27
<211> LENGTH: 21
<212> TYPE: DNA
<213> ORGANISM: Glycine max

<400> SEQUENCE: 27
tccaaaggga tcgcattgat c                                                21

<210> SEQ ID NO 28
<211> LENGTH: 487
<212> TYPE: DNA
<213> ORGANISM: Glycine max

<400> SEQUENCE: 28
tgaaaattac gttttcccct ttccttttgt tgccggttag cacttcaatg taaaaattaa     60
ttcaccataa aggatggttc gcatacaaaa gaataaaacc ttatgaaagg acacatgcaa    120
cgcaaaataa aggcatcgtt ccataggata tgccgatcct agtgagccat aaataacgtt    180
cccaaaggca ttcctctatg tgtgtggatc ttcccagttg cagctgcatt acagggcaag    240
ttctccattg gcaggtagcc actatgatat gcatctcata aatatttgca actttcttaa    300
tgtgcaatct gccaaaggag atttgcccag cgattctcct gcaacatctg cttcatgaaa    360
acagtattcg ttagtttctt caatcattca ttagaaacat ttcttgtact ggttgaaatg    420
ttgcatctcg aaccattcat atgccatatt tccttgttt tgtattttgg taaaaaccat     480
ttttccc                                                              487

<210> SEQ ID NO 29
<211> LENGTH: 21
<212> TYPE: DNA
<213> ORGANISM: Glycine max

<400> SEQUENCE: 29
tgccaaagga gatttgccca g                                                21

<210> SEQ ID NO 30
<211> LENGTH: 535
<212> TYPE: DNA
```

<213> ORGANISM: Glycine max

<400> SEQUENCE: 30

| | | | | | |
|---|---|---|---|---|---|
| ctgcagagta | agacctgaat | ttcactcatt | gttcctgcca | atgtccttag | ttagataaat | 60 |
| ctaattttt | ctctctctaa | agttgcatct | ataaatatga | gcctttccct | tggtgcagat | 120 |
| caatttgagc | tttcattacc | gttctcatga | agcttagggt | gcatgcaacg | gtctctactt | 180 |
| actactggtt | gagaagctcc | ttgttggaga | agcagggcac | gtgcaagtct | cttggatctc | 240 |
| aaatgccact | gaacccttg | cacgtgctcc | ccttctccaa | cacgggtttc | tccccttgct | 300 |
| tttctcctaa | ccaattgtgt | ccagcactta | tgaggtaatc | gctttcctcc | tatgtcttaa | 360 |
| tttggtccta | cgtaaagatc | tacaatatgc | atcttctttg | agatacgggc | tgaagcatgg | 420 |
| tacttttaaa | ttgaaggctt | caataactat | atttagaggg | aaaattcaac | atacaaagaa | 480 |
| ggaagaagtg | ttatgcatac | aatattttac | cgatgttcta | tgcgtatcaa | acata | 535 |

<210> SEQ ID NO 31
<211> LENGTH: 21
<212> TYPE: DNA
<213> ORGANISM: Glycine max

<400> SEQUENCE: 31
tggagaagca gggcacgtgc a                                                    21

<210> SEQ ID NO 32
<211> LENGTH: 663
<212> TYPE: DNA
<213> ORGANISM: Glycine max

<400> SEQUENCE: 32

| | | | | | |
|---|---|---|---|---|---|
| tctatataat | ttttttccta | ttttattttt | tattttattt | tgtatcatat | cacttataca | 60 |
| tcttttactt | tcactcatac | actaaatttt | cgggtgtagg | aatactccgg | caaagagaga | 120 |
| ataggtttgc | ttatttccta | attctgaagt | tagggtacgt | gcgtaattta | ctgtgtgttc | 180 |
| tgtgatgatg | agttaagtgg | tcctatttta | catgtaactt | ttgacaatct | gtttgggttg | 240 |
| agaatacaaa | ttaaggcccc | acacccaact | aagcttagct | ctctcccatt | tttagcaccc | 300 |
| atcccgcacc | caactttaaa | agcaccctca | attgcctctt | ctattatagg | agagtaggct | 360 |
| tcaaagcaca | caagaatatg | ataagatgaa | gaagttcagt | gtctcaaaat | tcaccacttc | 420 |
| tcttaaaacc | tccctcattt | gttttttcac | actttccttt | ccctcaccac | tctctctatt | 480 |
| acctcttgtt | tgttgttaag | agtactcaga | agaataactc | ctccaaccca | cttagcatgt | 540 |
| ggcaaaggtg | catgctgagc | aagatggaga | agcagggcac | gtgcaattct | aactcatgaa | 600 |
| accatagaat | catcttgttt | tttcttcttt | tcactctaac | caaatagatt | cctctacctg | 660 |
| cag | | | | | | 663 |

<210> SEQ ID NO 33
<211> LENGTH: 21
<212> TYPE: DNA
<213> ORGANISM: Glycine max

<400> SEQUENCE: 33
tggagaagca gggcacgtgc a                                                    21

<210> SEQ ID NO 34
<211> LENGTH: 443
<212> TYPE: DNA
<213> ORGANISM: Glycine max

```
<220> FEATURE:
<221> NAME/KEY: unsure
<222> LOCATION: (1)..(443)
<223> OTHER INFORMATION: unsure at all n locations

<400> SEQUENCE: 34
actcaagctt gaagcaccaa agttgcagtc ggaggagtca cagattaaat tcttcgcttc    60
tttaaccttt gtgtttctct tttcatacca ttgtttcttt ccctatagct gctttaattt   120
tcttgtgaga gtcagaaaag tatcactata tcaagtgaca tgatcatcag aattgaatta   180
tgtgcatgtt gtgcaagatg gagaagcagg gcacgtgcaa tactaactca tgaacactac   240
acggngcgtg aactcggaga atcatattct cttctgcttc atttcaccaa caagagagat   300
cctattagtt agttcttcat gtgcccctct ttcccatcat gacaacagca ccttatatat   360
attgcatttg gaaatgttga acgatgaagt tcgcttggct tctgctcata aatcagcacc   420
gagntttata ggttatgctc cat                                           443

<210> SEQ ID NO 35
<211> LENGTH: 21
<212> TYPE: DNA
<213> ORGANISM: Glycine max

<400> SEQUENCE: 35
tggagaagca gggcacgtgc a                                              21

<210> SEQ ID NO 36
<211> LENGTH: 21
<212> TYPE: DNA
<213> ORGANISM: Glycine max

<400> SEQUENCE: 36
tgagaccaaa tgagcagctg a                                              21

<210> SEQ ID NO 37
<211> LENGTH: 21
<212> TYPE: DNA
<213> ORGANISM: Glycine max

<400> SEQUENCE: 37
atgcactgcc tcttccctgg c                                              21

<210> SEQ ID NO 38
<211> LENGTH: 748
<212> TYPE: DNA
<213> ORGANISM: Glycine max

<400> SEQUENCE: 38
aaaattcatt acattgataa aacacaattc aaaagatcaa tgttccactt catgcaaaga    60
catttccaaa atatgtgtag gtagagggt tttacaggat cgtcctgaga ccaaatgagc    120
agctgaccac atgatgcagc tatgtttgct attcagctgc tcatctgttc tcaggtcgcc   180
cttgttggac tgtccaactc ctactgattg cggatgcact tgccacaaat gaaaatcaaa   240
gcgaggggaa aagaatgtag agtgtgacta cgattgcatg catgtgattt aggtaattaa   300
gttacatgat tgtctaattg tgtttatgga attgtatatt tcagaccag gcacctgtaa    360 ctaattatag gtaccatacc ttaaaataag tccaactaag tccatgtctg tgatttttta   420
gtgtcacaaa tcacaatcca ttgccattgg ttttttaatt tttcattgtc tgttgtttaa   480
ctaactctag cttttagct gcttcaagta cagattcctc aaagtggaaa atgttctttg    540
```

```
aagtcaataa aaagagcttt gatgatcatc tgcattgtct aagttggata aactaattag      600
agagaacttt tgaactttgt ctaccaaata tctgtcagtg tcatctgtca gttctgcaag      660
ctgaagtgtt gaatccacga ggtgcttgtt gcaaagttgt gatattaaaa gacatctacg      720
aagaagttca agcaaaactc tttttggc                                         748

<210> SEQ ID NO 39
<211> LENGTH: 960
<212> TYPE: DNA
<213> ORGANISM: Glycine max

<400> SEQUENCE: 39
ccgtggtggg cgaagggaat taacgcctat cgcgtggcga gagaaggagc agaacggcag       60 ggggggggccg gctccggggg ggcgccccgg tacgcaccgc gctctccgag tccctggggt     120
ccccccccca gaacatccta atcgaaaaat tcaagagtgc attttgtgcg taatgtagtt      180
aattagacaa atttctaatg tgagaatctt tctgagaatg agatgttgct aaatatttcg      240
gatgttgtcg acaaggatga ggtaataata gttagagaca ggacaaagca ggggaacagg      300
cagagcatgg atggagctat caacacaata ttgtcaagaa actgagagtg agaggagaaa      360
tatgttgtgg ttctgctcat gcactgcctc ttccctggct ctgtctccat ttctccttcc      420
cttatttatt ttttgattta ttgagtatga tctgttttca aatgtgttca taggttcaac      480
ttattaaggt acgaacatac tctgggcatt gaaaactggt ttgactcttg aacatattcc      540
gcaccactaa tctttcttgt aatccaggct cacgcacgat cactataagg tcccacattc      600
ttagtggcct aatcgttgga aaatgctact ttggcactac ttgatgaatt gtatggctgg      660 gattttttc cccttgcttg tagaatcctc tcaatttatg taaccatcgt gtactcattt       720
acatgtcatc attttgaat gagatgtgat atacatagag caaaaaaaa aaaaaaattg        780 tatgacctca ttttctgtgt ttatttctct ccatcaatat cattttctaa atctcaaaat      840
tctctctttt ttcttagttg tagaagttat tgtttactcg actcctcgcc tcacatccct      900
ctcacccctc tccccactac tgccccgcca gcgtcaccga tgctctcctt tgtggccggt      960

<210> SEQ ID NO 40
<211> LENGTH: 21
<212> TYPE: DNA
<213> ORGANISM: Glycine max

<400> SEQUENCE: 40
tgagatcaaa tgagcagctg a                                                 21

<210> SEQ ID NO 41
<211> LENGTH: 21
<212> TYPE: DNA
<213> ORGANISM: Glycine max

<400> SEQUENCE: 41
tgagaccaaa tgagcagctg t                                                 21

<210> SEQ ID NO 42
<211> LENGTH: 21
<212> TYPE: DNA
<213> ORGANISM: Glycine max

<400> SEQUENCE: 42
tgagaccaaa tgaccagctg a                                                 21
```

```
<210> SEQ ID NO 43
<211> LENGTH: 129
<212> TYPE: DNA
<213> ORGANISM: Zea mays

<400> SEQUENCE: 43
gttaaggggt ctgttgtctg gttcaaggtc gccacagcag gcaaataaag cccatttcgc      60
gcttagcatg caccatgcat gatgggtgta cctgttggtg atctcggacc aggcttcaat     120
ccctttaac                                                             129

<210> SEQ ID NO 44
<211> LENGTH: 86
<212> TYPE: DNA
<213> ORGANISM: Zea mays

<400> SEQUENCE: 44
gtcgagggga atgacgtccg gtccgaacga gccacggctg ctgctgcgcc gccgcgggct      60
tcggaccagg cttcattccc cgtgac                                           86

<210> SEQ ID NO 45
<211> LENGTH: 20
<212> TYPE: DNA
<213> ORGANISM: artificial sequence
<220> FEATURE:
<223> OTHER INFORMATION: Synthetic construct

<400> SEQUENCE: 45
gtgctcactc tcttctgtca                                                  20

<210> SEQ ID NO 46
<211> LENGTH: 21
<212> TYPE: DNA
<213> ORGANISM: artificial sequence
<220> FEATURE:
<223> OTHER INFORMATION: Synthetic construct

<400> SEQUENCE: 46
tagagctccc ttcaatccaa a                                                21

<210> SEQ ID NO 47
<211> LENGTH: 21
<212> TYPE: DNA
<213> ORGANISM: artificial sequence
<220> FEATURE:
<223> OTHER INFORMATION: Synthetic construct

<400> SEQUENCE: 47
tggcatccag ggagccaggc a                                                21

<210> SEQ ID NO 48
<211> LENGTH: 21
<212> TYPE: DNA
<213> ORGANISM: artificial sequence
<220> FEATURE:
<223> OTHER INFORMATION: Synthetic construct

<400> SEQUENCE: 48
ctggatgcag aggtttatcg a                                                21

<210> SEQ ID NO 49
<211> LENGTH: 21
<212> TYPE: DNA
<213> ORGANISM: artificial sequence
<220> FEATURE:
```

<223> OTHER INFORMATION: Synthetic construct

<400> SEQUENCE: 49
tgcacgtgcc ctgcttctcc a                                              21

<210> SEQ ID NO 50
<211> LENGTH: 21
<212> TYPE: DNA
<213> ORGANISM: artificial sequence
<220> FEATURE:
<223> OTHER INFORMATION: Synthetic construct

<400> SEQUENCE: 50
ggggaatgaa gcctggtccg a                                              21

<210> SEQ ID NO 51
<211> LENGTH: 21
<212> TYPE: DNA
<213> ORGANISM: artificial sequence
<220> FEATURE:
<223> OTHER INFORMATION: Synthetic construct

<400> SEQUENCE: 51
tagatcatgc tggcagcttc a                                              21

<210> SEQ ID NO 52
<211> LENGTH: 21
<212> TYPE: DNA
<213> ORGANISM: artificial sequence
<220> FEATURE:
<223> OTHER INFORMATION: Synthetic construct

<400> SEQUENCE: 52
ttcccgacct gcaccaagcg a                                              21

<210> SEQ ID NO 53
<211> LENGTH: 21
<212> TYPE: DNA
<213> ORGANISM: artificial sequence
<220> FEATURE:
<223> OTHER INFORMATION: Synthetic construct

<400> SEQUENCE: 53
tcggcaagtc atccttggct g                                              21

<210> SEQ ID NO 54
<211> LENGTH: 21
<212> TYPE: DNA
<213> ORGANISM: artificial sequence
<220> FEATURE:
<223> OTHER INFORMATION: Synthetic construct

<400> SEQUENCE: 54
gatattggcg cggctcaatc a                                              21

<210> SEQ ID NO 55
<211> LENGTH: 21
<212> TYPE: DNA
<213> ORGANISM: artificial sequence
<220> FEATURE:
<223> OTHER INFORMATION: Synthetic construct

<400> SEQUENCE: 55
ctgcagcatc atcaagattc t                                              21

<210> SEQ ID NO 56
<211> LENGTH: 21
<212> TYPE: DNA
<213> ORGANISM: artificial sequence
<220> FEATURE:
<223> OTHER INFORMATION: Synthetic construct

<400> SEQUENCE: 56
ggcgctatcc ctcctgagct t                                     21

<210> SEQ ID NO 57
<211> LENGTH: 21
<212> TYPE: DNA
<213> ORGANISM: artificial sequence
<220> FEATURE:
<223> OTHER INFORMATION: Synthetic construct

<400> SEQUENCE: 57
gatcaatgcg atccctttgg a                                     21

<210> SEQ ID NO 58
<211> LENGTH: 22
<212> TYPE: DNA
<213> ORGANISM: artificial sequence
<220> FEATURE:
<223> OTHER INFORMATION: Synthetic construct

<400> SEQUENCE: 58
tggggtcctt acaaggtcaa ga                                    22

<210> SEQ ID NO 59
<211> LENGTH: 20
<212> TYPE: DNA
<213> ORGANISM: artificial sequence
<220> FEATURE:
<223> OTHER INFORMATION: Synthetic construct

<400> SEQUENCE: 59
ggaggtggac agaatgccaa                                       20

<210> SEQ ID NO 60
<211> LENGTH: 21
<212> TYPE: DNA
<213> ORGANISM: artificial sequence
<220> FEATURE:
<223> OTHER INFORMATION: Synthetic construct

<400> SEQUENCE: 60
gagttccccc aaacacttca c                                     21

<210> SEQ ID NO 61
<211> LENGTH: 21
<212> TYPE: DNA
<213> ORGANISM: artificial sequence
<220> FEATURE:
<223> OTHER INFORMATION: Synthetic construct

<400> SEQUENCE: 61
catcaacgct gcgctcaatg a                                     21

<210> SEQ ID NO 62
<211> LENGTH: 21
<212> TYPE: DNA
<213> ORGANISM: artificial sequence
<220> FEATURE:
<223> OTHER INFORMATION: Synthetic construct

```
<400> SEQUENCE: 62
cgggggcgac ctgagaacac a                                              21

<210> SEQ ID NO 63
<211> LENGTH: 21
<212> TYPE: DNA
<213> ORGANISM: artificial sequence
<220> FEATURE:
<223> OTHER INFORMATION: Synthetic construct

<400> SEQUENCE: 63
agccagggaa gaggcagtgc a                                              21

<210> SEQ ID NO 64
<211> LENGTH: 20
<212> TYPE: RNA
<213> ORGANISM: Arabidopsis thaliana

<400> SEQUENCE: 64
gugcucucuc ucuucuguca                                                20

<210> SEQ ID NO 65
<211> LENGTH: 20
<212> TYPE: RNA
<213> ORGANISM: Arabidopsis thaliana

<400> SEQUENCE: 65
cugcucucuc ucuucuguca                                                20

<210> SEQ ID NO 66
<211> LENGTH: 20
<212> TYPE: RNA
<213> ORGANISM: Arabidopsis thaliana

<400> SEQUENCE: 66
uugcuuacuc ucuucuguca                                                20

<210> SEQ ID NO 67
<211> LENGTH: 20
<212> TYPE: RNA
<213> ORGANISM: Arabidopsis thaliana

<400> SEQUENCE: 67
ccgcucucuc ucuucuguca                                                20

<210> SEQ ID NO 68
<211> LENGTH: 21
<212> TYPE: RNA
<213> ORGANISM: Arabidopsis thaliana

<400> SEQUENCE: 68
uggagcuccc uucauuccaa u                                              21

<210> SEQ ID NO 69
<211> LENGTH: 21
<212> TYPE: RNA
<213> ORGANISM: Arabidopsis thaliana

<400> SEQUENCE: 69
ucgaguuccc uucauuccaa u                                              21

<210> SEQ ID NO 70
<211> LENGTH: 21
```

```
<212> TYPE: RNA
<213> ORGANISM: Arabidopsis thaliana

<400> SEQUENCE: 70
augagcucuc uucaaaccaa a                                              21

<210> SEQ ID NO 71
<211> LENGTH: 21
<212> TYPE: RNA
<213> ORGANISM: Arabidopsis thaliana

<400> SEQUENCE: 71
uggagcuccc uucauuccaa g                                              21

<210> SEQ ID NO 72
<211> LENGTH: 21
<212> TYPE: RNA
<213> ORGANISM: Arabidopsis thaliana

<400> SEQUENCE: 72
uagagcuucc uucaaaccaa a                                              21

<210> SEQ ID NO 73
<211> LENGTH: 21
<212> TYPE: RNA
<213> ORGANISM: Arabidopsis thaliana

<400> SEQUENCE: 73
uggagcucca uucgauccaa a                                              21

<210> SEQ ID NO 74
<211> LENGTH: 21
<212> TYPE: RNA
<213> ORGANISM: Arabidopsis thaliana

<400> SEQUENCE: 74
agcagcuccc uucaaaccaa a                                              21

<210> SEQ ID NO 75
<211> LENGTH: 21
<212> TYPE: RNA
<213> ORGANISM: Phaseolus vulgaris

<400> SEQUENCE: 75
cagagcuccc uucacuccaa u                                              21

<210> SEQ ID NO 76
<211> LENGTH: 21
<212> TYPE: RNA
<213> ORGANISM: Vitis vinifera

<400> SEQUENCE: 76
uggagcuccc uucacuccaa u                                              21

<210> SEQ ID NO 77
<211> LENGTH: 21
<212> TYPE: RNA
<213> ORGANISM: Hordeum vulgare

<400> SEQUENCE: 77
uggagcuccc uucacuccaa g                                              21

<210> SEQ ID NO 78
```

```
<211> LENGTH: 21
<212> TYPE: RNA
<213> ORGANISM: Oryza sativa

<400> SEQUENCE: 78
uggagcuccc uuuaauccaa u                                              21

<210> SEQ ID NO 79
<211> LENGTH: 21
<212> TYPE: RNA
<213> ORGANISM: Arabidopsis thaliana

<400> SEQUENCE: 79
uggcaugcag ggagccaggc a                                              21

<210> SEQ ID NO 80
<211> LENGTH: 21
<212> TYPE: RNA
<213> ORGANISM: Arabidopsis thaliana

<400> SEQUENCE: 80
aggaauacag ggagccaggc a                                              21

<210> SEQ ID NO 81
<211> LENGTH: 21
<212> TYPE: RNA
<213> ORGANISM: Arabidopsis thaliana

<400> SEQUENCE: 81
ggguuuacag ggagccaggc a                                              21

<210> SEQ ID NO 82
<211> LENGTH: 21
<212> TYPE: RNA
<213> ORGANISM: Oryza sativa

<400> SEQUENCE: 82
aggcauacag ggagccaggc a                                              21

<210> SEQ ID NO 83
<211> LENGTH: 21
<212> TYPE: RNA
<213> ORGANISM: Lotus corniculatus var. japonicus

<400> SEQUENCE: 83
aagcauacag ggagccaggc a                                              21

<210> SEQ ID NO 84
<211> LENGTH: 21
<212> TYPE: RNA
<213> ORGANISM: Arabidopsis thaliana

<400> SEQUENCE: 84
accugaugua aucacuuuca a                                              21

<210> SEQ ID NO 85
<211> LENGTH: 21
<212> TYPE: RNA
<213> ORGANISM: Arabidopsis thaliana

<400> SEQUENCE: 85
cccggaugua aucacuuuca g                                              21
```

```
<210> SEQ ID NO 86
<211> LENGTH: 21
<212> TYPE: RNA
<213> ORGANISM: Arabidopsis thaliana

<400> SEQUENCE: 86
uuguuacuuu caaugcauug a                                              21

<210> SEQ ID NO 87
<211> LENGTH: 21
<212> TYPE: RNA
<213> ORGANISM: Arabidopsis thaliana

<400> SEQUENCE: 87
cccugaugua uuuacuuuca a                                              21

<210> SEQ ID NO 88
<211> LENGTH: 21
<212> TYPE: RNA
<213> ORGANISM: Arabidopsis thaliana

<400> SEQUENCE: 88
uagucacguu caaugcauug a                                              21

<210> SEQ ID NO 89
<211> LENGTH: 21
<212> TYPE: RNA
<213> ORGANISM: Arabidopsis thaliana

<400> SEQUENCE: 89
cccugaugua uucacuuuca g                                              21

<210> SEQ ID NO 90
<211> LENGTH: 21
<212> TYPE: RNA
<213> ORGANISM: Arabidopsis thaliana

<400> SEQUENCE: 90
cccugauguu guuacuuuca g                                              21

<210> SEQ ID NO 91
<211> LENGTH: 21
<212> TYPE: RNA
<213> ORGANISM: Arabidopsis thaliana

<400> SEQUENCE: 91
uagucacuuu cagcgcauug a                                              21

<210> SEQ ID NO 92
<211> LENGTH: 21
<212> TYPE: RNA
<213> ORGANISM: Arabidopsis thaliana

<400> SEQUENCE: 92
uccaaaugua gucacuuuca g                                              21

<210> SEQ ID NO 93
<211> LENGTH: 21
<212> TYPE: RNA
<213> ORGANISM: Arabidopsis thaliana

<400> SEQUENCE: 93
uccaaaugua gucacuuuca a                                              21
```

```
<210> SEQ ID NO 94
<211> LENGTH: 21
<212> TYPE: RNA
<213> ORGANISM: Arabidopsis thaliana

<400> SEQUENCE: 94
uccaaaugua gucacuuuca g                                              21

<210> SEQ ID NO 95
<211> LENGTH: 21
<212> TYPE: RNA
<213> ORGANISM: Arabidopsis thaliana

<400> SEQUENCE: 95
uccaaaugua gucacuuuca a                                              21

<210> SEQ ID NO 96
<211> LENGTH: 21
<212> TYPE: RNA
<213> ORGANISM: Arabidopsis thaliana

<400> SEQUENCE: 96
uuguaacuuu cagugcauug a                                              21

<210> SEQ ID NO 97
<211> LENGTH: 21
<212> TYPE: RNA
<213> ORGANISM: Arabidopsis thaliana

<400> SEQUENCE: 97
uagucacguu caaugcauug a                                              21

<210> SEQ ID NO 98
<211> LENGTH: 21
<212> TYPE: RNA
<213> ORGANISM: Arabidopsis thaliana

<400> SEQUENCE: 98
uuguuacuuu cagugcauug a                                              21

<210> SEQ ID NO 99
<211> LENGTH: 21
<212> TYPE: RNA
<213> ORGANISM: Arabidopsis thaliana

<400> SEQUENCE: 99
cccugauguu gucacuuuca c                                              21

<210> SEQ ID NO 100
<211> LENGTH: 21
<212> TYPE: RNA
<213> ORGANISM: Arabidopsis thaliana

<400> SEQUENCE: 100
uuguuacuua caaugcauug a                                              21

<210> SEQ ID NO 101
<211> LENGTH: 21
<212> TYPE: RNA
<213> ORGANISM: Arabidopsis thaliana

<400> SEQUENCE: 101
uagucuuuuu caacgcauug a                                              21
```

<210> SEQ ID NO 102
<211> LENGTH: 22
<212> TYPE: RNA
<213> ORGANISM: Arabidopsis thaliana

<400> SEQUENCE: 102
cuggaugcag agguauuauc ga                                              22

<210> SEQ ID NO 103
<211> LENGTH: 22
<212> TYPE: RNA
<213> ORGANISM: Populus tremula

<400> SEQUENCE: 103
cuggaugcag aggucuuauc ga                                              22

<210> SEQ ID NO 104
<211> LENGTH: 22
<212> TYPE: RNA
<213> ORGANISM: Oryza sativa

<400> SEQUENCE: 104
cuggaugcag agguuuuauc ga                                              22

<210> SEQ ID NO 105
<211> LENGTH: 23
<212> TYPE: RNA
<213> ORGANISM: Arabidopsis thaliana

<400> SEQUENCE: 105
aucgaguucc aaguccucuu caa                                             23

<210> SEQ ID NO 106
<211> LENGTH: 23
<212> TYPE: RNA
<213> ORGANISM: Arabidopsis thaliana

<400> SEQUENCE: 106
aucgaguucc agguccucuu caa                                             23

<210> SEQ ID NO 107
<211> LENGTH: 23
<212> TYPE: RNA
<213> ORGANISM: Arabidopsis thaliana

<400> SEQUENCE: 107
aucgaguucc aaguuucuu caa                                              23

<210> SEQ ID NO 108
<211> LENGTH: 21
<212> TYPE: RNA
<213> ORGANISM: Arabidopsis thaliana

<400> SEQUENCE: 108
agcacguacc cugcuucucc a                                               21

<210> SEQ ID NO 109
<211> LENGTH: 21
<212> TYPE: RNA
<213> ORGANISM: Arabidopsis thaliana

<400> SEQUENCE: 109
uuuacgugcc cugcuucucc a                     21

<210> SEQ ID NO 110
<211> LENGTH: 21
<212> TYPE: RNA
<213> ORGANISM: Arabidopsis thaliana

<400> SEQUENCE: 110
agcacguguc cuguuucucc a                     21

<210> SEQ ID NO 111
<211> LENGTH: 21
<212> TYPE: RNA
<213> ORGANISM: Arabidopsis thaliana

<400> SEQUENCE: 111
ucuacgugcc cugcuucucc a                     21

<210> SEQ ID NO 112
<211> LENGTH: 21
<212> TYPE: RNA
<213> ORGANISM: Arabidopsis thaliana

<400> SEQUENCE: 112
cucacgugac cugcuucucc g                     21

<210> SEQ ID NO 113
<211> LENGTH: 21
<212> TYPE: RNA
<213> ORGANISM: Oryza sativa

<400> SEQUENCE: 113
cgcacgugac cugcuucucc a                     21

<210> SEQ ID NO 114
<211> LENGTH: 21
<212> TYPE: RNA
<213> ORGANISM: Medicago truncatula

<400> SEQUENCE: 114
cuuacguguc cugcuucucc a                     21

<210> SEQ ID NO 115
<211> LENGTH: 21
<212> TYPE: RNA
<213> ORGANISM: Glycine max

<400> SEQUENCE: 115
cuuacgugcc cugcuucucc a                     21

<210> SEQ ID NO 116
<211> LENGTH: 21
<212> TYPE: RNA
<213> ORGANISM: Lycopersicum esculentum

<400> SEQUENCE: 116
gccacgugca cugcuucucc a                     21

<210> SEQ ID NO 117
<211> LENGTH: 21
<212> TYPE: RNA
<213> ORGANISM: Arabidopsis thaliana

<400> SEQUENCE: 117

```
uugggaugaa gccuggaccg g                                              21

<210> SEQ ID NO 118
<211> LENGTH: 21
<212> TYPE: RNA
<213> ORGANISM: Arabidopsis thaliana

<400> SEQUENCE: 118
cugggaugaa gccugguccg g                                              21

<210> SEQ ID NO 119
<211> LENGTH: 21
<212> TYPE: RNA
<213> ORGANISM: Arabidopsis thaliana

<400> SEQUENCE: 119
cuggaaugaa gccugguccg g                                              21

<210> SEQ ID NO 120
<211> LENGTH: 21
<212> TYPE: RNA
<213> ORGANISM: Populus tremula

<400> SEQUENCE: 120
ccgggaugaa gccugguccg g                                              21

<210> SEQ ID NO 121
<211> LENGTH: 21
<212> TYPE: RNA
<213> ORGANISM: Arabidopsis thaliana

<400> SEQUENCE: 121
gagaucaggc uggcagcuug u                                              21

<210> SEQ ID NO 122
<211> LENGTH: 21
<212> TYPE: RNA
<213> ORGANISM: Arabidopsis thaliana

<400> SEQUENCE: 122
uagaucaggc uggcagcuug u                                              21

<210> SEQ ID NO 123
<211> LENGTH: 21
<212> TYPE: RNA
<213> ORGANISM: Oryza sativa

<400> SEQUENCE: 123
aagaucaggc uggcagcuug u                                              21

<210> SEQ ID NO 124
<211> LENGTH: 21
<212> TYPE: RNA
<213> ORGANISM: Arabidopsis thaliana

<400> SEQUENCE: 124
uucccgagcu gcaucaagcu a                                              21

<210> SEQ ID NO 125
<211> LENGTH: 21
<212> TYPE: RNA
<213> ORGANISM: Arabidopsis thaliana
```

```
<400> SEQUENCE: 125
aagggaaguc auccuuggcu g                                              21

<210> SEQ ID NO 126
<211> LENGTH: 21
<212> TYPE: RNA
<213> ORGANISM: Arabidopsis thaliana

<400> SEQUENCE: 126
acgggaaguc auccuuggcu a                                              21

<210> SEQ ID NO 127
<211> LENGTH: 21
<212> TYPE: RNA
<213> ORGANISM: Arabidopsis thaliana

<400> SEQUENCE: 127 agggggaaguc auccuuggcu a                                             21

<210> SEQ ID NO 128
<211> LENGTH: 21
<212> TYPE: RNA
<213> ORGANISM: Arabidopsis thaliana

<400> SEQUENCE: 128
aggcaaauca ucuuuggcuc a                                              21

<210> SEQ ID NO 129
<211> LENGTH: 21
<212> TYPE: RNA
<213> ORGANISM: Arabidopsis thaliana

<400> SEQUENCE: 129
gcggcaauuc auucuuggcu u                                              21

<210> SEQ ID NO 130
<211> LENGTH: 21
<212> TYPE: RNA
<213> ORGANISM: Arabidopsis thaliana

<400> SEQUENCE: 130
ccggcaaauc auucuuggcu u                                              21

<210> SEQ ID NO 131
<211> LENGTH: 21
<212> TYPE: RNA
<213> ORGANISM: Arabidopsis thaliana

<400> SEQUENCE: 131
aagggaaguc auccuuggcu a                                              21

<210> SEQ ID NO 132
<211> LENGTH: 21
<212> TYPE: RNA
<213> ORGANISM: Zea mays

<400> SEQUENCE: 132
guggcaacuc auccuuggcu c                                              21

<210> SEQ ID NO 133
<211> LENGTH: 21
<212> TYPE: RNA
<213> ORGANISM: Vitis vinifera
```

<400> SEQUENCE: 133
ugggcaauuc auccuuggcu u                                             21

<210> SEQ ID NO 134
<211> LENGTH: 21
<212> TYPE: RNA
<213> ORGANISM: Oryza sativa

<400> SEQUENCE: 134
auggcaaauc auccuuggcu u                                             21

<210> SEQ ID NO 135
<211> LENGTH: 21
<212> TYPE: RNA
<213> ORGANISM: Glycine max

<400> SEQUENCE: 135
uagggaaguc auccuuggcu c                                             21

<210> SEQ ID NO 136
<211> LENGTH: 21
<212> TYPE: RNA
<213> ORGANISM: Gossypium hirsutum

<400> SEQUENCE: 136
cugggaaguc auccuuggcu c                                             21

<210> SEQ ID NO 137
<211> LENGTH: 21
<212> TYPE: RNA
<213> ORGANISM: Arabidopsis thaliana

<400> SEQUENCE: 137
gauauuggcg cggcucaauc a                                             21

<210> SEQ ID NO 138
<211> LENGTH: 21
<212> TYPE: RNA
<213> ORGANISM: Arabidopsis thaliana

<400> SEQUENCE: 138
cugcagcauc aucaggauuc u                                             21

<210> SEQ ID NO 139
<211> LENGTH: 21
<212> TYPE: RNA
<213> ORGANISM: Arabidopsis thaliana

<400> SEQUENCE: 139
cagcagcauc aucaggauuc u                                             21

<210> SEQ ID NO 140
<211> LENGTH: 21
<212> TYPE: RNA
<213> ORGANISM: Arabidopsis thaliana

<400> SEQUENCE: 140
augcagcauc aucaggauuc u                                             21

<210> SEQ ID NO 141
<211> LENGTH: 21
<212> TYPE: RNA

<213> ORGANISM: Arabidopsis thaliana

<400> SEQUENCE: 141
uggcagcauc aucaggauuc u                     21

<210> SEQ ID NO 142
<211> LENGTH: 21
<212> TYPE: RNA
<213> ORGANISM: Arabidopsis thaliana

<400> SEQUENCE: 142
uuguagcauc aucaggauuc c                     21

<210> SEQ ID NO 143
<211> LENGTH: 21
<212> TYPE: RNA
<213> ORGANISM: Arabidopsis thaliana

<400> SEQUENCE: 143
uugcagcauc aucaggauuc c                     21

<210> SEQ ID NO 144
<211> LENGTH: 21
<212> TYPE: RNA
<213> ORGANISM: Arabidopsis thaliana

<400> SEQUENCE: 144 caggggggacc cuucagucca a                    21

<210> SEQ ID NO 145
<211> LENGTH: 21
<212> TYPE: RNA
<213> ORGANISM: Arabidopsis thaliana

<400> SEQUENCE: 145
gagggguccc cuucagucca u                     21

<210> SEQ ID NO 146
<211> LENGTH: 21
<212> TYPE: RNA
<213> ORGANISM: Arabidopsis thaliana

<400> SEQUENCE: 146
gagggguccc cuucagucca g                     21

<210> SEQ ID NO 147
<211> LENGTH: 21
<212> TYPE: RNA
<213> ORGANISM: Arabidopsis thaliana

<400> SEQUENCE: 147
aagggguacc cuucagucca g                     21

<210> SEQ ID NO 148
<211> LENGTH: 21
<212> TYPE: RNA
<213> ORGANISM: Arabidopsis thaliana

<400> SEQUENCE: 148 uaggggggacc cuucagucca a                    21

<210> SEQ ID NO 149
<211> LENGTH: 21

```
<212> TYPE: RNA
<213> ORGANISM: Oryza sativa

<400> SEQUENCE: 149
gaggggaccc cuucagucca g                                              21

<210> SEQ ID NO 150
<211> LENGTH: 21
<212> TYPE: RNA
<213> ORGANISM: Oryza sativa

<400> SEQUENCE: 150
ucggggcaca cuucagucca a                                              21

<210> SEQ ID NO 151
<211> LENGTH: 21
<212> TYPE: RNA
<213> ORGANISM: Arabidopsis thaliana

<400> SEQUENCE: 151
aaacaaugcg aucccuuugg a                                              21

<210> SEQ ID NO 152
<211> LENGTH: 21
<212> TYPE: RNA
<213> ORGANISM: Arabidopsis thaliana

<400> SEQUENCE: 152
agaccaugcg aucccuuugg a                                              21

<210> SEQ ID NO 153
<211> LENGTH: 21
<212> TYPE: RNA
<213> ORGANISM: Arabidopsis thaliana

<400> SEQUENCE: 153
ggucagagcg aucccuuugg c                                              21

<210> SEQ ID NO 154
<211> LENGTH: 21
<212> TYPE: RNA
<213> ORGANISM: Arabidopsis thaliana

<400> SEQUENCE: 154
agacaaugcg aucccuuugg a                                              21

<210> SEQ ID NO 155
<211> LENGTH: 21
<212> TYPE: RNA
<213> ORGANISM: Arabidopsis thaliana

<400> SEQUENCE: 155
ggagguugac agaaugccaa a                                              21

<210> SEQ ID NO 156
<211> LENGTH: 21
<212> TYPE: RNA
<213> ORGANISM: Arabidopsis thaliana

<400> SEQUENCE: 156 gaguccucc aaaacacuuca u                                              21

<210> SEQ ID NO 157
```

```
<211> LENGTH: 21
<212> TYPE: RNA
<213> ORGANISM: Arabidopsis thaliana

<400> SEQUENCE: 157
gaguuccucc aaacucuuca u                                              21

<210> SEQ ID NO 158
<211> LENGTH: 21
<212> TYPE: RNA
<213> ORGANISM: Arabidopsis thaliana

<400> SEQUENCE: 158
aaguucuccc aaacacuuca a                                              21

<210> SEQ ID NO 159
<211> LENGTH: 22
<212> TYPE: RNA
<213> ORGANISM: Arabidopsis thaliana

<400> SEQUENCE: 159
ucguucaaga aagccugugg aa                                             22

<210> SEQ ID NO 160
<211> LENGTH: 22
<212> TYPE: RNA
<213> ORGANISM: Arabidopsis thaliana

<400> SEQUENCE: 160
ccguucaaga aagccugugg aa                                             22

<210> SEQ ID NO 161
<211> LENGTH: 22
<212> TYPE: RNA
<213> ORGANISM: Arabidopsis thaliana

<400> SEQUENCE: 161
ucguucaaga aagcaugugg aa                                             22

<210> SEQ ID NO 162
<211> LENGTH: 22
<212> TYPE: RNA
<213> ORGANISM: Arabidopsis thaliana

<400> SEQUENCE: 162
acguucaaga aagcuugugg aa                                             22

<210> SEQ ID NO 163
<211> LENGTH: 22
<212> TYPE: RNA
<213> ORGANISM: Arabidopsis thaliana

<400> SEQUENCE: 163
ccguucaaga aagccugugg aa                                             22

<210> SEQ ID NO 164
<211> LENGTH: 21
<212> TYPE: RNA
<213> ORGANISM: Arabidopsis thaliana

<400> SEQUENCE: 164
aaucaaugcu gcacucaaug a                                              21
```

```
<210> SEQ ID NO 165
<211> LENGTH: 21
<212> TYPE: RNA
<213> ORGANISM: Arabidopsis thaliana

<400> SEQUENCE: 165
agucaacgcu gcacuuaaug a                                              21

<210> SEQ ID NO 166
<211> LENGTH: 21
<212> TYPE: RNA
<213> ORGANISM: Arabidopsis thaliana

<400> SEQUENCE: 166
aaucaaugcu gcacuuaaug a                                              21

<210> SEQ ID NO 167
<211> LENGTH: 21
<212> TYPE: RNA
<213> ORGANISM: Arabidopsis thaliana

<400> SEQUENCE: 167
aagggguuuc cugagaucac a                                              21

<210> SEQ ID NO 168
<211> LENGTH: 22
<212> TYPE: RNA
<213> ORGANISM: Arabidopsis thaliana

<400> SEQUENCE: 168
ugcgggugac cugggaaaca ua                                             22

<210> SEQ ID NO 169
<211> LENGTH: 22
<212> TYPE: RNA
<213> ORGANISM: Arabidopsis thaliana

<400> SEQUENCE: 169
aaggugugac cugagaauca ca                                             22

<210> SEQ ID NO 170
<211> LENGTH: 22
<212> TYPE: RNA
<213> ORGANISM: Arabidopsis thaliana

<400> SEQUENCE: 170
gugauuuuuc ucaacaagcg aa                                             22

<210> SEQ ID NO 171
<211> LENGTH: 22
<212> TYPE: RNA
<213> ORGANISM: Arabidopsis thaliana

<400> SEQUENCE: 171
gugauuuuuc ucuacaagcg aa                                             22

<210> SEQ ID NO 172
<211> LENGTH: 22
<212> TYPE: RNA
<213> ORGANISM: Arabidopsis thaliana

<400> SEQUENCE: 172
gugauuuuuc ucuccaagcg aa                                             22
```

```
<210> SEQ ID NO 173
<211> LENGTH: 21
<212> TYPE: RNA
<213> ORGANISM: Arabidopsis thaliana

<400> SEQUENCE: 173
uagggcauau cuccuuuggc a                                              21

<210> SEQ ID NO 174
<211> LENGTH: 21
<212> TYPE: RNA
<213> ORGANISM: Arabidopsis thaliana

<400> SEQUENCE: 174
uugggcaaau cuccuuuggc a                                              21

<210> SEQ ID NO 175
<211> LENGTH: 21
<212> TYPE: RNA
<213> ORGANISM: Arabidopsis thaliana

<400> SEQUENCE: 175
ucgagcaaau cuccuuuggc a                                              21

<210> SEQ ID NO 176
<211> LENGTH: 21
<212> TYPE: RNA
<213> ORGANISM: Arabidopsis thaliana

<400> SEQUENCE: 176
uagagcaaau cuccuuuggc a                                              21

<210> SEQ ID NO 177
<211> LENGTH: 21
<212> TYPE: RNA
<213> ORGANISM: Arabidopsis thaliana

<400> SEQUENCE: 177
uagggcaaau cuucuuuggc a                                              21

<210> SEQ ID NO 178
<211> LENGTH: 21
<212> TYPE: RNA
<213> ORGANISM: Oryza sativa

<400> SEQUENCE: 178
uagggcaaau cuccuuuggc a                                              21

<210> SEQ ID NO 179
<211> LENGTH: 21
<212> TYPE: RNA
<213> ORGANISM: Oryza sativa

<400> SEQUENCE: 179
cugggcaaau cuccuuuggc a                                              21

<210> SEQ ID NO 180
<211> LENGTH: 21
<212> TYPE: RNA
<213> ORGANISM: Oryza sativa

<400> SEQUENCE: 180
ucgggcaaau cuccuuuggc a                                              21
```

<210> SEQ ID NO 181
<211> LENGTH: 21
<212> TYPE: RNA
<213> ORGANISM: Oryza sativa

<400> SEQUENCE: 181
ccgggcaaau cuccuuuggc a						21

<210> SEQ ID NO 182
<211> LENGTH: 21
<212> TYPE: RNA
<213> ORGANISM: Populus tremula

<400> SEQUENCE: 182
gcgggcaaau cuucuuuggc a						21

<210> SEQ ID NO 183
<211> LENGTH: 21
<212> TYPE: RNA
<213> ORGANISM: Medicago truncatula

<400> SEQUENCE: 183
aagggcaaau cuccuuuggc a						21

<210> SEQ ID NO 184
<211> LENGTH: 21
<212> TYPE: RNA
<213> ORGANISM: Triticum aestivum

<400> SEQUENCE: 184
uagggcaaau cuccuuuggc g						21

<210> SEQ ID NO 185
<211> LENGTH: 21
<212> TYPE: RNA
<213> ORGANISM: Triticum aestivum

<400> SEQUENCE: 185
cugggcaaau cuccuuuggc g						21

<210> SEQ ID NO 186
<211> LENGTH: 21
<212> TYPE: RNA
<213> ORGANISM: Triticum aestivum

<400> SEQUENCE: 186
uucggcaaau cuccuuuggc a						21

<210> SEQ ID NO 187
<211> LENGTH: 22
<212> TYPE: RNA
<213> ORGANISM: Arabidopsis thaliana

<400> SEQUENCE: 187
ggaguuugug cgugaaucua au					22

<210> SEQ ID NO 188
<211> LENGTH: 22
<212> TYPE: RNA
<213> ORGANISM: Arabidopsis thaliana

<400> SEQUENCE: 188

-continued cuugucuauc ccuccugagc ua                                    22

<210> SEQ ID NO 189
<211> LENGTH: 22
<212> TYPE: RNA
<213> ORGANISM: Sorghum bicolor

<400> SEQUENCE: 189
uaugucuauc ccuucugagc ug                                    22

<210> SEQ ID NO 190
<211> LENGTH: 22
<212> TYPE: RNA
<213> ORGANISM: Saccharum officinarum

<400> SEQUENCE: 190
uaugucuauc ccuucugagc ua                                    22

<210> SEQ ID NO 191
<211> LENGTH: 22
<212> TYPE: RNA
<213> ORGANISM: Zea mays

<400> SEQUENCE: 191
uaugucuauc ccuucugagc ug                                    22

<210> SEQ ID NO 192
<211> LENGTH: 22
<212> TYPE: RNA
<213> ORGANISM: Oryza sativa

<400> SEQUENCE: 192
ucggucuauc ccuccugagc ug                                    22

<210> SEQ ID NO 193
<211> LENGTH: 22
<212> TYPE: RNA
<213> ORGANISM: Pennisetum glaucum

<400> SEQUENCE: 193
uuagucuauc ccuccugagc ua                                    22

<210> SEQ ID NO 194
<211> LENGTH: 22
<212> TYPE: RNA
<213> ORGANISM: Vitis vinifera

<400> SEQUENCE: 194
auugccuauc ccuccugagc ug                                    22

<210> SEQ ID NO 195
<211> LENGTH: 22
<212> TYPE: RNA
<213> ORGANISM: Theobroma cacao

<400> SEQUENCE: 195
ccuugcuauc ccuccugagc ug                                    22

<210> SEQ ID NO 196
<211> LENGTH: 22
<212> TYPE: RNA
<213> ORGANISM: Lycopersicum esculentum

<400> SEQUENCE: 196

-continued cuugcuauc ccuccugagc ug                    22

<210> SEQ ID NO 197
<211> LENGTH: 22
<212> TYPE: RNA
<213> ORGANISM: Zea mays

<400> SEQUENCE: 197
cccuucuauc ccuccugagc ua                    22

<210> SEQ ID NO 198
<211> LENGTH: 22
<212> TYPE: RNA
<213> ORGANISM: Populus tremula

<400> SEQUENCE: 198 cuugcuauc ccuccugagc ua                    22

<210> SEQ ID NO 199
<211> LENGTH: 22
<212> TYPE: RNA
<213> ORGANISM: Oryza sativa

<400> SEQUENCE: 199
cccuucuauc ccuccugagc ua                    22

<210> SEQ ID NO 200
<211> LENGTH: 22
<212> TYPE: RNA
<213> ORGANISM: Triticum aestivum

<400> SEQUENCE: 200
cccuucuauc ccuccugagc ua                    22

<210> SEQ ID NO 201
<211> LENGTH: 22
<212> TYPE: RNA
<213> ORGANISM: Hordeum vulgare

<400> SEQUENCE: 201 ccuucuauc ccuccugagc ua                    22

<210> SEQ ID NO 202
<211> LENGTH: 22
<212> TYPE: RNA
<213> ORGANISM: Populus tremula

<400> SEQUENCE: 202 ccugcuauc ccuccugagc ua                    22

<210> SEQ ID NO 203
<211> LENGTH: 22
<212> TYPE: RNA
<213> ORGANISM: Mesembryanthemum crystallinum

<400> SEQUENCE: 203 ugugcuauc ccuccugagc ua                    22

<210> SEQ ID NO 204
<211> LENGTH: 21
<212> TYPE: RNA
<213> ORGANISM: Arabidopsis thaliana -continued

<400> SEQUENCE: 204
ugacaaacau cucguccca a                                    21

<210> SEQ ID NO 205
<211> LENGTH: 21
<212> TYPE: RNA
<213> ORGANISM: Arabidopsis thaliana

<400> SEQUENCE: 205
ugacaaacau cucguuccua a                                   21

<210> SEQ ID NO 206
<211> LENGTH: 21
<212> TYPE: RNA
<213> ORGANISM: Arabidopsis thaliana

<400> SEQUENCE: 206
ccaagggaag aggcagugca u                                   21

<210> SEQ ID NO 207
<211> LENGTH: 21
<212> TYPE: RNA
<213> ORGANISM: Arabidopsis thaliana

<400> SEQUENCE: 207
accagugaag aggcugugca g                                   21

<210> SEQ ID NO 208
<211> LENGTH: 21
<212> TYPE: RNA
<213> ORGANISM: Arabidopsis thaliana

<400> SEQUENCE: 208
gccagggaag aggcagugca u                                   21

<210> SEQ ID NO 209
<211> LENGTH: 21
<212> TYPE: RNA
<213> ORGANISM: Arabidopsis thaliana

<400> SEQUENCE: 209
gccggugaag aggcugugca a                                   21

<210> SEQ ID NO 210
<211> LENGTH: 21
<212> TYPE: RNA
<213> ORGANISM: Arabidopsis thaliana

<400> SEQUENCE: 210
gccggugaag aggcugugca g                                   21

<210> SEQ ID NO 211
<211> LENGTH: 21
<212> TYPE: RNA
<213> ORGANISM: Arabidopsis thaliana

<400> SEQUENCE: 211
agggucuugc aaggucaaga a                                   21

<210> SEQ ID NO 212
<211> LENGTH: 21
<212> TYPE: RNA
<213> ORGANISM: Arabidopsis thaliana

```
<400> SEQUENCE: 212
aaggucuugc aaggucaaga a                                                    21

<210> SEQ ID NO 213
<211> LENGTH: 21
<212> TYPE: RNA
<213> ORGANISM: Oryza sativa

<400> SEQUENCE: 213
gaggucuugc aaggucaaga a                                                    21

<210> SEQ ID NO 214
<211> LENGTH: 21
<212> TYPE: RNA
<213> ORGANISM: Oryza sativa

<400> SEQUENCE: 214
acggucuugc aaggucaaga a                                                    21

<210> SEQ ID NO 215
<211> LENGTH: 21
<212> TYPE: RNA
<213> ORGANISM: Arabidopsis thaliana

<400> SEQUENCE: 215
agaacuagag aaagcauugg a                                                    21

<210> SEQ ID NO 216
<211> LENGTH: 21
<212> TYPE: RNA
<213> ORGANISM: Arabidopsis thaliana

<400> SEQUENCE: 216
agaguaagau ggagcuugau a                                                    21

<210> SEQ ID NO 217
<211> LENGTH: 21
<212> TYPE: RNA
<213> ORGANISM: Arabidopsis thaliana

<400> SEQUENCE: 217
agauggugga aaugggauau c                                                    21

<210> SEQ ID NO 218
<211> LENGTH: 21
<212> TYPE: RNA
<213> ORGANISM: Arabidopsis thaliana

<400> SEQUENCE: 218
uuguugaucg uaugguagaa g                                                    21

<210> SEQ ID NO 219
<211> LENGTH: 21
<212> TYPE: RNA
<213> ORGANISM: Arabidopsis thaliana

<400> SEQUENCE: 219
gguauucgag uaucugcaaa a                                                    21

<210> SEQ ID NO 220
<211> LENGTH: 1242
<212> TYPE: DNA
```

<213> ORGANISM: artificial sequence
<220> FEATURE:
<223> OTHER INFORMATION: Synthetic construct

<400> SEQUENCE: 220

| | | | | | |
|---|---|---|---|---|---|
| acacgctgaa | accatcttcc | acacactcaa | gccacactat | tggagaacac | acagggacaa | 60 |
| cacaccataa | ccgccgccgc | cggtagaaga | tggcgcccac | cgtgatgatg | gcctcgtcgg | 120 |
| ccaccgccgt | cgctccgttc | caggggctca | agtccaccgc | cagcctcccc | gtcgcccgcc | 180 |
| gctcctccag | aagcctcggc | aacgtcagca | acggcggaag | gatccggtgc | atgcaggtgt | 240 |
| ggccggccta | cggcaacaag | aagttcgaga | cgctgtcgta | cctgccgccg | ctgtcgaccg | 300 |
| gcgggcgcat | ccgctgcatg | caggccatgg | ccttcttcaa | ccgggtgatc | accctcacgg | 360 |
| tgccgtcgtc | agacgtggtc | aactactcgg | agatctacca | ggtggctcct | cagtatgtca | 420 |
| accaggccct | gaccctggcc | aagtacttcc | agggcgccat | cgacggcagc | accctgaggt | 480 |
| tcgacttcga | gaaggcgtta | cagatcgcca | acgacatccc | gcaggccgcg | gtggtcaaca | 540 |
| ccctgaacca | gaccgtccag | caggggaccg | tccaggtcag | cgtcatgatc | gacaagatcg | 600 |
| tggacatcat | gaagaatgtc | ctgtccatcg | tgatagacaa | caagaagttt | tgggatcagg | 660 |
| tcacggctgc | catcaccaac | accttcacga | acctgaacag | ccaggagtcg | gaggcctgga | 720 |
| tcttctatta | caaggaggac | gcccacaaga | cgtcctacta | ttacaacatc | ctcttcgcca | 780 |
| tccaggacga | agagacgggt | ggcgtgatgg | ccacgctgcc | catcgccttc | gacatcagtg | 840 |
| tggacatcga | gaaggagaag | gtcctgttcg | tgaccatcaa | ggacactgag | aattacgccg | 900 |
| tcaccgtcaa | ggcgatcaac | gtggtccagg | cactccagtc | tagcagggat | tctaaggtgg | 960 |
| ttgatgcgtt | caaatcgcca | cggcacttac | cccggaagag | gcataagatt | tgctctaact | 1020 |
| cgtgatgact | gctggatgca | gaggtattat | cgatgcgttt | ggacgtatgc | tcattcaggt | 1080 |
| tggagccaat | ttggttgatg | tgtgtgcgag | ttcttgcgag | tctgatgaga | catctctgta | 1140 |
| ttgtgtttct | ttccccagtg | ttttctgtac | ttgtgtaatc | ggctaatcgc | caacagattc | 1200 |
| ggcgatgaat | aaatgagaaa | taaattgttc | tgattttgag | tg | | 1242 |

<210> SEQ ID NO 221
<211> LENGTH: 956
<212> TYPE: DNA
<213> ORGANISM: artificial sequence
<220> FEATURE:
<223> OTHER INFORMATION: Synthetic construct

<400> SEQUENCE: 221

| | | | | | |
|---|---|---|---|---|---|
| acacgctgac | aagctgactc | tagcagatcc | tctagaacca | tcttccacac | actcaagcca | 60 |
| cactattgga | gaacacacag | ggacaacaca | ccataagatc | caaggaggc | ctccgccgcc | 120 |
| gccggtagaa | gtgatcaacc | atggccttct | tcaaccgggt | gatcaccctc | acggtgccgt | 180 |
| cgtcagacgt | ggtcaactac | tcggagatct | accaggtggc | ctcagtat | gtcaaccagg | 240 |
| ccctgaccct | ggccaagtac | ttccagggcg | ccatcgacgg | cagcaccctg | aggttcgact | 300 |
| tcgagaaggc | gttacagatc | gccaacgaca | tcccgcaggc | cgcggtggtc | aaccctga | 360 |
| accagaccgt | ccagcagggg | accgtccagg | tcagcgtcat | gatcgacaag | atcgtggaca | 420 |
| tcatgaagaa | tgtcctgtcc | atcgtgatag | acaacaagaa | gttttgggat | caggtcacgg | 480 |
| ctgccatcac | caacaccttc | acgaacctga | acagccagga | gtcggaggcc | tggatcttct | 540 |
| attacaagga | ggacgcccac | aagacgtcct | actattacaa | catcctcttc | gccatccagg | 600 |
| acgaagagac | gggtggcgtg | atggccacgc | tgcccatcgc | cttcgacatc | agtgtggaca | 660 |

```
tcgagaagga gaaggtcctg ttcgtgacca tcaaggacac tgagaattac gccgtcaccg      720
tcaaggcgat caacgtggtc caggcactcc agtctagcag ggattctaag gtggttgatg      780
cgttcaaatc gccacggcac ttaccccgga agaggcataa gatttgctct aactcgtgat      840
gaatgtacgt gccctgcttc tccatctgca tgcgtttgga cgtatgctca ttcaggttgg      900
agccaatttg gttgatgtgt gtgcgagttc ttgcgagtct gatgagacat ctctgt         956

<210> SEQ ID NO 222
<211> LENGTH: 1683
<212> TYPE: DNA
<213> ORGANISM: Zea mays

<400> SEQUENCE: 222
atgtattgct gatgacgctg cgccttcttg ttttttgct gcaactttga gaaagataga      60
tccatctgca tgcttttttc cgctgctatg gtgtatggtt gtgtgctgca gattttggat     120
ctgacttgtg agaaccgtcg acggacccct gcacacagta cgtgagacga tcgaggagga     180
tggaggcacg cagtacgttt tgttctcgat ctctgctaca gcatgtcatc ttaattaagc     240
ctactggttg catgcatggg tgaggattat tcatcgctaa gtttccatgt acgtagcata     300
ctatcacatg tacaatgaaa taggcaaata gcctagacgt tcttctcatg cgaccatgt     360 ctgccaatta aatatattgc aggtagtaaa cctcaagtac tgatagccat taattcttgg     420
ttggagttcg acagagaaga tcgaaaagac atgtatagaa tactgatcgt ctgatcatat     480
cgtccctacc tatctgtctg tctctaccaa agtgggctac agtacgttag ctagctgtct     540
cttcgaagac actgatagga tgtttgatta caagtccaac ggaaccactt gactgcatac     600
ggttaccact tactcatgca agaaaaaaaa ttgcattttc aaattcgaac cccaagtcgt     660
ctagtgtagg gtcttatgtt cataaccagg tgggataaca acatattaa tcgatctgca     720 tatatatata tatacacaaa agggctacac agattacaga tgcagtgcat agaacctaat     780
tgcaggtggg ggaccccggc cctcccccgg tggacaataa aaaaaatcca gtttccaagc     840
ccaagctata ggtaggcagt ccagagcggt ggtcttgtca ctttcttact tccaaaacca     900
ggccactgtt gatgtaggct ggctggctgg ctcatgtgcc acagttgctg ttcgttatta     960
actgtagtaa acatcagtgt ggacgggcgc cagaatttca gatctcggta cgtatgctgt    1020
gtggattcag cgttatttga acaccgtaat aatgctctcc agcagattgt gaattgtgaa    1080
tacagttcgt agagaacact atttataatg cagacgttat gtttacatag tttagtttaa    1140
aatgggagat aagatagaag agatagaatg agtaattggc tggagatcaa atcgtgcata    1200
ttattgtgca aaacactgtt tttccatata gtggagtttt aaagtatggg acgagagagc    1260
agatagcaaa tcgtgtatat ggtcgtgcaa atattatata tgtggttgtg caaaactccg    1320
aaatttgaaa taggagacac agttgataat tctacgctct acgcacgggc ggcggactgc    1380
actactagtt catcggatgc gttagcgtgc cactcctcat cttgtttcct tgtacgtact    1440
agtgcaatcc gtcagccgca cggctccagt ccactccagt ccagcaacag cgtcacctcc    1500
agctccgaaa ggcttatcct tgcaacaaac atcgtacgaa aaaggcgcag acaaaagaa     1560 aatggatcga aatgcaacaa ataaaaaagg gcatcaaaat acgctgcgag tgagcgagac    1620
gttggcctcc ccatcccata tatatatagc tatagctatc cctcggttct tcaattcatt    1680
cct                                                                  1683

<210> SEQ ID NO 223
```

<211> LENGTH: 674
<212> TYPE: DNA
<213> ORGANISM: Zea mays

<400> SEQUENCE: 223

```
acgtatgctg tgtggattca gcgttatttg aacaccgtaa taatgctctc cagcagattg      60
tgaattgtga atacagttcg tagagaacac tatttataat gcagacgtta tgtttacata     120
gtttagttta aaatgggaga taagatagaa gagatagaat gagtaattgg ctggagatca     180
aatcgtgcat attattgtgc aaaacactgt ttttccatat agtggagttt taaagtatgg     240
gacgagagag cagatagcaa atcgtgtata tggtcgtgca aatattatat atgtggttgt     300
gcaaaactcc gaaatttgaa ataggagaca cagttgataa ttctacgctc tacgcacggg     360
cggcggactg cactactagt tcatcggatg cgttagcgtg ccactcctca tcttgtttcc     420
ttgtacgtac tagtgcaatc cgtcagccgc acggctccag tccactccag tccagcaaca     480
gcgtcacctc cagctccgaa aggcttatcc ttgcaacaaa catcgtacga aaaggcgca      540
ggacaaaaga aaatggatcg aaatgcaaca aataaaaaag ggcatcaaaa tacgctgcga     600
gtgagcgaga cgttggcctc cccatcccat atatatatag ctatagctat ccctcggttc     660
ttcaattcat tcct                                                       674
```

<210> SEQ ID NO 224
<211> LENGTH: 6
<212> TYPE: DNA
<213> ORGANISM: artificial sequence
<220> FEATURE:
<223> OTHER INFORMATION: Synthetic construct

<400> SEQUENCE: 224

```
tgtctc                                                                  6
```

<210> SEQ ID NO 225
<211> LENGTH: 768
<212> TYPE: DNA
<213> ORGANISM: Zea mays

<400> SEQUENCE: 225

```
tcagcgttat ttgaacaccg taaagcctct ccggcagatt gtgaatacac agttgtggag      60
aacgctattt ataacgcaga cactatttat aatgcagatg tgtaaaagtg aaatttaaaa     120
tagtagatga gataggagag atagaatgag taaactgctg gagagcaaat cgtgcatatg     180
atcgtgcaaa acaccgtttt tcgtagagtg aagtttaaaa tagcaggtga gagagtagat     240
aggatgagta agctgatgga gagcaaatat tgtatatacg tggtcggtgc aatagagtga     300
aatttgaaat aactgacaca gttttggtgc gtggaaatag acgaggataa ttctagtgca     360
atccgcactg ccagtggacc ccgcccgacg ataattctac gcacgggcgg cgcactgcac     420
tactagttca tcgatcggat gcgttagcgt gcccctcctc atattgtttc cttgtacgta     480
ctagtgcaat ccgtcagccg cacggctcca gtccactcca gtccagcaac agcgtcacct     540
ccagctccga aaggcttatc cttgcaacaa acatcgtacg aaaaaggcgc aggaaaaarga     600
aaagtgtcga aatacgacat aaaaaaagca tcaaaatacg ctgcgagtga gygagacatt     660
ggcctcccca tcccatatat atatagctat agctaycect cggttcttca attcatctat     720
cccccgctct ctccatctct ctacccttc tctctctcgg atagctag                   768
```

<210> SEQ ID NO 226
<211> LENGTH: 407

<212> TYPE: DNA
<213> ORGANISM: Zea mays

<400> SEQUENCE: 226

```
tttgaaataa ctgacacagt tttggtgcgt ggaaatagac gaggataatt ctagtgcaat      60
ccgcactgcc agtggacccc gcccgacgat aattctacgc acgggcggcg cactgcacta     120
ctagttcatc gatcggatgc gttagcgtgc ccctcctcat attgtttcct tgtacgtact     180
agtgcaatcc gtcagccgca cggctccagt ccactccagt ccagcaacag cgtcacctcc     240
agctccgaaa ggcttatcct tgcaacaaac atcgtacgaa aaaggcgcag gaaaargaaa     300
agtgtcgaaa tacgacataa aaaaagcatc aaaatacgct gcgagtgagy gagacattgg     360
cctcccccatc ccatatatat atagctatag ctayccctcg gttcttc                  407
```

<210> SEQ ID NO 227
<211> LENGTH: 485
<212> TYPE: DNA
<213> ORGANISM: Zea mays

<400> SEQUENCE: 227

```
gcatctgctg ttctttattt ctatacatac atatatacta tcaccggtta tttgcttctc      60
tattctgtcc gagtacttta cggtgttccg cacatagatc tcgtggccgg cggttttgcg     120
ctttcgcttg cgtttcttgg ccctgctggt gtttgaccgg accgaacggg ggcagatcga     180
tgctttgggt ttgaagcgga gctcctatca ttccaatgaa gggtcgttcc gaagggctgg     240
ttccgctgct cgttcatggt tcccactatc ctatctcatc atgtgtatat atgtattcca     300
tgggggaggg tttctctcgt ctttgagata ggcttgtggt ttgcatgacc gaggagctgc     360
accgcccct tgctggccgc tctttggatt gaagggagct ctgcatcctg atccacccct     420
ccatttttt ttgcttgttg tgtccttcct gggacctgag atctgaggct cgtggtggct     480
cactg                                                                 485
```

<210> SEQ ID NO 228
<211> LENGTH: 539
<212> TYPE: DNA
<213> ORGANISM: Zea mays

<400> SEQUENCE: 228

```
ccttgtatgt tctccgctca ctcccccatt ccactctcat ccatctctca agctacacac      60
atataaaaaa aaaagagtag agaaggaccg ccgttagagc acttgatgca tgcgtacgtc     120
gatccggcgg accgatctgc ttttgcttgt gtgcttggtg agaaggtccc tgttggagaa     180
gcagggcacg tgcagagaca cgccggagca cggccgccgc cgatctaccg acctcccaca     240
cctgccttgt ggtgtggggg tggaggtcgt cggtggaagc gatagctgtc gttgttgctt     300
cgatgttgtt agctcctcct gcacgtgctc cccttctcca ccacggcctt ctcaccaccc     360
tcctcccccg gcggcggcgg cggcggaccg cccttgccgc gatcaataat gaaaccaaaa     420
gccgacagta tttgagcagg aaatacaaga ggcggatatc ccactgctag cacttctgcg     480
ttgatcatgt tcatctggaa caaaataata ctcggcgact ttacagcgag tgcagcatg     539
```

<210> SEQ ID NO 229
<211> LENGTH: 485
<212> TYPE: DNA
<213> ORGANISM: artificial sequence
<220> FEATURE:
<223> OTHER INFORMATION: Synthetic construct

<400> SEQUENCE: 229

```
gcatctgctg ttctttattt ctatacatac atatatacta tcaccggtta tttgcttctc    60
tattctgtcc gagtacttta cggtgttccg cacatagatc tcgtggccgg cggttttgcg   120
ctttcgcttg cgtttcttgg ccctgctggt gtttgaccgg accgaacggg ggcagatcga   180
tgctttgggt ttgaagatac gtggcaaaac taggaatgaa gggtcgttcc gaagggctgg   240
ttccgctgct cgttcatggt tcccactatc ctatctcatc atgtgtatat atgtattcca   300
tgggggaggg tttctctcgt ctttgagata ggcttgtggt ttgcatgacc gaggagctgc   360
accgccccct tgctggccgc tctttcctgg ttctgccacg tatcatcctg atccacccct   420
ccattttttt ttgcttgttg tgtccttcct gggacctgag atctgaggct cgtggtggct   480
cactg                                                              485
```

<210> SEQ ID NO 230
<211> LENGTH: 21
<212> TYPE: RNA
<213> ORGANISM: artificial sequence
<220> FEATURE:
<223> OTHER INFORMATION: Synthetic construct

<400> SEQUENCE: 230

```
uuuccugguu cugccacgua u                                             21
```

<210> SEQ ID NO 231
<211> LENGTH: 485
<212> TYPE: DNA
<213> ORGANISM: artificial sequence
<220> FEATURE:
<223> OTHER INFORMATION: Synthetic construct

<400> SEQUENCE: 231

```
gcatctgctg ttctttattt ctatacatac atatatacta tcaccggtta tttgcttctc    60
tattctgtcc gagtacttta cggtgttccg cacatagatc tcgtggccgg cggttttgcg   120
ctttcgcttg cgtttcttgg ccctgctggt gtttgaccgg accgaacggg ggcagatcga   180
tgctttgggt ttgaagtctc tggcagtaac tgacaatgaa gggtcgttcc gaagggctgg   240
ttccgctgct cgttcatggt tcccactatc ctatctcatc atgtgtatat atgtattcca   300
tgggggaggg tttctctcgt ctttgagata ggcttgtggt ttgcatgacc gaggagctgc   360
accgccccct tgctggccgc tctttgtccg tttctgccag agacatcctg atccacccct   420
ccattttttt ttgcttgttg tgtccttcct gggacctgag atctgaggct cgtggtggct   480
cactg                                                              485
```

<210> SEQ ID NO 232
<211> LENGTH: 230
<212> TYPE: DNA
<213> ORGANISM: Diabrotica virgifera

<400> SEQUENCE: 232

```
agaagcctgg caatttccaa ggtgattttg tccgttctg ccagagatgc tttacctacc    60
agctgcacaa tttcggctag atcatcttct tcctgaagaa tttccttaac tttggttcta   120
agaggaataa actcttggaa gttttttgtca taaaagtcgt ccaatgctct taaatatttg   180
gaatatgatc caagccagtc tactgaaggg aagtgcttac gttgggcaag               230
```

<210> SEQ ID NO 233
<211> LENGTH: 21

```
<212> TYPE: RNA
<213> ORGANISM: artificial sequence
<220> FEATURE:
<223> OTHER INFORMATION: Synthetic construct

<400> SEQUENCE: 233
uuuguccguu ucugccagag a                                              21

<210> SEQ ID NO 234
<211> LENGTH: 21
<212> TYPE: RNA
<213> ORGANISM: Glycine max

<400> SEQUENCE: 234
ugagaccaaa ugagcagcug a                                              21

<210> SEQ ID NO 235
<211> LENGTH: 20
<212> TYPE: RNA
<213> ORGANISM: Glycine max

<400> SEQUENCE: 235
gcugcucauc uguucucagg                                                20

<210> SEQ ID NO 236
<211> LENGTH: 762
<212> TYPE: DNA
<213> ORGANISM: Glycine max

<400> SEQUENCE: 236
aaaattcatt acattgataa aacacaattc aaaagatcaa tgttccactt catgcaaaga     60
catttccaaa atatgtgtag gtagaggggt tttacaggat cgtcctgaga ccaaatgagc    120
agctgaccac atgatgcagc tatgtttgct attcagctgc tcatctgttc tcaggtcgcc    180
cttgttggac tgtccaactc ctactgattg cggatgcact tgccacaaat gaaaatcaaa    240
gcgaggggaa aagaatgtag agtgtgacta cgattgcatg catgtgattt aggtaattaa    300
gttacatgat tgtctaattg tgtttatgga attgtatatt ttcagaccag gcacctgtaa    360
ctaattatag gtaccatacc ttaaaataag tccaactaag tccatgtctg tgattttta     420 gtgtcacaaa tcacaatcca ttgccattgg ttttttaatt tttcattgtc tgttgtttaa    480
ctaactctag cttttagct gcttcaagta cagattcctc aaagtggaaa atgttctttg     540
aagtcaataa aaagagcttt gatgatcatc tgcattgtct aagttggata aactaattag    600
agagaacttt tgaactttgt ctaccaaata tctgtcagtg tcatctgtca gttctgcaag    660
ctgaagtgtt gaatccacga ggtgcttgtt gcaaagttgt gatattaaaa gacatctacg    720
aagaagttca agcaaaactc tttttggcaa aaaaaaaaaa aa                       762

<210> SEQ ID NO 237
<211> LENGTH: 21
<212> TYPE: RNA
<213> ORGANISM: Glycine max

<400> SEQUENCE: 237
uagaagcucc ccauguucuc a                                              21

<210> SEQ ID NO 238
<211> LENGTH: 19
<212> TYPE: RNA
<213> ORGANISM: Glycine max
```

```
<400> SEQUENCE: 238
gagcaugggu aacuucuau                                                    19

<210> SEQ ID NO 239
<211> LENGTH: 346
<212> TYPE: DNA
<213> ORGANISM: Glycine max
<220> FEATURE:
<221> NAME/KEY: unsure
<222> LOCATION: (1)..(346)
<223> OTHER INFORMATION: unsure at all n locations

<400> SEQUENCE: 239
ttttctccta actttgagag catgggtaac ttctattttt atctctgncc ccntttcctt       60
catcttttct tcaaccttta ttcgttcctt tttcaactgt taaaaggcct gactatgttg      120
aggaaattaa gaaatgggt tgttgccga tgccagcaga atagaagctc cccatgttct        180
caccgttagc agaaaacggg tgttatctgg ataagaccgc caggttccat tcccttgttt     240
gccagcacca ccatcacttc ttcactctag tatccgattt ttttaaagga tcgttgtccc     300
ttgccttctg gtggacttct atggagaagt ttcttcacac cctatg                    346

<210> SEQ ID NO 240
<211> LENGTH: 21
<212> TYPE: RNA
<213> ORGANISM: Glycine max

<400> SEQUENCE: 240
uguugcgggu aucuuugccu c                                                21

<210> SEQ ID NO 241
<211> LENGTH: 20
<212> TYPE: RNA
<213> ORGANISM: Glycine max

<400> SEQUENCE: 241
ggcguagauc cccacaacag                                                  20

<210> SEQ ID NO 242
<211> LENGTH: 434
<212> TYPE: RNA
<213> ORGANISM: Glycine max

<400> SEQUENCE: 242
aacacuaggg uuugcauucc uccuuuagcc gcaacccaua uucuaagcuu ccuuucuccu       60
acuguucugu gucgggccag caaaacuguu gcgggguaucu uugccucuga aggaaaguug    120
ugccuauuau uauggcuuau ugcuuagug gcguagauc cccacaacagu uaugcuugca      180 cugccuuuug ucuccgagac uaacaaauuu gauugauguu ucucuuguug cuaaacuuuu     240
gauuuugacc cgaacugcau gaggcaugaa aguuucauag uggucaaacc acaguaaaau      300
aggaugguca guuuaugucu ggguuuuaua agaauuuuua gaucugucuu gauuacugga     360
ccauuggaug aacacccugu ugguguugaa aaaguagcuu cagccuucug gauguggguua    420 ugagcuuucg augc                                                       434

<210> SEQ ID NO 243
<211> LENGTH: 21
<212> TYPE: RNA
<213> ORGANISM: Glycine max

<400> SEQUENCE: 243
```
ugcgagugus uucgccucug a              21

<210> SEQ ID NO 244
<211> LENGTH: 21
<212> TYPE: RNA
<213> ORGANISM: Glycine max

<400> SEQUENCE: 244
ggaggcguag auacucacac c              21

<210> SEQ ID NO 245
<211> LENGTH: 439
<212> TYPE: DNA
<213> ORGANISM: Glycine max

<400> SEQUENCE: 245
aattagggtt ctctggtcct cccgcccccg gtgctggcat tctcaagcca gtgaaatcgg    60
tgcgagtgtc ttcgcctctg agagagatac tatgagatct caagcctcgg aggcgtagat   120
actcacacct cttttctgg ctatctcacc actgctcttt tccgccgggg cacgaaggtc    180
cttcgcctca ccaaatttcg ttctttaaat ttcacctata tatgtgtata ttttaataa    240
taataattag gtttaaaggg aaaaaaagtc gcttcttaat cctttattca ttgtatgcag   300
aacgatttga ttcgtgatga taatgtatgg atctgtatag tcggttgctc tagtatccaa   360
taatttgatt tctaacaaat taatatgtag tggccttctt ggacatgaaa aaaattcttg   420
aaattgggtt gttaggtta                                                439

<210> SEQ ID NO 246
<211> LENGTH: 22
<212> TYPE: RNA
<213> ORGANISM: Glycine max

<400> SEQUENCE: 246
uugccgauuc cacccauucc ua             22

<210> SEQ ID NO 247
<211> LENGTH: 20
<212> TYPE: RNA
<213> ORGANISM: Glycine max

<400> SEQUENCE: 247
gcugcucauc uguucucagg               20

<210> SEQ ID NO 248
<211> LENGTH: 495
<212> TYPE: DNA
<213> ORGANISM: Glycine max

<400> SEQUENCE: 248
gactagatgt gaatgtgatt catattcata gagagagaaa gggaaaggga gaagagcttg    60
aggaagtgat gggagatggg agggtcggta aagaatatat ctgagactcg actcaatctc   120
gatctctctc agtgttgtgt tgttttgttt atccttttgc cgattccacc cattcctatg   180
atttccttcg gttcctctct ttccactctc ctctccgctc tttcctcttg ttatggtaag   240
cacctttctt cttcagatct gctctttata ccatacactt attatagatc taagtttta    300
tggaccttaa ctatcttcct tgatctctta ttaatttaa ccgctctctc tttgttgctg   360
gacatgttac ttcaagataa caaattgctt ttttattttt catcttttct ctcgttctct   420

```
tgtttaaggt ttctataaat catcgatgag atacctataa taatatactt attacagaca    480
aaaaaaaaaa aaaaa                                                     495

<210> SEQ ID NO 249
<211> LENGTH: 825
<212> TYPE: DNA
<213> ORGANISM: Glycine max

<400> SEQUENCE: 249
ctgttctata ttgatagagt gagaaaggga aggaagaag agcttgagga agtgatggga      60
gatgggaggg tcggtaaagg ataacagcgt ctctatgatt aattgttgtg ttgtttattc    120
ttttgccgat tccacccatt cctatgattt tctttggttc ctttctttcc actctcctct   180
ccgctctcca caatctgtta tggtcatgaa gctgccggtc tgactgggtt acattcaaga   240
caagaaaaaa caacaaatcg cttctttctt tttcgtctt ttctttcctt tttcttgttt    300
aaggcttaac aaattatctc agctctagta gatgtagatt attacagaca gatgctagtt   360
aattagctag ctccacaaga tgtttaaaaa tgtgatctat ccatatcaag ctggaccaaa   420
tccaaataat tttactggag ctttctttc ttggtaaaag ctggacattt ttaaaggttt    480
gggtgccact ataacgccac caaagttttc tttcttgatt tttaaccaag ttacattttt   540
ttccctaaat tattccagcg ctaataaata ctgaattttc tgtttttttt ataaaaagaa   600
ttttacatta aattctttga aaataatttc attttggttg ttaatatttt ttttagttc    660 ataacaaatt aacgaatttt gtatttattt tttttataaaa aattattaga aaataacata  720
ttaaatcaag caaaaaaatg tatttttatta aaataaaaaa gtgaaggaaa aaattattta  780
aaaccaacac accaacatat tttaactttt ttattaaact aaacg                   825

<210> SEQ ID NO 250
<211> LENGTH: 21
<212> TYPE: RNA
<213> ORGANISM: Glycine max

<400> SEQUENCE: 250
ccagcugcuc auuuggucac u                                              21

<210> SEQ ID NO 251
<211> LENGTH: 21
<212> TYPE: RNA
<213> ORGANISM: Glycine max

<400> SEQUENCE: 251
agaggacaug gggagguucu a                                              21

<210> SEQ ID NO 252
<211> LENGTH: 21
<212> TYPE: RNA
<213> ORGANISM: Glycine max

<400> SEQUENCE: 252
ucagcugcuc aucuguucuc a                                              21

<210> SEQ ID NO 253
<211> LENGTH: 21
<212> TYPE: RNA
<213> ORGANISM: Glycine max

<400> SEQUENCE: 253
ccagcugcuc auuuggucac u                                              21
```

<210> SEQ ID NO 254
<211> LENGTH: 21
<212> TYPE: RNA
<213> ORGANISM: Glycine max

<400> SEQUENCE: 254
ucagcucuuc uuuggucuc u                                                    21

<210> SEQ ID NO 255
<211> LENGTH: 21
<212> TYPE: RNA
<213> ORGANISM: Glycine max

<400> SEQUENCE: 255
ucagcuacug aucuggucuc a                                                   21

<210> SEQ ID NO 256
<211> LENGTH: 21
<212> TYPE: RNA
<213> ORGANISM: Glycine max

<400> SEQUENCE: 256
ucagcuguuc cuuuguucuc u                                                   21

<210> SEQ ID NO 257
<211> LENGTH: 21
<212> TYPE: RNA
<213> ORGANISM: Glycine max

<400> SEQUENCE: 257
ucagcuguuc cuuuguucuc u                                                   21

<210> SEQ ID NO 258
<211> LENGTH: 21
<212> TYPE: RNA
<213> ORGANISM: Glycine max

<400> SEQUENCE: 258
guagcuucuc acuuggucuu a                                                   21

<210> SEQ ID NO 259
<211> LENGTH: 21
<212> TYPE: RNA
<213> ORGANISM: Glycine max

<400> SEQUENCE: 259
uuagcugcuu cuucggucuc u                                                   21

<210> SEQ ID NO 260
<211> LENGTH: 21
<212> TYPE: RNA
<213> ORGANISM: Glycine max

<400> SEQUENCE: 260
uuagaugcuu guuuggucuu u                                                   21

<210> SEQ ID NO 261
<211> LENGTH: 21
<212> TYPE: RNA
<213> ORGANISM: Glycine max

<400> SEQUENCE: 261
ugagaacaug gggagccucu a            21

<210> SEQ ID NO 262
<211> LENGTH: 21
<212> TYPE: RNA
<213> ORGANISM: Glycine max

<400> SEQUENCE: 262
agaggacaug gggagauucu a            21

<210> SEQ ID NO 263
<211> LENGTH: 21
<212> TYPE: RNA
<213> ORGANISM: Glycine max

<400> SEQUENCE: 263
agaggacaug gggagguucu a            21

<210> SEQ ID NO 264
<211> LENGTH: 21
<212> TYPE: RNA
<213> ORGANISM: Glycine max

<400> SEQUENCE: 264
ugagaacaug ggaaucuucu a            21

<210> SEQ ID NO 265
<211> LENGTH: 21
<212> TYPE: RNA
<213> ORGANISM: Glycine max

<400> SEQUENCE: 265
aaagaacaug gggagccucu a            21

<210> SEQ ID NO 266
<211> LENGTH: 21
<212> TYPE: RNA
<213> ORGANISM: Glycine max

<400> SEQUENCE: 266
ugagaacaug ggggauuucu a            21

<210> SEQ ID NO 267
<211> LENGTH: 21
<212> TYPE: RNA
<213> ORGANISM: Glycine max

<400> SEQUENCE: 267
ugugaaggug gggagcuucu u            21

<210> SEQ ID NO 268
<211> LENGTH: 21
<212> TYPE: RNA
<213> ORGANISM: Glycine max

<400> SEQUENCE: 268
ggagaacaug cagagcuucu g            21

<210> SEQ ID NO 269
<211> LENGTH: 21
<212> TYPE: RNA
<213> ORGANISM: Glycine max

<400> SEQUENCE: 269

```
ugagaaacug gggagcuuuu c                                              21

<210> SEQ ID NO 270
<211> LENGTH: 20
<212> TYPE: RNA
<213> ORGANISM: Glycine max

<400> SEQUENCE: 270
ugagaacugg ugagcuucug                                                20

<210> SEQ ID NO 271
<211> LENGTH: 20
<212> TYPE: RNA
<213> ORGANISM: Glycine max

<400> SEQUENCE: 271
ugaguacugg ggagcuucuc                                                20

<210> SEQ ID NO 272
<211> LENGTH: 21
<212> TYPE: RNA
<213> ORGANISM: Glycine max

<400> SEQUENCE: 272
ugagagcaug gguaacuucu a                                              21

<210> SEQ ID NO 273
<211> LENGTH: 20
<212> TYPE: RNA
<213> ORGANISM: Glycine max

<400> SEQUENCE: 273
ugagcacugg ggagcuucuc                                                20

<210> SEQ ID NO 274
<211> LENGTH: 20
<212> TYPE: RNA
<213> ORGANISM: Glycine max

<400> SEQUENCE: 274
ugagcacugg ggagcuucuc                                                20

<210> SEQ ID NO 275
<211> LENGTH: 20
<212> TYPE: RNA
<213> ORGANISM: Glycine max

<400> SEQUENCE: 275
ugagcacugg ggagcuucuc                                                20

<210> SEQ ID NO 276
<211> LENGTH: 21
<212> TYPE: RNA
<213> ORGANISM: Glycine max

<400> SEQUENCE: 276
ugagaacaug ggaacuuucu a                                              21

<210> SEQ ID NO 277
<211> LENGTH: 21
<212> TYPE: RNA
<213> ORGANISM: Glycine max
```

-continued

```
<400> SEQUENCE: 277
ugagagcaug gguaacuucu a                                          21

<210> SEQ ID NO 278
<211> LENGTH: 21
<212> TYPE: RNA
<213> ORGANISM: Glycine max

<400> SEQUENCE: 278
ugagaaccug guaagcuucu g                                          21

<210> SEQ ID NO 279
<211> LENGTH: 21
<212> TYPE: RNA
<213> ORGANISM: Glycine max

<400> SEQUENCE: 279
ugagaacauc gaaagcuucu u                                          21

<210> SEQ ID NO 280
<211> LENGTH: 21
<212> TYPE: RNA
<213> ORGANISM: Glycine max

<400> SEQUENCE: 280
ugaggacaag gggagcuuau g                                          21

<210> SEQ ID NO 281
<211> LENGTH: 21
<212> TYPE: RNA
<213> ORGANISM: Glycine max

<400> SEQUENCE: 281
cuaaaacaug gggagcuucu u                                          21

<210> SEQ ID NO 282
<211> LENGTH: 21
<212> TYPE: RNA
<213> ORGANISM: Glycine max

<400> SEQUENCE: 282
ugaggaaaua gggaguuucu g                                          21

<210> SEQ ID NO 283
<211> LENGTH: 21
<212> TYPE: RNA
<213> ORGANISM: Glycine max

<400> SEQUENCE: 283
ugagaacaua gugaguuuuu u                                          21

<210> SEQ ID NO 284
<211> LENGTH: 21
<212> TYPE: RNA
<213> ORGANISM: Glycine max

<400> SEQUENCE: 284
uaggaucgug gggagcuucu c                                          21

<210> SEQ ID NO 285
<211> LENGTH: 21
<212> TYPE: RNA
<213> ORGANISM: Glycine max
```

<400> SEQUENCE: 285
uaggaucgug gggagcuucu c                                              21

<210> SEQ ID NO 286
<211> LENGTH: 21
<212> TYPE: RNA
<213> ORGANISM: Glycine max

<400> SEQUENCE: 286
uaggaucgug gggagcuucu c                                              21

<210> SEQ ID NO 287
<211> LENGTH: 21
<212> TYPE: RNA
<213> ORGANISM: Glycine max

<400> SEQUENCE: 287
gaugaauaug gggaguuucu a                                              21

<210> SEQ ID NO 288
<211> LENGTH: 21
<212> TYPE: RNA
<213> ORGANISM: Glycine max

<400> SEQUENCE: 288
ggggcaagga cauccgcaac g                                              21

<210> SEQ ID NO 289
<211> LENGTH: 21
<212> TYPE: RNA
<213> ORGANISM: Glycine max

<400> SEQUENCE: 289
aaggcaaagu ugcccgcgac g                                              21

<210> SEQ ID NO 290
<211> LENGTH: 21
<212> TYPE: RNA
<213> ORGANISM: Glycine max

<400> SEQUENCE: 290
gaggcaaaga ugcgagcaac g                                              21

<210> SEQ ID NO 291
<211> LENGTH: 21
<212> TYPE: RNA
<213> ORGANISM: Glycine max

<400> SEQUENCE: 291
gcggcaaaga uacucacaac c                                              21

<210> SEQ ID NO 292
<211> LENGTH: 21
<212> TYPE: RNA
<213> ORGANISM: Glycine max

<400> SEQUENCE: 292
aacgcaaaga gaccuguaac a                                              21

<210> SEQ ID NO 293
<211> LENGTH: 21
<212> TYPE: RNA

<213> ORGANISM: Glycine max

<400> SEQUENCE: 293
aaggcaaaga ugccagcgac g         21

<210> SEQ ID NO 294
<211> LENGTH: 21
<212> TYPE: RNA
<213> ORGANISM: Glycine max

<400> SEQUENCE: 294
gagccaaaga gacccgugac g         21

<210> SEQ ID NO 295
<211> LENGTH: 21
<212> TYPE: RNA
<213> ORGANISM: Glycine max

<400> SEQUENCE: 295
aaggcauaga uagucgcagc a         21

<210> SEQ ID NO 296
<211> LENGTH: 21
<212> TYPE: RNA
<213> ORGANISM: Glycine max

<400> SEQUENCE: 296
aaggcaaaga ugccagcaau g         21

<210> SEQ ID NO 297
<211> LENGTH: 21
<212> TYPE: RNA
<213> ORGANISM: Glycine max

<400> SEQUENCE: 297
uagggaaaga uacauguaac a         21

<210> SEQ ID NO 298
<211> LENGTH: 21
<212> TYPE: RNA
<213> ORGANISM: Glycine max

<400> SEQUENCE: 298
gaggcaaagu uguucgcaau g         21

<210> SEQ ID NO 299
<211> LENGTH: 21
<212> TYPE: RNA
<213> ORGANISM: Glycine max

<400> SEQUENCE: 299
caggcaaaga ugucugcaau u         21

<210> SEQ ID NO 300
<211> LENGTH: 21
<212> TYPE: RNA
<213> ORGANISM: Glycine max

<400> SEQUENCE: 300
uagguaugga uacuugcaac a         21

<210> SEQ ID NO 301
<211> LENGTH: 21

```
<212> TYPE: RNA
<213> ORGANISM: Glycine max

<400> SEQUENCE: 301
aaggcaaagc ugcccgcgau g                                              21

<210> SEQ ID NO 302
<211> LENGTH: 21
<212> TYPE: RNA
<213> ORGANISM: Glycine max

<400> SEQUENCE: 302
ucaggggagg agacacucgc a                                              21

<210> SEQ ID NO 303
<211> LENGTH: 21
<212> TYPE: RNA
<213> ORGANISM: Glycine max

<400> SEQUENCE: 303
uuagaggcaa agacacucgu c                                              21

<210> SEQ ID NO 304
<211> LENGTH: 21
<212> TYPE: RNA
<213> ORGANISM: Glycine max

<400> SEQUENCE: 304
ucagaggaga agauacucgu g                                              21

<210> SEQ ID NO 305
<211> LENGTH: 21
<212> TYPE: RNA
<213> ORGANISM: Glycine max

<400> SEQUENCE: 305
ucagaggaga agacacgcgc a                                              21

<210> SEQ ID NO 306
<211> LENGTH: 21
<212> TYPE: RNA
<213> ORGANISM: Glycine max

<400> SEQUENCE: 306
ucagagggga agacacacgc u                                              21

<210> SEQ ID NO 307
<211> LENGTH: 21
<212> TYPE: RNA
<213> ORGANISM: Glycine max

<400> SEQUENCE: 307
ucagagggga agacacacgc u                                              21

<210> SEQ ID NO 308
<211> LENGTH: 21
<212> TYPE: RNA
<213> ORGANISM: Glycine max

<400> SEQUENCE: 308
ucagagguga ggacacacgc u                                              21

<210> SEQ ID NO 309
```

```
<211> LENGTH: 21
<212> TYPE: RNA
<213> ORGANISM: Glycine max

<400> SEQUENCE: 309
ccagaggcgg augcauucgc a                                              21

<210> SEQ ID NO 310
<211> LENGTH: 21
<212> TYPE: RNA
<213> ORGANISM: Glycine max

<400> SEQUENCE: 310
acagaggcag ggacacuugc a                                              21

<210> SEQ ID NO 311
<211> LENGTH: 21
<212> TYPE: RNA
<213> ORGANISM: Glycine max

<400> SEQUENCE: 311
gcagagguga agaagcuugc a                                              21

<210> SEQ ID NO 312
<211> LENGTH: 21
<212> TYPE: RNA
<213> ORGANISM: Glycine max

<400> SEQUENCE: 312
uuagaggaga ggauacucgc g                                              21

<210> SEQ ID NO 313
<211> LENGTH: 21
<212> TYPE: RNA
<213> ORGANISM: Glycine max

<400> SEQUENCE: 313
gcagagguga agaagcuugc a                                              21

<210> SEQ ID NO 314
<211> LENGTH: 21
<212> TYPE: RNA
<213> ORGANISM: Glycine max

<400> SEQUENCE: 314
ucagaggcaa agauacccgc a                                              21

<210> SEQ ID NO 315
<211> LENGTH: 21
<212> TYPE: RNA
<213> ORGANISM: Glycine max

<400> SEQUENCE: 315 uuagaggga agacacgcgc u                                               21

<210> SEQ ID NO 316
<211> LENGTH: 21
<212> TYPE: RNA
<213> ORGANISM: Glycine max

<400> SEQUENCE: 316
ucagagggga agacacccgu g                                              21
```

-continued

<210> SEQ ID NO 317
<211> LENGTH: 21
<212> TYPE: RNA
<213> ORGANISM: Glycine max

<400> SEQUENCE: 317
ucagaggcua agagacuugu a                                              21

<210> SEQ ID NO 318
<211> LENGTH: 21
<212> TYPE: RNA
<213> ORGANISM: Glycine max

<400> SEQUENCE: 318
ucagagggga agacacgcgu g                                              21

<210> SEQ ID NO 319
<211> LENGTH: 21
<212> TYPE: RNA
<213> ORGANISM: Glycine max

<400> SEQUENCE: 319
ucagagggga agacacccgu g                                              21

<210> SEQ ID NO 320
<211> LENGTH: 21
<212> TYPE: RNA
<213> ORGANISM: Glycine max

<400> SEQUENCE: 320
ucagagggga agacacacgu u                                              21

<210> SEQ ID NO 321
<211> LENGTH: 21
<212> TYPE: RNA
<213> ORGANISM: Glycine max

<400> SEQUENCE: 321
ucagagggga agacacacgu u                                              21

<210> SEQ ID NO 322
<211> LENGTH: 21
<212> TYPE: RNA
<213> ORGANISM: Glycine max

<400> SEQUENCE: 322
ucagggguga agacacacgu a                                              21

<210> SEQ ID NO 323
<211> LENGTH: 21
<212> TYPE: RNA
<213> ORGANISM: Glycine max

<400> SEQUENCE: 323
ucagagggga agacacccgu g                                              21

<210> SEQ ID NO 324
<211> LENGTH: 21
<212> TYPE: RNA
<213> ORGANISM: Glycine max

<400> SEQUENCE: 324
ucagaaacga agacgcucgu u                                              21

```
<210> SEQ ID NO 325
<211> LENGTH: 21
<212> TYPE: RNA
<213> ORGANISM: Glycine max

<400> SEQUENCE: 325
uccgagggga agauacucgu u                                              21

<210> SEQ ID NO 326
<211> LENGTH: 21
<212> TYPE: RNA
<213> ORGANISM: Glycine max

<400> SEQUENCE: 326
uccgagggga agauacucgu c                                              21

<210> SEQ ID NO 327
<211> LENGTH: 21
<212> TYPE: RNA
<213> ORGANISM: Glycine max

<400> SEQUENCE: 327
uccgagggga agauacucgu c                                              21

<210> SEQ ID NO 328
<211> LENGTH: 21
<212> TYPE: RNA
<213> ORGANISM: Glycine max

<400> SEQUENCE: 328
gcagaggcug uggcacucgc a                                              21

<210> SEQ ID NO 329
<211> LENGTH: 21
<212> TYPE: RNA
<213> ORGANISM: Glycine max

<400> SEQUENCE: 329
uuagaggcga ggacacacgu u                                              21

<210> SEQ ID NO 330
<211> LENGTH: 21
<212> TYPE: RNA
<213> ORGANISM: Glycine max

<400> SEQUENCE: 330
uccgaggaga agauacucgu u                                              21

<210> SEQ ID NO 331
<211> LENGTH: 21
<212> TYPE: RNA
<213> ORGANISM: Glycine max

<400> SEQUENCE: 331
ucaguggcga aggcguucgu c                                              21

<210> SEQ ID NO 332
<211> LENGTH: 21
<212> TYPE: RNA
<213> ORGANISM: Glycine max

<400> SEQUENCE: 332
uuagagguga uggcacucgu g                                              21
```

<210> SEQ ID NO 333
<211> LENGTH: 22
<212> TYPE: RNA
<213> ORGANISM: Glycine max

<400> SEQUENCE: 333
ggggaauggg uggaaacggc aa                                              22

<210> SEQ ID NO 334
<211> LENGTH: 22
<212> TYPE: RNA
<213> ORGANISM: Glycine max

<400> SEQUENCE: 334
ugggaauggg ugggaugggu aa                                              22

<210> SEQ ID NO 335
<211> LENGTH: 22
<212> TYPE: RNA
<213> ORGANISM: Glycine max

<400> SEQUENCE: 335
ugggaauggg ugggauggu aa                                               22

<210> SEQ ID NO 336
<211> LENGTH: 22
<212> TYPE: RNA
<213> ORGANISM: Glycine max

<400> SEQUENCE: 336
auggaacugg uggaauuggc aa                                              22

<210> SEQ ID NO 337
<211> LENGTH: 22
<212> TYPE: RNA
<213> ORGANISM: Glycine max

<400> SEQUENCE: 337
cgggaaaggu uggaauuggc aa                                              22

<210> SEQ ID NO 338
<211> LENGTH: 22
<212> TYPE: RNA
<213> ORGANISM: Glycine max

<400> SEQUENCE: 338
uaggaauggg uggauuuugc aa                                              22

<210> SEQ ID NO 339
<211> LENGTH: 20
<212> TYPE: RNA
<213> ORGANISM: Glycine max

<400> SEQUENCE: 339
ggaaugggug gcgugggcaa                                                 20

<210> SEQ ID NO 340
<211> LENGTH: 22
<212> TYPE: RNA
<213> ORGANISM: Glycine max

<400> SEQUENCE: 340

```
caggaaaggg gggaguuggc aa                                                  22

<210> SEQ ID NO 341
<211> LENGTH: 22
<212> TYPE: RNA
<213> ORGANISM: Glycine max

<400> SEQUENCE: 341
uagcaauggg uuggaucggu ga                                                  22

<210> SEQ ID NO 342
<211> LENGTH: 22
<212> TYPE: RNA
<213> ORGANISM: Glycine max

<400> SEQUENCE: 342
guugaauggg uggaauugga aa                                                  22

<210> SEQ ID NO 343
<211> LENGTH: 22
<212> TYPE: RNA
<213> ORGANISM: Glycine max

<400> SEQUENCE: 343
guugaauggg uggaauugga aa                                                  22

<210> SEQ ID NO 344
<211> LENGTH: 22
<212> TYPE: RNA
<213> ORGANISM: Glycine max

<400> SEQUENCE: 344
aaggaauugg gggaauuggu ac                                                  22

<210> SEQ ID NO 345
<211> LENGTH: 22
<212> TYPE: RNA
<213> ORGANISM: Glycine max

<400> SEQUENCE: 345
cacgaguggg gggaaucggc gg                                                  22

<210> SEQ ID NO 346
<211> LENGTH: 22
<212> TYPE: RNA
<213> ORGANISM: Glycine max

<400> SEQUENCE: 346
guggaauggg uggucuuggu aa                                                  22

<210> SEQ ID NO 347
<211> LENGTH: 112
<212> TYPE: RNA
<213> ORGANISM: artificial sequence
<220> FEATURE:
<223> OTHER INFORMATION: synthetic construct

<400> SEQUENCE: 347
guugagggga auguugucug gcucgaggac auuaacaaga uauacauaug auuuacauau         60
gaauuaugau aagccuuaua ggguucucgg accaggcuuc auuccccca ac                 112

<210> SEQ ID NO 348
<211> LENGTH: 311
```

<212> TYPE: PRT
<213> ORGANISM: artificial sequence
<220> FEATURE:
<223> OTHER INFORMATION: synthetic construct

<400> SEQUENCE: 348

Met Ala Pro Thr Val Met Met Ala Ser Ser Ala Thr Ala Val Ala Pro
1               5                   10                  15

Phe Gln Gly Leu Lys Ser Thr Ala Ser Leu Pro Val Ala Arg Arg Ser
            20                  25                  30

Ser Arg Ser Leu Gly Asn Val Ser Asn Gly Gly Arg Ile Arg Cys Met
        35                  40                  45

Gln Val Trp Pro Ala Tyr Gly Asn Lys Lys Phe Glu Thr Leu Ser Tyr
    50                  55                  60

Leu Pro Pro Leu Ser Thr Gly Gly Arg Ile Arg Cys Met Gln Ala Met
65                  70                  75                  80

Ala Phe Phe Asn Arg Val Ile Thr Leu Thr Val Pro Ser Ser Asp Val
                85                  90                  95

Val Asn Tyr Ser Glu Ile Tyr Gln Val Ala Pro Gln Tyr Val Asn Gln
            100                 105                 110

Ala Leu Thr Leu Ala Lys Tyr Phe Gln Gly Ala Ile Asp Gly Ser Thr
        115                 120                 125

Leu Arg Phe Asp Phe Glu Lys Ala Leu Gln Ile Ala Asn Asp Ile Pro
    130                 135                 140

Gln Ala Ala Val Val Asn Thr Leu Asn Gln Thr Val Gln Gln Gly Thr
145                 150                 155                 160

Val Gln Val Ser Val Met Ile Asp Lys Ile Val Asp Ile Met Lys Asn
                165                 170                 175

Val Leu Ser Ile Val Ile Asp Asn Lys Lys Phe Trp Asp Gln Val Thr
            180                 185                 190

Ala Ala Ile Thr Asn Thr Phe Thr Asn Leu Asn Ser Gln Glu Ser Glu
        195                 200                 205

Ala Trp Ile Phe Tyr Tyr Lys Glu Asp Ala His Lys Thr Ser Tyr Tyr
    210                 215                 220

Tyr Asn Ile Leu Phe Ala Ile Gln Asp Glu Glu Thr Gly Gly Val Met
225                 230                 235                 240

Ala Thr Leu Pro Ile Ala Phe Asp Ile Ser Val Asp Ile Glu Lys Glu
                245                 250                 255

Lys Val Leu Phe Val Thr Ile Lys Asp Thr Glu Asn Tyr Ala Val Thr
            260                 265                 270

Val Lys Ala Ile Asn Val Val Gln Ala Leu Gln Ser Ser Arg Asp Ser
        275                 280                 285

Lys Val Val Asp Ala Phe Lys Ser Pro Arg His Leu Pro Arg Lys Arg
    290                 295                 300

His Lys Ile Cys Ser Asn Ser
305                 310

<210> SEQ ID NO 349
<211> LENGTH: 232
<212> TYPE: PRT
<213> ORGANISM: artificial sequence
<220> FEATURE:
<223> OTHER INFORMATION: synthetic construct

<400> SEQUENCE: 349

Met Ala Phe Phe Asn Arg Val Ile Thr Leu Thr Val Pro Ser Ser Asp
1               5                   10                  15

-continued

```
Val Val Asn Tyr Ser Glu Ile Tyr Gln Val Ala Pro Gln Tyr Val Asn
            20                  25                  30

Gln Ala Leu Thr Leu Ala Lys Tyr Phe Gln Gly Ala Ile Asp Gly Ser
        35                  40                  45

Thr Leu Arg Phe Asp Phe Glu Lys Ala Leu Gln Ile Ala Asn Asp Ile
    50                  55                  60

Pro Gln Ala Ala Val Val Asn Thr Leu Asn Gln Thr Val Gln Gln Gly
65                      70                  75                  80

Thr Val Gln Val Ser Val Met Ile Asp Lys Ile Val Asp Ile Met Lys
                85                  90                  95

Asn Val Leu Ser Ile Val Ile Asp Asn Lys Lys Phe Trp Asp Gln Val
                100                 105                 110

Thr Ala Ala Ile Thr Asn Thr Phe Thr Asn Leu Asn Ser Gln Glu Ser
            115                 120                 125

Glu Ala Trp Ile Phe Tyr Tyr Lys Glu Asp Ala His Lys Thr Ser Tyr
        130                 135                 140

Tyr Tyr Asn Ile Leu Phe Ala Ile Gln Asp Glu Glu Thr Gly Gly Val
145                 150                 155                 160

Met Ala Thr Leu Pro Ile Ala Phe Asp Ile Ser Val Asp Ile Glu Lys
                165                 170                 175

Glu Lys Val Leu Phe Val Thr Ile Lys Asp Thr Glu Asn Tyr Ala Val
            180                 185                 190

Thr Val Lys Ala Ile Asn Val Val Gln Ala Leu Gln Ser Ser Arg Asp
        195                 200                 205

Ser Lys Val Val Asp Ala Phe Lys Ser Pro Arg His Leu Pro Arg Lys
    210                 215                 220

Arg His Lys Ile Cys Ser Asn Ser
225                 230
```